United States Patent
Van Berkel et al.

(10) Patent No.: US 10,544,223 B2
(45) Date of Patent: Jan. 28, 2020

(54) COMBINATION THERAPY WITH AN ANTI-AXL ANTIBODY-DRUG CONJUGATE

(71) Applicants: ADC THERAPEUTICS SA, Epalinges (CH); MEDIMMUNE LIMITED, Cambridge, Cambridgeshire (GB)

(72) Inventors: Patricius Hendrikus Cornelis Van Berkel, Epalinges (CH); Jens Wuerthner, Epalinges (CH); John Hartley, London (GB); Francesca Zammarchi, Epalinges (CH)

(73) Assignees: ADC THERAPEUTICS SA, Epalinges (CH); MEDIMMUNE LIMTIED, Cambridge (GB)

( * ) Notice: Subject to any disclaimer, the term of this patent is extended or adjusted under 35 U.S.C. 154(b) by 0 days.

(21) Appl. No.: 16/197,891

(22) Filed: Nov. 21, 2018

(65) Prior Publication Data

US 2019/0218291 A1 Jul. 18, 2019

Related U.S. Application Data

(63) Continuation of application No. PCT/EP2018/060209, filed on Apr. 20, 2018.

(30) Foreign Application Priority Data

| Apr. 20, 2017 | (GB) | ................................. | 1706223.3 |
| Apr. 20, 2017 | (GB) | ................................. | 1706224.1 |
| Apr. 20, 2017 | (GB) | ................................. | 1706225.8 |
| Apr. 20, 2017 | (GB) | ................................. | 1706226.6 |
| Apr. 20, 2017 | (GB) | ................................. | 1706227.4 |
| Apr. 20, 2017 | (GB) | ................................. | 1706228.2 |
| Apr. 20, 2017 | (GB) | ................................. | 1706229.0 |
| Apr. 20, 2017 | (GB) | ................................. | 1706230.8 |
| Apr. 20, 2017 | (GB) | ................................. | 1706231.6 |

(51) Int. Cl.

| *A61K 39/00* | (2006.01) |
| *C07K 16/28* | (2006.01) |
| *A61K 31/7068* | (2006.01) |
| *A61K 47/68* | (2017.01) |
| *A61P 35/00* | (2006.01) |
| *A61K 47/54* | (2017.01) |
| *A61K 47/55* | (2017.01) |
| *A61K 31/20* | (2006.01) |

(52) U.S. Cl.
CPC .......... *C07K 16/2818* (2013.01); *A61K 31/20* (2013.01); *A61K 31/7068* (2013.01); *A61K 47/542* (2017.08); *A61K 47/55* (2017.08); *A61K 47/6803* (2017.08); *A61P 35/00* (2018.01)

(58) Field of Classification Search
CPC .................................................. C07K 16/2818
See application file for complete search history.

(56) References Cited

U.S. PATENT DOCUMENTS

| 3,361,742 A | 1/1968 | Julius et al. |
| 3,523,941 A | 8/1970 | Leimgruber et al. |
| 3,524,849 A | 8/1970 | Batcho et al. |
| 3,794,644 A | 2/1974 | Karlyone et al. |
| 4,185,016 A | 1/1980 | Takanabe et al. |
| 4,239,683 A | 12/1980 | Takanabe et al. |
| 4,309,437 A | 1/1982 | Ueda et al. |
| 4,353,827 A | 10/1982 | Hunkeler et al. |
| 4,382,032 A | 5/1983 | Hunkeler et al. |
| 4,386,028 A | 5/1983 | Hunkeler et al. |
| 4,405,516 A | 9/1983 | Hunkeler et al. |
| 4,405,517 A | 9/1983 | Hunkeler et al. |
| 4,407,752 A | 10/1983 | Hunkeler et al. |
| 4,427,587 A | 1/1984 | Kaneko et al. |
| 4,427,588 A | 1/1984 | Kaneko et al. |
| 4,701,325 A | 10/1987 | Ueda et al. |
| 4,816,567 A | 3/1989 | Cabilly et al. |
| 4,923,984 A | 5/1990 | Matsumura et al. |
| 4,923,990 A | 5/1990 | Nakano et al. |
| 5,362,852 A | 11/1994 | Geoghegan |
| 5,418,241 A | 5/1995 | Jegham et al. |
| 5,440,021 A | 8/1995 | Chuntharapai et al. |
| 5,468,634 A | 11/1995 | Liu |
| 5,538,861 A | 7/1996 | Scheider et al. |
| 5,583,024 A | 12/1996 | McElroy et al. |
| 5,621,002 A | 4/1997 | Bosslet et al. |
| 5,644,033 A | 7/1997 | Seon |
| 5,674,713 A | 10/1997 | McElroy et al. |
| 5,700,670 A | 12/1997 | Yamagishi et al. |
| 5,773,223 A | 6/1998 | Shyamala et al. |
| 5,792,616 A | 8/1998 | Persico et al. |

(Continued)

FOREIGN PATENT DOCUMENTS

| EP | 0522868 | 1/1993 |
| EP | 0875569 | 11/1998 |

(Continued)

OTHER PUBLICATIONS

Strome et al., The Oncologist, 2007; 12:1084-95 (Year: 2007).*
Brand et al., Anticancer Res. 2006; 26:463-70 (Year: 2006).*
3-Aminobenzamide, NCBI Pubchem reference 1645.
Adair, J.R. et al., "Antibody-drug conjugates—a perfect synergy," Exp. Opin. Biol. Ther. (2012), pp. 1-16.
Adams et al., "Molecular modelling of a sequence-specific DNA-binding agent based on the pyrrolo[2,1-c][1,4]benzodiazepines," Pharm. Pharmacol. Commun. (1999) 5:555-560.
Aird, R.E. et al., "ABCB1 genetic polymorphism influences the pharmacology of the new pyrrolobenzodiazepine derivative SJG-136," Pharmacogenomics Journal (2008) 8(4):289-296.

(Continued)

*Primary Examiner* — Sheela J. Huff
(74) *Attorney, Agent, or Firm* — Casimir Jones, S.C.; Melissa E. Kolom

(57) ABSTRACT

The present disclosure relates to combination therapies for the treatment of pathological conditions, such as cancer. In particular, the present disclosure relates to combination therapies comprising treatment with an Antibody Drug Conjugate (ADC) and a secondary agent.

21 Claims, 10 Drawing Sheets

Specification includes a Sequence Listing.

(56) References Cited

U.S. PATENT DOCUMENTS

| | | |
|---|---|---|
| 5,854,399 A | 12/1998 | Salomon et al. |
| 5,869,445 A | 2/1999 | Cheever et al. |
| 5,968,508 A | 10/1999 | Goldfine et al. |
| 5,976,551 A | 11/1999 | Mottez et al. |
| 6,011,146 A | 1/2000 | Mottez et al. |
| 6,087,144 A | 7/2000 | Scadden |
| 6,153,408 A | 11/2000 | Abastado et al. |
| 6,211,142 B1 | 4/2001 | Hammonds et al. |
| 6,214,345 B1 | 4/2001 | Firestone et al. |
| 6,218,519 B1 | 4/2001 | Kenten et al. |
| 6,235,769 B1 | 5/2001 | Clary et al. |
| 6,268,488 B1 | 7/2001 | Barbas, III et al. |
| 6,362,331 B1 | 3/2002 | Kamal et al. |
| 6,518,404 B1 | 2/2003 | Li et al. |
| 6,534,482 B1 | 3/2003 | Fikes et al. |
| 6,555,339 B1 | 4/2003 | Liaw et al. |
| 6,562,806 B1 | 5/2003 | Thurston et al. |
| 6,602,677 B1 | 8/2003 | Wood et al. |
| 6,608,192 B1 | 8/2003 | Thurston et al. |
| 6,660,742 B2 | 12/2003 | Lee |
| 6,660,856 B2 | 12/2003 | Wang |
| 6,677,435 B2 | 1/2004 | Barbas, III et al. |
| 6,747,144 B1 | 6/2004 | Thurston et al. |
| 6,759,509 B1 | 7/2004 | King et al. |
| 6,835,807 B1 | 12/2004 | Sasaki et al. |
| 6,884,799 B2 | 4/2005 | Kamal et al. |
| 6,909,006 B1 | 6/2005 | Thurston et al. |
| 7,049,311 B1 | 5/2006 | Thurston et al. |
| 7,067,511 B2 | 6/2006 | Thurston et al. |
| 7,223,837 B2 | 5/2007 | De Groot et al. |
| 7,244,724 B2 | 7/2007 | Liu et al. |
| 7,265,105 B2 | 9/2007 | Thurston et al. |
| 7,375,078 B2 | 5/2008 | Feng |
| 7,407,951 B2 | 8/2008 | Thurston et al. |
| 7,429,658 B2 | 9/2008 | Howard et al. |
| 7,498,298 B2 | 3/2009 | Doronina et al. |
| 7,511,032 B2 | 3/2009 | Liu et al. |
| 7,521,541 B2 | 4/2009 | Eigenbrot et al. |
| 7,528,126 B2 | 5/2009 | Howard et al. |
| 7,557,099 B2 | 7/2009 | Howard et al. |
| 7,612,062 B2 | 11/2009 | Gregson et al. |
| 7,704,924 B2 | 4/2010 | Thurston et al. |
| 7,723,485 B2 | 5/2010 | Junutula et al. |
| 7,741,319 B2 | 6/2010 | Howard et al. |
| 8,034,808 B2 | 11/2011 | Delavault et al. |
| 8,163,736 B2 | 4/2012 | Gauzy et al. |
| 8,487,092 B2 | 7/2013 | Howard et al. |
| 8,501,934 B2 | 8/2013 | Howard et al. |
| 8,592,576 B2 | 11/2013 | Howard et al. |
| 8,609,089 B2 | 12/2013 | Langermann |
| 8,633,185 B2 | 1/2014 | Howard et al. |
| 8,637,664 B2 | 1/2014 | Howard et al. |
| 8,697,688 B2 | 4/2014 | Howard et al. |
| 8,735,553 B1 | 5/2014 | Li et al. |
| 8,829,184 B2 | 9/2014 | Howard et al. |
| 8,940,733 B2 | 1/2015 | Howard et al. |
| 9,321,774 B2 | 4/2016 | Howard et al. |
| 9,376,440 B2 | 6/2016 | Howard et al. |
| 9,399,641 B2 | 7/2016 | Howard et al. |
| 9,624,227 B2 | 4/2017 | Howard et al. |
| 9,889,207 B2 | 2/2018 | Howard |
| 2001/0055751 A1 | 12/2001 | Reiter et al. |
| 2002/0034749 A1 | 3/2002 | Billing-Medel et al. |
| 2002/0042366 A1 | 4/2002 | Thompson et al. |
| 2002/0150573 A1 | 10/2002 | Nussenzweig |
| 2002/0193567 A1 | 12/2002 | Jacobs et al. |
| 2003/0060612 A1 | 3/2003 | Goddard et al. |
| 2003/0062401 A1 | 4/2003 | Hasz et al. |
| 2003/0064397 A1 | 4/2003 | Spancake et al. |
| 2003/0065143 A1 | 4/2003 | Eaton et al. |
| 2003/0091580 A1 | 5/2003 | Mitcham et al. |
| 2003/0096743 A1 | 5/2003 | Senter et al. |
| 2003/0096961 A1 | 5/2003 | Baker et al. |
| 2003/0105292 A1 | 6/2003 | Liaw et al. |
| 2003/0109676 A1 | 6/2003 | Li et al. |
| 2003/0118592 A1 | 6/2003 | Ledbetter et al. |
| 2003/0119121 A1 | 6/2003 | Baker et al. |
| 2003/0119122 A1 | 6/2003 | Baker et al. |
| 2003/0119125 A1 | 6/2003 | Baker et al. |
| 2003/0119126 A1 | 6/2003 | Baker et al. |
| 2003/0119128 A1 | 6/2003 | Baker et al. |
| 2003/0119129 A1 | 6/2003 | Baker et al. |
| 2003/0119130 A1 | 6/2003 | Baker et al. |
| 2003/0119131 A1 | 6/2003 | Baker et al. |
| 2003/0124140 A1 | 7/2003 | Bangur et al. |
| 2003/0124579 A1 | 7/2003 | Mack et al. |
| 2003/0129192 A1 | 7/2003 | Chenault et al. |
| 2003/0130189 A1 | 7/2003 | Senter et al. |
| 2003/0134790 A1 | 7/2003 | Langenfeld |
| 2003/0143557 A1 | 7/2003 | Penner |
| 2003/0157089 A1 | 8/2003 | Xu et al. |
| 2003/0165504 A1 | 9/2003 | Retter et al. |
| 2003/0185830 A1 | 10/2003 | Xu et al. |
| 2003/0186372 A1 | 10/2003 | Baker et al. |
| 2003/0186373 A1 | 10/2003 | Baker et al. |
| 2003/0194704 A1 | 10/2003 | Penn et al. |
| 2003/0195196 A1 | 10/2003 | Thurston et al. |
| 2003/0206918 A1 | 11/2003 | Fanger et al. |
| 2003/0219806 A1 | 11/2003 | Glucksmann et al. |
| 2003/0224411 A1 | 12/2003 | Stanton et al. |
| 2003/0224454 A1 | 12/2003 | Ryseck et al. |
| 2003/0228319 A1 | 12/2003 | Frantz et al. |
| 2003/0232056 A1 | 12/2003 | Fanger et al. |
| 2003/0232350 A1 | 12/2003 | Afar et al. |
| 2004/0001827 A1 | 1/2004 | Dennis |
| 2004/0005320 A1 | 1/2004 | Thompson et al. |
| 2004/0005538 A1 | 1/2004 | Chen et al. |
| 2004/0005563 A1 | 1/2004 | Mack et al. |
| 2004/0005598 A1 | 1/2004 | Devaux et al. |
| 2004/0018194 A1 | 1/2004 | Francisco et al. |
| 2004/0018553 A1 | 1/2004 | Billing-Medel et al. |
| 2004/0022727 A1 | 2/2004 | Stanton et al. |
| 2004/0044179 A1 | 3/2004 | Baker et al. |
| 2004/0044180 A1 | 3/2004 | Baker et al. |
| 2004/0052793 A1 | 3/2004 | Carter et al. |
| 2004/0101874 A1 | 5/2004 | Ghosh et al. |
| 2004/0101899 A1 | 5/2004 | Dillon et al. |
| 2004/0121940 A1 | 6/2004 | De Groot et al. |
| 2004/0138269 A1 | 7/2004 | Sun et al. |
| 2004/0197325 A1 | 10/2004 | Law et al. |
| 2004/0198722 A1 | 10/2004 | Thurston et al. |
| 2004/0249130 A1 | 12/2004 | Stanton et al. |
| 2005/0271615 A1 | 12/2005 | Shabat et al. |
| 2006/0116422 A1 | 6/2006 | De Groot et al. |
| 2007/0072846 A1 | 3/2007 | Vishnuvajjala et al. |
| 2007/0185336 A1 | 8/2007 | Rossen et al. |
| 2007/0191349 A1 | 8/2007 | Howard et al. |
| 2007/0232592 A1 | 10/2007 | Delavault et al. |
| 2007/0249591 A1 | 10/2007 | Howard et al. |
| 2008/0090812 A1 | 4/2008 | Pepper et al. |
| 2008/0092940 A1 | 4/2008 | Nakajima |
| 2008/0112961 A1 | 5/2008 | Stavenhagen et al. |
| 2008/0206239 A1 | 8/2008 | Jones et al. |
| 2008/0213289 A1 | 9/2008 | Francisco et al. |
| 2008/0214525 A1 | 9/2008 | Howard et al. |
| 2009/0036431 A1 | 2/2009 | Gauzy et al. |
| 2009/0148942 A1 | 6/2009 | McDonagh et al. |
| 2009/0149449 A1 | 6/2009 | Liu et al. |
| 2009/0304710 A1 | 12/2009 | Park et al. |
| 2010/0047257 A1 | 2/2010 | Blanc et al. |
| 2010/0113425 A1 | 5/2010 | Howard et al. |
| 2010/0203007 A1 | 8/2010 | Li et al. |
| 2011/0070227 A1 | 3/2011 | Novotney-Barry et al. |
| 2011/0160192 A1 | 6/2011 | Howard et al. |
| 2011/0196148 A1 | 8/2011 | Howard et al. |
| 2011/0201803 A1 | 8/2011 | Howard et al. |
| 2011/0256157 A1 | 10/2011 | Howard et al. |
| 2013/0028917 A1 | 1/2013 | Howard et al. |
| 2013/0028919 A1 | 1/2013 | Howard et al. |
| 2013/0266595 A1 | 10/2013 | Flygare et al. |
| 2014/0066435 A1 | 3/2014 | Howard et al. |
| 2014/0120118 A1 | 5/2014 | Howard |
| 2014/0127239 A1 | 5/2014 | Howard |
| 2014/0234346 A1 | 8/2014 | Howard |

(56) References Cited

U.S. PATENT DOCUMENTS

| | | |
|---|---|---|
| 2014/0274907 A1 | 9/2014 | Howard et al. |
| 2014/0275522 A1 | 9/2014 | Howard et al. |
| 2014/0294868 A1 | 10/2014 | Howard et al. |
| 2016/0074527 A1 | 7/2016 | Flygare et al. |
| 2016/0304607 A1 | 10/2016 | Sadineni et al. |

FOREIGN PATENT DOCUMENTS

| | | |
|---|---|---|
| EP | 1295944 | 3/2003 |
| EP | 1347046 | 9/2003 |
| EP | 1394274 | 3/2004 |
| EP | 1439393 | 7/2004 |
| EP | 1813614 | 8/2007 |
| EP | 2019104 | 1/2009 |
| EP | 2267454 A2 | 12/2010 |
| EP | 2298817 | 3/2011 |
| EP | 2528625 | 7/2013 |
| FR | 2027356 | 12/1969 |
| FR | 2586683 | 3/1987 |
| GB | 1299198 | 12/1972 |
| GB | 1410826 | 10/1975 |
| GB | 2053894 | 2/1981 |
| JP | 5382792 | 7/1978 |
| JP | 57131791 | 8/1982 |
| JP | 58180487 | 10/1983 |
| JP | 05003790 | 1/1993 |
| JP | 2004113151 | 4/2004 |
| WO | WO 199102536 | 3/1991 |
| WO | WO 9216221 | 3/1992 |
| WO | WO 199207574 | 5/1992 |
| WO | WO 199217497 | 10/1992 |
| WO | WO 199219620 | 11/1992 |
| WO | WO 199318045 | 9/1993 |
| WO | WO 199410312 | 5/1994 |
| WO | WO 199428931 | 12/1994 |
| WO | WO 199504718 | 2/1995 |
| WO | WO 199630514 | 10/1996 |
| WO | WO 199707198 | 2/1997 |
| WO | WO 199744452 | 11/1997 |
| WO | WO 199813059 | 4/1998 |
| WO | WO 199837193 | 8/1998 |
| WO | WO 199840403 | 9/1998 |
| WO | WO 199851805 | 11/1998 |
| WO | WO 199851824 | 11/1998 |
| WO | WO 199928468 | 6/1999 |
| WO | WO 199946284 | 9/1999 |
| WO | WO 1999049894 | 10/1999 |
| WO | WO 199958658 | 11/1999 |
| WO | WO 200003291 | 1/2000 |
| WO | WO 200012506 | 3/2000 |
| WO | WO 200012507 | 3/2000 |
| WO | WO 200012508 | 3/2000 |
| WO | WO 200012509 | 3/2000 |
| WO | WO 200014228 | 3/2000 |
| WO | WO 200020579 | 4/2000 |
| WO | WO 200022129 | 4/2000 |
| WO | WO 200032752 | 6/2000 |
| WO | WO 200036107 | 6/2000 |
| WO | WO 200040614 | 7/2000 |
| WO | WO 200044899 | 8/2000 |
| WO | WO 200012130 | 9/2000 |
| WO | WO 200053216 | 9/2000 |
| WO | WO 200055351 | 9/2000 |
| WO | WO 2000053216 | 9/2000 |
| WO | WO 200075655 | 12/2000 |
| WO | WO 2000076309 | 12/2000 |
| WO | WO 200100244 | 1/2001 |
| WO | WO 200116104 | 3/2001 |
| WO | WO 200116318 | 3/2001 |
| WO | WO 2001016181 | 3/2001 |
| WO | WO 200138490 | 5/2001 |
| WO | WO 2001032926 | 5/2001 |
| WO | WO 200140269 | 6/2001 |
| WO | WO 200140309 | 6/2001 |
| WO | WO 200141787 | 6/2001 |
| WO | WO 200145746 | 6/2001 |
| WO | WO 200146232 | 6/2001 |
| WO | WO 200146261 | 6/2001 |
| WO | WO 200148204 | 7/2001 |
| WO | WO 200153463 | 7/2001 |
| WO | WO 200157188 | 8/2001 |
| WO | WO 200162794 | 8/2001 |
| WO | WO 200166689 | 9/2001 |
| WO | WO 200172830 | 10/2001 |
| WO | WO 200172962 | 10/2001 |
| WO | WO 200175177 | 10/2001 |
| WO | WO 200177172 | 10/2001 |
| WO | WO 200188133 | 11/2001 |
| WO | WO 200190304 | 11/2001 |
| WO | WO 200194641 | 12/2001 |
| WO | WO 200198351 | 12/2001 |
| WO | WO 200202587 | 1/2002 |
| WO | WO 200202624 | 1/2002 |
| WO | WO 200202634 | 1/2002 |
| WO | WO 200206317 | 1/2002 |
| WO | WO 200206339 | 1/2002 |
| WO | WO 200210187 | 2/2002 |
| WO | WO 200210382 | 2/2002 |
| WO | WO 200212341 | 2/2002 |
| WO | WO 200213847 | 2/2002 |
| WO | WO 200214503 | 2/2002 |
| WO | WO 200216413 | 2/2002 |
| WO | WO 200222153 | 3/2002 |
| WO | WO 200222636 | 3/2002 |
| WO | WO 200222660 | 3/2002 |
| WO | WO 200222808 | 3/2002 |
| WO | WO 200224909 | 3/2002 |
| WO | WO 200226822 | 4/2002 |
| WO | WO 200230268 | 4/2002 |
| WO | WO 200238766 | 5/2002 |
| WO | WO 200254940 | 7/2002 |
| WO | WO 200259377 | 8/2002 |
| WO | WO 200260317 | 8/2002 |
| WO | WO 200261087 | 8/2002 |
| WO | WO 200264798 | 8/2002 |
| WO | WO 200271928 | 9/2002 |
| WO | WO 200272596 | 9/2002 |
| WO | WO 200278524 | 10/2002 |
| WO | WO 200281646 | 10/2002 |
| WO | WO 200283866 | 10/2002 |
| WO | WO 200286443 | 10/2002 |
| WO | WO 200288170 | 11/2002 |
| WO | WO 200288172 | 11/2002 |
| WO | WO 200289747 | 11/2002 |
| WO | WO 200292836 | 11/2002 |
| WO | WO 200294852 | 11/2002 |
| WO | WO 02098897 | 12/2002 |
| WO | WO 200298358 | 12/2002 |
| WO | WO 200299074 | 12/2002 |
| WO | WO 200299122 | 12/2002 |
| WO | WO 2002101075 | 12/2002 |
| WO | WO 2002102235 | 12/2002 |
| WO | WO 200216429 | 1/2003 |
| WO | WO 2003000842 | 1/2003 |
| WO | WO 2003002717 | 1/2003 |
| WO | WO 2003003906 | 1/2003 |
| WO | WO 2003003984 | 1/2003 |
| WO | WO 2003004529 | 1/2003 |
| WO | WO 2003004989 | 1/2003 |
| WO | WO 2003008537 | 1/2003 |
| WO | WO 2003009814 | 2/2003 |
| WO | WO 2003014294 | 2/2003 |
| WO | WO 2003016475 | 2/2003 |
| WO | WO 2003016494 | 2/2003 |
| WO | WO 2003018621 | 3/2003 |
| WO | WO 2003022995 | 3/2003 |
| WO | WO 2003023013 | 3/2003 |
| WO | WO 2003024392 | 3/2003 |
| WO | WO 2003025138 | 3/2003 |
| WO | WO 2003025148 | 3/2003 |
| WO | WO 2003025228 | 3/2003 |
| WO | WO 2003026493 | 4/2003 |
| WO | WO 2003026577 | 4/2003 |
| WO | WO 2003029262 | 4/2003 |

(56) References Cited

FOREIGN PATENT DOCUMENTS

| | | |
|---|---|---|
| WO | WO 2003029277 | 4/2003 |
| WO | WO 2003029421 | 4/2003 |
| WO | WO 2003034984 | 5/2003 |
| WO | WO 2003035846 | 5/2003 |
| WO | WO 2003042661 | 5/2003 |
| WO | WO 2003043583 | 5/2003 |
| WO | WO 2003045422 | 6/2003 |
| WO | WO 2003048202 | 6/2003 |
| WO | WO 2003054152 | 7/2003 |
| WO | WO 2003055439 | 7/2003 |
| WO | WO 2003055443 | 7/2003 |
| WO | WO 2003060612 | 7/2003 |
| WO | WO 2003062401 | 7/2003 |
| WO | WO 2003068983 | 8/2003 |
| WO | WO 2003072035 | 9/2003 |
| WO | WO 2003072036 | 9/2003 |
| WO | WO 2003077836 | 9/2003 |
| WO | WO 2003081210 | 10/2003 |
| WO | WO 2003083041 | 10/2003 |
| WO | WO 2003083047 | 10/2003 |
| WO | WO 2003083074 | 10/2003 |
| WO | WO 2003087306 | 10/2003 |
| WO | WO 2003087768 | 10/2003 |
| WO | WO 2003088808 | 10/2003 |
| WO | WO 2003089624 | 10/2003 |
| WO | WO 2003089904 | 10/2003 |
| WO | WO 2003093444 | 11/2003 |
| WO | WO 2003097803 | 11/2003 |
| WO | WO 2003101283 | 12/2003 |
| WO | WO 2003101400 | 12/2003 |
| WO | WO 2003104270 | 12/2003 |
| WO | WO 2003104275 | 12/2003 |
| WO | WO 2003104399 | 12/2003 |
| WO | WO 2003105758 | 12/2003 |
| WO | WO 2004000221 | 12/2003 |
| WO | WO 2004000997 | 12/2003 |
| WO | WO 2004001004 | 12/2003 |
| WO | WO 2004005598 | 1/2004 |
| WO | WO 2004009622 | 1/2004 |
| WO | WO 2004011611 | 2/2004 |
| WO | WO 2004015426 | 2/2004 |
| WO | WO 2004016225 | 2/2004 |
| WO | WO 2004020583 | 3/2004 |
| WO | WO 2004020595 | 3/2004 |
| WO | WO 2004022709 | 3/2004 |
| WO | WO 2004022778 | 3/2004 |
| WO | WO 2004027049 | 4/2004 |
| WO | WO 2004031238 | 4/2004 |
| WO | WO 2004032828 | 4/2004 |
| WO | WO 2004032842 | 4/2004 |
| WO | WO 2004040000 | 5/2004 |
| WO | WO 2004042346 | 5/2004 |
| WO | WO 2004043361 | 5/2004 |
| WO | WO 2004043963 | 5/2004 |
| WO | WO 2004044178 | 5/2004 |
| WO | WO 2004045516 | 6/2004 |
| WO | WO 2004045520 | 6/2004 |
| WO | WO 2004045553 | 6/2004 |
| WO | WO 2004046342 | 6/2004 |
| WO | WO 2004047749 | 6/2004 |
| WO | WO 2004048938 | 6/2004 |
| WO | WO 2004053079 | 6/2004 |
| WO | WO 2004058309 | 7/2004 |
| WO | WO 2004063355 | 7/2004 |
| WO | WO 2004063362 | 7/2004 |
| WO | WO 2004063709 | 7/2004 |
| WO | WO 2004065576 | 8/2004 |
| WO | WO 2004065577 | 8/2004 |
| WO | WO 2004074320 | 9/2004 |
| WO | WO 2005023814 | 3/2005 |
| WO | WO 2005040170 | 5/2005 |
| WO | WO 2005042535 | 5/2005 |
| WO | WO 2005079479 | 9/2005 |
| WO | WO 2005082023 | 9/2005 |
| WO | WO 2005085177 | 9/2005 |
| WO | WO 2005085250 | 9/2005 |
| WO | WO 2005085251 | 9/2005 |
| WO | WO 2005085259 | 9/2005 |
| WO | WO 2005085260 | 9/2005 |
| WO | WO 2005105113 | 11/2005 |
| WO | WO 2005110423 | 11/2005 |
| WO | WO 2006065533 A2 | 6/2006 |
| WO | WO 2006105021 | 10/2006 |
| WO | WO 2006111759 | 10/2006 |
| WO | WO 2007005874 | 1/2007 |
| WO | WO 2007039752 | 4/2007 |
| WO | WO 2007044515 | 4/2007 |
| WO | WO 2007085930 | 8/2007 |
| WO | WO 2008010101 | 1/2008 |
| WO | WO 2008047242 | 4/2008 |
| WO | WO 2008070593 | 6/2008 |
| WO | WO 2009009116 | 1/2009 |
| WO | WO 2009062690 A1 | 1/2009 |
| WO | WO 2009016516 | 2/2009 |
| WO | WO 2009052249 | 4/2009 |
| WO | WO 2009063965 | 5/2009 |
| WO | WO 2009117531 | 9/2009 |
| WO | WO 2010010347 | 1/2010 |
| WO | WO 2010043877 | 4/2010 |
| WO | WO 2010043880 | 4/2010 |
| WO | WO 2010091150 | 8/2010 |
| WO | WO 2010130751 A1 | 11/2010 |
| WO | WO 2011005481 | 1/2011 |
| WO | WO 2011014457 A1 | 2/2011 |
| WO | WO 2011023883 | 3/2011 |
| WO | WO 2011028683 | 3/2011 |
| WO | WO 2011028811 | 3/2011 |
| WO | WO 2011038159 | 3/2011 |
| WO | WO 2011100227 | 8/2011 |
| WO | WO 2011130598 | 10/2011 |
| WO | WO 2011130613 | 10/2011 |
| WO | WO 2011130615 | 10/2011 |
| WO | WO 2011130616 | 10/2011 |
| WO | WO 2011159980 A1 | 12/2011 |
| WO | WO 2011161699 | 12/2011 |
| WO | WO 2012064733 A2 | 5/2012 |
| WO | WO 2012112687 | 8/2012 |
| WO | WO 2012112708 | 8/2012 |
| WO | WO 2012128868 | 9/2012 |
| WO | WO 2012145493 | 10/2012 |
| WO | WO 2012175691 A1 | 12/2012 |
| WO | WO 2012175692 A1 | 12/2012 |
| WO | WO 2013041606 | 3/2013 |
| WO | WO 2013053871 | 4/2013 |
| WO | WO 2013053873 | 4/2013 |
| WO | WO 2013055987 | 4/2013 |
| WO | WO 2013055990 | 4/2013 |
| WO | WO 2013055993 | 4/2013 |
| WO | WO 2013093809 | 6/2013 |
| WO | WO 2013177481 | 11/2013 |
| WO | WO 2014011518 | 1/2014 |
| WO | WO 2014022679 | 2/2014 |
| WO | WO 2014055648 | 4/2014 |
| WO | WO 2014057072 | 4/2014 |
| WO | WO 2014057073 | 4/2014 |
| WO | WO 2014057074 | 4/2014 |
| WO | WO 2014057113 | 4/2014 |
| WO | WO 2014057114 | 4/2014 |
| WO | WO 2014057115 | 4/2014 |
| WO | WO 2014057117 | 4/2014 |
| WO | WO 2014057118 | 4/2014 |
| WO | WO 2014057119 | 4/2014 |
| WO | WO 2014057120 | 4/2014 |
| WO | WO 2014057122 | 4/2014 |
| WO | WO 2014174111 A1 | 10/2014 |
| WO | WO 2015031693 A1 | 3/2015 |
| WO | WO 2015095423 | 6/2015 |
| WO | WO 2015153514 | 8/2015 |
| WO | WO 2016000619 | 1/2016 |
| WO | WO 2016007235 | 1/2016 |
| WO | WO 2016011160 | 1/2016 |
| WO | WO 2016053107 | 4/2016 |
| WO | WO 2016057667 | 4/2016 |
| WO | WO 2016073380 | 5/2016 |

(56) References Cited

FOREIGN PATENT DOCUMENTS

| WO | WO 2016081384 | 5/2016 | | |
|---|---|---|---|---|
| WO | WO 2016127052 | 8/2016 | | |
| WO | WO 2016166297 | 10/2016 | | |
| WO | WO 2016166302 | 10/2016 | | |
| WO | WO 2016179517 | 11/2016 | | |
| WO | WO 2016189124 | 12/2016 | | |
| WO | WO 2016196792 | 12/2016 | | |
| WO | WO 2017004016 | 1/2017 | | |
| WO | WO 2017130076 | 8/2017 | | |
| WO | WO-2017137456 | A1 * | 8/2017 | ......... A61K 47/6889 |
| WO | WO 2018146189 | 8/2018 | | |
| WO | WO 2015042246 | 3/2019 | | |

OTHER PUBLICATIONS

Alley, M.C. et al., ""SJG-136 (NSC 694501), a novel rationally designed DNA minor groove interstrand cross-linking agent with potent and broad spectrum antitumor activity. Part 2: Efficacy evaluations,"" Cancer Res. (2004) 64:6700-6706.

Alley, M.C., "Efficacy evaluations of SJG-136 (NSC 694501), a novel pyrrolobenzodiazepine dimer with broad spectrum antitumor activity," Proceedings of the American Association for Cancer Research Annual Meeting (Mar. 2002) 43:63.

Alley, S. C., "Contribution of Linker Stability to the Activities of Anticancer Immunoconjugates" Bioconjugate Chem 2008, 19, 759-765.

Althius, T. H. and Hess, H. J., "Synthesis and Identification of the Major Metabolites of Prazosin Formed in Dog and Rat," J. Medicinal Chem. (1977) 20(1):146-148.

Altuvia et al., "Ranking potential binding peptides to MHC molecules by a computational threading approach." J. Mol. Biol., 249, 244-250 (1995).

Amiel J., et al., "Heterozygous endothelin receptor B {EDNRB} mutations in isolated Hirschsprung disease," Hum. Mol. Genet. 5, 355-357, 1996.

Amir et al., "Self-Immolative Dendrimers," (2003) Angew. Chem. Int. Ed. 42:4494-4499.

Amsberry, et al, "The Lactonization of 2'-Hydroxyhydrocinnamic Acid Amides: A Potential Prodrug for Amines," (1990) J. Org. Chem. 55:5867-5877.

Anti-GITR Agonistic Monoclonal Antibody BMS-986156, NCI Thesaurus, Code C132267.

Anti-GITR Monoclonal Antibody GWN 323, NCI Thesaurus Code C128028.

Anti-GITR Monoclonal Antibody MK-4166, NCI Thesauruse Code C116065.

Anti-human GITR Monoclonal Antibody TRX518, NCI thesaurus code C95023.

Anti-OX40 Agonist Monoclonal Antibody PF-04518600, NCI thesaurus code C121927.

Antonow, D. et al., ""Synthesis of DNA-Interactive Pyrrolo [2,1-c][1,4] benzodiazepines (PBDs)"" Chemical Reviews, 2011, 111(4):2815-2864.

Antonow, D. et al., "Structure-activity relationships of monomeric C2-aryl pyrrolo[2,1-c][1,4]benzodiazepine (PBD) antitumor agents." J Med Chem. Apr. 8, 2010;53(7):2927-41.

Antonow, D. et al.,"Parallel synthesis of a novel C2-aryl pyrrolo[2,1-c][1,4]benzodiazepine (PBD) library," J. Comb. Chem. (2007) 9:437-445.

Arai H., et al., ""Molecular cloning of human endothelin receptors and their expressiOn in vascular endothelial cells and smooth muscle cells,"" Jpn. Circ. J. 56, 1303-1307, 1992.

Arai H., et al., "The Human Endotbelin-B Receptor Gene. Structural Organization and Chromosomal Assignment," J. Biol. Chem. 268, 3463-3470, 1993.

Arima et al., "Studies on Tomaymycin, a New Antibiotic. I. Isolation and Properties of Tomaymycin," J. Antibiotics (1972) 25:437-444.

Arnould, S., ""Impact on the cell cycle and involvement of ATM, ATR, chk1 and chk2 kinases in the cytotoxicity of SJG-136, a new pyrrolobenzodiazepine dimer,"" Proceedings of the American Association for Cancer Research Annual Meeting (Mar. 2004) 45:1298, Abstract No. 5618.

Arnould, S., "Time-dependent cytotoxicity induced by SJG-136 (NSC 694501): influence of the rate of interstrand cross-link formation on DNA damage signaling," Mol. Canc. Therap. 5(6):1602-1609 (2006).

Atezolizumab, Drug Bank Accession No. DB11595.

Attie T., et al., "Mutation of the endothelin-receptor B gene in Waardenburg-Hirschsprung disease," Hum. Mol. Genet. 4, 2407-2409, 1995.

Auricchio A., et al., "Endothelin-B receptor mutations in patients with isolated Hirschsprung disease from a non-inbred population," Hum. Mol. Genet. 5:351-354, 1996.

Axup et al., "Synthesis of site-specific antibody-drug conjugates using unnatural amino acids." Proc Natl Acad Sci U S A. Oct. 2, 2012; 109(40)16101-6.

Azacitidine, NCBI Pubchem reference 9444.

Babb et al. "Cancer phase I clinical trials: efficient dose escalation with overdose control." Stat Med. May 30, 1998; 17(10):1103-20.

Bahrenberg et al., ""Reduced Expression of PSCA, a Member of the LY-6 Family of Cell Surface Antigens, in Bladder, Esophagus, and Stomach Tumors,"" Biochem. Biophys. Res. Commun. (2000) 275(3):783-788.

Banker, G.S. et al., "Modern Pharmaceutics", Third edition, Marcel Dekker, New York (1996) 451 and 596.

Barel M., et al., "Evidence fora new transcript of the Epstein-Barr virus/C3d receptor (CR2, CD21) which is due to alternative exon usage," Mol. Immunol. 35, 1025-1031, 1998.

Barella et al., "Sequence variation of a novel heptahelical leucocyte receptor through alternative transcript formation," (1995) Biochem. J. 309:773-779.

Barnett T., et al., "Carcinoembryonic Antigen Family: Characterization of cDNAs Coding for NCA and CEA and Suggestion of Nonrandom Sequence Variation in Their Conserved Loop-Domains," Genomics 3, 59-66, 1988.

Batisse, et al., "A new delivery system for Auristatin in STxB-drug conjugate therapy." European J. Medicinal Chemistry, 2015, 95: 483-491.

Beck et al., "DNA Sequence Analysis of 66 kb of the Human MHC Class II Region Encoding a Cluster of Genes for Antigen Processing," (1992) J. Mol. Biol. 228:433-441.

Beck et al., "Evolutionary Dynamics of Non-coding Sequences Within the Class II Region of the Human Mhc," (1996) J. Mol. Biol. 25 255:1-13.

Ben-Batalla et al., "Axl, a prognostic and therapeutic target in acute myeloid leukemia mediates paracrine crosstalk of leukemia cells with bone marrow stroma" Blood Oct. 2013, 122:2443-2452.

Berge et al., "Pharmaceutical Salts," J. Pharm. Sci. (1977) 66:1-19.

Berry, J. M. et al., "Solid-phase synthesis of DNA-interactive pyrrolo[2,1-c][1,4]benzodiazepines," Tetrahedron Letters (2000) 41:6171-6174.

Blanc et al., "SAR3419: an anti-CD19-Maytansinoid Immunoconjugate for the treatment of B-cell malignancies," Clin Cancer Res., 2011, 17(20):6448-58.

Bloom et al., "Intrachain disulfide bond in the core hinge region of human IgG4." Protein Sci. Feb. 1997; 6(2):407-15.

Blumberg H., et al., ""Interleukin 20: Discovery, Receptor Identification, and Role in Epidermal Function,"" Cell 104, 9-19, 2001.

Borch et al., "Reorienting the immune system in the treatment of cancer by using anti-PD-1 and anti-PD-L1 antibodies." Drug Discov Today. Sep. 2015; 20(9):1127-34.

Bose et al., "New Approaches to Pyrrolo[2,1-c][1,4]benzodiazepines: Synthesis, DNA-binding and cytotoxicity of DC-81," Tetrahedron, 48, 751-758 (1992).

Bose, D.S. et al., "Effect of linker length on DNA-binding affinity, cross-linking efficiency and cytotoxicity of C8 linked pyrrolobenzodiazepine dimers," J. Chem. Soc. Chem. Commun. (1992) 20:1518-1520.

(56) References Cited

OTHER PUBLICATIONS

Bose, D.S. et al., "Rational Design of a Highly Efficient Irreversible DNA Interstrand Cross-Linking Agent Based on the Pyrrolobenzodiazepine Ring System," J. Am. Chem. Soc., 114, 4939-4941 (1992).
Bourgeois C., et al., "Endothelin-1 and ETA Receptor Expression in Vascular Smooth Muscle Cells from Human Placenta: A New ETA Receptor Messenger Ribonucleic Acid Is Generated by Alternative Splicing of Exon 3," J. Clin. Endocrinol. Metab. 82, 3116-3123, 1997.
Brand et al., Prospect for anti-HER2 receptor therapy in breast cancer. Anticancer Res. Jan.-Feb. 2006;26(16):463-70.
Brinster et al., ""Introits increase transcriptional efficiency in transgenic mice,"" (1988) Proc. Natl. Acad. Sci. USA 85:836-840.
Buchman et al., "Comparison of Intron-Dependent and Intron-Independent Gene Expression," (1988) Mol. Cell. Biol. 8:4395-4405.
Buhrow, S.A., "LC-MS/MS assay and dog pharmacokinetics of the dimeric pyrrolobenzodiazepine SJG-136 (NSC 694501)," J. Chromat. B: Anal. Tech. Biomed. Life Sci. (2006) 840(1):56-62.
Burke, P.J. et al., "Anti-CD70 antibody-drug conjugates containing pyrrolobenzodiazepine dimers demonstrate robust antitumor activity," AACR National Meeting, Apr. 2012, Chicago, Illinois, Abstract No. 4631.
Burke, P.J. et al., "Novel immunoconjugates comprised of streptonigrin and 17-amino-geldanamycin attached via a dipeptide-p-aminobenzylamine linker system," Bioorg. Med. Chem. Lett., Apr. 2009, 19(10):2650-2653.
Burton, "Immunoglobulin G: functional sites." Mol Immunol. Mar. 1985; 22(3):161-206.
Byers et al. "An Epithelial-Mesenchymal Transition Gene Signature Predicts Resistance to EGFR and PI3K Inhibitors and Identifies Axl as a Therapeutic Target for Overcoming EGFR Inhibitor Resistance." Clin Cancer Res 2013; 19:279-290.
Calcutt, M.W., "Determination of chemically reduced pyrrolobenzodiazepine SJG-136 in human plasma by HPLC-MS/MS: application to an anticancer phase I dose escalation study," J. Mass Spectrom. (2008) 43(1):42-52.
Camrelizumab, NCI Thesaurus code C123816.
Capellas et al., "Enzymatic condensation of cholecystokinin CCK-8 (4-6) and CCK-8 (7-8) peptide fragments in organic media." Biotechnol Bioeng. Nov. 20, 1997; 56(4):456-63.
Carl et al., "A Novel Connector Linkage Applicable in Prodrug Design," (1981) J. Med. Chem. 24:479-480.
Carlsson et al., "Protein Thiolation and Reversible Protein-Protein Conjugation," (1978) Biochem. J. 173:723-737.
Carter, P., "Potent antibody therapeutics by design," (2006) Nature Reviews Immunology 6:343-357.
Casset et al., "A peptide mimetic of an anti-CD4 monoclonal antibody by rational design." Biochem Biophys Res Commun. Jul. 18, 2003; 307(1):198-205.
CellTiter-Glo Luminescent Cell Viability Assay, Promega Corp. Technical Bulletin TB288, dated Jan. 13, 2012 (14 pages).
Cemiplimab, NCI thesaurus code C121540.
Chakravarty et al., ""Plasmin-Activated Prodrugs for Cancer Chemotherapy. 2. Synthesis and Biological Activity of Peptidyl Derivatives of Doxorubicin,"" (1983) J. Med. Chem. 26:638-644.
Chan, J. and Watt, V.M., "eek and erk, new members of the eph subclass of receptor protein-tyrosine kinases," Oncogene 6 (6), 1057-1061 (1991).
Chang et al., "Molecular cloning of mesothelin, a differentiation antigen present on mesothelium, mesotheliomas, and ovarian cancers," Proc. Natl. Acad. Sci. U.S.A. 93(1):136-140 (1996).
Chen, Z. et al., "A novel approach to the synthesis of cytotoxic C2-C3 unsaturated pyrrolo[2,1-c][1,4]benzodiazepines (PBDs) with conjugated acrylyl C2-substituents," Biorg. Med. Chem. Lett. (2004) 14:1547-1549.
Cheung, A., "Direct liquid chromatography determination of the reactive imine SJG-136 (NSC 694501)," J. Chromat. B: Anal. Techn. Biomed. Life Sci. (2005) 822(1-2):10-20.

Child et al., "Translational Control by an Upstream Open Reading Frame in the HER-2/neu Transcript," (1999) J. Bioi. Chern. 274: 24335-24341.
Cho et al., ""Structure of the extracellular region of HER2 alone and in complex with the Herceptin Fab,"" Nature 421, 756-760, 2003.
Chothia et al., "Domain association in immunoglobulin molecules. The packing of variable domains," J Mol. Biol. 1985, 186(3):651-663.
Ciccodicola, A., et al., ""Molecular characterization of a gene of the 'EGF family' expressed in undifferentiated human NTERA2 teratocarcinoma cells,"" EMBO J. 8(7):1987-1991 (1989).
Cipolla, L., "Pyrrolo[2,1-c][1,4]benzodiazepine as a scaffold for the design and synthesis of anti-tumour drugs," Anti-Cancer Agents in Medicinal Chemistry (Jan. 2009) 9(1):1-31.
Clackson et al., "Making antibody fragments using phage display libraries," (1991) Nature, 352:624-628.
Clark H.F., et al., "The Secreted Protein Discovery Initiative (SPDI], a Large-Scale Effort to Identify Novel Human Secreted and Transmembrane Proteins: A Bioinformatics Assessment," Genome Res. 13, 2265-2270, 2003.
Clingen, P.H., "The role of nucleotide excision repair and homologous recomination in the sensitivity of mammalian cells to the minor groove crosslinking pyrrolo[2,1-c][1,4]benzodiazepine dimer SJG-136 (NSC694501)," Proceedings of the American Association for Cancer Research Annual Meeting (Jul. 2003) 44:524.
Clingen, P.H., "the XPF-ERCC1 endonuclease and homologous recombination contribute to the repair of minor groove DNA interstrand crosslinks in mammalian cells produced by the pyrrolo[2,1-c][1,4]benzodiazepine dimer SJG-136," Nucl. Acids Res. (2005) 33(10):3283-3291.
Clinical Trial, "Translational research: 4 ways to fix the clinical trial." 2011, http://www.nature.com/news/2011/110928/full/477526a.html.
Clinical Trials Identifier: NCT01239134, "ITrial of TRX518 (Anti-GITR mAb) in Stage III or IV Malignant Melanoma or Other Solid Tumors (TRX518-001)," Actual Study Completion Date: Sep. 2018; Leap Therapeutics, Inc.
Clinical Trials Identifier: NCT02013804; Study Completion Date: May 18, 2017, "A Phase 1 Multicenter Open-label Study to Evaluate the Safety Tolerability and PK of MEDI0680 (AMP-514) in Subjects with Advanced Malignancies", Medimmune LLC.
Clinical Trials Identifier: NCT02028403, "Safety and Immune Response of BMS-936559 in HIV-Infected People Taking Combination Antiretroviral Therapy" Study Start Date: Jun. 2014; Completion Date: Nov. 2015; National Cancer Institute (NCI).
Clinical Trials Identifier: NCT02132754, "Study of MK-4166 and MK-4166 in Combination with Pembrolizumab (MK-3475) in Participants With Advanced Solid Tumors (MK-4166-001)" Study Start Date: Jun. 27, 2014; Estimated Completion Date: Oct. 17, 2019; Merck Sharp & Dohme Corp.
Clinical Trials Identifier: NCT02221960, "A Phase 1 Study to Evaluate MED16383 Alone and in Combination with MED14736 in Adult Subjects With Select Advanced Solid Tumors." Study Start Date: Sep. 15, 2014; Completion Date: Jul. 3, 2017; MedImmune LLC.
Clinical Trials Identifier: NCT02271945; Study Completion Date: May 24, 2016, "Safety/Efficacy of MEDI-551 in Combination With Immunomodulating Therapies in Subjects With Aggressive B-cell Lymphomas", Medimmune LLC.
Clinical Trials Identifier: NCT02298946, "AMP-224, a PD-1 Inhibitor, With Stereotactic Body Radiation Therapy in Metastatic Colorectal Cancer" Study Start Date: Nov. 21, 2014; Completion Date: Mar. 7, 2017; National Cancer Institute (NCI).
Clinical Trials Identifier: NCT02315066, "Study of OX40 Agonist PF-04518600 Alone and in Combination With 4-1BB Agonist PF-05082566." Study Start Date: Apr. 23, 2015; Estimated Completion Date: Apr. 30, 2020; Pfizer.
Clinical Trials Identifier: NCT02318394, "AA Phase 1 Study of MED10562 in Adult Subjects with Selected Advanced Solid Tumors." Study Start Date: Mar. 2, 2015; Completion Date: Jan. 9, 2018; MedImmune LLC.
Clinical Trials Identifier: NCT02528357, "GSK3174998 Alone or With Pembrolizumab in Subjects with Advanced Solid Tumors

(56) References Cited

OTHER PUBLICATIONS (ENGAGE-1)." Study Start Date: Sep. 11, 2015; Estimated Completion Date: Apr. 8, 2021; GlaxoSmithKline.

Clinical Trials Identifier: NCT02553499, "Study of MK-1248 With and Without Pembrolizumab (MK-3475) for Participants With Advanced Solid Tumors (MK-1248-001)," Study Start Date: Nov. 12, 2015; Completion Date: Oct. 17, 2018; Merck Sharp & Dohme Corp.

Clinical Trials Identifier: NCT02583165, "A Study in Adult Subjects With Select Advanced Solid Tumors," Study Completion Date: Dec. 19, 2018; MedImmune LLC.

Clinical Trials Identifier: NCT02598960, "An Investigational Immunotherapy Study of Experimental Medication BMS-986156, Given by Itself or in Combination With Nivolumab in Patients With Solid Cancers or Cancers That Have Spread." Study Start Date: Oct. 9, 2015; Estimated Completion Date: Jan. 31, 2020; Bristol-Myers Squibb.

Clinical Trials Identifier: NCT02628574, "Phase 1 Open-label Study of TRX518 Monotherapy and TRX518 in Combination With Gemcitabine, Pembrolizumab, or Nivolumab," Study Start Date: Jan. 2016; Leap Therapeutics, Inc.

Clinical Trials Identifier: NCT02923349, "A Phase 1/2, Open-Label, Dose-Escalation, Safety Study of INCAGN01949 in Subjects With Advanced or Metastatic Solid Tumors." Study Start Date: Oct. 2016; Completion Date: Mar. 26, 2019; Incyte Biosciences International Sàrl.

Clinical Trials Identifier: NCT03277352, "INCAGN01876 in Combination With Immune Therapies in Subjects With Advanced or Metastatic Malignancies," Estimated Study Completion Date: May 2020; Incyte Biosciences International Sàrl.

Collins, "Generation and initial analysis of more than 15,000 full-length human and mouse eDNA sequences," Proc. Natl. Acad. Sci. U.S.A. 99 (26):16899-16903 (2002).

Cooper, N. et al., "Synthesis of novel PBDs as anti-tumour agents," Chem. Commun. (2002) 16:1764-1765.

Cooper, N., "Design, Synthesis and Evaluation of Novel C2-Aryl Pyrrolobenzodiazepines as Potential Anticancer Agents," Thesis submitted to School of Pharmacy, University of London, Dated Oct. 5, 2006.

Corey et al., "LuCap35: a new model of prostate cancer progression to androgen independence." The Prostate 2003;55:239-46.

Courtney, S. M. et al., "A new convenient procedure for the synthesis of pyrrolo[2,1-c][1,4]benzodiazepines", Tetrahedron Letters, vol. 34, No. 33, 5327-28 (1993).

Coussens et al., "Tyrosine Kinase Receptor with Extensive Homology to EGF Receptor Shares Chromosomal Location With neu Oncogene," Science (1985) 230(4730):1132-1139.

Cragg et al., "The alternative transcript of CD79b is overexpressed in B-CLL and inhibits signaling for apoptosis," Blood (2002) 100 (9):3068-3076.

Cree et al., "Methotrexate chemosensitivity by ATP luminescence in human leukemia cell lines and in breast cancer primary cultures: comparison of the TCA-100 assay with a clonogenic assay," (1995) AntiCancer Drugs 6:398-404.

Crouch et al., "The use• of ATP bioluminescence as a measure of cell proliferation and cytotoxicity," (1993) J. Immunol. Meth. 160:81-88.

Cytarabine; NCBI Pubchem reference 6253.

Dall'Acqua, W. F. et al., "Antibody humanization by framework shuffling" Methods, 36, 43-60 (2005).

Dattolo, G. et al., "Polycondensed nitrogen heterocycles. IX. 5,6-dihydro-7H-pyrrolo[1,2- d][1,4]benzodiazepin-6-one," J. Heterocyclic. Chem. (1980) 17:701-703.

Davis et al., "Identification of a family of Fe receptor homo logs with preferential B cell expression," (2001) Proc. Natl. Acad. Sci. USA 98(17):9772-9777.

De Groot et al., ""Cascade-Release Dendrimers"" Liberate All End Groups upon a Single Triggering Event in the Dendritic Core, (2003) Angew. Chem. Int. Ed. 42:4490-4494.

De Groot et al., "Elongated Multiple Electronic Cascade and Cyclization Spacer Systems in Activatible Anticancer Prodrug for Enhanced Drug Release," (2001) J. Org. Chem. 66:8815-8830.

De Pascalis, "Grafting of "abbreviated" complementarity-determining regions containing specificity-determining residues essential for ligand contact to engineer a less immunogenic humanized monoclonal antibody." J Immunol. Sep. 15, 2002;169(6):3076-84.

Decitabine, NCBI Pubchem reference 451668.

Dennis et al., (2002) "Albumin Binding as a General Strategy for Improving the Pharmacokinetics of Proteins" J Biol Chem. 277:35035-35043.

Dijke, P., et al., "Characterization of Type I Receptors for Transforming Growth Factor-beta and Activin," Science 264 (5155):101-104 (1994).

Dobner et al., "Differentiation-specific expression of a novel G protein-coupled receptor from Burkitt's lymphoma," (1992) Eur. J. Immunol. 22:2795-2799.

Dong, Q. et al., "Reductive cleavage of TROC groups under neutral conditions with cadmium-lead couple," Tetrahedron Lett. (1995) 36(32):5681-5682.

Dono et al., "Isolation and Characterization of the CRI PTO Autosomal Gene and its X-linked Related Sequence," Am. J. Hum. Genet. 49:555-565, 1991.

Dornan et al., "Therapeutic potential of an anti-CD79b antibody-drug conjugate, anti-CD79b-vc-MMAE, for the treatment of non-Hodgkin lymphoma," (2009) Blood 114(13):2721-2729.

Doronina et al., "Enhanced Activity of Monomethylauristatin F through Monoclonal Antibody Delivery: Effects of Linker Technology on Efficacy and Toxicity," (2006) Bioconj. Chem. 17:114-124.

Doronina, S.O. et al., "Development of potent monoclonal antibody auristatin conjugates for cancer therapy," Nature Biotech. (2003) 21:778-784.

Dorwald, F.Z., Side Reactions in Organic Synthesis: a Guide to Successful Synthesis Design, Weinheim: Wiley-VCH Verlag GmbH & Co., KGaA (2005) Preface.

Doyle, M., "Response of staphylococcus aureus to subinhibitory concentrations of a sequence-selective, DNA minor groove cross-linking pyrrolobenzodiazepine dimer," J. Antimicrob. Chemo., Aug. 2009, 64(5):949-959.

Dubowchik et al, "Cathepsin B-sensitive dipeptide prodrugs. 1. A model study of structural requirements for efficient release of doxorubicin." Bioorg Med Chem Lett. Dec. 1, 1998; 8(23):3341-6.

Dubowchik et al, "Cathepsin B-sensitive dipeptide prodrugs. 2. Models of anticancer drugs paclitaxel (Taxol), mitomycin C and doxorubicin." Bioorganic & Medicinal Chemistry Letters, 8:3347-3352, (1998).

Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity," Bioconjugate Chem. (2002) 13, 855-869.

Dubowchik, et al., "Monomethoxytrityl (MMT) as a Versatile Amino Protecting Group for Complex Prodrugs of Anticancer Compounds Sensitive to Strong Acids, Bases and Nucleophiles," (1997) Tetrahedron Letters. 38:5257-5260.

Dumoutier L., et al., "Cutting Edge: STAT Activation by IL-19, IL-20 and mda-7 Through IL-20 Receptor Complexes of Two Types," J. Immunol. 167, 3545-3549, 2001.

Dupont, C. et al., "Synthesis of rhazinilam analogue acting as an inhibitor of tubulin assembly," Tetrahedron Lett. (2000) 41:5853-5856.

Efizonerimod, NCI Thesaurus, Code C118282.

Ehsani A., et al., "Characterization of a New Allele of the Human ERBB2 Gene by Allele-Specific Competition Hybridization," (1993) Genomics 15, 426-429.

Elshourbagy N.A., et al., "Molecular Characterization and Regulation of the Human Endothelin Receptors," J. Biol. Chem. 268, 3873-3879, 1993.

Erickson et al., "Antibody-Maytansinoid Conjugates Are Activated in Targeted Cancer Cells by Lysosomal Degradation and Linker-Dependent Intracellular Processing," (2006) Cancer Res. 66(8): 4426-4433.

(56) References Cited

OTHER PUBLICATIONS

Farmer, J.D. et al., "Synthesis and DNA crosslinking ability of a dimeric anthramycin analog," Tetrahedron Letters (1988) 29(40):5105-5108, Abstract only.
Farmer, J.D. et al., "DNA binding properties of a new class of linked anthramycin analogs," Chemical Abstracts, Abstract No. 239940r, vol. 114, No. 25, 25 899-903 (1991).
Feild, J.A., et al., "Cloning and Functional Characterization of a Sodium-Dependent Phosphate Transporter Expressed in Human Lung and Small Intestine," (1999) Biochem. Biophys. Res. Commun. 258 (3):578-582.
Fey, T. et al., "Silica-supported TEMPO catalyst: synthesis and application in the anelli oxidation of alcohols," J. Org. Chem. (2001) 66:8154-8159.
Fields, G. and Noble, R. (1990) "Solid phase peptide synthesis utilizing 9-fluoroenylmethoxycarbonyl amino acids", Int. J. Peptide Protein Res. 35:161-214.
Firsching, A. et al., "Antiproliferative and angiostatic activity of suramin analogues," Cancer Res. (1995) 55:4957-4961.
Fisch et al., "Site-specific modification of a fragment of a chimeric monoclonal antibody using reverse proteolysis." Bioconjug Chem. Mar.-Apr. 1992; 3(2):147-53.
Flanagan et al., "The ephrins and Eph receptors in neural development," Annu. Rev. Neurosci. 21:309-345 (1998).
Fludarabine, NCBI Pubchem reference 657237.
Foloppe, M.P. et al., "DNA-binding properties of pyrrolo[2,1-c][1,4]benzodiazepine N10-C11 amidines," Eur. J. Med. Chem., 31, 407-410 (1996).
Foote & Winter, "Antibody framework residues affecting the conformation of the hypervariable loops," J Mol. Biol. 1992, 224(2):487-499.
Fox et al., "cDNA cloning and tissue distribution of five human EPH-like receptor protein-tyrosine kinases," Oncogene 10 (5):897-905 (1995).
Fuchs S., et al., "Functional Characterization of Three Mutations of the Endothelin B Receptor Gene in Patients with Hirschsprung's Disease: Evidence for Selective Loss of Gi Coupling," Mol. Med. 7, 115-124, 2001.
Fujisaku et al., "Genomic Organization and Polymorphisms of the Human C3d/Epstein-Barr Virus Receptor," (1989) J. Biol. Chem. 264 (4):2118-2125.
Fujisawa Pharmaceutical Co. Ltd., "Benzodiazepine derivatives," SciFinder Scholar, 2-3 (2002).
Fujisawa Pharmaceutical Co., Ltd., Abstract No. 139983k,"Benzodiazepine derivatives", Chemical Abstracts, vol. 99, No. 17, 603 (1983).
Fujisawa Pharmaceutical Co., Ltd., Abstract No. 72145x,"Benzodiazepine derivatives", Chemical Abstracts, vol. 98, No. 9, 638 (1983).
Fukuyama, T. et al., "Total Synthesis of (+)-Porothramycin B," Tetrahedron Letters, vol. 34, 16, 2577-2580 (1993).
Gallmeier, E., "Targeted disruption of FANCC and FANCG in human cancer provides a preclinical model for specific therapeutic options," Gastroenterology (2006) 130(7):2145-2154.
Gary S.C., et al., "cDNA cloning chromosomal localization, and expression analysis of human BEHAB/brevican, a brain specific proteoglycan regulated during cortical development and in glioma," Gene 256, 139-147, 2000.
Gaugitsch, H.W., et al., "A novel transiently expressed, integral membrane protein linked to cell activation. Molecular cloning via the rapid degradation signal AUUUA.," (1992) J. Biol. Chem. 267 (16):11267-11273.
Gavezzotti, A., "Are crystal structures predictable?" Acc. Chem. Res. (1994) 27:309-314.
Geiser et al "Automation of solid-phase peptide synthesis" in Macromolecular Sequencing and Synthesis, Alan R. Liss, Inc., 1988, pp. 199-218.
Gemcitabine, DrugBank reference DB00441.
Gemcitabine, NCBI Pubchem reference 60750.
Genbank accession No. 11038674 (2013).
Genbank accession No. AAA60137, 1995.
Genbank accession No. AAC51773, 2005.
Genbank accession No. AAD22635, 1999.
Genbank accession No. AAF25807, Mar. 10, 2010.
Genbank accession No. AAH32229 (2006).
Genbank accession No. AAH46618 (2006).
Genbank accession No. AAL07473, 2001.
Genbank accession No. AB040878 (2001).
Genbank accession No. AF116456 (1999).
Genbank accession No. AF125304.1, 1999.
Genbank accession No. AF177937, version No. AF177937.1, Mar. 10, 2010.
Genbank accession No. AF179274 (2001).
Genbank accession No. AF229053 (2000).
Genbank accession No. AF343662 (2001).
Genbank accession No. AF343663 (2001).
Genbank accession No. AF343664 (2001).
Genbank accession No. AF343665 (2001).
Genbank accession No. AF361486 (2003).
Genbank accession No. AF369794 (2001).
Genbank accession No. AF397453 (2001).
Genbank accession No. AF414120.1, 2001.
Genbank accession No. AF455138 (2003).
Genbank accession No. AJ297436 (2008).
Genbank accession No. AK026467 (2006).
Genbank accession No. AK089756 (2010).
Genbank accession No. AK090423 (2006).
Genbank accession No. AK090475 (2006).
Genbank accession No. AL834187 (2008).
Genbank accession No. AX092328 (2001).
Genbank accession No. AY158090 (2003).
Genbank accession No. AY260763 (2003).
Genbank accession No. AY275463 (2003).
Genbank accession No. AY358085 (2003).
Genbank accession No. AY358628 (2003).
Genbank accession No. AY358907 (2003).
Genbank accession No. AY506558 (2004).
Genbank Accession No. BAB15489.1 (2006).
Genbank accession No. BC017023 (2006).
Genbank accession No. CAA53576.1, 2008.
Genbank accession No. CAA76847.1 (2001).
Genbank accession No. CAF85723 (2004).
Genbank accession No. CQ782436 (2004).
GenBank Accession No. gi:23238190.
GenBank Accession No. gi:23238193.
GenBank Accession No. gi:23238196.
GenBank Accession No. gi:40354198, 2007.
Genbank accession No. M11730 (1995).
Genbank accession No. M18112.1, 1995.
Genbank accession No. M18728 (1995).
Genbank accession No. M26004 (1993).
Genbank accession No. M76125 (1995).
Genbank accession No. NM_000626 (2013).
Genbank accession No. NM_001203 (2013).
Genbank accession No. NM_003212 (2013).
Genbank accession No. NM_003486 (2013).
Genbank accession No. NM_004442 (2013).
Genbank accession No. NM_005823 (2013).
Genbank accession No. NM_006424 (2013).
Genbank accession No. NM_009465 (2019).
Genbank accession No. NM_012449 (2013).
Genbank accession No. NM_017636 (2013).
Genbank accession No. NM_030764 (2013).
Genbank accession No. NP 002111.1 (2013).
Genbank accession No. NP_001194 (2013).
Genbank accession No. NP_001707.1 (2013).
Genbank accession No. NP_001773.1 (2013).
Genbank accession No. NP_001774.10 (2013).
Genbank accession No. NP_002552.2 (2013).
Genbank accession No. NP_003203 (2013).
Genbank accession No. NP_005573.1 (2007).
Genbank accession No. NP_112571.1 (2007).
Genbank accession No. U64863, 2005.

(56) References Cited

OTHER PUBLICATIONS

Genbank accession No. X75962, 2008.
Geoghegan & Stroh, "Site-Directed Conjugation of Nonpeptide Groups to Peptides and Proteins via Periodate Oxidation of a 2-Amino Alcohol. Application to Modification at N-Terminal Serine," (1992) Bioconjugate Chem. 3:138-146.
Getz Et al., "A Comparison between the Sulfhydryl Reductants Tris(2-carboxyethyl)phosphine and Dithiothreitol for Use in Protein Biochemistry," (1999) Anal. Biochem. vol. 273:73-80.
GITR Agonist MEDI1873, NCI thesaurus code C124651.
Gjerdrum, "Axl is an essential epithelial-to-mesenchymal transition-induced regulator of breast cancer metastasis and patient survival." Proc natl Acad Sci USA 2010, 107:1124-1129.
Glynne-Jones et al., "Tenb2, A Proteogl Ycan Identified in Prostate Cancer That Is Associated With Disease Progression and Androgen Independence," (2001) Int J Cancer. Oct 15; 94(2): 178-184.
Gomez et al., "Effect of temperature, pH, dissolved oxygen, and hydrolysate on the formation of triple light chain antibodies in cell culture." Biotechnol Prog. Sep.-Oct. 2010; 26(5):1438-45.
Gomez et al., "Triple light chain antibodies: factors that influence its formation in cell culture." Biotechnol Bioeng. Mar. 1, 2010; 105(4):748-60.
Gonzalez et al. "Abstract 3204: INCAGN01949: an anti-OX40 agonist antibody with the potential to enhance tumor-specific T-cell responsiveness, while selectively depleting intratumoral regulatory T cells." Proceedings: AACR 107th Annual Meeting 2016; Apr. 16-20, 2016.
Gordon et al., "Somatic hypermutation of the B cell receptor genes B29 (Igβ, CD79b) and mb1 (Igα, CD79a)," PNAS, 2003, vol. 100, No. 7, 4126-4131.
Greene & Wuts, Protective Groups in Organic Synthesis, John Wiley & Sons, 2nd ed., Ch 7, 315-345 (1991).
Greene, et al., Protective Groups in Organic Synthesis, John Wiley & Sons (1999) 3rd Edition, 23-200.
Greene, et al., Protective Groups in Organic Synthesis, John Wiley & Sons (1999) 3rd Edition, 503-549.
Gregson, S. et al., "Synthesis of a novel C2/C2'-exo unsaturated pyrrolobenzodiazepine cross-linking agent with remarkable DNA binding affinity and cytotoxicity," Chemical Communications, 797-798 (1999).
Gregson, S.J. et al., "Effect of C2/C3-endo unsaturation on the cytotoxicity and DNA-binding reactivity of pyrrolo-[2,1-c][1,4]-benzodiazepines," Bioorg. Med. Chem. Lett. (2000) 10(16):1849-1851.
Gregson, S.J. et al., "Linker length modulates DNA cross-linking reactivity and cytotoxic potency of C8/C8' ether-linked C2-exo-unsaturated pyrrolo[2,1-c][1,4]benzodiazepine (PBD) dimers," J. Med. Chem. (2004) 1161-1174.
Gregson, S.J. et al., "Synthesis of the first example of a C2-C3/C2'-C3'-endo unsaturated pyrrolo[2,1-c][1,4]benzodiazepine dimer," Biorg. Med. Chem. Lett. (2001) 11:2859-2862.
Gregson, S.J. et al., "Synthesis of the first examples of A-C8/C-C2 amide-linked pyrrolo[2,1-c][1,4]benzodiazepine dimers," Biorg. Med. Chem. Lett. (2003) 13:2277-2280.
Gregson, S.J. et al., "Design, Synthesis and Evaluation of a Novel Pyrrolobenzodiazepine DNA-Interactive Agent with Highly Efficient Cross-Linking Ability and Potent Cytotoxicity", J. Med. Chem., 44: 737-748 (2001).
Gregson, S.J. et al., "Effect of C2-exo Unsaturation on the Cytotoxicity and DNA-Binding Reactivity of Pyrrolo[2,1-c][1,4]benzodiazepines", Bioorganic & Medicinal Chemistry Letters, 10: 1845-1847 (2000).
Gu Z., et al., "Prostate stem cell antigen (PSCA) expression increases with high gleason score, advanced stage and bone metastasis in prostate cancer," Oncogene 19, 1288-1296, 2000.
Guichard, S.M., "Influence of P-glycoprotein expression on in vitro cytotoxicity and in vivo antitumour activity of the novel pyrrolobenzodiazepine dimer SJG-136," Eur. J. Cancer (2005) 41(12):1811-1818.
Guiotto, A. et al., "Synthesis of novel C7-aryl substituted pyrrolo[2,1-c][1,4]benzodiazepines (PBDs) via Pro-N10-troc protection and suzuki coupling," Bioorganic & Medicinal Chemistry Letters, 8, No. 21, 3017-3018 (1998).
Guselnikov et al., "A family of highly diverse human and mouse genes structurally links leukocyte FcR, gp42 and PECAM-1," Immunogenetics 54 (2):87-95 (2002).
Ha et al., "Molecular Cloning and Expression Pattern of a Human Gene Homologous to The Murine mb-1 Gene," (1992) J. Immunol. 148(5):1526-1531.
Hadjivassileva, T., "Antibacterial activity of pyrrolobenzodiazepine dimers, a novel group of DNA-binding compounds," Abstracts of the Interscience Conference on Antimicrobial Agents and Chemotherapy (Oct.-Nov. 2004) 44:202.
Hadjivassileva, T., "Interactions of pyrrolobenzodiazepine dimers and duplex DNA from methicillin-resistant *Staphylococcus aureus*," Int. J. Antimicrob. Agents (2007) 29(6):672-678.
Hadjivassileva, T., "Pyrrolobenzodiazepine dimers: novel sequence-selective, DNA-interactive, cross-linking agents with activity against Gram-positive bacteria," J. Antimicrob. Chemo. (2005) 56(3):513-518.
Haendler B., et al., "Molecular Cloning of Human Endothelin (ET) Receptors ETA and ETB," J. Cardiovasc. Pharmacal. 20, s1-S4, 1992.
Hamaguchi, A., "DNA cross-linking and in vivo antitumour activity of the extended pyrrolo[2,1-c][1,4]benzodiazepine dimer SG2057 (DRG-16)," EJC Supplements (Nov. 2006) 4(12):96.
Hamann P. "Monoclonal antibody-drug conjugates," (2005) Expert Opin. Ther. Patents 15(9):1087-1103.
Hamblett et al., "Effects of Drug Loading on the Antitumor Activity of a Monoclonal Antibody Drug Conjugate," (2004) Clin. Cancer Res. 10:7063-7070.
Handbook of Food Additives, 2nd Ed. (eds. M. Ash and I. Ash), Synapse Information Resources, Inc., Endicott, New York, USA (2001).
Handbook of Pharmaceutical Excipients, 2nd edition, 1994, Edited by Ainley Wade and Paul J. Weller.
Hara et al., "DC 102, a new glycosidic pyrrolo(1,4)benzodiazepine antibiotic produced by *Streptomyces* sp.", J. Antibiotics, 41, 702-704 (1988).
Hartley, "The development of pyrrolobenzodiazepines as antitumour agents", Expert Opinion on Investigational Drugs, Ashley Publications Ltd., vol. 28, No. 6, Jan. 1, 2011, pp. 733-744.
Hartley, J.A. et al., "SG2285, a novel C2-aryl-substituted pyrrolobenzodiazepine dimer prodrug that cross-links DNA and exerts highly potent antitumor activity," Cancer Res., Sep. 2010, 70(17):6849-6858.
Hartley, J.A. et al., "SJG-136 (NSC 694501), a novel rationally designed DNA minor groove interstrand cross-linking agent with potent and broad spectrum antitumor activity. Part 1: Cellular pharmacology, in vitro and initial in vivo antitumor activity," Cancer Res. (2004) 64:6693-6699.
Hartley, J.A., "In vitro antitumor activity and in vivo DNA interstrand crosslinking by the novel pyrrolobenzodiazepine dimer SJG-136 (NSC 694501)," Proceedings of the American Association for Cancer Research Annual Meeting (Mar. 2002) 43:489.
Hartley, J.A., "SJG-136 (NSC-D694501)—a novel DNA sequence specific minor groove crosslinking agent with significant antitumor activity," Proceedings of the American Association for Cancer Research Annual Meeting (Mar. 2000) 41:425.
Hashimoto et al., "Chromosomal localization, genomic structure, and allelic polymorphism of the human CD79a (Ig-alpha/mb-1) gene," (1994) Immunogenetics 40(4):287-295.
Hay et al., "A 2-Nitroimidazole Carbamate Prodrug of 5-Amin0-1-(Chloromethyl)-3-[(5,6,7-Trimethoxyindol-2-Yl)Carbonyl]-1,2-Dihydr0-3h-Benz[E]Indole (Amino-Seco-Cbi-Tmi) for Use With Adept and Gdept," (1999) Bioorg. Med. Chern. Lett. 9:2237-2242.
Herdwijn et al., "Synthesis of trans(+)6-phenoxyacetamido-1-methylene-3,3-dicarboxymethyl-1-carbapenam," Canadian Journal of Chemistry. 1982, 60, 2903-2907.
Hermanson, G.T., "Heterobifunctional Cross-linkers," (1996) Bioconjugate Techniques; Academic Press: New York, p. 228-286.

(56) References Cited

OTHER PUBLICATIONS

Hermanson, G.T., Bioconjugate Techniques, Academic Press: San Diego, Calif. (1996)—(Table of Contents Only).
Hezareh et al., "Effector function activities of a panel of mutants of a broadly neutralizing antibody against human immunodeficiency virus type 1." J Virol. Dec. 2001; 75(24):12161-8.
Hochhauser, D., "Phase I study of sequence-selective minor groove DNA binding agent SJG-136 in patients with advanced solid tumors," Clin. Cancer Res., Mar. 2009, 15(6):2140-2147.
Hochlowski, J. et al., "Abbeymycin, a new anthramycin-type antibiotic produced by a streptomycete," J. Antibiotics, 40, 145-148 (1987).
Hofstra R.M.W., et al., "A homozygous mUtation in the endothelin-3 gene associated with a combined Waardenburg type 2 and Hirschsprung phenotype (Shah-Waardenburg syndrome)" Nat. Genet. 12, 445-447, 1996.
Hofstra R.M.W., et al., "Mutations in Hirschsprung Disease: When Does a Mutation Contribute to the Phenotype," Eur. J. Hum. Genet. 5, 180-185, 1997.
Holland et al. "R428, a Selective Small Molecule Inhibitor of Axl Kinase, Blocks Tumor Spread and Prolongs Survival in Models of Metastatic Breast Cancer." Cancer Res 2010; 70:1544-1554.
Holland et al., "Multiple roles for the receptor tyrosine kinase axl in tumor formation." Cancer Res. Oct. 15, 2005; 65(20):9294-303.
Horie et al., "Identification and Characterization of TMEFF2, a Novel Survival Factor for Hippocampal and Mesencephalic Neurons," (2000) Genomics 67: 146-152.
Howard, et al., "Design, synthesis and biological evaluation of ZC-423, a novel C2-aryl substituted pyrrolobenzodiazepine (PBD) dimer," Clinical Cancer Research (2005) 11(23):9015S-9016S (A205).
Howard, P.W. et al., "Synthesis of a novel C2/C2'-aryl-substituted pyrrolo[2,1-c][1,4]benzodiazepine dimer prodrug with improved water solubility and reduced DNA reaction rate," Bioorg. Med. Chem., Sep. 2009, In Press, 4 pages now: Sep. 2009, 19:6463-6466.
Howard, P.W. et al., "The design, synthesis and biological evaluation of a set of C2-aryl substituted pyrrolo[2,1-c][1,4]benzodiazepine dimers," EJC Supplements (2006) 4(12):95—Poster Abstract 301.
Howard, P.W., "Design, synthesis and biological evaluation of novel C2-aryl-substituted pyrrolo[2,1-c][1,4]benzodiazepine monomers," Proceedings of the American Association for Cancer Research Annual Meeting (Apr. 2006) 47:132.
Hubert, R.S., et al., "STEAP: A prostate-specific cell-surface antigen highly expressed in human prostate tumors," (1999) Proc. Natl. Acad. Sci. U.S.A. 96(25):14523-14528.
Humphreys et al., "Formation of dimeric Fabs in *Escherichia coli*: effect of hinge size and isotype, presence of interchain disulphide bond, Fab' expression levels, tail piece sequences and growth conditions." J Immunol Methods. Dec. 1, 1997; 209(2):193-202.
Hurley, L. and Needham-Vandevanter, D., "Covalent Binding of Antitumor Antibiotics in the Minor Groove of DNA. Mechanism of Action of CC-1065 and the yrrolo(1,4)benzodiazepines," Acc. Chem. Res., 19, 230-237 (1986).
Hutterer et al., "Axl and growth arrest-specific gene 6 are frequently overexpressed in human gliomas and predict poor prognosis in patients with glioblastoma multiforme." Clin Cancer Res. Jan. 1, 2008;14(1):130-8.
Ide et al., "Cloning of human bone morphogenetic protein type IB receptor (BMPRIB) and its expression in prostate cancer in comparison with other BMPRs," Oncogene (1997) 14, 1377-1382.
Iida, H. et al. "Design and synthesis of pyrrolo[2,1-c][1,4]benzodiazepine (PBD)-polyaminoalkyl conjugates by the use of SNA4 reaction 2-nitro-5-fluorobenzoate precursor as key reaction," Heterocycles (2004) 62:693-711.
International Search Report and Written Opinion for Application No. PCT/EP2012/070233 dated Jan. 28, 2013 (8 pages).
International Search Report and Written Opinion for Application No. PCT/EP2013/071352 dated Feb. 5, 2014 (14 pages).
International Search Report and Written Opinion for Application No. PCT/GB2015/052629 dated Nov. 2, 2015 (12 pages).
International Search Report and Written Opinion for Application No. PCT/US2011/032668 dated May 26, 2011 (12 pages).
Ishikawa et al., "Higher Expression of Receptor Tyrosine Kinase Axl, and Differential Expression of its Ligand, Gas6, Predict Poor Survival in Lung Adenocarcinoma Patients" Ann Surg Oncol (2013) 20: S467-S476.
Itoh et al., "Application of Inverse Substrates to Trypsin-Catalyzed Peptide Synthesis" Bioorg. Chem., 24(1): 59-68 (1996).
Itoh et al., "Sibanomicin, a new pyrrolo(1,4)benzodiazepine antitumor antibiotic produced by a *Micromonospora* sp." J. Antibiotics, 41, 1281-1284 (1988).
Janjigian, Y.Y., "A phase I trial of SJG-136 (NSC#694501) in advanced solid tumors," Cancer Chemotherapy and Pharmacology , Aug. 2009, 65(5):833-838.
Jeffrey et al., "Development and properties of beta-glucuronide linkers for monoclonal antibody-drug conjugates." Bioconjugate Chemistry, 5, 2006, 17, 831-840. (Abstract).
Jeffrey, S.C., "Design, synthesis, and in vitro evaluation of dipeptide-based antibody minor groove binder conjugates," J. Med. Chem. (2005) 48(5):1344-1358.
Jespers, L. S., "Guiding the Selection of Human Antibodies from Phage Display Repertoires to a Single Epitope of an Antigen" Nature Biotech., 12, 899-903 (1994).
Jia, L., "Interspecies differences in pharmacokinetics and time-dissociated toxicokinetics of SJG-136," Proceedings of the American Association for Cancer Research Annual Meeting (Mar. 2004) 45:487.
Jia, L., "Use of the comet assay as a surrogate biomarker for the in vivo measurement of DNA damage to lymphocytes," Proceedings of the American Association for Cancer Research Annual Meeting (Mar. 2004) 45:452-453.
Johnson & Goldin, "The clinical impact of screening and other experimental tumor studies." Cancer Treat Rev. Mar. 1975; 2(1):1-31.
Jones et al., "Releasable Luciferin—Transporter Conjugates: Tools for the Real-Time Analysis of Cellular Uptake and Release," J. Am. Chem. Soc., 2006, 128, 6526-6527.
Jonsson et al., "Human class II DNA and DOB genes display low sequence variability," (1989) Immunogenetics 29(6):411-413.
Jordan, V.C., "Tamoxifen: a most unlikely pioneering medicine," Nature Reviews: Drug Discovery (2003) 2:205-213.
Junutula et al., "Rapid identification of reactive cysteine residues for site-specific labeling of antibody-Fabs," (2008) Jour of Immun. Methods 332:41-52.
Junutula, et al., "Site-specific conjugation of a cytotoxic drug to an antibody improves the therapeutic index," 2008b Nature Biotech., 26(8):925-932.
Kabat et al., Sequences of proteins of immunological interest, 5 ed. (NIH National Technical Information Service, 1991).
Kamal et al., "Synthesis and DNA-binding affinity of A-C8/C-C2 alkoxyamido-linked pyrrolo[2,1-c][1,4]benzodiazepine dimers" Biorg. Med. Chem. Lett. (2003) 13(22): 3955-3958.
Kamal, A. et al., "Design, synthesis and evaluation of new noncross-linking pyrrolobenzodiazepine dimers with efficient DNA binding ability and potent antitumor activity," J. Med. Chem. (2002) 45:4679-4688.
Kamal, A., "Development of pyrrolo[2,1-c][1,4]benzodiazepine beta-galactoside prodrugs for selective therapy of cancer by ADEPT and PMT," Chemmedchem (2008) 3:794-802.
Kamal, A., "Remarkable DNA binding affinity and potential anticancer activity of pyrrolo[2,1-c][1,4]benzodiazepine-naphthalamide conjugates linked through piperazine side-armed alkane spacers," Bioorg. Med. Chem. (2008) 16(15):7218-7224.
Kamal, A., "Remarkable enhancement in the DNA-binding ability of C2-fluoro substituted pyrrolo[2,1-c][1,4]benzodiazepines and their anticancer potential," Bioorg. Med. Chem., Jan. 2009, 17(4):1557-1572.
Kamal, A., "Synthesis of fluorinated analogues of SJG-136 and their DNA-binding potential," Bioorg. Med. Chem. Lett (2004) 14(22):5699-5702.
Kamal, A., et al., "An Efficient Synthesis of Pyrrolo[2,1-c][1,4] Benzodiazepine Antibiotics via Reductive Cyclization," Bioorg. Med. Chem. Ltrs, 7, No. 14, 1825-1828 (1997).

(56) References Cited

OTHER PUBLICATIONS

Kamal, A., et al., "Synthesis of Pyrrolo [2,1-c][1,4]-Benzodiazepene Antibiotics: Oxidation of Cyclic Secondary Amine with TPAP", Tetrahedron, v. 53, No. 9, 3223-3230 (1997).
Kamal, et al., "Synthesis of pyrrolo[2,1-c][1,4]benzodiazepines via reductive cyclization of w-azido carbonyl compounds by TMSI: an efficient preparation of antibiotic DC-81 and its dimers," Biorg. Med. Chem. Lett. (2000) 10:2311-2313.
Kaneko, T. et al., "Bicyclic and tricyclic analogues of anthramycin," J. Med. Chem. (1985) 28:388-392.
Kang, G.-D. et al., "Synthesis of a novel C2-aryl substituted 1,2-unsaturated pyrrolobenzodiazepine," Chem. Commun. (2003) 1680-1689.
Kasahara et al., "Nucleotide sequence of a chimpanzee DOB eDNA clone," (1989) Immunogenetics 30(1):66-68.
King et al., "Facile synthesis of maleimide bifunctional Jinkers," (2002) Tetrahedron Letters 43:1987-1990.
Kingsbury et al., ""A Novel Peptide Delivery System Involving Peptidase Activated Prodrugs as Antimicrobial Agents. Synthesis and Biological Activity of Peptidyl Derivatives of 5 Fluorouracil,"" (1984) J. Med. Chem. 27:1447-1451.
Kohler et al., "Continuous cultures of fused cells secreting antibody of predefined specificity," (1975) Nature 256:495-497.
Kohn, K., "Anthramycin," Antibiotics III, Springer-Verlag, NY, 3-11 (1975).
Kojima et al., "Molecular Cloning and Expression of Megakaryocyte Potentiating Factor eDNA," The Journal of Biological Chemistry, vol. 270, No. 37, Issue of Sep. 15, pp. 21984-21990, 1995.
Konishi, M. et al., "Chicamycin, a new antitumor antibiotic II. Structure determination of chicamycins A and B," J. Antibiotics, 37, 200-206 (1984).
Korshunov, "Axl-dependent signaling: A clinical update." Clinical Science 2012, 122:361-368.
Kovtun et al., "Antibody-Drug Conjugates Designed to Eradicate Tumors with Homogeneous and Heterogeneous Expression of the Target Antigen," (2006) Cancer Res. 66(6):3214-3121.
Kreitman & Pastan "Immunotoxins for targeted cancer therapy." Adv Drug Deliv Rev. Apr. 6, 1998; 31(1-2):53-88.
Kuhns J.J., et al., "Poor Binding of a HER-2/neu Epitope (GP2) to HLA-A2.1 is due to a Lack of Interactions with the Center of the Peptide," J. Biol. Chem. 274, 36422-36427, 1999.
Kumaran et al., "Conformationally driven protease-catalyzed splicing of peptide segments: V8 protease-mediated synthesis of fragments derived from thermolysin and ribonuclease A." Protein Sci. Oct. 1997; 6(10):2233-41.
Kunimoto et al., "Mazethramycin, a new member of anthramycin group antibiotics," J. Antibiotics, 33, 665-667 (1980).
Kurebayashi et al., "Isolation and characterization of a new human breast cancer cell line, KPL-4, expressing the Erb B family receptors and interleukin•6," (1999) Brit. Jour. Cancer 79(5-6):707-717.
Lambert J., "Drug-conjugated monoclonal antibodies for the treatment of cancer," (2005) Current Opin. In Pharmacol. 5:543-549.
Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," J. Org. Chem., 52, 91-97 (1987).
Langlois, N. et al., "Synthesis and cytotoxicity on sensitive and doxorubicin-resistant cell lines of new pyrrolo[2,1-c][1,4]benzodiazepines related to anthramycin," J. Med. Chem. (2001) 44:3754-3757.
Larhammar et al., "Sequence of Gene and eDNA Encoding Murine Major Histocompatibility Complex Class II Gene AP2*," (1985) J. Biol. Chem. 260(26):14111-14119.
Launay et al., "TRPM4 is a Ca2+-Activated Nonselective Cation Channel Mediating Cell Membrane Depolarization," Cell 109 (3):397-407 (2002).

Law et al., "Lymphocyte Activation Antigen CD70 Expressed by Renal Cell Carcinoma is a Potential Therapeutic Target for Anti-CD70 Antibody-Drug Conjugates," (2006) Cancer Res. 66(4):2328-2337.
Lazar et al., "A molecular immunology approach to antibody humanization and functional optimization" Molecular Immunology, 2007, 44(8), 1986-1998.
Le et al., "Primary structure and expression of a naturally truncated human P2X ATP receptor subunit from brain and immune system," (1997) Febs Lett. 418(1-2):195-199.
Leabman; et al., "Effects of altered FcγR binding on antibody pharmacokinetics in cynomolgus monkeys." MAbs. Nov.-Dec. 2013; 5(6):896-903.
Leber, J.D. et al., "A revised structure for sibiromycin," J. Am. Chem. Soc., 110, 2992-2993 (1988).
Leimgruber, W. et al., "Isolation and characterization of anthramycin, a new antitumor antibiotic," J. Am. Chem. Soc., 87, 5791-5793 (1965).
Leimgruber, W. et al., "The structure of anthramycin," J. Am. Chem. Soc., 87, 5793-5795 (1965).
Leimgruber, W. et al., "Total synthesis of anthramycin," J. Am. Chem. Soc., 90, 5641-5643 (1968).
Leonard et al., "Phase I/II trial of epratuzumab (humanized anti-CD22 antibody) in indolent non-Hodgkin's lymphoma," J. Clin. Oncology (2003) 21(16):3051-3059.
Leonard et al., "Preclinical and clinical evaluation of epratuzumab (anti-CD22 IgG) in B-cell malignancies," Oncogene (2007) 26:3704-3713.
Leung et al., "Construction and characterization of a humanized, internalizing, B-cell (CD22)-specific, leukemia/lymphoma antibody, LL2," Mol. Immunol. (1995) 32(17-18):1413-1427.
Levenson et al., "MCF-7: The First Hormone-responsive Breast Cancer Cell Line," (1997) Cancer Res. 57(15):3071-3078.
Lewis Phillips et al., "Targeting HER2-Positive Breast Cancer with Trastuzumab-DM1, an Antibody-Cytotoxic Drug Conjugate," Cancer Res, 2008, 68: (22).
Li et al., "A Mini-Review for Cancer Immunotherapy: Molecular Understanding of PD-1/PD-L1 Pathway & Translational Blockade of Immune Checkpoints." Int. J. Mol. Sci. 2016, 17(7), 1151.
Liang et al., "The Gene for a Novel Transmembrane Protein Containing Epidermal Growth Factor and Follistatin Domains is Frequently Hypermethylated in Human Tumor Cells," (2000) Cancer Res. 60:4907-4912.
Lin et al., "The PD-1/PD-L1 complex resembles the antigen-binding Fv domains of antibodies and T cell receptors" PNAS, Feb. 26, 2008., 105(8): 3011-3016.
Linden et al., "Dose-fractionated radioimmunotherapy in non-Hodgkin's lymphoma using DOTA-conjugated, 90Y-radiolabeled, humanized anti-CD22 monoclonal antibody, epratuzumab," J. Clin. Cancer Res. (2005) 11:5215-5222.
Linger et al., "Taking aim at Mer and Axl receptor tyrosine kinases as novel therapeutic targets in solid tumors." Expert Opin Ther Targets. Oct. 2010; 14(10):1073-90.
Linger et al., "TAM receptor tyrosine kinases: biologic functions, signaling, and potential therapeutic targeting in human cancer." Adv Cancer Res. 2008; 100:35-83.
Loges et al., "Malignant cells fuel tumor growth by educating infiltrating leukocytes to produce the mitogen Gas6." Blood. 115(11):2264-2273.
Lonberg, "Fully Human antibodies from transgenic mouse and phage display platforms" Curr. Opinion, 20(4), 450-459 (2008).
Lown et al., "Molecular Mechanism of Binding of Pyrrolo(1,4)benzodiazepine antitumour agents to deoxyribonucleic acid-anthramycin and tomaymycin," Biochem. Pharmacol. (1979), 28 (13), 2017-2026.
Lu et al., "Homeostatic regulation of the immune system by receptor tyrosine kinases of the Tyro 3 family." Science. Jul. 13, 2001; 293(5528):306-11.
Manfre et al., "Syntheses of Proline Analogues as Potential Mechanism-Based Inhibitors of Proline Dehydrogenase: 4-Methylene-L-, (E)- and (Z)-4-(Fluoromethylene)-L-, cis- and trans-5-Ethynyl-(±)-, and cis- and trans-5-Vinyl-L-proline," J. Org. Chem. 1992, 57, 2060-2065.

(56) References Cited

OTHER PUBLICATIONS

Marin, D., "Voltammetric studies of the interaction of pyrrolo[2,1-c][1,4]benzodiazepine (PDB) monomers and dimers with DNA," J. Electroanal. Chem. (2006) 593(1-2):241-246.

Marks et al., "By-passing Immunization, Human Antibodies from V-gene Libraries Displayed on Phage," (1991) J. Mol. Biol., 222:581-597.

Martin, C. et al., "Sequence-selective interaction of the minor-groove interstrand cross-linking agent SJG-136 with naked and cellular DNA: footprinting and enzyme inhibition studies," Biochem. (2005) 44(11):4135-4147.

Mastroberardino et al., "Amino-acid transport by heterodimers of 4F2hc/CD98 and members of a permease family," Nature 395 (6699):288-291 (1998).

McDonagh, "Engineered antibody-drug conjugates with defined sites and stoichiometries of drug attachment," (2006) Protein Eng. Design & Sel. 19(7): 299-307.

Melaragno et al., "Increased expression of Axl tyrosine kinase after vascular injury and regulation by G protein-coupled receptor agonists in rats." Circ Res. Oct. 5, 1998;83(7):697-704.

Melaragono et al., "The Gas6/Axl system: a novel regulator of vascular cell function." Trends Cardiovasc Med. Nov. 1999; 9(8):250-3.

Mendoza et al., "Inhibition of Ligand-mediated HER2 Activation in Androgen-independent Prostate Cancer," (2002) Cancer Res. 62:5485-5488.

Miller et al., "Design, Construction, and In Vitro Analyses of Multivalent Antibodies," (2003) Jour. of Immunology 170:4854-4861.

Miller et al., "IRTAs: a new family of immunoglobulinlike receptors differentially expressed in B cells," Blood 99 (8):2662-2669 (2002).

Miller et al., "Reduced Proteolytic Shedding of Receptor Tyrosine Kinases Is a Post-Translational Mechanism of Kinase Inhibitor Resistance." Cancer Discov. Apr. 2016; 6(4):382-99.

Miura et al., "Molecular cloning of a human RP105 homologue and chromosomal localization of the mouse and human RP105 genes (Ly64 and LY64)." Genomics. Dec. 15, 1996; 38(3):299-304.

Miura et al., "RPIOS Is Associated With MD-1 and Transmits an Activation Signal in Human B Cells," (1998) Blood 92:2815-2822.

Moore M., et al., "Molecular cloning of the eDNA encoding the Epstein-Barr virus/C3d receptor (complement receptor type 2) of human B lymphocytes," Proc. Natl. Acad. Sci. U.S.A. 84, 9194-9198, 1987.

Morea et al., "Antibody modeling: implications for engineering and design." Methods. Mar. 2000; 20(3):267-79.

Mori, M. et al., "Total syntheses of prothracarcin and tomaymicin by use of palladium catalyzed carbonylation," Tetrahedron (1986) 42(14):3793-3806.

Morrison et al., "Chimeric human antibody molecules: Mouse antigen-binding domains with human constant region domains," (1984) Proc. Natl. Acad. Sci. USA, 81:6851-6855.

Mountzouris, J.A. et al., "Comparison of a DSB-120 DNA interstrand cross-linked adduct with the corresponding bis-Tomamycin adduct," J. Med. Chem. (1994) 37:3132-3140.

Muller et al., "Cloning and sequencing of the eDNA encoding the human homologue of the murine immunoglobulin-associated protein B29," (1992) Eur. J. Immunol. 22 (6): 1621-1625.

Mungall A.J., et al., "The DNA sequence and analysis of human chromosome 6," Nature 425, 805-811, 2003.

Nagasaka, T. et al., "Stereoselective Synthesis of Tilivalline," Tetrahedron Letters, 30:14, 1871-1872 (1989).

Nagase T., et al., "Prediction of the Coding Sequences of Unidentified Human Genes. XVII. The Complete Sequences of 100 New eDNA Clones from Brain Which Code for Large Proteins in vitro," (2000) DNA Res. 7 (2):143-150.

Nakamuta M., et al., "Cloning and Sequence Analysis of a cDNA Encoding Human Non-Selective Type of Endothelin Receptor," Biochem. Biophys. Res. Commun. 177, 34-39, 1991.

Nakayama et al., "Altered Gene Expression upon BCR Cross-Linking in Burkitt's Lymphoma B Cell Line," (2000) Biochem. Biophys. Res. Commun. 277(1):124-127.

Narayanaswamy, M., "A novel HPLC/MS assay to measure DNA interstrand cross-linking efficacy in oligonucleotides of varying sequence," EJC Supplements (Nov. 2006) 4(12):92-93.

Narayanaswamy, M., "An assay combining high-performance liquid chromatography and mass spectrometry to measure DNA interstrand cross-linking efficiency in oligonucleotides of varying sequences," Anal. Biochem. (2008) 374(1):173-181.

Narayanaswamy, M., "Use of HPLC-MS to characterize novel mono and intrastrand cross-linked DNA adducts formed by the sequence-selective Dna-interactive agent SJG-136," Proceedings of the American Association for Cancer Research Annual Meeting (Apr. 2007) 48:760-761.

Narukawa, Y., "General and efficient synthesis of 2-alkylcarbapenems synthesis of dethia carba analogs of clinically useful carbapenems via palladium-catalyzed cross-coupling reaction," Tetrahedron (1997) 53:539-556.

Naruse et al., "The HLA-DOB gene displays limited polymorphism with only one amino acid substitution," (2002) Tissue Antigens 59:512-519.

Neuberger and Williams, "The intron requirement for immunoglobulin gene expression is dependent upon the promoter," (1988) Nucleic Acids Res. 16:6713-6724.

Neuenschwander et al., "Critical aspects of the Bayesian approach to phase I cancer trials." Statistics in Medicine 2008, 27:2420-2439.

Nicolaou et al., "Calicheamicin θ: A Rationally Designed Molecule with Extremely Potent and Selective DNA Cleaving Properties and Apoptosis Inducing Activity," Angew Chem. Intl. Ed. Engl. (1994) 33:183-186.

Nilius et al., "Voltage Dependence of the Ca2+-activated Cation Channel TRPM4," The Journal of Biological Chemistry, vol. 278, No. 33, Issue of Aug. 15, pp. 30813-30820, 2003.

Niraparib, NCBI Pubchem reference 24958200.

Nivolumab, DrugBank Reference DB09035.

Nocentini et al. "A new member of the tumor necrosis factor/nerve growth factor receptor family inhibits T cell receptor-induced apoptosis."Proc Natl Acad Sci U S A. Jun. 10, 1997;94(12):6216-21.

Nomi et al. "Clinical significance and therapeutic potential of the programmed death-1 ligand/programmed death-1 pathway in human pancreatic cancer." Clin Cancer Res. Apr. 1, 2007; 13(7):2151-7.

O'Neil, Chemical Abstract No. 171573p, "The synthesis of Functionalized Pyrrolo-[2,1-c][1,4]-Benzodiazepines", Chemical Abstracts, vol. 126, No. 13, 618 (1997).

O'Neil, I.A., et al., "The Synthesis of Functionalized Pyrrolo-[2,1-c][1,4]-Benzodiazepines," Synlett, 75-78 (1997).

O'Bryan et al., "The transforming receptor tyrosine kinase, Axl, is post-translationally regulated by proteolytic cleavage." J Biol Chem. Jan. 13, 1995;270(2):551-7.

Ogawa et al., "Molecular cloning of a non-isopeptide-selective human endothelin receptor," Biochem. Biophys. Res. Commun. 178, 248-255, 1991.

Okamoto Y., et al. "Palmitoylation of Human Endothelin B," Biol. Chem. 272, 21589-21596, 1997.

Olaparib, NCBI Pubchem reference 23725625.

O'Neil, I.A. et al., "DPPE: A Convenient Replacement for Triphenylphosphine in the Staudinger and Mitsunobu Reactions", Tetrahedron Letters, vol. 39, No. 42, 7787-7790 (1998).

Paccez et al., "The receptor tyrosine kinase Axl is an essential regulator of prostate cancer proliferation and tumor growth and represents a new therapeutic target" Oncogene 2013, 32: 689-698.

Paolino et al., "The Role of TAM Family Receptors in Immune Cell Function: Implications for Cancer Therapy." Cancers (Basel) Oct. 21, 2016; 8(10).

Parrish-Novak J., et al., "Interleukins 19, 20, and 24 Signal through Two Distinct Receptor Complexes," J. Biol. Chem. 277, 47517-47523, 2002.

Paul, Fundamental Immunology, 3rd Edition, pp. 292-295, (1994).

Payne, G. "Progress in immunoconjugate cancer therapeutics," (2003) Cancer Cell 3:207-212.

(56) References Cited

OTHER PUBLICATIONS

PD1 polypeptide corresponds to Uniprot/Swiss-Prot accession No. Q9NZQ7, 2005.
Peggs et al., "Cancer immunotherapy: co-stimulatory agonists and co-inhibitory antagonists." Clin Exp Immunol. Jul. 2009;157(1):9-19.
Pepper, C., "Fludarabine-mediated suppression of the excision repair enzyme ERCC1 contributes to the cytotoxic synergy with the DNA minor groove crosslinking agent SJG-136 (NSC 694501) in chronic lymphocytic leukaemia cells," Br. J. Cancer (2007) 97(2):253-259.
Pepper, C.J. et al., "The novel sequence-specific DNA cross-linking agent SJG-136 (NSC 694501) has potent and selective in vitro cytotoxicity in human B-cell chronic lymphocytic leukemia cells with evidence of a p53- independent mechanism of cell kill," Cancer Res. (2004) 64:6750-6755.
Phillips et al., "Targeting HER2-Positive Breast Cancer with Trastuzumab-DM1, an Antibody-Cytotoxic Drug Conjugate," (2008) Cancer Res. 68(22):9280-9290.
Pingault V., et al., "SOX10 mutations in chronic intestinal pseudo-obstruction suggest a complex physiopathological mechanism," (2002) Hum. Genet. 111, 198-206.
Pletnev S., et al., "Characterization of the Recombinant Extracellular Domains of Human Interleukin-20 Receptors and Their Complexe with Interleukin-19 and Interleukin-20," (2003) Biochemistry 42:12617-12624.
Porkaa et al., "Cloning and Characterization of a Novel Six-Transmembrane Protein STEAP2, Expressed in Normal and Malignant Prostate," Lab. Invest. 82 (11):1573-1582 (2002).
Prasad et al.,"Human LAT1, a Subunit of System L Amino Acid Transporter: Molecular Cloning and Transport Function," Biochem. Biophys. Res. Commun. 255 (2), 283-288 (1999).
Preud'Homme et al., "Structure and expression of the mb-1 transcript in human lymphoid cells," (1992) Clin. Exp. Immunol. 90(1):141-146.
Puffenberger E.G., et al., "A Missense Mutation of the Endothelin-B Receptor Gene in Multigenic Hirschsprung's Disease," Cell 79, 1257-1266, 1994.
Puzanov, I., "Phase I and pharmacokinetic trial of SJG-136 administered on a daily x5 schedule," EJC Supplements (Nov. 2006) 4(12):93.
Quintas-Cardama, A., "Sequencing of subcloned PCR products facilitates earlier detetction of BCR-ABL1 and other mutants compared to direct sequencing of the ABL1 kinase domain," Leukemia (2008) 22(4):877-878.
Rahman et al. "Antistaphylococcal activity of DNA-interactive pyrrolobenzodiazepine (PBD) dimers and PBD-biaryl conjugates." J Antimicrob Chemother. Jul. 2012; 67(7):1683-96.
Rahman, K.M., "Effect of microwave irradiation on covalent ligand-DNA interactions," Chem. Commun. (Cambridge, UK), Apr. 2009, 20:2875-2877.
Rahman, K.M., "Rules of DNA adduct formation for pyrrolobenzodiazepine (PBD) dimers," Proceedings of the American Association for Cancer Research Annual Meeting (Apr. 2010) 51:851.
Rahman, K.M., "The pyrrolobenzodiazepine dimer SJG-136 forms sequence-dependent intrastrand DNA cross-lins and monoalkylated adducts in addition to interstrand cross-links," J. Am. Chem. Soc., Sep. 2009, 131(38):13756-13766.
Rao et al., "Influence of diet on mammary cancer in transgenic mice bearing an oncogene expressed in mammary tissue," (1997) Breast Cancer Res. and Treatment 45:149-158.
Reid, J.M., "LC-MS/MS assay and rat pharmacokinetics and metabolism of the dimeric pyrrolobenzodiazepine SJG-136," Proceedings of the American Association for Cancer Research Annual Meeting (Mar. 2004) 45:1248.
Reiter R.E., et al., "Prostate stem cell antigen: A cell surface marker overexpressed in prostate cancer," Proc. Natl. Acad. Sci. U.S.A. 95, 1735-1740, 1998.

Remmers et al., "Conformations of complexes between pyrrolo[1,4]benzodiazepines and DNA segments," J Med Chem. Dec. 1986;29(12):2492-2503.
Rich, I.N., "Validation and development of a predictive paradigm for hemotoxicology using a multifunctional bioluminescence colony-forming proliferation assay," Toxicological Sci. (2005) 87(2):427-441.
Rodrigues et al., "Synthesis and beta-lactamase-mediated activation of a cephalosporin-taxol prodrug," (1995) Chemistry Biology 2:223-227.
Ross et al., "Prostate Stem Cell Antigen as Therapy Target: Tissue Expression and in Vivo Efficacy of an Immunoconjugate," (2002) Cancer Res. 62:2546-2553.
Sagnou, M.J. et al., "Design and Synthesis of Novel Pyrrolobenzodiazepine (PDB) Prodrugs for ADEPT and GDEPT," Bioorganic & Medicinal Chemistry Letters, 10, 2083-2086 (2000).
Sakaguchi et al., "8 lymphocyte lineage-restricted expression of mb-1, a gene with CD3-like structural properties," (1988) EMBO J. 7(11):3457-3464.
Sakamoto A, Yanagisawa M., et al., "Cloning and Functional Expression of Human cDNA for the ETB Endothelin Receptor," Biochem. Biophys. Res. Commun. 178, 656-663, 1991.
Sanderson et al., "In vivo Drug-Linker Stability of an Anti-CD30 Dipeptide-Linked Auristatin Immunoconjugate," (2005) Clin. Cancer Res. 11:843-852.
Scholler et al., "Soluble member(s) of the mesothelin/ megakaryocyte potentiating factor family are detectable in sera from patients with ovarian carcinoma," Proc. Natl. Acad. Sci. USA vol. 96, pp. 11531-11536, Sep. 1999.
Schroder and Lubke, The Peptides, vol. 1. pp. 76-136 (1965) Academic Press.
Schweikart, K., "In vitro myelosuppression of SJG-136, a pyrrolobenzodiazepine dimer: comparison to bizelesin," Proceedings of the American Association for Cancer Research Annual Meeting (Mar. 2004) 45:486.
Segawa et al., "Growth-related Renal Type II Na/Pi Cotransporter," The Journal of Biolocjcal Chemistry, vol. 277. No. 22, Issue of May 31, pp. 19665-19672, 2002.
Semba K., et al., "A v-erbB-related protooncogene, c-erbB-2, is distinct from the c-erbB-1 /epidermal growth factor-receptor gene and is amplified in a human salivary gland adenocarcinoma," 15 Proc. Natl. Acad. Sci. U.S.A 82, 6497-6501, 1985.
Servenius et al., "Class II Genes of the Human Major Histocompatibility Complex, The DOBeta Gene is a Divergent Member of the Class II P Gene Family," (1987) J. Biol. Chem. 262:8759-8766.
Shamis et al., "Bioactivation of Self-Immolative Dendritic Prodrugs by Catalytic Antibody 38C2," (2004) J . Am. Chem. Soc. 126:1726-1731.
Sharkey et al., "Epratuzumab-SN-38: a new antibody-drug conjugate for the therapy of hematologic malignancies," Mol. Cancer Ther. (2012) 11(1):224-234.
Sheikh F., et al., "Cutting Edge: IL-26 Signals through a Novel Receptor Complex Composed of IL-20 Receptor 1 and IL-10 Receptor 21," (2004) J.Immunol, 172, 2006-2010.
Shen et al., "Conjugation site modulates the in vivo stability and therapeutic activity of antibody-drug conjugates," (2012) Nature Biotech., 30(2):184-191.
Shieh et al., "Expression of axl in lung adenocarcinoma and correlation with tumor progression." Neoplasia. Dec. 2005; 7(12):1058-64.
Shimizu, K et al., "Prothracarcin, a Novel Antitumor Antibiotic," J. Antibiotics, 35, 972-978 (1982).
Sinha S.K., et al., "Characterization of the EBV /C3d Receptor on the Human Jurkat T Cell Line: Evidence for a Novel Transcript," (1993) J. Immunol. 150, 5311-5320.
Smellie, M. et al., "Cellular pharmacology of novel C8-linked anthramycin-based sequence-selective DNA minor groove cross-linking agents," Br. J. Cancer (1994) 70:48-53.
Smellie, M. et al., "Sequence selective recognition of duplex DNA through covalent interstrand cross-linking," Biochem. (2003) 42:8232-8239.
Smith, P. K. et al., "Measurement of protein using bicinchoninic acid." Anal Biochem. Oct. 1985; 150(1):76-85.

(56) References Cited

OTHER PUBLICATIONS

Song et al., "Overexpression of Receptor Tyrosine Kinase Axl Promotes Tumor Cell Invasion and Survival in Pancreatic Ductal Adenocarcinoma" Cancer 2011, 117:734-743.
Souillac, P. et al., "Characterization of delivery systems, differential scanning calorimetry," Encyclopedia of Controlled Drug Delivery (1999) 212-227 (pp. 217-218).
Stimmel et al., "Site-specific conjugation on serine right-arrow cysteine variant monoclonal antibodies." J Biol Chem. Sep. 29, 2000; 275(39):30445-50.
Storm et al., "Effect of Small Changes in Orientation on Reaction Rate," (1972) J. Amer. Chem. Soc. 94:5815-5825.
Strausberg et al., "Generation and initial analysis of more than 15,000 full-length human and mouse Edna sequences," (2002) Proc. Natl. Acad. Sci USA 99:16899-16903.
Strop et al., "Location matters: site of conjugation modulates stability and pharmacokinetics of antibody drug conjugates." Chem Biol. Feb. 21, 2013; 20(2):161-7.
Suggitt, M., "The hollow fibre model-facilitating anti-cancer preclinical pharmacodynamics and improving animal welfare," Int. J. Oncol. (2006) 29(6):1493-1499.
Suggs, J.W. et al., "Synthesis and structure of anthramycin analogs via hydride reduction of dilactams," Tetrahedron Letters, 26, No. 40, 4871-4874 (1985).
Sukumar et al., "Characterization of MK-4166, a Clinical Agonistic Antibody That Targets Human GITR and Inhibits the Generation and Suppressive Effects of T Regulatory Cells." Cancer Res. Aug. 15, 2017; 77(16):4378-4388.
Sun et al., "Enabling ScFvs as Multi-Drug Carriers: A Dendritic Approach," (2003) Bioorganic & Medicinal Chemistry 11:1761-1768.
Sun et al., "Syntheses of Dendritic Linkers Containing Chlorambucil Residues for the Preparation of Antibody-Multidrug Immunoconjugates," (2002) Bioorganic & Medicinal Chemistry Letters 12:2213-2215.
Sutherland, M.S.K. et al., "SGN-CD33A: a novel CD33-directed antibody-drug conjugate, utilizing pyrrolobenzodiazepine dimers, demonstrates preclinical anti-tumor activity against multi-drug resistant human AML," American Society of Hematology (Dec. 8-12, 2012) Atlanta, Georgia, Abstract No. 3589.
Svensson P.J., et al., "Phenotypic variation in a family with mutations in two Hirschsprung-related genes (RET and endothelin receptor B)," Hum. Genet. 103, 145-148, 1998.
Swiercz J.M., et al., "Plexin-81 /RhoGEF-mediated Rho a activation involves the receptor tyrosine kinase ErbB-2," J. Cell Biol. 165, 869-880, 2004.
Syrigos and Epenetos, "Antibody Directed Enzyme Prodrug Therapy (ADEPT): A Review of the Experimental and Clinical Considerations," (1999) Anticancer Research 19:605-614.
Tai et al., "Axl promotes cell invasion by inducing MMP-9 activity through activation of NF-kappaB and Brg-1." Oncogene. Jul. 3, 2008; 27(29):4044-55.
Takahashi et al., "Human Fas ligand: gene structure, chromosomal location and species specificity." Int Immunol. Oct. 1994; 6(10):1567-74.
Takeuchi, T. et al., "Neothramycins A and B, New Antitumor Antibiotics," J. Antibiotics, 29, 93-96 (1976).
Tamoxifen, DrugBank reference DB00675, retrieved online https://www.drugbank.ca/.
Tamoxifen, NCBI Pubchem reference 2733526.
Tavolimab, NCI Thesaurus, Code C132267, Retrieved from https://ncit.nci.nih.gov/ncitbrowser/.
Tawaragi Y., et al., "Primary Structure of Nonspecific Crossreacting Antigen (Nca), A Member of Carcinoembryonic Antigen (Cea) Gene Family, Deduced From Cdna Sequence," Biochem. Biophys. Res. Commun. 150, 89-96, 1988.
Tercel, M. et al., "Unsymmetrical DNA cross-linking agents: combination of the CBI and PBD pharmacophores," J. Med. Chem. (2003) 46:2132-2151.

Thompson J.S., et al., "BAFF-R, a Newly Identified TNF Receptor That Specifically Interacts with BAFF," Science 293 (5537), 2108-2111 (2001 ).
Thurston, D. E., "Advances in the study of Pyrrolo[2,1-c][1,4] benzodiazepine (PBD) Antitumour Antibiotics", Molecular Aspects of Anticancer Drug-DNA Interaction, Neidle, S. and Waring, M.J., Eds.; Macmillan Press Ltd, 1:54-88 (1993).
Thurston, D.E. and Bose, D.S., "Synthesis of DNA-Interactive Pyrrolo[2,1-c][1,4]benzodiazepines," Chem. Rev., 94:433-465 (1994).
Thurston, D.E. and Thompson, A.S., "The molecular recognition of DNA," Chem. Brit., 26, 767-772 (1990).
Thurston, D.E. et al., "Effect of A-ring modifications on the DNA-binding behavior and cytotoxicity of pyrrolo[2,1-c][1,4]benzodiazepines", Journal of Medicinal Chemistry, 42:1951-1964 (1999).
Thurston, D.E. et al., "Synthesis of Sequence-selective C8-linked Pyrrolo [2,1c][1,4] Benzodiazepine Dna Interstrand Cross-linking Agent," J. Org. Chem., 61:8141-8147 (1996).
Thurston, D.E. et al., "Synthesis of a novel GC-specific covalent-binding DNA affinity-cleavage agent based on pyrrolobenzodiazepines (PBDs)," Chemical Communications, 563-565 (1996).
Thurston, D.E., "Nucleic acid targeting: therapeutic strategies for the 21st century," Brit. J. Cancer (1999) 80(1):65-85.
Tiberghien, A.C. et al., "Application of the stille coupling reaction to the synthesis of C2-substituted endo-exo unsaturated pyrrolo[2,1-c][1,4]benzodiazepines (PBDs)," Biorg. Med. Chem. Lett. (2004) 14:5041-5044.
Tiberghien, A.C., "Application of the stille coupling reaction to the synthesis of C2-substituted endo-exo unsaturated pyrrolo[2,1-c][1,4]benzodiazepines (PBDs)," Bioorg. Med. Chem. Lett. (2008) 18(6):2073-2077.
Tigue et al., "MEDI1873, a potent, stabilized hexameric agonist of human GITR with regulatory T-cell targeting potential." Oncoimmunology. Feb. 3, 2017; 6(3):e1280645.
Toki et al., "Protease-Mediated Fragmentation of p-Amidobenzyl Ethers: A New Strategy for the Activation of Anticancer Prodrugs," (2002) J. Org. Chem. 67:1866-1872.
Tonnelle et al., "DO Beta a new chain gene in HLA-D with a distinct regulation of expression," (1985) EMBO J. 4(11):2839-2847.
Touchman et al., "The Genomic Region Encompassing the Nephropathic Cystinosis Gene (CTNS): Complete Sequencing of a 200-kb Segment and Discovery of a Novel Gene within the Common Cystinosis-Causing Deletion," (2000) Genome Res. 10:165-173.
Tozuka et al., "Studies on tomaymycin. II. Total synthesis of the antitumor antibiotics, E-and Z-tomaymycins," J. Antibiotics (Tokyo) (1983) 36:276-282.
Trail et al., "Monoclonal antibody drug immunoconjugates for targeted treatment of cancer," (2003) Cancer Immunol. Immunother. 52:328-337.
Tsunakawa, M. et al., "Porothramycin, a new antibiotic of the anthramycin group: Production, isolation, structure and biological activity," J. Antibiotics, 41:1366-1373 (1988).
Tsushima et al., "Predominant expression of B7-H1 and its immunoregulatory roles in oral squamous cell carcinoma." Oral Oncol. Mar. 2006; 42(3):268-74.
Tsutsumi M., et al., "Novel endothelin B receptor transcripts with the potential of generating a new receptor," Gene 228, 43-49, 1999.
Uchida et al., "A Novel Epidermal Growth Factor-like Molecule Containing Two Follistatin Modules Stimulates Tyrosine Phosphorylation of erbB-4 in MKN28 Gastric Cancer Cells," (1999) Biochem. Biophys. Res. Commun. 266:593-602.
Umezawa, H. et al., "Mazethramycins," SciFinder Scholar, 2-3 (2002).
Umezawa, H. et al., Chemical Abstract No. 4427a, "Mazethramycins" Chemical Abstracts, vol. 90, No. 1, 428 (1979).
Uniprot Swiss-Prot accession No. P09874, 2019.
Uniprot Swiss-Prot accession No. Q15116, 1997.
Uniprot/Swiss-Prot accession No. P16410, 2019.
Uniprot/Swiss-Prot accession No. P43489, 2019.
UniProtKB/Swiss-Prot: Q9Y5U5.1, 2001.

(56) References Cited

OTHER PUBLICATIONS

Vajkoczy et al., "Dominant-negative inhibition of the Axl receptor tyrosine kinase suppresses brain tumor cell growth and invasion and prolongs survival." Proc Natl Acad Sci U S A. Apr. 11, 2006; 103(15):5799-804.
Van Geel et al., "Chemoenzymatic Conjugation of Toxic Payloads to the Globally Conserved N-Glycan of Native mAbs Provides Homogeneous and Highly Efficacious Antibody-Drug Conjugates." Bioconjug Chem. Nov. 18, 2015;26(11):2233-42.
Veliparib, NCBI Pubchem reference 11960529.
Vemurafenib, DrugBank reference DB08881, retrieved online.
Verheij J.B., et al., "ABCD Syndrome is Caused by a Homozygous Mutation in the EDNRB Gene," Am. J. Med. 15 Genet. 108, 223-225, 2002.
Vippagunta, S.R. et al., "Crystalline solids," Adv. Drug Delivery Rev. (2001) 48:3-26.
Von Hoegen et al., "Identifigation of a Human Protein Homologous to the Mouse Lyb-2 B Cell Differentiation Antigen and Sequence of the Corresponding cDNA," (1990) J. Immunol. 144(12):4870-4877.
Wang et al., "Clinical experience of MEK inhibitors in cancer therapy." Biochim Biophys Acta. Aug. 2007;1773(8):1248-55.
Wang, J.H., "Determination of antitumor agent AJG-136 in human serum by HPLC with tandem mass spectrometric detection (HPLC-MS/MS)," Abstracts of Papers American Chemical Society (Mar. 13, 2005) 229(1):U119.
Webster et al., "Mammary tumorigenesis and metastasis in transgenic mice," (1994) Semin. Cancer Biol. 5:69-76.
Weidner-Wells, M.A. et al., "Photochemical approach to the synthesis of the pyrrolo[1,4]benzodiazepine antibiotics," J. Org. Chem. (1989) 54:5746-5758.
Weinberg, "Anti-OX40 (CD134) administration to nonhuman primates: immunostimulatory effects and toxicokinetic study." J Immunother. Nov.-Dec. 2006; 29(6):575-85.
Weis J.J., et al., "Identification of a partial cDNA clone for the C3d/Epstein-Barr virus receptor of human B lymphocytes: Homology with the receptor for fragments C3b and C4b of the third and fourth components of complement," Proc. Natl. Acad. Sci. U.S.A. 83, 5639-5643, 1986.
Weis J.J., et al., "Structure of the human b lymphocyte receptor for c3d and the epstein-barr virus and relatedness to other members of the family of c3/c4 binding proteins," J. Exp. Med. 167, 1047-1066, 1988.
Wells, G. et al., "Design, synthesis and biophysical and biological evaluation of a series of pyrrolobenzodiazepine-poly(N-methylpyrrole) conjugates," J. Med. Chem. (2006) 49:5442-5461.
Werlen et al., "Site-specific conjugation of an enzyme and an antibody fragment." Bioconjug Chem. Sep.-Oct. 1994; 5(5):411-7.
Wikipedia, "How many types of cancer are there?", 2012, 3 pages; http://wiki.answers.com/Q/How-many-different-types_of_cancer_are_there.
Wikipedia, "Management of Cancer," 2012, 1 page; http://en.wikipedia.org/wiki/Management of cancer.
Wilkinson, G.P., "Pharmacokinetics and intracellular pharmacological characteristics of the novel pyrrolobenzodiazepine (PBD) dimer SJG-136," Proceedings of the American Association for Cancer Research Annual Meeting (Jul. 2003) 44:320.
Wilkinson, G.P., "Pharmacokinetics, metabolism and glutathione reactivity of SJG-136," Br. J. Cancer (2003) 88(Supp. 1):S29.
Wilkinson, G.P., "Preliminary pharmacokinetic and bioanalytical studies of SJG-136 (NSC 694501), a sequence-selective pyrrolobenzodiazepine dimer DNA-cross-linking agent," Investigational New Drugs (2004) 22(3):231-240.
Wilson et al., "cDNA Cloning of the B Cell Membrane Protein CD22: A Mediator of B-B Cell Interactions," (1991) J. Exp. Med. 173:137-146.
Wilson, S.C. et al., "Design and Synthesis of a Novel Epoxide-Containing Pyrrolo[2,1-c][1,4]benzodiazepine (PBD) via a New Cyclization Procedure," Tetrahedron Letters, 36, No. 35, 6333-6336 (1995).
Wilson, S.C. et al., "Design, Synthesis, and Evaluation of a Novel Sequence-Selective Epoxide-Containing Dna Cross-Linking Agent Based on the Pyrrolo[2,1-c][1,4]benzodiazepine System", J. Med. Chem. 42: 4028-4041 (1999).
Wines et al., "The IgG Fc contains distinct Fc receptor (FcR) binding sites: the leukocyte receptors Fc gamma RI and Fc gamma RIIa bind to a region in the Fc distinct from that recognized by neonatal FcR and protein A." J Immunol. May 15, 2000; 164(10):5313-8.
Wolff, M.E., Burger's Medicinal Chemistry, 4th Edition, Part I, Wiley: New York (1979) 336-337.
Wolff, M.E., Burger's Medicinal Chemistry, 5th Edition, Part I, John Wiley & Sons (1995) 975-977.
Workman, P. et al., "United Kingdom Co-ordinating Committee on Cancer Research (UKCCCR) guidelines for the welfare of animals in experimental neoplasia (second edition)," Br. J. Cancer (1998) 77(1):1-10.
Wu et al., "Arming antibodies: prospects and challenges for immunoconjugates," (2005) Nature Biotech. 23(9):1137-1145.
Xie et al., "In vivo behaviour of antibody- drug conjugates for the targeted treatment of cancer," (2006) Expert. Opin Biol. Ther. 6(3):281-291.
Xie, G. et al., "Bisindolylmaleimides linked to DNA minor groove binding lexitropsins: synthesis, inhibitory activity against topoisomerasel, and biological evaluation," J. Med. Chem. (1996) 39:1049-1055.
Xu et al., "Molecular Cloning, Functional Characterization, Tissue Distribution, and Chromosomal Localization of a Human, Small Intestinal Sodium-Phosphate (Na +-Pi) Transporter (SLC34A2)," Genomics 62 (2):281-284 (1999).
Xu, M.J., et al., "Molecular Cloning and Characterization of SPAP1, an Inhibitory Receptor," (2001) Biochem. Biophys. Res. Commun. 280 (3):768-775.
Xu, X.Z., et al., "Regulation of melastatin, a TRP-related protein, through interaction with a cytoplasmic isoform," Proc. Natl. Acad. Sci. U.S.A. 98 (19):10692-10697 (2001).
Yamaguchi, N., et al., "A Novel Cytokine Exhibiting Megakaryocyte Potentiating Activity From a Human Pancreatic Tumor Cell Line HPC-Y5," Biol. Chem. 269 (2), 805-808 (1994).
Yamamoto T., et al., "Similarity of protein encoded by the human c-erb-B-2 gene to epidermal growth factor receptor," Nature 319, 230-234, 1986.
Yanagita et al., "Essential role of Gas6 for glomerular injury in nephrotoxic nephritis." J Clin Invest. Jul. 2002; 110(2):239-46.
Yang et al., "Murine Six-Transmembrane Epithelial Antigen of the Prostate, Prostate Stem Cell Antigen, and Prostate-specific Membrane Antigen: Prostate-specific Cell-Surface Antigens Highly Expressed in Prostate Cancer of Transgenic Adenocarcinoma Mouse Prostate Mice," Cancer Research, 61, 5857-5860. Aug. 1, 2001.
Yin & Lloyd, "Molecular Cloning of the CA125 Ovarian Cancer Antigen," J. Biol. Chem. 276 (29):27371-27375 (2001).
Yu et al., "Human mb-1 Gene: Complete cDNA Sequence and Its Expression in B Cells Bearing Membrane Ig of Various Isotypes," (1992) J. Immunol. 148(2) 633-637.
Yuen et al., "TAZ Expression as a Prognostic Indicator in Colorectal Cancer" PLoS One 2013, 8(1):e54211.
Zalevsky et al., "Enhanced antibody half-life improves in vivo activity." Nat Biotechnol. Feb. 2010; 28(2):157-9.
Zammarchi et al., "Pre-Clinical Development of Adct-402, a Novel Pyrrolobenzodiazepine (PBD)—Based Antibody Drug Conjugate (ADC) Targeting CD19-Expressing B-Cell Malignancies," Blood, 2015, 126:1564, Abstract.
Zhang et al., "Activation of the AXL Kinase Causes Resistance to EGFRTargeted Therapy in Lung Cancer" Nat Genet. 2013, 44(8): 852-860.
Zhang et al., "AXL is a potential target for therapeutic intervention in breast cancer progression." Cancer Res. Mar. 15, 2008;68(6):1905-15.
Zhang et al., "Structural and functional analysis of the costimulatory receptor programmed death-1." Immunity. Mar. 2004; 20(3):337-47.

\* cited by examiner

SEQUENCES

SEQ ID NO.1 [1H12 VH, CDR underline]
QVQLVESGGGVVQPGRSLRLSCAASGFTFS<u>SYGMS</u>WVRQAPGKGLEWVA<u>TISSGGSY
TYYPDSVKG</u>RFTISRDNSKNTLYLQMNSLRAEDTAVYYCAR<u>HPIYYTYDDTMDY</u>WGQG
TTVTVSS SEQ ID NO.2 [1H12 VL, CDR underline]
EIVLTQSPGTLSLSPGERATLSC<u>SASSSVSSGNFH</u>WYQQKPGLAPRLLIY<u>RTSNLAS</u>GIP
ARFSGSGSGTDFTLTISSLEPEDFAVYYC<u>QQWSGYPWT</u>FGGGTKLEIK SEQ ID NO.3 [1H12 Heavy Chain]
QVQLVESGGGVVQPGRSLRLSCAASGFTFSSYGMSWVRQAPGKGLEWVATISSGGSY
TYYPDSVKGRFTISRDNSKNTLYLQMNSLRAEDTAVYYCARHPIYYTYDDTMDYWGQG
TTVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKKVEPKSCDKTHTCPP
CPAPELLGGPSVFLFPPKPKDTLMISRTPEVTCVVVDVSHEDPEVKFNWYVDGVEVHNA
KTKPREEQY<u>N</u>*STYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGSFF
LYSKLTVDKSRWQQGNVFSCSVMHEALHNHYTQKSLSLSPG
  <u>N</u>* indicates Asn297 (numbering according to Kabat)

SEQ ID NO.4 [1H12 Light Chain]
EIVLTQSPGTLSLSPGERATLSCSASSSVSSGNFHWYQQKPGLAPRLLIYRTSNLASGIP
ARFSGSGSGTDFTLTISSLEPEDFAVYYCQQWSGYPWTFGGGTKLEIKRTVAAPSVFIFP
PSDEQLKSGTASVVCLLNNFYPREAKVQWKVDNALQSGNSQESVTEQDSKDSTYSLSS
TLTLSKADYEKHKVYACEVTHQGLSSPVTKSFNRGEC

SEQ ID NO.5 [1H12 VH CDR1]
SYGMS

SEQ ID NO.6 [1H12 VH CDR2]
TISSGGSYTYYPDSVKG

SEQ ID NO.7 [1H12 VH CDR3]
HPIYYTYDDTMDY

SEQ ID NO.8 [1H12 VL CDR1]
SASSSVSSGNFH

SEQ ID NO.9 [1H12 VL CDR2]
RTSNLAS

Figure 1A

SEQ ID NO.10 [1H12 VL CDR3]
QQWSGYPWT

SEQ ID NO.11 [murine 5F11 VH, CDR underline]
EVKLLESGGGLVQPGGSLKLSCAASGFDFSRYWMSWVRQAPGKGLEWIGEINPDSSTI
NYTPSLKDKFIISRDNAKNTLYLQMSKVRSEDTALYYCASPYYYGPFAYWGQGTLVTVS
S SEQ ID NO.12 [murine 5F11 VL, CDR underline]
DIVLTQSPASLAVSLGQRAIISCKASQSVSFAGTSLMHWYQQKPGQQPKLLIYRASNLEA
GFPTRFSGSGSRTDFTLNIHPVEEEDAATYYCQQSREYPRTFGGGTKLEVK

SEQ ID NO.13 [5F11 VH CDR1]
RYWMS

SEQ ID NO.14 [5F11 VH CDR2]
EINPDSSTINYTPSLKD

SEQ ID NO.15 [5F11 VH CDR3]
PYYYGPFAY

SEQ ID NO.16 [5F11 VL CDR1]
KASQSVSFAGTSLMH

SEQ ID NO.17 [5F11 VL CDR2]
RASNLEA

SEQ ID NO.18 [5F11 VL CDR3]
QQSREYPRT

SEQ ID NO.19 [5F11 RHA]
QVQLVESGGGVVQPGRSLRLSCAASGFTFSRYWMSWVRQAPGKGLEWVAEINPDSST
INYTPSLKDRFAISRDNSKNTLYLQMNSLRAEDTAVYYCASPYYYGPFAYWGQGTLVTV
S

SEQ ID NO.20 [5F11 RHB]
EVQLVESGGGLVQPGGSLRLSCAASGFTFSRYWMSWVRQAPGKGLEWVAEINPDSSTI
NYTPSLKDRFTISRDNAKNSLYLQMNSLRAEDTAVYYCASPYYYGPFAYWGQGTLVTVS

SEQ ID NO.21 [5F11 RHC]
EVQLLESGGGLVQPGGSLRLSCAASGFTFSRYWMSWVRQAPGKGLEWVSEINPDSSTI
NYTPSLKDRFTISRDNSKNTLYLQMNSLRAEDTAVYYCASPYYYGPFAYWGQGTLVTVS

Figure 1B

SEQ ID NO.22 [5F11 RKA]
EIVLTQSPLSLPVTPGEPASISCKASQSVSFAGTSLMHWYLQKPGQSPQLLIYRASNLEA
GVPDRFSGSGSGTDFTLKISRVEAEDVGVYYCQQSREYPRTFGQGTKVEIK

SEQ ID NO.23 [Human Axl]
MAWRCPRMGRVPLAWCLALCGWACMAPRGTQAEESPFVGNPGNITGARGLTGTLRC
QLQVQGEPPEVHWLRDGQILELADSTQTQVPLGEDEQDDWIVVSQLRITSLQLSDTGQY
QCLVFLGHQTFVSQPGYVGLEGLPYFLEEPEDRTVAANTPFNLSCQAQGPPEPVDLLW
LQDAVPLATAPGHGPQRSLHVPGLNKTSSFSCEAHNAKGVTTSRTATITVLPQQPRNLH
LVSRQPTELEVAWTPGLSGIYPLTHCTLQAVLSDDGMGIQAGEPDPPEEPLTSQASVPP
HQLRLGSLHPHTPYHIRVACTSSQGPSSWTHWLPVETPEGVPLGPPENISATRNGSQAF
VHWQEPRAPLQGTLLGYRLAYQGQDTPEVLMDIGLRQEVTLELQGDGSVSNLTVCVAA
YTAAGDGPWSLPVPLEAWRPGQAQPVHQLVKEPSTPAFSWPWWYVLLGAVVAAACVL
ILALFLVHRRKKETRYGEVFEPTVERGELVVRYRVRKSYSRRTTEATLNSLGISEELKEKL
RDVMVDRHKVALGKTLGEGEFGAVMEGQLNQDDSILKVAVKTMKIAICTRSELEDFLSE
AVCMKEFDHPNVMRLIGVCFQGSERESFPAPVVILPFMKHGDLHSFLLYSRLGDQPVYL
PTQMLVKFMADIASGMEYLSTKRFIHRDLAARNCMLNENMSVCVADFGLSKKIYNGDYY
RQGRIAKMPVKWIAIESLADRVYTSKSDVWSFGVTMWEIATRGQTPYPGVENSEIYDYL
RRGNRLKQPADCLDGLYALMSRCWELNPQDRPSFTELREDLENTLKALPPAQEPDEILY
VNMDEGGGYPEPPGAAGGADPPTQPDPKDSCSCLTAAEVHPAGRYVLCPSTTPSPAQ
PADRGSPAAPGQEDGA

Figure 1C

COMBINATION THERAPY WITH AN ANTI-AXL ANTIBODY-DRUG CONJUGATE

CROSS-REFERENCE TO RELATED APPLICATIONS

This application is a continuation of International Application No. PCT/EP2018/060209, filed 20 Apr. 2018, which claims the benefit of GB1706231.6, GB1706230.8, GB1706229.0, GB1706228.2, GB1706227.4, GB1706226.6, GB1706225.8, and GB1706224.1, GB1706223.3, all filed 20 Apr. 2017, each of which are hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on Apr. 3, 2019, is named 37414-US-1-CON_ST25 and is 74,784 bytes in size.

FIELD

The present disclosure relates to combination therapies for the treatment of pathological conditions, such as cancer. In particular, the present disclosure relates to combination therapies comprising treatment with an Antibody Drug Conjugate (ADC) and a secondary agent.

BACKGROUND

Antibody Therapy

Antibody therapy has been established for the targeted treatment of subjects with cancer, immunological and angiogenic disorders (Carter, P. (2006) Nature Reviews Immunology 6:343-357). The use of antibody-drug conjugates (ADC), i.e. immunoconjugates, for the local delivery of cytotoxic or cytostatic agents, i.e. drugs to kill or inhibit tumour cells in the treatment of cancer, targets delivery of the drug moiety to tumours, and intracellular accumulation therein, whereas systemic administration of these unconjugated drug agents may result in unacceptable levels of toxicity to normal cells (Xie et al (2006) Expert. Opin. Biol. Ther. 6(3):281-291; Kovtun et al (2006) Cancer Res. 66(6): 3214-3121; Law et al (2006) Cancer Res. 66(4):2328-2337; Wu et al (2005) Nature Biotech. 23(9):1137-1145; Lambert J. (2005) Current Opin. in Pharmacol. 5:543-549; Hamann P. (2005) Expert Opin. Ther. Patents 15(9):1087-1103; Payne, G. (2003) Cancer Cell 3:207-212; Trail et al (2003) Cancer Immunol. Immunother. 52:328-337; Syrigos and Epenetos (1999) Anticancer Research 19:605-614).

Axl

Axl is a member of the receptor tyrosine kinase subfamily. Although similar to other receptor tyrosine kinases, the Axl protein represents a unique structure of the extracellular region that juxtaposes IgL and FNIII repeats, and has an intracellular region containing an intracellular domain, part of which is the kinase domain. Axl transduces signals from the extracellular matrix into the cytoplasm by binding growth factors like vitamin K-dependent protein growth-arrest-specific gene 6 (Gas6). The extracellular domain of Axl can be cleaved and a soluble extracellular domain of 65 kDa can be released. Cleavage enhances receptor turnover and generates a partially activated kinase (O'Bryan J P, etal (1995) J Bioi Chern. 270 (2): 551-557).

Structural information relating to the human Axl gene and gene product is described in WO2003/068983. The following patent publications also relate to Axl or other tyrosine kinase receptors: U.S. Pat. Nos. 5,468,634; 6,087,144; 5,538,861; 5,968,508; 6,211,142; 6,235,769; WO1999/49894; WO2000/76309; WO2001/16181 and WO2001/32926.

Axl is involved in the stimulation of cell proliferation. Specifically, Axl is a chronic myelogenous leukaemia-associated oncogene, that is also associated with colon cancer and melanoma. It is in close vicinity to the bcl3 oncogene which is at 19q13.1-q13.2. The Axl gene is evolutionarily conserved among vertebrate species, and is expressed during development in the mesenchyme.

Upon interaction with the Gas6 ligand, Axl becomes autophosphorylated, and a cascade of signal transduction events takes place. PI3K, AKT, src, Bad, 14-3-3, PLC, ERK, S6K (mitogen-regulated kinase) and STAT are each known to be involved in this cascade. Gas6 has a region rich with y-carboxyglutamic acid (GLA domain) that allows for Ca++-dependent binding to membrane phospholipids. Gas6 is a weak mitogen and has an anti-apoptotic effect in NIH3T3 fibroblasts subjected to stress by TNF-induced cytotoxicity, or growth factor withdrawal. In NIH3T3 the binding of Gas6 to Axl results in activation of PI3K, AKT, src and Bad.

Studies have shown that Axl plays a number of different roles in tumour formation. Axl is a key regulator of angiogenic behaviours including endothelial cell migration, proliferation and tube formation. Axl is also required for human breast carcinoma cells to form a tumour in vivo, indicating that Axl regulates processes that are vital for both neovascularisation and tumorigenesis (Holland S. et al, Cancer Res 2005; 65 (20), Oct. 15, 2005).

The activity of Axl receptor tyrosine kinase is positively correlated with tumour metastasis. More specifically, studies have shown that Axl enhances expression of MMP-9, which is required for Axl-mediated invasion. Axl promotes cell invasion by inducing MMP-9 activity through activation of NF-BK and Brg-1 (Tai, K-Y et al, Oncogene (2008), 27, 4044-4055). Axl is overexpressed in human glioma cells and can be used to predict poor prognosis in patients with Glioblastoma Multiforme (GBM) (Vajkoczy P. et al, PNAS, Apr. 11, 2006, val 103, no. 15, 5799-5804; Hutterer M. etal, Clinical Cancer Res 2008; 14 (1) Jan. 1, 2008). Axl is also relatively overexpressed in highly invasive lung cancer cell lines compared to their minimally invasive counterparts (Shieh, Y-S etal, Neoplasia, val 7, no. 12, December 2005, 1058-1064). Axl is therefore believed to play an important role in tumour invasion and progression.

Likewise, Axl is expressed in highly invasive breast cancer cells, but not in breast cancer cells of low invasivity. More specifically, inhibition of Axl signalling (by dominant-negative Axl mutant, an antibody against the extracellular domain of Axl, or by short hairpin RNA knockdown of Axl) decreased the mobility and invasivity of highly invasive breast cancer cells. Small molecule Axl inhibitors interfered with motility and invasivity of breast cancer cells. Thus, Axl is understood to be a critical element in the signalling network that governs the motility/invasivity of breast cancer cells (Zhang, Y-X et al., Cancer Res 2008; 68 (6), Mar. 15, 2008).

In mesangial cells, Gas6 was found to have a mitogenic effect, indicative of a possible role in the progression of glomerulosclerosis. Evidence has suggested that the Gas6/Axl pathway also plays a role in glomerulonephritis (Yanagita M. at al, The Journal of Clinical Investigation;

2002, 110 (2) 239-246). Further studies have shown that Gas6 promotes the survival of endothelial cells in a model for arterial injury. Angiotensin II, via its AT1 receptor, was shown to increase Axl mRNA and protein receptor in vascular smooth muscle cells (Melaragno M. G. etal, Circ Res., 1998, 83 (7): 697-704). Axl has also been shown to be involved in cellular adhesion, cell proliferation and regulation of homeostasis in the immune system (Lu Q., 2001) Science 293 (5528): 306 311). Following Axl activation, the following phenomena have been observed: inhibition of apoptosis, increase in "normal" cell (non-transformed) survival of fibroblasts and endothelial cells, migration of Vascular Smooth Muscle Cell (VSMC) (inactivation of the Axl kinase blocks migration), enhancement of neointima formation in blood vessel wall (Melaragno M. G. etal, Trends Cardiovasc Med., 1999, (Review) 9 (8): 250-253) and involvement in lesion formation and the progression of atherosclerosis.

Therapeutic uses of anti-AXL ADCs

The efficacy of an Antibody Drug Conjugate comprising an anti-AXL antibody (an anti-AXL-ADC) in the treatment of, for example, cancer has been established—see, for example, WO2016/166297, WO2016/166302, GB1702029.8, GB1719906.8, and PCT/EP2018/053163.

Research continues to further improve the efficacy, tolerability, and clinical utility of anti-AXL ADCs. To this end, the present authors have identified clinically advantageous combination therapies in which an anti-AXL ADC is administered in combination with at least one secondary agent.

SUMMARY

The present authors have determined that the administration of a combination of an ADC and secondary agent to an individual leads to unexpected clinical advantages.

Accordingly, in one aspect the disclosure provides a method for treating a disorder in an individual, the method comprising administering to the individual an effective amount of an ADC and secondary agent.

The disorder may be a proliferative disease, for example a cancer. Cancers include metastatic cancers and metastatic cancer cells, such as circulating tumour cells, which may be found circulating in body fluids such as blood or lymph. Cancers of particular interest include, but are not limited to, breast, lung, gastric, head and neck, colorectal, renal, pancreatic, uterine, hepatic, bladder, endometrial and prostate cancers as well as lymphomas (e.g., non-Hodgkin's lymphoma, NHL) and leukemia (particularly acute myeloid leukemia, AML).

Other disorders of interest include any condition in which Axl is overexpressed, or wherein Axl antagonism will provide a clinical benefit. These include immune disorders, cardiovascular disorders, thrombosis, diabetes, immune checkpoint disorders, or fibrotic disorders (fibrosis) such as strabmisus, scleroderma, keloid, Nephrogenic systemic fibrosis, pulmonary fibrosis, idiopathic pulmonary fibrosis (IPF), cystic fibrosis (CF), systemic sclerosis, cardiac fibrosis, non-alcoholic steatohepatitis (NASH), other types of liver fibrosis, primary biliary cirrhosis, renal fibrosis, cancer, and atherosclerosis.

The proliferative disease may be characterised by the presence of a neoplasm comprising both AXL+ve and AXL−ve cells.

The proliferative disease may be characterised by the presence of a neoplasm composed of AXL−ve neoplastic cells, optionally wherein the AXL−ve neoplastic cells are associated with AXL+ve non-neoplastic cells.

The target neoplasm or neoplastic cells may be all or part of a solid tumour.

"Solid tumor" herein will be understood to include solid haematological cancers such as lymphomas (Hodgkin's lymphoma or non-Hodgkin's lymphoma) which are discussed in more detail herein.

Solid tumors may be neoplasms, including non-haematological cancers, comprising or composed of AXL+ve neoplastic cells. Solid tumors may be neoplasms, including non-haematological cancers, infiltrated with AXL+ve cells, such as AXL+ve immune suppressive dendritic cells, NK cells, or macrophages; such solid tumours may lack expression of AXL (that is, comprise or be composed of AXL−ve neoplastic cells).

For example, the solid tumour may be a tumour with high levels of infiltrating AXL+ve cells, such as infiltrating dendritic cells, NK cells, or macrophages (Paolino, M., et al., Cancers 2016, 8, 97; doi:10.3390/cancers8100097). Accordingly, the solid tumour may be pancreatic cancer, breast cancer, colorectal cancer, gastric and oesophageal cancer, leukemia and lymphoma, melanoma, non-small cell lung cancer, ovarian cancer, hepatocellular carcinoma, renal cell carcinoma, and head and neck cancer.

The ADC may be anti-AXL-ADC, such as ADCxAXL described herein.

The secondary agent may be a PD1 antagonist, a PD-L1 antagonist, a GITR agonist, an OX40 agonist, a CTLA-4 antagonist, Fludarabine or Cytarabine, a hypomethylating agent, a PARP inhibitor (PARPi), an agent that upregulates HER2 expression, an AXL inhibitor (AXLi), a BRAF inhibitor (BRAFi), or a MEK inhibitor (MEKi).

The individual may be human. The individual may have cancer, or may have been determined to have cancer. The individual may have, or have been determined to have, a AXL+ cancer or AXL+ tumour-associated non-tumour cells. The individual may have, or have been determined to have, a AXL+ cancer or AXL+ tumour-associated non-tumour cells.

The individual may have, or have been determined to have, a PD-L1+ cancer.

In the disclosed methods the ADC may be administered before the secondary agent, simultaneous with the secondary agent, or after the secondary agent. The disclosed methods may comprise administering a further chemotherapeutic agent to the individual.

In another aspect, the disclosure provides a first composition comprising an ADC for use in a method of treating a disorder in an individual, wherein the treatment comprises administration of the first composition in combination with a second composition comprising a secondary agent.

Also provided by this aspect is a first composition comprising a secondary agent for use in a method of treating a disorder in an individual, wherein the treatment comprises administration of the first composition in combination with a second composition comprising an ADC.

The disorder may be a proliferative disease, for example a cancer. Cancers include metastatic cancers and metastatic cancer cells, such as circulating tumour cells, which may be found circulating in body fluids such as blood or lymph. Cancers of particular interest include, but are not limited to, breast, lung, gastric, head and neck, colorectal, renal, pancreatic, uterine, hepatic, bladder, endometrial and prostate cancers as well as lymphomas (e.g., non-Hodgkin's lymphoma, NHL) and leukemia (particularly acute myeloid leukemia, AML).

Other disorders of interest include any condition in which Axl is overexpressed, or wherein Axl antagonism will provide a clinical benefit. These include immune disorders, cardiovascular disorders, thrombosis, diabetes, immune checkpoint disorders, or fibrotic disorders (fibrosis) such as strabmisus, scleroderma, keloid, Nephrogenic systemic fibrosis, pulmonary fibrosis, idiopathic pulmonary fibrosis (IPF), cystic fibrosis (CF), systemic sclerosis, cardiac fibrosis, non-alcoholic steatohepatitis (NASH), other types of liver fibrosis, primary biliary cirrhosis, renal fibrosis, cancer, and atherosclerosis.

The proliferative disease may be characterised by the presence of a neoplasm comprising both AXL+ve and AXL–ve cells.

The proliferative disease may be characterised by the presence of a neoplasm composed of AXL–ve neoplastic cells, optionally wherein the AXL–ve neoplastic cells are associated with AXL+ve non-neoplastic cells.

The target neoplasm or neoplastic cells may be all or part of a solid tumour.

"Solid tumor" herein will be understood to include solid haematological cancers such as lymphomas (Hodgkin's lymphoma or non-Hodgkin's lymphoma) which are discussed in more detail herein.

Solid tumors may be neoplasms, including non-haematological cancers, comprising or composed of AXL+ve neoplastic cells. Solid tumors may be neoplasms, including non-haematological cancers, infiltrated with AXL+ve cells, such as AXL+ve immune suppressive dendriti cells, NK cells, or macrophages; such solid tumours may lack expression of AXL (that is, comprise or be composed of AXL–ve neoplastic cells).

The ADC may be anti-AXL–ADC, such as ADC×AXL described herein.

The secondary agent may be a PD1 antagonist, a PD-L1 antagonist, a GITR agonist, an OX40 agonist, a CTLA-4 antagonist, Fludarabine or Cytarabine, a hypomethylating agent, a PARP inhibitor (PARPi), an agent that upregulates HER2 expression, an AXL inhibitor (AXLi), a BRAF inhibitor (BRAFi), or a MEK inhibitor (MEKi).

The individual may be human. The individual may have cancer, or may have been determined to have cancer. The individual may have, or have been determined to have, a AXL+ cancer or AXL+ tumour-associated non-tumour cells. The individual may have, or have been determined to have, a AXL+ cancer or AXL+ tumour-associated non-tumour cells.

The individual may have, or have been determined to have, a PD-L1+ cancer.

The first composition may be administered before the second composition, simultaneous with the second composition, or after the second composition. The treatment may comprise administering a further chemotherapeutic agent to the individual.

In a further aspect, the disclosure provides the use of n ADC in the manufacture of a medicament for treating a disorder in an individual, wherein the medicament comprises an ADC, and wherein the treatment comprises administration of the medicament in combination with a composition comprising secondary agent.

Also provided by this aspect is the use of secondary agent in the manufacture of a medicament for treating a disorder in an individual, wherein the medicament comprises a secondary agent, and wherein the treatment comprises administration of the medicament in combination with a composition comprising an ADC.

The disorder may be a proliferative disease, for example a cancer. Cancers include metastatic cancers and metastatic cancer cells, such as circulating tumour cells, which may be found circulating in body fluids such as blood or lymph. Cancers of particular interest include, but are not limited to, breast, lung, gastric, head and neck, colorectal, renal, pancreatic, uterine, hepatic, bladder, endometrial and prostate cancers as well as lymphomas (e.g., non-Hodgkin's lymphoma, NHL) and leukemia (particularly acute myeloid leukemia, AML).

Other disorders of interest include any condition in which Axl is overexpressed, or wherein Axl antagonism will provide a clinical benefit. These include immune disorders, cardiovascular disorders, thrombosis, diabetes, immune checkpoint disorders, or fibrotic disorders (fibrosis) such as strabmisus, scleroderma, keloid, Nephrogenic systemic fibrosis, pulmonary fibrosis, idiopathic pulmonary fibrosis (IPF), cystic fibrosis (CF), systemic sclerosis, cardiac fibrosis, non-alcoholic steatohepatitis (NASH), other types of liver fibrosis, primary biliary cirrhosis, renal fibrosis, cancer, and atherosclerosis.

The proliferative disease may be characterised by the presence of a neoplasm comprising both AXL+ve and AXL–ve cells.

The proliferative disease may be characterised by the presence of a neoplasm composed of AXL–ve neoplastic cells, optionally wherein the AXL–ve neoplastic cells are associated with AXL+ve non-neoplastic cells.

The target neoplasm or neoplastic cells may be all or part of a solid tumour.

"Solid tumor" herein will be understood to include solid haematological cancers such as lymphomas (Hodgkin's lymphoma or non-Hodgkin's lymphoma) which are discussed in more detail herein.

Solid tumors may be neoplasms, including non-haematological cancers, comprising or composed of AXL+ve neoplastic cells. Solid tumors may be neoplasms, including non-haematological cancers, infiltrated with AXL+ve cells, such as AXL+ve immune suppressive dendritic cells, NK cells, or macrophages; such solid tumours may lack expression of AXL (that is, comprise or be composed of AXL–ve neoplastic cells).

The ADC may be anti-AXL–ADC, such as ADC×AXL described herein.

The secondary agent may be a PD1 antagonist, a PD-L1 antagonist, a GITR agonist, an OX40 agonist, a CTLA-4 antagonist, Fludarabine or Cytarabine, a hypomethylating agent, a PARP inhibitor (PARPi), an agent that upregulates HER2 expression, an AXL inhibitor (AXLi), a BRAF inhibitor (BRAFi), or a MEK inhibitor (MEKi).

The individual may be human. The individual may have cancer, or may have been determined to have cancer. The individual may have, or have been determined to have, a AXL+ cancer or AXL+ tumour-associated non-tumour cells. The individual may have, or have been determined to have, a AXL+ cancer or AXL+ tumour-associated non-tumour cells.

The individual may have, or have been determined to have, a PD-L1+ cancer.

The medicament may be administered before the composition, simultaneous with the composition, or after the composition. The treatment may comprise administering a further chemotherapeutic agent to the individual.

Another aspect of the disclosure provides a kit comprising:
 a first medicament comprising an ADC;
 a second medicament comprising a secondary agent; and, optionally, a package insert comprising instructions for administration of the first medicament to an individual in combination with the second medicament for the treatment of a disorder.

Also provided by this aspect is a kit comprising a medicament comprising an ADC and a package insert comprising instructions for administration of the medicament to an individual in combination with a composition comprising a secondary agent for the treatment of a disorder.

Further provided by this aspect is a kit comprising a medicament comprising a secondary agent and a package insert comprising instructions for administration of the medicament to an individual in combination with a composition comprising an ADC for the treatment of a disorder.

The disorder may be a proliferative disease, for example a cancer. Cancers include metastatic cancers and metastatic cancer cells, such as circulating tumour cells, which may be found circulating in body fluids such as blood or lymph. Cancers of particular interest include, but are not limited to, breast, lung, gastric, head and neck, colorectal, renal, pancreatic, uterine, hepatic, bladder, endometrial and prostate cancers as well as lymphomas (e.g., non-Hodgkin's lymphoma, NHL) and leukemia (particularly acute myeloid leukemia, AML).

Other disorders of interest include any condition in which Axl is overexpressed, or wherein Axl antagonism will provide a clinical benefit. These include immune disorders, cardiovascular disorders, thrombosis, diabetes, immune checkpoint disorders, or fibrotic disorders (fibrosis) such as strabmisus, scleroderma, keloid, Nephrogenic systemic fibrosis, pulmonary fibrosis, idiopathic pulmonary fibrosis (IPF), cystic fibrosis (CF), systemic sclerosis, cardiac fibrosis, non-alcoholic steatohepatitis (NASH), other types of liver fibrosis, primary biliary cirrhosis, renal fibrosis, cancer, and atherosclerosis.

The proliferative disease may be characterised by the presence of a neoplasm comprising both AXL+ve and AXL−ve cells.

The proliferative disease may be characterised by the presence of a neoplasm composed of AXL−ve neoplastic cells, optionally wherein the AXL−ve neoplastic cells are associated with AXL+ve non-neoplastic cells.

The target neoplasm or neoplastic cells may be all or part of a solid tumour.

"Solid tumor" herein will be understood to include solid haematological cancers such as lymphomas (Hodgkin's lymphoma or non-Hodgkin's lymphoma) which are discussed in more detail herein.

Solid tumors may be neoplasms, including non-haematological cancers, comprising or composed of AXL+ve neoplastic cells. Solid tumors may be neoplasms, including non-haematological cancers, infiltrated with AXL+ve cells, such as AXL+ve immune suppressive dendritic cells, NK cells, or macrophages; such solid tumours may lack expression of AXL (that is, comprise or be composed of AXL−ve neoplastic cells).

The ADC may be anti-AXL-ADC, such as ADCxAXL described herein.

The secondary agent may be a PD1 antagonist, a PD-L1 antagonist, a GITR agonist, an OX40 agonist, a CTLA-4 antagonist, Fludarabine or Cytarabine, a hypomethylating agent, a PARP inhibitor (PARPi), an agent that upregulates HER2 expression, an AXL inhibitor (AXLi), a BRAF inhibitor (BRAFi), or a MEK inhibitor (MEKi).

The individual may be human. The individual may have cancer, or may have been determined to have cancer. The individual may have, or have been determined to have, a AXL+ cancer or AXL+ tumour-associated non-tumour cells. The individual may have, or have been determined to have, a AXL+ cancer or AXL+ tumour-associated non-tumour cells.

The individual may have, or have been determined to have, a PD-L1+ cancer.

The medicament or composition comprising the ADC may be administered before the medicament or composition comprising the secondary agent, simultaneous with the medicament or composition comprising the secondary agent, or after the medicament or composition comprising the secondary agent. The treatment may comprise administering a further chemotherapeutic agent to the individual.

In a yet further aspect, the disclosure provides a composition comprising an ADC and a secondary agent.

Also provided in this aspect of the disclosure is a method of treating a disorder in an individual, the method comprising administering to the individual an effective amount of the composition comprising an ADC and a secondary agent.

Also provided in this aspect of the disclosure is a composition comprising an ADC and a secondary agent for use in a method of treating a disorder in an individual.

Also provided in this aspect of the disclosure is the use of a composition comprising an ADC and a secondary agent in the manufacture of a medicament for treating a disorder in an individual.

Also provided in this aspect of the disclosure is a kit comprising composition comprising an ADC and a secondary agent and a set of instructions for administration of the medicament to an individual for the treatment of a disorder.

The disorder may be a proliferative disease, for example a cancer. Cancers include metastatic cancers and metastatic cancer cells, such as circulating tumour cells, which may be found circulating in body fluids such as blood or lymph. Cancers of particular interest include, but are not limited to, breast, lung, gastric, head and neck, colorectal, renal, pancreatic, uterine, hepatic, bladder, endometrial and prostate cancers as well as lymphomas (e.g., non-Hodgkin's lymphoma, NHL) and leukemia (particularly acute myeloid leukemia, AML).

Other disorders of interest include any condition in which Axl is overexpressed, or wherein Axl antagonism will provide a clinical benefit. These include immune disorders, cardiovascular disorders, thrombosis, diabetes, immune checkpoint disorders, or fibrotic disorders (fibrosis) such as strabmisus, scleroderma, keloid, Nephrogenic systemic fibrosis, pulmonary fibrosis, idiopathic pulmonary fibrosis (IPF), cystic fibrosis (CF), systemic sclerosis, cardiac fibrosis, non-alcoholic steatohepatitis (NASH), other types of liver fibrosis, primary biliary cirrhosis, renal fibrosis, cancer, and atherosclerosis.

The proliferative disease may be characterised by the presence of a neoplasm comprising both AXL+ve and AXL−ve cells.

The proliferative disease may be characterised by the presence of a neoplasm composed of AXL−ve neoplastic cells, optionally wherein the AXL−ve neoplastic cells are associated with AXL+ve non-neoplastic cells.

The target neoplasm or neoplastic cells may be all or part of a solid tumour.

"Solid tumor" herein will be understood to include solid haematological cancers such as lymphomas (Hodgkin's lymphoma or non-Hodgkin's lymphoma) which are discussed in more detail herein.

Solid tumors may be neoplasms, including non-haematological cancers, comprising or composed of AXL+ve neoplastic cells. Solid tumors may be neoplasms, including non-haematological cancers, infiltrated with AXL+ve cells, such as AXL+ve immune suppressive dendritic cells, NK cells, or macrophages; such solid tumours may lack expression of AXL (that is, comprise or be composed of AXL-ve neoplastic cells).

The ADC may be anti-AXL-ADC, such as ADCxAXL described herein.

The secondary agent may be a PD1 antagonist, a PD-L1 antagonist, a GITR agonist, an OX40 agonist, a CTLA-4 antagonist, Fludarabine or Cytarabine, a hypomethylating agent, a PARP inhibitor (PARPi), an agent that upregulates HER2 expression, an AXL inhibitor (AXLi), a BRAF inhibitor (BRAFi), or a MEK inhibitor (MEKi).

The individual may be human. The individual may have cancer, or may have been determined to have cancer. The individual may have, or have been determined to have, a AXL+ cancer or AXL+ tumour-associated non-tumour cells. The individual may have, or have been determined to have, a AXL+ cancer or AXL+ tumour-associated non-tumour cells.

The individual may have, or have been determined to have, a PD-L1+ cancer.

The treatment may comprise administering a further chemotherapeutic agent to the individual.

BRIEF DESCRIPTION OF THE FIGURES

Embodiments and experiments illustrating the principles of the disclosure will now be discussed with reference to the accompanying figures in which:

FIG. 1A shows the sequences of 1H12 VH, 1H12 VL, 1H12 Heavy Chain, 1H12 Light Chain, 1H12 VH CDR1, 1H12 VH CDR2, 1H12 VH CDR3, 1H12 VL CDR1, and 1H12 VL CDR2. FIG. 1B shows the sequences of 1H12 VL CDR3, murine 5F11 VH, murine 5F11 VL, 5F11 VH CDR1, 5F11 VH CDR2, 5F11 VH CDR3, 5F11 VL CDR1, 5F11 VL CDR2, 5F11 VL CDR3, 5F11 RHA, 5F11 RHB, and 5F11 RHC. FIG. 1C shows the sequences of 5F11 RKA and Human Axl.

DETAILED DESCRIPTION

Antibody Drug Conjugates (ADCs)

Figure 2:
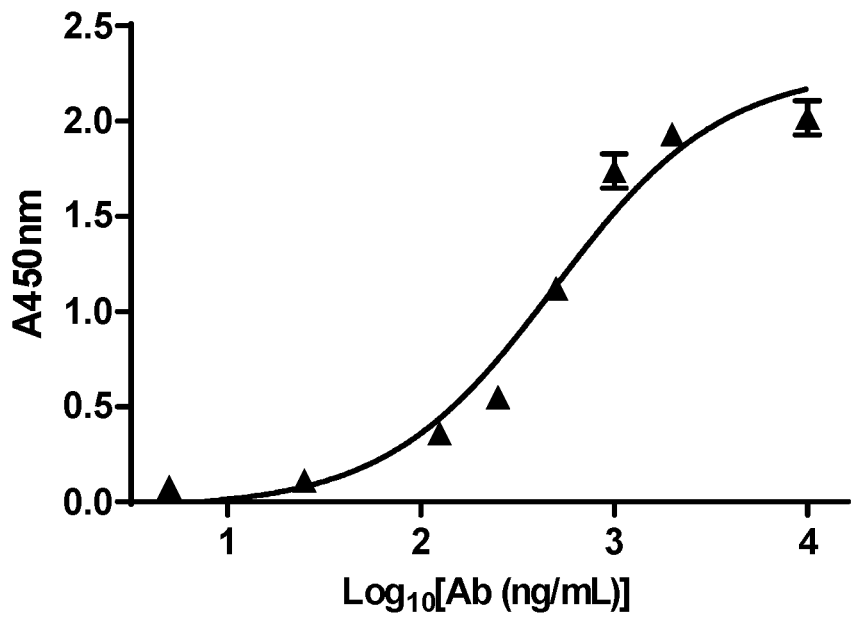
FIG. 2. Graph showing binding of a conjugate according to the invention to AXL.

The present disclosure relates to the improved efficacy of combinations of an ADC and a secondary agent.

The ADC of present disclosure provides a PBD dimer with a linker connected through the N10 position on one of the PBD moieties conjugated to an antibody as defined below.

The present disclosure is suitable for use in providing a PBD compound to a preferred site in a subject. The conjugate allows the release of an active PBD compound that does not retain any part of the linker. There is no stub present that could affect the reactivity of the PBD compound. Thus the conjugate of formula (I) would release the compound RelA:

ReIA

[Chemical structure]

The specified link between the PBD dimer and the antibody in the present invention is preferably stable extracellularly. Before transport or delivery into a cell, the antibody-drug conjugate (ADC) is preferably stable and remains intact, i.e. the antibody remains linked to the drug moiety. The linkers are stable outside the target cell and may be cleaved at some efficacious rate inside the cell. An effective linker will: (i) maintain the specific binding properties of the antibody; (ii) allow intracellular delivery of the conjugate or drug moiety; (iii) remain stable and intact, i.e. not cleaved, until the conjugate has been delivered or transported to its targeted site; and (iv) maintain a cytotoxic, cell-killing effect or a cytostatic effect of the PBD drug moiety. Stability of the ADC may be measured by standard analytical techniques such as mass spectroscopy, HPLC, and the separation/analysis technique LC/MS.

Delivery of the compounds of formulae RelA is achieved at the desired activation site of the conjugate of formula (I) by the action of an enzyme, such as cathepsin, on the linking group, and in particular on the valine-alanine dipeptide moiety.

The disclosure also particularly relates treatment with an anti-AXL ADC disclosed in GB1702029.8, GB1719906.8, PCT/EP2018/053163, and as herein described.

anti-AXL ADCs

As used herein, the term "AXL-ADC" refers to an ADC in which the antibody component is an anti-AXL antibody. The term "PBD-ADC" refers to an ADC in which the drug component is a pyrrolobenzodiazepine (PBD) warhead. The term "anti-AXL-ADC" refers to an ADC in which the antibody component is an anti-AXL antibody, and the drug component is a PBD warhead.

The ADC may comprise a conjugate of formula (I):

$$\text{Ab-(DL)}_p \tag{I}$$

wherein:
Ab is an antibody that binds to AXL;
DL is

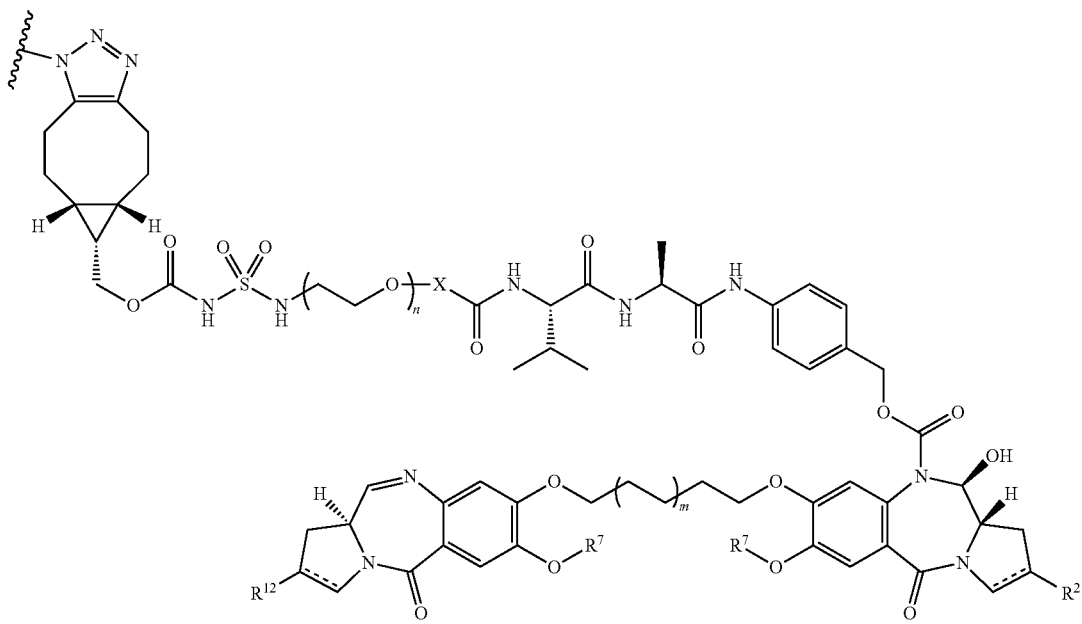

wherein:

X is selected from the group comprising: a single bond, —CH$_2$— and —C$_2$H$_4$—;

n is from 1 to 8;

m is 0 or 1;

R$^7$ is either methyl or phenyl;

when there is a double bond between C2 and C3, R$^2$ is selected the group consisting of:

(ia) C$_{5-10}$ aryl group, optionally substituted by one or more substituents selected from the group comprising: halo, nitro, cyano, ether, carboxy, ester, C$_{1-7}$ alkyl, C$_{3-7}$ heterocyclyl and bis-oxy-C$_{1-3}$ alkylene;

(ib) C$_{1-5}$ saturated aliphatic alkyl;

(ic) C$_{3-6}$ saturated cycloalkyl;

(id)

$$\begin{array}{c} R^{22} \\ | \\ \sim\!\!\!\sim\!\!\!\sim\!\!\!-\!\!\!\!\!\!\diagdown\!\!\!\!\!\!R^{23}, \\ | \\ R^{21} \end{array}$$

wherein each of R$^{21}$, R$^{22}$ and R$^{23}$ are independently selected from H, C$_{1-3}$ saturated alkyl, C$_{2-3}$ alkenyl, C$_{2-3}$ alkynyl and cyclopropyl, where the total number of carbon atoms in the R$^{12}$ group is no more than 5;

(ie)

$$\begin{array}{c} R^{25b} \\ | \\ \sim\!\!\!\sim\!\!\!\sim\!\!\!=\!\!\!\!\!\diagdown\!\!\!\!\!R^{25a}, \end{array}$$

wherein one of R$^{25a}$ and R$^{25b}$ is H and the other is selected from: phenyl, which phenyl is optionally substituted by a group selected from halo, methyl, methoxy; pyridyl; and thiophenyl; and (if)

$$\sim\!\!\!\sim\!\!\!\sim\!\!\!-\!\!\!\equiv\!\!\!-R^{24},$$

where R$^{24}$ is selected from: H; C$_{1-3}$ saturated alkyl; C$_{2-3}$ alkenyl; C$_{2-3}$ alkynyl; cyclopropyl; phenyl, which phenyl is optionally substituted by a group selected from halo, methyl, methoxy; pyridyl; and thiophenyl;

when there is a single bond between C2 and C3, R$^2$ is $$\begin{array}{c} \sim\!\!\!\sim\!\!\!\sim\!\!\!-\!\!\!\!\!\diagdown\!\!\!\!R^{26a}, \\ | \\ R^{26b} \end{array}$$

where R$^{26a}$ and R$^{26b}$ are independently selected from H, F, C$_{1-4}$ saturated alkyl, C$_{2-3}$ alkenyl, which alkyl and alkenyl groups are optionally substituted by a group selected from C$_{1-4}$ alkyl amido and C$_{1-4}$ alkyl ester; or, when one of R$^{26a}$ and R$^{26b}$ is H, the other is selected from nitrile and a C$_{1-4}$ alkyl ester;

when there is a double bond between C2' and C3', R$^{12}$ is selected the group consisting of:

(ia) C$_{5-10}$ aryl group, optionally substituted by one or more substituents selected from the group comprising: halo, nitro, cyano, ether, carboxy, ester, C$_{1-7}$ alkyl, C$_{3-7}$ heterocyclyl and bis-oxy-C$_{1-3}$ alkylene;

(ib) C$_{1-5}$ saturated aliphatic alkyl;

(ic) C$_{3-6}$ saturated cycloalkyl;

(id)

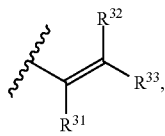

wherein each of $R^{31}$, $R^{32}$ and $R^{33}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

(ie)

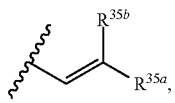

wherein one of $R^{35a}$ and $R^{35b}$ is H and the other is selected from: phenyl, which phenyl is optionally substituted by a group selected from halo, methyl, methoxy; pyridyl; and thiophenyl; and (if)

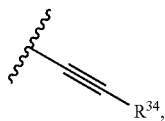

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond between C2' and C3', $R^{12}$ is

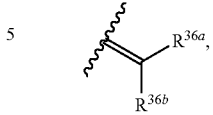

where $R^{36a}$ and $R^{36b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{36a}$ and $R^{36b}$ is H, the other is selected from nitrile and a $C_{1-4}$ alkyl ester;

and p is from 1 to 8.

It has previously been shown that such ADCs are useful in the treatment of AXL expressing cancers (see, for example, GB1702029.8, GB1719906.8, and PCT/EP2018/053163, which are incorporated by reference herein in their entirety).

The term anti-AXL-ADC may include any embodiment described in GB1702029.8. In particular, in preferred embodiments the ADC may have the chemical structure:

$$Ab\text{-}(DL)_p \qquad (I)$$

wherein:

Ab is an antibody that binds to AXL;

DL is:

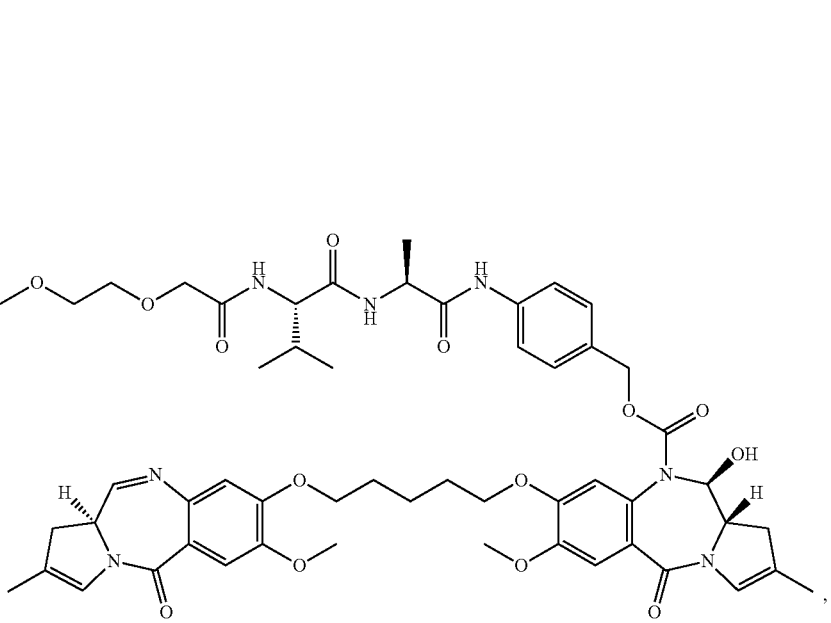

wherein the Ab is an anti-AXL antibody.

DL may be conjugated to the antibody through the sidechain of an antibody asparagine residue, for example Asn297 according to the numbering system of Kabat. The structure of the linkage to the antibody may be N-[sugar]-DL, wherein N is the asparagine residue, and [sugar] represents a sugar residue, such as a GlcNAc residue. p may be 1 to 4, preferably 2.

In some embodiments Ab is an antibody that binds to AXL, the antibody comprising:
(a) a heavy chain having the sequence according to SEQ ID NO. 3, wherein DL is conjugated to the antibody through the asparagine at position 302 of SEQ ID NO.3; and
(b) a light chain having the sequence according to SEQ ID NO. 4.

DL Embodiments

X
In some embodiments, X is a single bond.
In other embodiments, X is —$CH_2$—.
In further embodiments, X is —$C_2H_4$—.
In some embodiments, n is 1 to 4.
In some of these embodiments, n is 1.
In other of these embodiments, n is 2.
In further of these embodiments, n is 4.
$R^7$
In one embodiment, $R^7$ is methyl.
In another embodiment, $R^7$ is phenyl.
$R^2$
When there is a double bond present between C2 and C3, $R^2$ is selected from: (a) $C_{5-10}$ aryl group, optionally substituted by one or more substituents selected from the group comprising: halo, nitro, cyano, ether, $C_{1-7}$ alkyl, $C_{3-7}$ heterocyclyl and bis-oxy-$C_{1-3}$ alkylene;
(b) $C_{1-5}$ saturated aliphatic alkyl;
(c) $C_{3-6}$ saturated cycloalkyl;
(d)

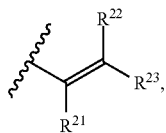

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5;
(e)

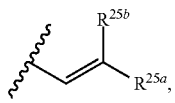

wherein one of $R^{25a}$ and $R^{25b}$ is H and the other is selected from: phenyl, which phenyl is optionally substituted by a group selected from halo methyl, methoxy; pyridyl; and thiophenyl; and
(f)

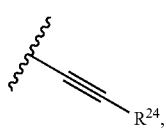

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo methyl, methoxy; pyridyl; and thiophenyl.

When $R^2$ is a $C_{5-10}$ aryl group, it may be a $C_{5-7}$ aryl group. A $C_{5-7}$ aryl group may be a phenyl group or a $C_{5-7}$ heteroaryl group, for example furanyl, thiophenyl and pyridyl. In some embodiments, $R^2$ is preferably phenyl. In other embodiments, $R^{12}$ is preferably thiophenyl, for example, thiophen-2-yl and thiophen-3-yl.

When $R^2$ is a $C_{5-10}$ aryl group, it may be a $C_{8-10}$ aryl, for example a quinolinyl or isoquinolinyl group. The quinolinyl or isoquinolinyl group may be bound to the PBD core through any available ring position. For example, the quinolinyl may be quinolin-2-yl, quinolin-3-yl, quinolin-4yl, quinolin-5-yl, quinolin-6-yl, quinolin-7-yl and quinolin-8-yl. Of these quinolin-3-yl and quinolin-6-yl may be preferred. The isoquinolinyl may be isoquinolin-1-yl, isoquinolin-3-yl, isoquinolin-4yl, isoquinolin-5-yl, isoquinolin-6-yl, isoquinolin-7-yl and isoquinolin-8-yl. Of these isoquinolin-3-yl and isoquinolin-6-yl may be preferred.

When $R^2$ is a $C_{5-10}$ aryl group, it may bear any number of substituent groups. It preferably bears from 1 to 3 substituent groups, with 1 and 2 being more preferred, and singly substituted groups being most preferred. The substituents may be any position.

Where $R^2$ is $C_{5-7}$ aryl group, a single substituent is preferably on a ring atom that is not adjacent the bond to the remainder of the compound, i.e. it is preferably β or γ to the bond to the remainder of the compound. Therefore, where the $C_{5-7}$ aryl group is phenyl, the substituent is preferably in the meta- or para-positions, and more preferably is in the para-position.

Where $R^2$ is a $C_{8-10}$ aryl group, for example quinolinyl or isoquinolinyl, it may bear any number of substituents at any position of the quinoline or isoquinoline rings. In some embodiments, it bears one, two or three substituents, and these may be on either the proximal and distal rings or both (if more than one substituent).

$R^2$ Substituents, when $R^2$ is a $C_{5-10}$ Aryl Group

If a substituent on $R^2$ when $R^2$ is a $C_{5-10}$ aryl group is halo, it is preferably F or Cl, more preferably Cl.

If a substituent on $R^2$ when $R^2$ is a $C_{5-10}$ aryl group is ether, it may in some embodiments be an alkoxy group, for example, a $C_{1-7}$ alkoxy group (e.g. methoxy, ethoxy) or it may in some embodiments be a $C_{5-7}$ aryloxy group (e.g phenoxy, pyridyloxy, furanyloxy). The alkoxy group may itself be further substituted, for example by an amino group (e.g. dimethylamino).

If a substituent on $R^2$ when $R^2$ is a $C_{5-10}$ aryl group is $C_{1-7}$ alkyl, it may preferably be a $C_{1-4}$ alkyl group (e.g. methyl, ethyl, propryl, butyl).

If a substituent on $R^2$ when $R^2$ is a $C_{5-10}$ aryl group is $C_{3-7}$ heterocyclyl, it may in some embodiments be $C_6$ nitrogen containing heterocyclyl group, e.g. morpholino, thiomorpholino, piperidinyl, piperazinyl. These groups may be bound to the rest of the PBD moiety via the nitrogen atom. These groups may be further substituted, for example, by $C_{1-4}$ alkyl groups. If the $C_6$ nitrogen containing heterocyclyl group is piperazinyl, the said further substituent may be on the second nitrogen ring atom.

If a substituent on $R^2$ when $R^2$ is a $C_{5-10}$ aryl group is bis-oxy-$C_{1-3}$ alkylene, this is preferably bis-oxy-methylene or bis-oxy-ethylene.

If a substituent on $R^2$ when $R^2$ is a $C_{5-10}$ aryl group is ester, this is preferably methyl ester or ethyl ester.

Particularly preferred substituents when $R^2$ is a $C_{5-10}$ aryl group include methoxy, ethoxy, fluoro, chloro, cyano, bis-oxy-methylene, methyl-piperazinyl, morpholino and methyl-thiophenyl. Other particularly preferred substituent for $R^2$ are dimethylaminopropyloxy and carboxy.

Particularly preferred substituted $R^2$ groups when $R^2$ is a $C_{5-10}$ aryl group include, but are not limited to, 4-methoxyphenyl, 3-methoxyphenyl, 4-ethoxy-phenyl, 3-ethoxy-phenyl, 4-fluoro-phenyl, 4-chloro-phenyl, 3,4-bisoxymethylene-phenyl, 4-methylthiophenyl, 4-cyanophenyl, 4-phenoxyphenyl, quinolin-3-yl and quinolin-6-yl, isoquinolin-3-yl and isoquinolin-6-yl, 2-thienyl, 2-furanyl, methoxynaphthyl, and naphthyl. Another possible substituted $R^2$ group is 4-nitrophenyl. $R^2$ groups of particular interest include 4-(4-methylpiperazin-1-yl)phenyl and 3,4-bisoxymethylene-phenyl.

When $R^2$ is $C_1$-5 saturated aliphatic alkyl, it may be methyl, ethyl, propyl, butyl or pentyl. In some embodiments, it may be methyl, ethyl or propyl (n-pentyl or isopropyl). In some of these embodiments, it may be methyl. In other embodiments, it may be butyl or pentyl, which may be linear or branched.

When $R^2$ is $C_{3-6}$ saturated cycloalkyl, it may be cyclopropyl, cyclobutyl, cyclopentyl or cyclohexyl. In some embodiments, it may be cyclopropyl.

When $R^2$ is

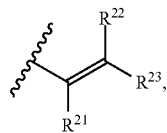

each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5. In some embodiments, the total number of carbon atoms in the $R^2$ group is no more than 4 or no more than 3.

In some embodiments, one of $R^{21}$, $R^{22}$ and $R^{23}$ is H, with the other two groups being selected from H, $C_{1-3}$ saturated alkyl, $C_{2-3}$ alkenyl, $C_{2-3}$ alkynyl and cyclopropyl.

In other embodiments, two of $R^{21}$, $R^{22}$ and $R^{23}$ are H, with the other group being selected from H, $C_{1-3}$ saturated alkyl, $C_{2-3}$ alkenyl, $C_{2-3}$ alkynyl and cyclopropyl.

In some embodiments, the groups that are not H are selected from methyl and ethyl. In some of these embodiments, the groups that are not H are methyl.

In some embodiments, $R^{21}$ is H.

In some embodiments, $R^{22}$ is H.

In some embodiments, $R^{23}$ is H.

In some embodiments, $R^{21}$ and $R^{22}$ are H.

In some embodiments, $R^{21}$ and $R^{23}$ are H.

In some embodiments, $R^{22}$ and $R^{23}$ are H.

A $R^2$ group of particular interest is:

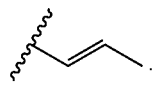 [SMILES: */C=C/C]

When $R^2$ is

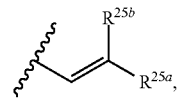

one of $R^{25a}$ and $R^{25b}$ is H and the other is selected from: phenyl, which phenyl is optionally substituted by a group selected from halo, methyl, methoxy; pyridyl; and thiophenyl. In some embodiments, the group which is not H is optionally substituted phenyl. If the phenyl optional substituent is halo, it is preferably fluoro. In some embodiment, the phenyl group is unsubstituted.

When $R^2$ is

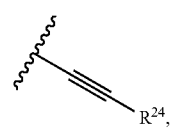

$R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo methyl, methoxy; pyridyl; and thiophenyl. If the phenyl optional substituent is halo, it is preferably fluoro. In some embodiment, the phenyl group is unsubstituted. In some embodiments, $R^{24}$ is selected from H, methyl, ethyl, ethenyl and ethynyl. In some of these embodiments, $R^{24}$ is selected from H and methyl.

When there is a single bond present between C2 and C3, $R^2$ is

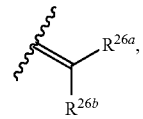

where $R^{26a}$ and $R^{26b}$ are independently selected from H, F, C1-4 saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester.

In some embodiments, it is preferred that $R^{26a}$ and $R^{26b}$ are both H.

In other embodiments, it is preferred that $R^{26a}$ and $R^{26b}$ are both methyl.

In further embodiments, it is preferred that one of $R^{26a}$ and $R^{26b}$ is H, and the other is selected from $C_{1-4}$ saturated alkyl, $C_{2-3}$ alkenyl, which alkyl and alkenyl groups are optionally substituted. In these further embodiment, it may be further preferred that the group which is not H is selected from methyl and ethyl.

$R^{12}$

The above preferences for $R^2$ apply equally to $R^{12}$

In one preferred embodiment of the invention, DL is

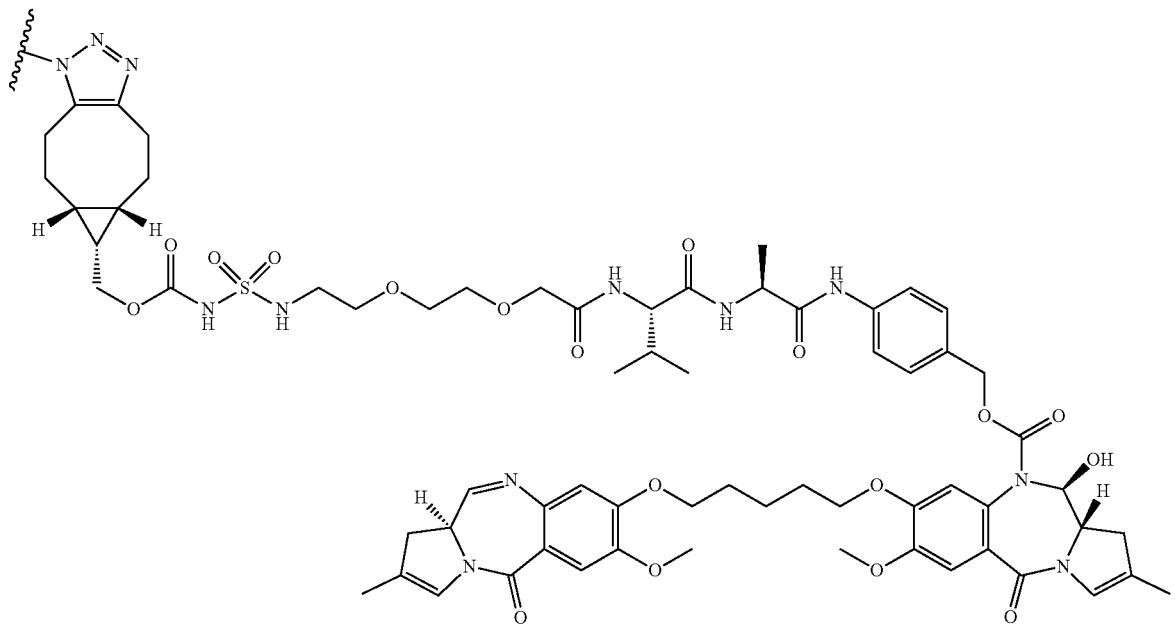 [SMILES: *n1nnc2c1CC[C@@H]1[C@H](CC2)[C@@H]1COC(=O)NS(=O)(=O)NCCOCCOCC(=O)N[C@H](C(=O)N[C@@H](C)C(=O)Nc1ccc(COC(=O)N2c3cc(OCCCCCOc4cc5c(cc4OC)C(=O)N4C=C(C)C[C@H]4C=N5)c(OC)cc3C(=O)N3C=C(C)C[C@H]3[C@@H]2O)cc1)C(C)C]

The above DL may be preferably comprised in an ADC having the formula Ab-(DL)$_p$, wherein Ab is an antibody that binds to AXL. DL may be conjugated to the antibody through the sidechain of an antibody asparagine residue, for example Asn297 according to the numbering system of Kabat. The structure of the linkage to the antibody may be N-[sugar]-DL, wherein N is the asparagine residue, and [sugar] represents a sugar residue, such as a GlcNAc residue. p may be 1 to 4, for example 2.

For example, in one embodiment the invention provides a conjugate having the formula:

Ab-([N]-[GlcNAc]-DL)$_2$     (II)

wherein:

Ab is an antibody comprising:
(a) two heavy chains, each having the sequence according to SEQ ID NO. 3; and
(b) two light chains, each having the sequence according to SEQ ID NO. 4;

[N] is the sidechain of the asparagine at position 302 of each SEQ ID NO.3;

[GlcNAc] is a N-acytel glucsamine residue; and

DL is the drug-linker described immediately above.

The Antibody Component of the Anti-AXL ADC

In one aspect the antibody is an antibody that binds to AXL.

1H12

In some embodiments the antibody comprises a VH domain having a VH CDR3 with the amino acid sequence of SEQ ID NO.7. In some embodiments the VH domain further comprises a VH CDR2 with the amino acid sequence of SEQ ID NO.6, and/or a VH CDR1 with the amino acid sequence of SEQ ID NO.5. In some embodiments the antibody comprises a VH domain having a VH CDR1 with the amino acid sequence of SEQ ID NO.5, a VH CDR2 with the amino acid sequence of SEQ ID NO.6, and a VH CDR3 with the amino acid sequence of SEQ ID NO.7. In preferred embodiments the antibody comprises a VH domain having the sequence according to SEQ ID NO. 1.

The antibody may further comprise a VL domain. In some embodiments the antibody comprises a VL domain having a VL CDR3 with the amino acid sequence of SEQ ID NO.10. In some embodiments the VL domain further comprises a VL CDR2 with the amino acid sequence of SEQ ID NO.9, and/or a VL CDR1 with the amino acid sequence of SEQ ID NO.8. In some embodiments the antibody comprises a VL domain having a VL CDR1 with the amino acid sequence of SEQ ID NO.8, a VL CDR2 with the amino acid sequence of SEQ ID NO.9, and a VL CDR3 with the amino acid sequence of SEQ ID NO.10. In preferred embodiments the antibody comprises a VL domain having the sequence according to SEQ ID NO. 2.

In preferred embodiments the antibody comprises a VH domain and a VL domain. Preferably the VH comprises the sequence of SEQ ID NO.1 and the VL domain comprises the sequence of SEQ ID NO.2.

The VH and VL domain(s) may pair so as to form an antibody antigen binding site that binds AXL.

In some embodiments the antibody is an intact antibody comprising a VH domain paired with a VL domain, the VH and VL domains having sequences of SEQ ID NO.1 paired with SEQ ID NO.2.

In some embodiments the antibody comprises a heavy chain having the sequence of SEQ ID NO. 3 paired with a light chain having the sequence of SEQ ID NO.4. In some embodiments the antibody is an intact antibody comprising two heavy chains having the sequence of SEQ ID NO.3, each paired with a light chain having the sequence of SEQ ID NO.4.

In one aspect the antibody is an antibody as described herein which has been modified (or further modified) as described below. In some embodiments the antibody is a humanised, deimmunised or resurfaced version of an antibody disclosed herein.

In some embodiments the antibody is a fully human monoclonal IgG1 antibody, preferably IgG1,κ.

In an aspect the antibody is an antibody as described herein which has been modified (or further modified) as described below. In some embodiments the antibody is a humanised, deimmunised or resurfaced version of an antibody disclosed herein.

The most preferred anti-AXL-ADC for use with the aspects of the present disclosure is ADCxAXL, as described herein below.

5F11

In some embodiments the antibody comprises a VH domain having a VH CDR3 with the amino acid sequence of SEQ ID NO.15. In some embodiments the VH domain further comprises a VH CDR2 with the amino acid sequence of SEQ ID NO.14, and/or a VH CDR1 with the amino acid sequence of SEQ ID NO.13. In some embodiments the the antibody comprises a VH domain having a VH CDR1 with the amino acid sequence of SEQ ID NO.13, a VH CDR2 with the amino acid sequence of SEQ ID NO.14, and a VH CDR3 with the amino acid sequence of SEQ ID NO.15.

In some embodiments the antibody comprises a VH domain having the sequence according to SEQ ID NO. 11. In some embodiments the antibody comprises a VH domain having the sequence according to SEQ ID NO. 19. In some embodiments the antibody comprises a VH domain having the sequence according to SEQ ID NO. 20. In some embodiments the antibody comprises a VH domain having the sequence according to SEQ ID NO. 21.

The antibody may further comprise a VL domain. In some embodiments the antibody comprises a VL domain having a VL CDR3 with the amino acid sequence of SEQ ID NO.18. In some embodiments the VL domain further comprises a VL CDR2 with the amino acid sequence of SEQ ID NO.17, and/or a VL CDR1 with the amino acid sequence of SEQ ID NO.16. In some embodiments the the antibody comprises a VL domain having a VL CDR1 with the amino acid sequence of SEQ ID NO.16, a VL CDR2 with the amino acid sequence of SEQ ID NO.17, and a VL CDR3 with the amino acid sequence of SEQ ID NO.18.

In some embodiments the antibody comprises a VL domain having the sequence according to SEQ ID NO. 22.

In preferred embodiments the antibody comprises a VH domain and a VL domain. In some embodiments the VH comprises a VH CDR1 with the amino acid sequence of SEQ ID NO.13, a VH CDR2 with the amino acid sequence of SEQ ID NO.14, and a VH CDR3 with the amino acid sequence of SEQ ID NO.15; and the VL domain comprises a VL CDR1 with the amino acid sequence of SEQ ID NO.16, a VL CDR2 with the amino acid sequence of SEQ ID NO.17, and a VL CDR3 with the amino acid sequence of SEQ ID NO.18.

In some embodiments the antibody comprises a VH domain having the sequence of SEQ ID NO.19 and the VL domain having the sequence of SEQ ID NO.22. In some embodiments the antibody comprises a VH domain having the sequence of SEQ ID NO.20 and the VL domain having the sequence of SEQ ID NO.22. In some embodiments the antibody comprises a VH domain having the sequence of SEQ ID NO.21 and the VL domain having the sequence of SEQ ID NO.22.

In one aspect the antibody is an antibody as described herein which has been modified (or further modified) as described below. In some embodiments the antibody is a humanised, deimmunised or resurfaced version of an antibody disclosed herein.

In some embodiments the antibody is a fully human monoclonal IgG1 antibody, preferably IgG1,κ.

In an aspect the antibody is an antibody as described herein which has been modified (or further modified) as described below. In some embodiments the antibody is a humanised, deimmunised or resurfaced version of an antibody disclosed herein.

Modification of Antibodies

The antibodies disclosed herein may be modified. For example, to make them less immunogenic to a human subject. This may be achieved using any of a number of techniques familiar to the person skilled in the art. Some of these techniques are described in more detail below.

Humanisation

Techniques to reduce the in vivo immunogenicity of a non-human antibody or antibody fragment include those termed "humanisation".

A "humanized antibody" refers to a polypeptide comprising at least a portion of a modified variable region of a human antibody wherein a portion of the variable region, preferably a portion substantially less than the intact human variable domain, has been substituted by the corresponding sequence from a non-human species and wherein the modified variable region is linked to at least another part of another protein, preferably the constant region of a human antibody. The expression "humanized antibodies" includes human antibodies in which one or more complementarity determining region ("CDR") amino acid residues and/or one or more framework region ("FW" or "FR") amino acid residues are substituted by amino acid residues from analogous sites in rodent or other non-human antibodies. The expression "humanized antibody" also includes an immunoglobulin amino acid sequence variant or fragment thereof that comprises an FR having substantially the amino acid sequence of a human immunoglobulin and a CDR having substantially the amino acid sequence of a non-human immunoglobulin.

"Humanized" forms of non-human (e.g., murine) antibodies are chimeric antibodies that contain minimal sequence derived from non-human immunoglobulin. Or, looked at another way, a humanized antibody is a human antibody that also contains selected sequences from non-human (e.g. murine) antibodies in place of the human sequences. A humanized antibody can include conservative amino acid substitutions or non-natural residues from the same or different species that do not significantly alter its binding and/or biologic activity. Such antibodies are chimeric antibodies that contain minimal sequence derived from non-human immunoglobulins.

There are a range of humanisation techniques, including 'CDR grafting', 'guided selection', 'deimmunization', 'resurfacing' (also known as 'veneering'), 'composite antibodies', 'Human String Content Optimisation' and framework shuffling.

CDR Grafting

In this technique, the humanized antibodies are human immunoglobulins (recipient antibody) in which residues from a complementary-determining region (CDR) of the recipient antibody are replaced by residues from a CDR of a non-human species (donor antibody) such as mouse, rat, camel, bovine, goat, or rabbit having the desired properties (in effect, the non-human CDRs are 'grafted' onto the human framework). In some instances, framework region (FR) residues of the human immunoglobulin are replaced by corresponding non-human residues (this may happen when, for example, a particular FR residue has significant effect on antigen binding).

Furthermore, humanized antibodies can comprise residues that are found neither in the recipient antibody nor in the imported CDR or framework sequences. These modifications are made to further refine and maximize antibody performance. Thus, in general, a humanized antibody will comprise all of at least one, and in one aspect two, variable domains, in which all or all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), or that of a human immunoglobulin.

Guided Selection

The method consists of combining the $V_H$ or $V_L$ domain of a given non-human antibody specific for a particular epitope with a human $V_H$ or $V_L$ library and specific human V domains are selected against the antigen of interest. This selected human VH is then combined with a VL library to generate a completely human VH×VL combination. The method is described in Nature Biotechnology (N.Y.) 12, (1994) 899-903.

Composite Antibodies

In this method, two or more segments of amino acid sequence from a human antibody are combined within the final antibody molecule. They are constructed by combining multiple human VH and VL sequence segments in combinations which limit or avoid human T cell epitopes in the final composite antibody V regions. Where required, T cell epitopes are limited or avoided by, exchanging V region segments contributing to or encoding a T cell epitope with alternative segments which avoid T cell epitopes. This method is described in US 2008/0206239 A1.

Deimmunization

This method involves the removal of human (or other second species) T-cell epitopes from the V regions of the therapeutic antibody (or other molecule). The therapeutic antibodies V-region sequence is analysed for the presence of MHC class II-binding motifs by, for example, comparison with databases of MHC-binding motifs (such as the "motifs" database hosted wehi.edu.au). Alternatively, MHC class II-binding motifs may be identified using computational threading methods such as those devised by Altuvia et al. (J. Mol. Biol. 249 244-250 (1995)); in these methods, consecutive overlapping peptides from the V-region sequences are testing for their binding energies to MHC class II proteins. This data can then be combined with information on other sequence features which relate to successfully presented peptides, such as amphipathicity, Rothbard motifs, and cleavage sites for cathepsin B and other processing enzymes.

Once potential second species (e.g. human) T-cell epitopes have been identified, they are eliminated by the alteration of one or more amino acids. The modified amino acids are usually within the T-cell epitope itself, but may also be adjacent to the epitope in terms of the primary or secondary structure of the protein (and therefore, may not be adjacent in the primary structure). Most typically, the alteration is by way of substitution but, in some circumstances amino acid addition or deletion will be more appropriate.

All alterations can be accomplished by recombinant DNA technology, so that the final molecule may be prepared by expression from a recombinant host using well established methods such as Site Directed Mutagenesis. However, the use of protein chemistry or any other means of molecular alteration is also possible.

Resurfacing

This method involves:
(a) determining the conformational structure of the variable region of the non-human (e.g. rodent) antibody (or fragment thereof) by constructing a three-dimensional model of the non-human antibody variable region;
(b) generating sequence alignments using relative accessibility distributions from x-ray crystallographic structures of a sufficient number of non-human and human antibody variable region heavy and light chains to give a set of heavy and light chain framework positions wherein the alignment positions are identical in 98% of the sufficient number of non-human antibody heavy and light chains;
(c) defining for the non-human antibody to be humanized, a set of heavy and light chain surface exposed amino acid residues using the set of framework positions generated in step (b);
(d) identifying from human antibody amino acid sequences a set of heavy and light chain surface exposed amino acid residues that is most closely identical to the set of surface exposed amino acid residues defined in step (c), wherein the heavy and light chain from the human antibody are or are not naturally paired;
(e) substituting, in the amino acid sequence of the non-human antibody to be humanized, the set of heavy and light chain surface exposed amino acid residues defined in step (c) with the set of heavy and light chain surface exposed amino acid residues identified in step (d);
(f) constructing a three-dimensional model of the variable region of the non-human antibody resulting from the substituting specified in step (e);
(g) identifying, by comparing the three-dimensional models constructed in steps (a) and (f), any amino acid residues from the sets identified in steps (c) or (d), that are within 5 Angstroms of any atom of any residue of the complementarity determining regions of the non-human antibody to be humanized; and
(h) changing any residues identified in step (g) from the human to the original non-human amino acid residue to thereby define a non-human antibody humanizing set of surface exposed amino acid residues; with the proviso that step (a) need not be conducted first, but must be conducted prior to step (g).

Superhumanization

The method compares the non-human sequence with the functional human germline gene repertoire. Those human genes encoding canonical structures identical or closely related to the non-human sequences are selected. Those selected human genes with highest homology within the CDRs are chosen as FR donors. Finally, the non-human CDRs are grafted onto these human FRs. This method is described in patent WO 2005/079479 A2.

Human String Content Optimization

This method compares the non-human (e.g. mouse) sequence with the repertoire of human germline genes and the differences are scored as Human String Content (HSC) that quantifies a sequence at the level of potential MHC/T-cell epitopes. The target sequence is then humanized by maximizing its HSC rather than using a global identity measure to generate multiple diverse humanized variants (described in Molecular Immunology, 44, (2007) 1986-1998).

Framework Shuffling

The CDRs of the non-human antibody are fused in-frame to cDNA pools encompassing all known heavy and light chain human germline gene frameworks. Humanised antibodies are then selected by e.g. panning of the phage displayed antibody library. This is described in *Methods* 36, 43-60 (2005).

Modification of Antibody with Azide crosslinks that do not distort the DNA double helix and which are not recognized by nucleotide excision repair factors, allowing for a longer effective period (Hartley 2011).

It has the chemical structure:

wherein:

DL is:

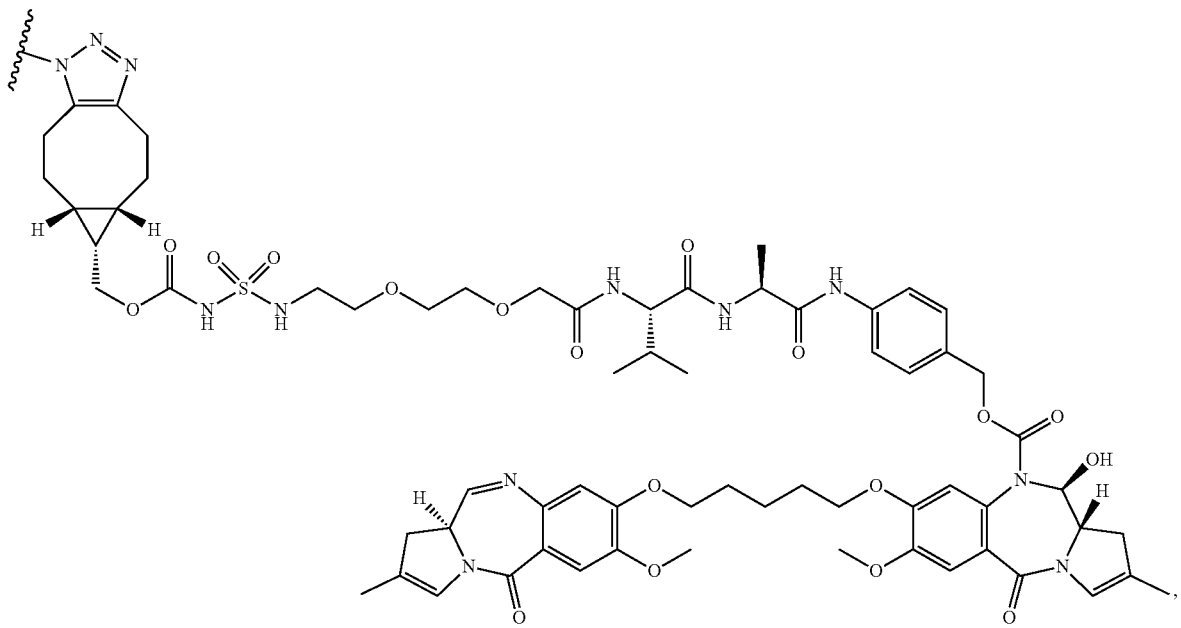 [SMILES: *n1nnc2c1CC[C@@H]1[C@H](CC2)[C@@H]1COC(=O)NS(=O)(=O)NCCOCCOCC(=O)N[C@H](C(=O)N[C@@H](C)C(=O)Nc1ccc(COC(=O)N2c3cc(OCCCCCOc4cc5c(cc4OC)C(=O)N4C=C(C)C[C@H]4C=N5)c(OC)cc3C(=O)N3C=C(C)C[C@H]3[C@@H]2O)cc1)C(C)C]

The antibody may prepared for conjugation with the drug linker through a three step process:
(1) Expression of antibody (Ab) bearing the core N-glycan in a suitable expression system (e.g. a CHO cell line). The core N-glycan is typically conjugated to Asn-297 of the heavy chain according to the numbering system of Kabat;
(2) trimming of all glycan isoforms (complex, hybrid, high-mannose) with an endoglycosidase to leave the core GlcNAc; and
(3) enzymatic transfer to the core GlcNAc of a N-acetylgalactose residue harboring an azide group for conjugation to the drug linker.

An overview of the above process is set out in van Geel, R., et al., Bioconjugate Chemistry, 2015, 26, 2233-2242; DOI: 10.1021/acs.bioconjchem.5b00224. Alternatively, a one-pot process may be used—see the examples.

ADCxAXL

ADCxAXL is an antibody drug conjugate composed of a humanized antibody against human AXL attached to a pyrrolobenzodiazepine (PBD) warhead via a cleavable linker. The mechanism of action of ADCxAXL depends on AXL binding. The AXL specific antibody targets the antibody drug conjugate (ADC) to cells expressing AXL. Upon binding, the ADC internalizes and is transported to the lysosome, where the protease sensitive linker is cleaved and free PBD dimer is released inside the target cell. The released PBD dimer inhibits transcription in a sequence-selective manner, due either to direct inhibition of RNA polymerase or inhibition of the interaction of associated transcription factors. The PBD dimer produces covalent Ab is an antibody that binds to AXL, the antibody comprising:
(a) a heavy chain having the sequence according to SEQ ID NO. 3;
(b) a light chain having the sequence according to SEQ ID NO. 4.

It is noted that "having the sequence" has the same meaning as "comprising the sequence"; in particular, in some embodiments the heavy chain of ADCxAXL is expressed with an additional terminal 'K' residue (so, ending . . . SPGK), with the terminal K being optionally removed post-translationally to improve the homogeneity of the final therapeutic ADC product.

DL may be conjugated to the antibody through the sidechain of the asparagine at position 302 of SEQ ID NO.3. The structure of the linkage to the antibody may be N-[GlcNAc]-DL, wherein N is the asparagine residue, and [GlcNac] represents a GlcNAc residue. p may be up to 2, and is typically greater than 1.9.

Definitions

AXL binding

The "first target protein" (FTP) as used herein may be AXL.

As used herein, "binds AXL" is used to mean the antibody binds AXL with a higher affinity than a non-specific partner such as Bovine Serum Albumin (BSA, Genbank accession no. CAA76847, version no. CAA76847.1 G1:3336842, record update date: Jan. 7, 2011 02:30 PM). In some embodiments the antibody binds AXL with an association constant ($K_a$) at least 2, 3, 4, 5, 10, 20, 50, 100, 200, 500, 1000, 2000, 5000, $10^4$, $10^5$ or $10^6$-fold higher than the antibody's association constant for BSA, when measured at physiological conditions. The antibodies of the invention can bind AXL with a high affinity. For example, in some embodiments the antibody can bind AXL with a $K_D$ equal to or less than about $10^{-6}$ M, such as $1 \times 10^{-6}$, $10^{-7}$, $10^{-8}$, $10^{-9}$, $10^{-10}$, $10^{-11}$, $10^{-12}$, $10^{-13}$ or $10^{-14}$.

As used herein, "binds AXL" is used to mean the antibody binds AXL with a higher affinity than a non-specific partner such as Bovine Serum Albumin (BSA, Genbank accession no. CAA76847, version no. CAA76847.1 GI:3336842, record update date: Jan. 7, 2011 02:30 PM). In some embodiments the antibody binds AXL with an association constant (Ka) at least 2, 3, 4, 5, 10, 20, 50, 100, 200, 500, 1000, 2000, 5000, 104, 105 or 106-fold higher than the antibody's association constant for BSA, when measured at physiological conditions. The antibodies of the invention can bind AXL with a high affinity. For example, in some embodiments the antibody can bind AXL with a $K_D$ equal to or less than about 10-6 M, such as 1×10-6, 10-7, 10-8, 10-9,10-10, 10-11, 10-12, 10-13 or 10-14.

AXL is member of the human TAM family of receptor tyrosine kinases. In some embodiments, the AXL polypeptide corresponds to Genbank accession no. AAH32229, version no. AAH32229.1 GI:21619004, record update date: Mar. 6, 2012 01:18 PM (SEQ ID NO.9). In one embodiment, the nucleic acid encoding AXL polypeptide corresponds to Genbank accession no. M76125, version no. M76125.1 GI:292869, record update date: Jun. 23, 2010 08:53 AM. In some embodiments, the AXL polypeptide has the sequence of SEQ ID NO.23.

Substituents

The phrase "optionally substituted" as used herein, pertains to a parent group which may be unsubstituted or which may be substituted.

Unless otherwise specified, the term "substituted" as used herein, pertains to a parent group which bears one or more substituents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Examples of substituents are described in more detail below.

$C_{1-12}$ alkyl: The term "$C_{1-12}$ alkyl" as used herein, pertains to a monovalent moiety obtained by removing a hydrogen atom from a carbon atom of a hydrocarbon compound having from 1 to 12 carbon atoms, which may be aliphatic or alicyclic, and which may be saturated or unsaturated (e.g. partially unsaturated, fully unsaturated). The term "$C_{1-4}$ alkyl" as used herein, pertains to a monovalent moiety obtained by removing a hydrogen atom from a carbon atom of a hydrocarbon compound having from 1 to 4 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{2-12}$ Alkenyl: The term "$C_{2-12}$ alkenyl" as used herein, pertains to an alkyl group having one or more carbon-carbon double bonds.

Examples of unsaturated alkenyl groups include, but are not limited to, ethenyl (vinyl, —CH=$CH_2$), 1-propenyl (—CH=CH—$CH_3$), 2-propenyl (allyl, —CH—CH=$CH_2$), isopropenyl (1-methylvinyl, —C($CH_3$)=$CH_2$), butenyl ($C_4$), pentenyl ($C_5$), and hexenyl ($C_6$).

$C_{2-12}$ alkynyl: The term "$C_{2-12}$ alkynyl" as used herein, pertains to an alkyl group having one or more carbon-carbon triple bonds.

Examples of unsaturated alkynyl groups include, but are not limited to, ethynyl (—C≡CH) and 2-propynyl (propargyl, —$CH_2$—C≡CH).

$C_{3-12}$ cycloalkyl: The term "$C_{3-12}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:

saturated monocyclic hydrocarbon compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$) and methylcyclohexane ($C_7$);

unsaturated monocyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$) and methylcyclohexene ($C_7$); and saturated polycyclic hydrocarbon compounds:
norcarane ($C_7$), norpinane ($C_7$), norbornane ($C_7$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of an aromatic compound, which moiety has from 3 to 20 ring atoms. The term "$C_{5-7}$ aryl", as used herein, pertains to a monovalent moiety obtained by removing a hydrogen atom from an aromatic ring atom of an aromatic compound, which moiety has from 5 to 7 ring atoms and the term "$C_{5-10}$ aryl", as used herein, pertains to a monovalent moiety obtained by removing a hydrogen atom from an aromatic ring atom of an aromatic compound, which moiety has from 5 to 10 ring atoms. Preferably, each ring has from 5 to 7 ring atoms.

In this context, the prefixes (e.g. $C_{3-20}$, $C_{5-7}$, $C_{5-6}$, $C_{5-10}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

The ring atoms may be all carbon atoms, as in "carboaryl groups".

Examples of carboaryl groups include, but are not limited to, those derived from benzene (i.e. phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{1-3}$), phenalene ($C_{1-3}$), acephenanthrene ($C_{15}$), and aceanthrene ($C_{16}$).

Alternatively, the ring atoms may include one or more heteroatoms, as in "heteroaryl groups". Examples of monocyclic heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$);

$N_1S_1$: thiazole ($C_5$), isothiazole ($C_5$);

$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);

$N_3$: triazole ($C_5$), triazine ($C_6$); and, $N_4$: tetrazole ($C_5$).

Examples of heteroaryl which comprise fused rings, include, but are not limited to:

$C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran (Si), benzothiazole ($N_1S_1$), benzothiadiazole ($N_2S$);

$C_{10}$ (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$ (with 2 fused rings) derived from benzodiazepine ($N_2$);

$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$ (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

The above groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

Alkoxy: —OR, wherein R is an alkyl group, for example, a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Carboxy (carboxylic acid): —C(=O)OH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Amino: —NR$^1$R$^2$, wherein R$^1$ and R$^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Nitro: —NO$_2$.

Azido: —N$_3$.

Cyano (nitrile, carbonitrile): —CN.

Drug Loading

The drug loading is the average number of PBD drugs per antibody, e.g. antibody.

The average number of drugs per antibody in preparations of ADC from conjugation reactions may be characterized by conventional means such as UV, reverse phase HPLC, HIC, mass spectroscopy, ELISA assay, and electrophoresis. The quantitative distribution of ADC in terms of p may also be determined. By ELISA, the averaged value of p in a particular preparation of ADC may be determined (Hamblett et al (2004) Clin. Cancer Res. 10:7063-7070; Sanderson et al (2005) Clin. Cancer Res. 11:843-852). However, the distribution of p (drug) values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues. In some instances, separation, purification, and characterization of homogeneous ADC where p is a certain value from ADC with other drug loadings may be achieved by means such as reverse phase HPLC or electrophoresis. Such techniques are also applicable to other types of conjugates.

For the present antibody-drug conjugates, p is limited by the number of attachment sites on the antibody, i.e. the number of azide groups. For example, the antibody may have only one or two azide groups to which the drug linker may be attached.

Typically, fewer than the theoretical maximum of drug moieties are conjugated to an antibody during a conjugation reaction. The loading (drug/antibody ratio) of an ADC may be controlled in several different manners, including: (i) limiting the molar excess of drug-linker intermediate (D-L) or linker reagent relative to antibody, and (ii) limiting the conjugation reaction time or temperature.

Where more than one nucleophilic or electrophilic group of the antibody reacts with a drug-linker intermediate, or linker reagent followed by drug moiety reagent, then the resulting product is a mixture of ADC compounds with a distribution of drug moieties attached to an antibody, e.g. 1, 2, 3, etc. Liquid chromatography methods such as polymeric reverse phase (PLRP) and hydrophobic interaction (HIC) may separate compounds in the mixture by drug loading value. Preparations of ADC with a single drug loading value (p) may be isolated, however, these single loading value ADCs may still be heterogeneous mixtures because the drug moieties may be attached, via the linker, at different sites on the antibody.

Thus the antibody-drug conjugate compositions of the invention include mixtures of antibody-drug conjugate compounds where the antibody has one or more PBD drug moieties and where the drug moieties may be attached to the antibody at various amino acid residues.

In one embodiment, the average number of dimer pyrrolobenzodiazepine groups per antibody is in the range 1 to 8. In some embodiments the range is selected from 1 to 4, 1 to 4, 2 to 4, and 1 to 3.

In some embodiments, there are one or two dimer pyrrolobenzodiazepine groups per antibody.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO—), a salt or solvate thereof, as well as conventional protected forms. Similarly, a reference to an amino group includes the protonated form (—N+HR$^1$R$^2$), a salt or solvate of the amino group, for example, a hydrochloride salt, as well as conventional protected forms of an amino group. Similarly, a reference to a hydroxyl group also includes the anionic form (—O—), a salt or solvate thereof, as well as conventional protected forms.

Salts

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —COO—), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$ Examples of suitable organic cations include, but are not limited to, ammonium ion (i.e. NH$_4$) and substituted ammonium ions (e.g. NH$_3$R+, NH$_2$R$_2$+, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g. —NH$_2$ may be —NH$_3$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic acid and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

The invention includes compounds where a solvent adds across the imine bond of the PBD moiety, which is illustrated below where the solvent is water or an alcohol ($R^4OH$, where $R^4$ is $C_{1-4}$ alkyl):

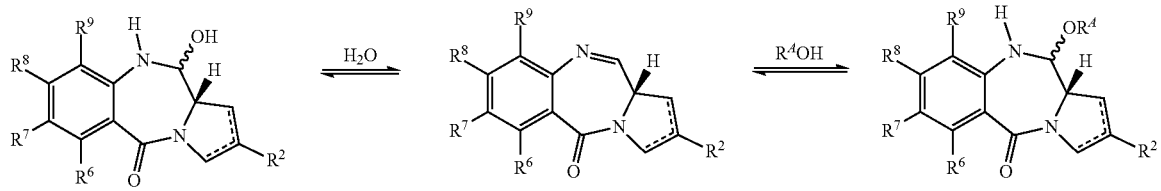

These forms can be called the carbinolamine and carbinolamine ether forms of the PBD (as described in the section relating to $R^{10}$ above). The balance of these equilibria depend on the conditions in which the compounds are found, as well as the nature of the moiety itself.

These particular compounds may be isolated in solid form, for example, by lyophilisation.

Isomers

Certain compounds of the invention may exist in one or more particular geometric, optical, enantiomeric, diastereomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities.

Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light.

In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g. $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

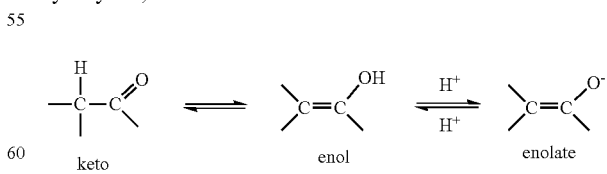

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Examples of isotopes that can be incorporated into compounds of the invention include isotopes of hydrogen, carbon, nitrogen, oxygen, phosphorous, fluorine, and chlorine, such as, but not limited to $^2H$ (deuterium, D), $^3H$ (tritium), $^{11}C$, $^{13}C$, $^{14}C$ $^{15}N$, $^{18}F$, $^{31}P$, $^{32}$, $^{35}S$, $^{36}Cl$, and $^{125}I$. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent. The concentration of such a heavier isotope, specifically deuterium, may be defined by an isotopic enrichment factor. In the compounds of this invention any atom not specifically designated as a particular isotope is meant to represent any stable isotope of that atom.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Secondary Agents

The recent development of agents that enhance anti-tumor immunity is rapidly changing the treatment of a broad range of cancers. However, these treatments are not effective in all cancer types, responses are often not durable, and many patients receive little or no benefit from treatment. The prevailing assumption in the oncology field is that only combinations of immune-therapies with other treatment options will ultimately be able to cure cancer patients.

The ADC is well tolerated and active across a range of cancer types, and will likely be one component of combination therapies that increase the response rate and durability of treatment. The purpose of this disclosure is to combine the ADC with the secondary agent.

A secondary agent as described herein may be an Immune-oncology (IO) drug.

Immune-oncology (IO) drugs, a type of cancer therapy relying on the body's immune system to help fight cancer, have shown enhanced durability of anti-tumor response. There are different types of IO, including but not limited to PD1 inhibitors, PD-L1 inhibitors, CLTL4 inhibitors, GITR agonists and OX40 agonists. Due to the considerable fraction of patients who are not cured by single agent immunotherapies and ultimately relapse, combination treatments with alternative 10 drugs or different therapeutic modalities are needed (see K S Peggs et al. 2009, Clinical and Experimental Immunology, 157: 9-19 [doi:10.1111/j.1365-2249.2009.03912.x]; D M Pardoll 2012 [doi: 10.1038/nrc3239]).

Immunogenic cell death (ICD) is a particular form of cell death that stimulates an immune response against dead-cell antigens (released by dying cells) and it is considered as one of the best way to induce an adaptive immune response and improve the efficacy of anti-cancer treatment. This process is frequently suboptimal, calling for combinatorial strategies that attempt to restore the full immunogenicity of cell death for therapeutic purposes. There are several anti-neoplastic agents that can induce ICD such as various anthracyclines (including doxorubicin, epirubicin and idarubicin), alkylating agents (including oxaliplatin and cyclophosphamide), the topoisomerase II inhibitor mitoxantrone, and the proteasomal inhibitor Bortezomib.

Antibody-drug conjugates, including those with a PBD warhead, may be particularly suited as combination partners because they are more targeted compared to conventional chemotherapy and expected to offer an increased antigen presentation to infiltrating cells as has been shown for auristatin-based ADCs.

Combining ADCs with 10 therefore allows for dual benefits: on the one hand, the ADC will directly kill the tumor expressing the target, providing immediate anti-tumor activity, and on the other the immunogenic cell death induced by ADC mediated cell kill may boost a stronger and more durable adaptive immune response, as compared to when the 10 is given as a single agent.

The secondary agent may be:
(a) a PD1 antagonist, such as pembrolizumab, nivolumab, MEDI0680, PDR001 (spartalizumab), Camrelizumab, AUNP12, Pidilizumab, Cemiplimab (REGN-2810), AMP-224, BGB-A317 (Tisleizumab), or BGB-108;
(b) a PD-L1 antagonist, such as atezolizumab (Tecentriq), BMS-936559/MDX-1105, durvalumab/MED14736, or MSB0010718C (Avelumab);
(c) a GITR (Glucocorticoid-Induced TNFR-Related protein) agonist, such as MEDI1873, TRX518, GWN323, MK-1248, MK-4166, BMS-986156 or INCAGN1876;
(d) an OX40 agonist, such as MED10562, MED16383, MOXR0916, RG7888, OX40mAb24, INCAGN1949, GSK3174998, or PF-04518600;
(e) a CTLA-4 antagonist, such as ipilimumab (brand name Yervoy) or Tremelimumab (Originally developed by Pfizer, now Medimmune);
(f) Fludarabine or Cytarabine;
(g) a hypomethylating agent, such as cytidine analogs—for example, 5-azacytidine (azacitidine) and 5-aza-2'-deoxycytidine (decitabine); or (h) a PARP inhibitor (PARPi), such as Olaparib, CEP-9722, BMN-673/talazoparib, Rucaparib, Iniparib/SAR24-550/BSI-201, Veliparib (ABT-888), Niraparib/MK-4827, BGB-290, 3-aminobenzamide, and E7016;

(i) an agent that upregulates HER2 expression, such as gemcitabine and tamoxifen;

(j) an AXL-kinase inhibitor (AXLi) such as BGB324 (bemcentinib), TP0903, Gilteritinib (ASP2215), Cabozantinib (XL184), SG17079, Merestinib, amuvatinib (MP-470), bosutinib (SKI-606), MGCD265, and foretinib (GSK1363089/XL880);

(k) a BRAF inhibitor (BRAFi), such as vemurafenib, PLX4720, dabrafenib, Sorafenib, Encorafenib, and GDC0879; or (l) a MEK inhibitor (MEKi), such as Trametinib, Cobimetinib, Binimetinib, Selumetinib, PD-325901, CI-1040, PD035901, U0126 and TAK-733.

Each of these classes of secondary agent is described in more detail below.

PD1 Antagonists

Programmed death receptor I (PD1) is an immune-inhibitory receptor that is primarily expressed on activated T and B cells. Interaction with its ligands has been shown to attenuate T-cell responses both in vitro and in vivo. Blockade of the interaction between PD1 and one of its ligands, PD-L1, has been shown to enhance tumor-specific CD8+ T-cell immunity and may therefore be helpful in clearance of tumor cells by the immune system.

PD1 (encoded by the gene Pdcd1) is an Immunoglobulin superfamily member related to CD28, and CTLA-4. PD1 has been shown to negatively regulate antigen receptor signalling upon engagement of its ligands (PD-L1 and/or PD-L2). The structure of murine PD1 has been solved as well as the co-crystal structure of mouse PD1 with human PD-L1 (Zhang, X., et al., (2004) Immunity 20: 337-347; Lin, et al., (2008) Proc. Natl. Acad. Sci. USA 105: 3011-6). PD1 and like family members are type I transmembrane glycoproteins containing an Ig Variable-type (V-type) domain responsible for ligand binding and a cytoplasmic tail that is responsible for the binding of signaling molecules. The cytoplasmic tail of PD1 contains two tyrosine-based signaling motifs, an ITIM (immunoreceptor tyrosine-based inhibition motif) and an ITSM (immunoreceptor tyrosine-based switch motif).

In humans, expression of PD1 (on tumor infiltrating lymphocytes) and/or PD-L1 (on tumor cells) has been found in a number of primary tumor biopsies assessed by immunohistochemistry. Such tissues include cancers of the lung, liver, ovary, cervix, skin, colon, glioma, bladder, breast, kidney, esophagus, stomach, oral squamous cell, urothelial cell, and pancreas as well as tumors of the head and neck (Brown, J. A., et al., (2003) J Immunol. I 70: I257-I266; Dong H., et al., (2002) Nat. Med. 8: 793-800; Wintterle, et al., (2003) Cancer Res. 63: 7462-7467; Strome, S. E., et al., (2003) Cancer Res. 63: 6501-6505; Thompson, R. H., et al., (2006) Cancer Res. 66: 3381-5; Thompson, et al., (2007) Clin. Cancer Res. 13: I 757-61; Nomi, T., et al., (2007) Clin. Cancer Res. 13: 2151-7). More strikingly, PD-ligand expression on tumor cells has been correlated to poor prognosis of cancer patients across multiple tumor types (reviewed in Okazaki and Honjo, (2007) Int. Immunol. 19: 813-824).

To date, numerous studies have shown that interaction of PD1 with its ligands (PD-L1 and PD-L2) leads to the inhibition of lymphocyte proliferation in vitro and in vivo. Blockade of the PD1/PD-L1 interaction could lead to enhanced tumor-specific T-cell immunity and therefore be helpful in clearance of tumor cells by the immune system. To address this issue, a number of studies were performed. In a murine model of aggressive pancreatic cancer (Nomi, T., et al. (2007) Clin. Cancer Res. 13: 2151-2157), the therapeutic efficacy of PD1/PD-L1 blockade was demonstrated. Administration of either PD1 or PD-L1 directed antibody significantly inhibited tumor growth. Antibody blockade effectively promoted tumor reactive CD8+ T cell infiltration into the tumor resulting in the up-regulation of anti-tumor effectors including IFN gamma, granzyme Band perforin. Additionally, the authors showed that PD1 blockade can be effectively combined with chemotherapy to yield a synergistic effect. In another study, using a model of squamous cell carcinoma in mice, antibody blockade of PD1 or PD-L1 significantly inhibited tumor growth (Tsushima, F., et al., (2006) Oral Oneal. 42: 268-274).

"PD1 antagonist" means any chemical compound or biological molecule that stimulates an immune reaction through inhibition of PD1 signalling.

To examine the extent of enhancement of, e.g., PD1 activity, samples or assays comprising a given, e.g., protein, gene, cell, or organism, are treated with a potential activating or inhibiting agent and are compared to control samples treated with an inactive control molecule. Control samples are assigned a relative activity value of 100%.

Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 20%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Combining an ADC, which targets a first target protein (FTP) with PD1 inhibitors is advantageous, because on the one hand, the ADC will directly kill the FTP positive tumor cells, while on the other hand the PD1 inhibitor will engage the patient's own immune system to eliminate the cancer cells. Next to FTP(+) tumor cells, FTP negative tumor cells in close proximity to FTP(+) tumor cells will potentially be killed by the bystander mechanism of the PBD-dimer released after cell kill of CD19(+) or CD22(+) cells. Hence, the ADC will directly kill the tumor cells.

The resulting release of tumor associated antigens from cells that are killed with the PBD dimer will trigger the immune system, which will be further enhanced by the use of programmed cell death protein 1 (PD1) inhibitors, expressed on a large proportion of tumour infiltrating lymphocytes (TILs) from many different tumour types. Blockade of the PD1 pathway may enhance antitumour immune responses against the antigens released from the tumors killed by the ADC by diminishing the number and/or suppressive activity of intratumoral TReg cells.

The major function of PD1 is to limit the activity of T-cells at the time of an anti-inflammatory response to infection and to limit autoimmunity. PD1 expression is induced when T-cells become activated, and binding of one of its own ligands inhibits kinases involved in T-cell activation. Hence, in the tumor environment this may translate into a major immune resistance, because many tumours are highly infiltrated with TReg cells that probably further suppress effector immune responses. This resistance mechanism is alleviated by the use of PD1 inhibitors in combination with the ADC.

PD1 antagonists suitable for use as secondary agents in the present disclosure include:
  a) a PD1 antagonist which inhibits the binding of PD1 to its ligand binding partners.
  b) a PD1 antagonist which inhibits the binding of PD1 to PD-L1.
  c) a PD1 antagonist which inhibits the binding of PD-1 to PDL2.
  d) a PD1 antagonist which inhibits the binding of PD-1 to both PDL1 and PDL2.
  e) a PD1 antagonist of parts (a) to (d) which is an antibody.

Specific PD1 antagonists suitable for use as secondary agents in the present disclosure include:
  a) pembrolizumab (brand name Keytruda)
    i. CAS Number→1374853-91-4
      (see cas.org/content/chemical-substances/faqs)
    ii. NCBI Pubchem reference→254741536
      (see pubchem.ncbi.nlm.nih.gov/)
    iii. DrugBank reference→DB09037
      (see drugbank.ca/)
    iv. Unique Ingredient Identifier (UNII)→DPT0-O3T46P
      (see fda.gov/ForIndustry/DataStandards/SubstanceRegistrationSystem-UniqueIngredientIdentifierUNII/default.htm)
  b) nivolumab (brand name Opdivo)
    i. CAS Number→946414-94-4
      (see cas.org/content/chemical-substances/faqs)
    ii. DrugBank reference→DB09035
      (see drugbank.ca/)
  c) MED10680 (formerly AMP-514)
    As described in WO2014/055648, WO2015/042246, WO2016/127052, WO2017/004016, WO2012/145493, U.S. Pat. No. 8,609,089, WO2016/007235, WO2016/011160; Int. J. Mol. Sci. 2016 July; 17(7):1151, doi: 10.3390/ijms17071151; and Drug Discov Today, 2015 September; 20(9):1127-34. doi: 10.1016/j.drudis.2015.07.003.
    See also clinical trials NCT02271945 and NCT-02013804 at clinicaltrials.gov/ct2/home
  d) PDR001 (spartalizumab)
    i. CAS Number→1935694-88-4
      (see cas.org/content/chemical-substances/faqs)
    ii. Unique Ingredient Identifier (UNII)→QOG25-L6Z8Z
      (see fda.gov/ForIndustry/DataStandards/SubstanceRegistrationSystem-UniqueIngredientIdentifierUNII/default.htm)
    As described in WO2016/007235 and WO2016/011160
    NCI thesaurus code→C121625
      (see ncit.nci.nih.gov/ncitbrowser/)
  e) Camrelizumab [INCSHR-1210] (Incyte)
    i. CAS Number→1798286-48-2
      (see cas.org/content/chemical-substances/faqs)
    ii. Unique Ingredient Identifier (UNII)→73096E137E
      (see fda.gov/ForIndustry/DataStandards/SubstanceRegistrationSystem-UniqueIngredientIdentifierUNII/default.htm)
  f) AUNP12 (peptide) (Aurigene/PierreFabre)
    i. Disclosed in WO2011/161699 as "compound 8", see Example 2 on page 77 of the A2 publication of WO2011/161699.
    ii. CAS Number→1353563-85-5
      (see cas.org/content/chemical-substances/faqs)

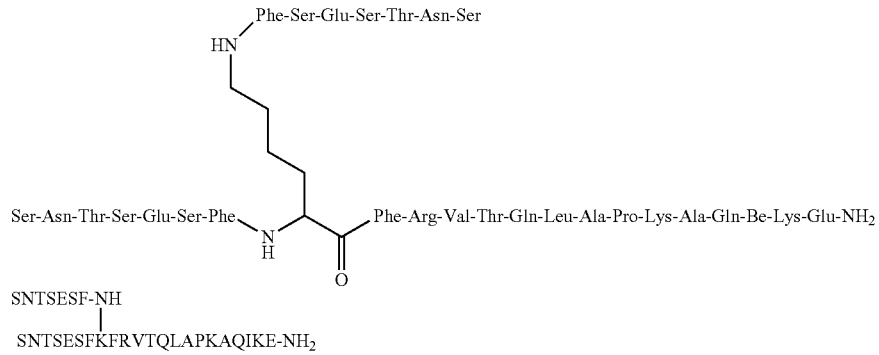

SNTSESF-NH
|
SNTSESFKFRVTQLAPKAQIKE-NH$_2$ g) Pidilizumab (CT-011)
    i. CAS Number→1036730-42-3
      (see cas.org/content/chemical-substances/faqs)
    ii. Unique Ingredient Identifier (UNII)→B932PA-Q1BQ
      (see fda.gov/ForIndustry/DataStandards/SubstanceRegistrationSystem-UniqueIngredientIdentifierUNII/default.htm)
  h) Cemiplimab (formerly REGN-2810, SAR-439684)
    i. CAS Number→1801342-60-8
      (see cas.org/content/chemical-substances/faqs)
    ii. Unique Ingredient Identifier (UNII)→6QVL0571NT
      (see fda.gov/ForIndustry/DataStandards/SubstanceRegistrationSystem-UniqueIngredientIdentifierUNII/default.htm)
    As described in WO2016/007235
    NCI thesaurus code→$C_{121540}$
      (see ncit.nci.nih.gov/ncitbrowser/)
  i) BGB-A317 (Tislelizumab)
    i. As described in U.S. Pat. No. 9,834,606 B2
    ii. See clinical trial NCT03209973 (clinicaltrials.gov/)
    iii. NCI thesaurus code $C_{121775}$
      (see ncit.nci.nih.gov/ncitbrowser/)
  j) BGB-108
    See WO2016/000619 and U.S. Pat. No. 8,735,553
  k) AMP-224
    see clinical trial NCT02298946, clinicaltrials.gov/ct2/home In some embodiments, PD1 polypeptide corresponds to Genbank accession no. AAC51773, version no.

AAC51773.1, record update date: Jun. 23, 2010 09:24 AM. In one embodiment, the nucleic acid encoding PD1 polypeptide corresponds to Genbank accession no. U64863, version no. U64863.1, record update date: Jun. 23, 2010 09:24 AM. In some embodiments, PD1 polypeptide corresponds to Uniprot/Swiss-Prot accession No. Q15116.

PD-L1 Antagonists

"PD-L1 antagonist" means any chemical compound or biological molecule that stimulates an immune reaction through inhibition of PD-L1 signalling.

To examine the extent of enhancement of, e.g., PD-L1 activity, samples or assays comprising a given, e.g., protein, gene, cell, or organism, are treated with a potential activating or inhibiting agent and are compared to control samples treated with an inactive control molecule. Control samples are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 20%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Combining an ADC, which targets a first target protein (FTP) positive lymphomas and leukemias with PD-L1 inhibitors is advantageous because, on the one hand, the ADC will directly kill the FTP positive tumor cells while, on the other hand, the PD-L1 inhibitor will engage the patient's own immune system to eliminate the cancer cells.

Next to FTP(+) tumor cells, target negative tumor cells in close proximity to FTP(+) tumor cells will potentially be killed by the bystander mechanism of the PBD-dimer released after cell kill of FTP(+) cells. Hence, the ADC will directly kill the tumor cells. The resulting release of tumor associated antigens from cells that are killed with the PBD dimer will trigger the immune system, which will be further enhanced by the use of programmed cell death protein 1 ligand inhibitors (PD-L1, aka B7-H1 or CD274).

PD-L1 is commonly upregulated on the tumour cell surface from many different human tumours. Interfering with the PD1 ligand expressed on the tumor will avoid the immune inhibition in the tumor microenvironment and therefore blockade of the PD1 pathway using PDL1 inhibitors may enhance antitumour immune responses against the antigens released from the tumors killed by the ADC.

Combining an ADC, which targets a first target protein (FTP) with PD1 inhibitors is advantageous, because on the one hand, the ADC will directly kill the FTP positive tumor cells, while on the other hand the PD1 inhibitor will engage the patient's own immune system to eliminate the cancer cells. Next to FTP(+) tumor cells, FTP negative tumor cells in close proximity to FTP(+) tumor cells will potentially be killed by the bystander mechanism of the PBD-dimer released after cell kill of CD19(+) or CD22 (+) cells. Hence, the ADC will directly kill the tumor cells.

PD-L1 antagonists suitable for use as secondary agents in the present disclosure include PD-L1 antagonists that:
(a) are PD-L1 binding antagonists;
(b) inhibit the binding of PD-L1 to PD1;
(c) inhibit the binding of PD-L1 to B7-1;
(d) inhibit the binding of PD-L1 to both PD1 and B7-1;
(e) are anti-PD-L1 antibodies.

Specific PD-L1 antagonists suitable for use as secondary agents in the present disclosure include:
a) atezolizumab (MPDL3280A, brand name Tecentriq)
   i. CAS Number→1380723-44-3
      (see cas.org/content/chemical-substances/faqs)
   ii. DrugBank reference→DB11595
      (see drugbank.ca/)
   iii. Unique Ingredient Identifier (UNII)→52CM10-WC3Y
      (see fda.gov/ForIndustry/DataStandards/Substance-RegistrationSystem-UniqueIngredientIdentifierUNII/default.htm)
b) BMS-936559/MDX-1105
   I. CAS Number→1422185-22-5
      (see cas.org/content/chemical-substances/faqs)
   II. see clinical trial NCT02028403, clinicaltrials.gov/ct2/home
   III. See WO2007/005874 for antibody sequences, in particular the:
      i. Antibody having:

```
a. VH CDR1 = DYGFS
   (SEQ ID NO: 400)

b. VH CDR2 = WITAYNGNTNYAQKLQG
   (SEQ ID NO: 401)

c. VH CDR3 = DYFYGMDV
   (SEQ ID NO: 402)

d. VL CDR1 = RASQSVSSYLV
   (SEQ ID NO: 403)

e. VL CDR2 = DASNRAT
   (SEQ ID NO: 404)

f. VL CDR3 = QQRSNWPRT
   (SEQ ID NO: 405)
``` ii. Antibody having:

```
a. VH CDR1 = TYAIS
   (SEQ ID NO: 406)

b. VH CDR2 = GIIPIFGKAHYAQKFQG
   (SEQ ID NO: 407)

c. VH CDR3 = KFHFVSGSPFGMDV
   (SEQ ID NO: 408)

d. VL CDR1 = RASQSVSSYLA
   (SEQ ID NO: 409)

e. VL CDR2 = DASNRAT
   (SEQ ID NO: 410)

f. VL CDR3 = QQRSNWPT
   (SEQ ID NO: 411)
``` iii. Antibody having:

```
a. VH CDR1 = SYDVH
   (SEQ ID NO: 412)

b. VH CDR2 = WLHADTGITKFSQKFQG
   (SEQ ID NO: 413)

c. VH CDR3 = ERIQLWFDY
   (SEQ ID NO: 414)
```

-continued d. VL CDR1 = RASQGISSWLA
   (SEQ ID NO: 415)

e. VL CDR2 = AASSLQS
   (SEQ ID NO: 416)

f. VL CDR3 = QQYNSYPYT
   (SEQ ID NO: 417)

c) durvalumab/MED14736
  i. CAS Number→1428935-60-7
     (see cas.org/content/chemical-substances/faqs)
  ii. Unique Ingredient Identifier (UNII)→28X-28X9OKV
     (see fda.gov/ForIndustry/DataStandards/Substance-RegistrationSystem-UniqueIngredientIdentifierUNII/default.htm)
  iii. VH sequence

EVQLVESGGGLVQPGGSLRLSCAASGFTFSRYWMSWVRQAPGKGLEW

VANIKQDGSEKYYVDSVKGRFTISRDNAKNSLYLQMNSLRAEDTAVYYC

AREGGWFGELAFDYWGQGTLVTVSS (SEQ ID NO: 418)

iv. VL sequence

EIVLTQSPGTLSLSPGERATLSCRASQRVSSSYLAWYQQKPGQAPRLLIY

DASSRATGIPDRFSGSGSGTDFTLTISRLEPEDFAVYYCQQYGSLPWTF

GQGTKVEIK (SEQ ID NO: 419)

d) Avelumab/MSB0010718C
  i. CAS Number→1537032-82-8
     (see cas.org/content/chemical-substances/faqs)
  ii. Unique Ingredient Identifier (UNII)→KXG2PJ551I
     (see fda.gov/ForIndustry/DataStandards/Substance-RegistrationSystem-UniqueIngredientIdentifierUNII/default.htm)

In some embodiments, PD-L1 polypeptide corresponds to Genbank accession no. AAF25807, version no. AAF25807.1, record update date: Mar. 10, 2010 10:14 PM. In one embodiment, the nucleic acid encoding PD1 polypeptide corresponds to Genbank accession no. AF177937, version no. AF177937.1, record update date: Mar. 10, 2010 10:14 PM. In some embodiments, PD1 polypeptide corresponds to Uniprot/Swiss-Prot accession No. Q9NZQ7.

GITR Agonists

The term "glucocorticoid-induced TNF receptor" (abbreviated herein as "GITR"), also known as TNF receptor superfamily 18 (TNFRSF18, CD357), TEASR, and 312C2, as used herein, refers to a member of the tumor necrosis factor/nerve growth factor receptor family. GITR is a 241 amino acid type I transmembrane protein characterized by three cysteine pseudo-repeats in the extracellular domain and specifically protects T-cell receptorinduced apoptosis, although it does not protect cells from other apoptotic signals, including Fas triggering, dexamethasone treatment, or UV irradiation (Nocentini, G., et al. (1997) Proc. Natl. Acad. Sci. USA 94:6216-622).

GITR activation increases resistance to tumors and viral infections, is involved in autoimmune/inflammatory processes and regulates leukocyte extravasation (Nocentini supra; Cuzzocrea, et al. (2004) J Leukoc. Biol. 76:933-940; Shevach, et al. (2006) Nat. Rev. Immunol. 6:613-618; Cuzzocrea, et al. (2006) J Immunol. I 77:631-641; and Cuzzocrea, et al. (2007) FASEB J 21:1 I 7-129). In tumor mouse models, agonist GITR antibody, DTA-I, was combined with an antagonist CTLA-4 antibody, and showed synergistic results in complete tumor regression of advanced stage tumors in some test group mice (Ko, et al. (2005) J Exp. Med. 7:885-891).

The nucleic acid and amino acid sequences of human GITR (hGITR), of which there are three splice variants, are known and can be found in, for example GenBank Accession Nos. gi:40354198, gi:23238190, gi:23238193, and gi:23238196.

"GITR agonist" means any chemical compound or biological molecule that stimulates an immune reaction through activation of GITR signalling. Also contemplated are soluble GITR-L proteins, a GITR binding partner.

To examine the extent of enhancement of, e.g., GITR activity, samples or assays comprising a given, e.g., protein, gene, cell, or organism, are treated with a potential activating or inhibiting agent and are compared to control samples treated with an inactive control molecule. Control samples are assigned a relative activity value of 100%.

Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 20%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Combining an ADC, which targets a first target protein (FTP) positive lymphomas and leukemias with GITR agonists is advantageous, because on the one hand the ADC will directly kill the FTP positive tumor cells, while on the other hand the GITR agonist will engage the patient's own immune system to eliminate the cancer cells. Next to FTP(+) tumor cells, target negative tumor cells in close proximity to FTP(+) tumor cells will potentially be killed by the bystander mechanism of the PBD-dimer released after cell kill of FTP(+) cells. Hence, the ADC will directly kill the tumor. The resulting release of tumor associated antigens from cells killed with the PBD dimer will trigger the immune system, which will be further enhanced by the use of a GITR agonist.

GITR (Glucocorticoid-Induced TNFR-Related protein) is expressed transiently on activated T-cells and expressed constitutively at high levels on T-regs with further induction following activation. GITR ligation via its ligand GITRL stimulates both proliferation and function of both effector and regulatory CD4+ T cells. This promotes T-cell survival, and differentiation into effector cells, while abrogating suppression. Therefore it will be beneficial to target a FTP(+) tumor with the ADC, causing the antigenic cell death, while the GITR agonist induces a stronger, durable immune response.

Specific GITR agonists suitable for use as secondary agents in the present disclosure include:
  a) MED11873, a GITR ligand fusion protein developed by MedImmune
     See WO2016/196792, US20160304607
     NCI thesaurus code→C124651

(see ncit.nci.nih.gov/ncitbrowser)
See also clinical trial NCT023126110 at clinicaltrials.gov/ct2/home
See Tigue N J, Bamber L, Andrews J, et al. MED11873, a potent, stabilized hexameric agonist of human GITR with regulatory T-cell targeting potential. Oncoimmunology. 2017; 6(3):e1280645. doi:10.1080/2162402X.2017.1280645.

b) INCAGN1876, is an agonist antibody targeting the glucocorticoid-induced TNFR-related protein, or GITR. Discovered during a collaboration with Ludwig Cancer Research. INCAGN1876 is being co-developed with Incyte
See clinical trials NCT02583165 and NCT03277352 at clinicaltrials.gov/ct2/home c) TRX518, a humanized agylcosylated (Fc disabled) IgG1 anti-GITR mAb with immune-modulating activity developed by Leap Therapeutics
See WO2006/105021 for sequences 58, 60-63; and EP2175884 sequences 1-7:
VL comprising the sequence (CDR underline):

```
EIVMTQSPATLSVSPGERATLSCKASQNVGTNVAWYQQKPG

QAPRLLIYSASYRYSGIPARFSGSGSGTEFTLTISSLQSEDFA

VYYCQQYNTDPLTFGGGTKVEIK (SEQ ID NO: 500)
```

VH comprising the sequence (CDR underline):

```
QVTLRESGPALVKPTQTLTLTCTFSGFSLSTSGMGVGWIRQP

PGKALEWLAHIWWDDDKYYNPSLKSRLTISKDTSKNQVVLTM

TNMDPVDTATYYCARTRRYFPFAYWGQGTLVTVS
(SEQ ID NO: 501)

QVTLRESGPALVKPTQTLTLTCTFSGFSLSTSGMGVGWIRQP

PGKALEWLAHIWWDDDKYYQPSLKSRLTISKDTSKNQVVLTM

TNMDPVDTATYYCARTRRYFPFAYWGQGTLVTVS
(SEQ ID NO: 502)
```

See clinical trials NCT01239134 and NCT02628574 at clinicaltrials.gov/ct2/home
NCI thesaurus code→C95023
(see ncit.nci.nih.gov/ncitbrowser)

d) GWN323, an anti-GITR agonistic monoclonal antibody, which activates GITRs found on multiple types of T-cells. GWN323 is developed by Novartis
See WO2016/196792
NCI thesaurus code→C128028
(see ncit.nci.nih.gov/ncitbrowser)
See clinical trial NCT02740270 at clinicaltrials.gov/ct2/home e) MK-1248, a humanized IgG4 anti-human g ucocorticoid-induced tumor necrosis factor receptor (GITR) agonistic monoclonal antibody (MoAb) with significantly reduced effector function
See clinical trial NCT02553499 at clinicaltrials.gov/ct2/home
MK-1248 has the same CDR as MK4166 (see Sukumar et al., Cancer Res. 2017)

f) MK-4166, a humanized IgG1 anti-human glucocorticoid-induced tumor necrosis factor receptor (GITR) agonistic monoclonal antibody (MoAb) with potential immunomodulating activity (see Sukumar et al., Cancer Res. 2017).
See clinical trial NCT02132754 at clinicaltrials.gov/ct2/home
See Sukumar, et al., (2017), Cancer Research. 77. canres.1439.2016. 10.1158/0008-5472. CAN-16-1439.
NCI thesaurus code C116065
(see ncit.nci.nih.gov/ncitbrowser/)

g) BMS-986156, An anti-human glucocorticoid-induced tumor necrosis factor receptor (GITR; tumor necrosis factor superfamily member 18; TNFRSF18; CD357) agonistic monoclonal antibody
See clinical trial NCT02598960 at clinicaltrials.gov/ct2/home
NCI thesaurus code C132267
(see ncit.nci.nih.gov/ncitbrowser/)

Sequences of agonist anti-GITR antibodies are provided in WO2011/028683 and WO2006/105021.

In some embodiments, GITR polypeptide corresponds to Genbank accession no. AAD22635, version no. AAD22635.1, record update date: Mar. 10, 2010 09:42 PM. In one embodiment, the nucleic acid encoding GITR polypeptide corresponds to Genbank accession no. AF125304, version no. AF125304.1, record update date: Mar. 10, 2010 09:42 PM. In some embodiments, GITR polypeptide corresponds to Uniprot/Swiss-Prot accession No. Q9Y5U5.

OX40 Agonists

OX40 (CD134; TNFRSF4) is a member of the TNFR super-family and is expressed by CD4 and CD8 T cells during antigen-specific priming. OX40 expression is largely transient following TCR/CD3 cross-linking, and by the presence of inflammatory cytokines. In the absence of activating signals, relatively few mature T cell subsets express OX40 at biologically relevant levels. Generating optimal "killer" CD8 T cell responses requires T cell receptor activation plus co-stimulation, which can be provided through ligation of OX40 using a OX40 agonist. This activating mechanism augments T cell differentiation and cytolytic function leading to enhanced anti-tumor immunity. Therefore it will be beneficial to target a FTP(+) tumor with the ADC, causing the antigenic cell death, while the OX40 agonist induces a stronger, durable immune response.

The OX40 agonist may be selected from the group consisting of an OX40 agonist antibody, an OX40L agonist fragment, an OX40 oligomeric receptor, and an OX40 immunoadhesin. In some embodiments, the OX40 binding agonist is a trimeric OX40L-Fc protein.

In some embodiments, the OX40 binding agonist is an OX40L agonist fragment comprising one or more extracellular domains of OX40L. In some embodiments, the OX40 binding agonist is an OX40 agonist antibody that binds human OX40. In some embodiments, the OX40 agonist antibody depletes cells that express human OX40. In some embodiments, the OX40 agonist antibody depletes cells that express human OX40 in vitro. In some embodiments, the cells are CD4+ effector T cells. In some embodiments, the cells are Treg cells. In some embodiments, the depleting is by ADCC and/or phagocytosis. In some embodiments, the depleting is by ADCC. In some embodiments, the OX40 agonist antibody binds human OX40 with an affinity of less than or equal to about 1 nM. In some embodiments, the OX40 agonist antibody increases CD4+ effector T cell proliferation and/or increasing cytokine production by the CD4+ effector T cell as compared to proliferation and/or cytokine production prior to treatment with anti-human OX40 agonist antibody. In some embodiments, the cytokine is gamma interferon. In some embodiments, the OX40 agonist antibody increases memory T cell proliferation and/or increasing cytokine production by the memory cell. In some embodiments, the cytokine is gamma interferon. In some embodiments, the OX40 agonist antibody inhibits Treg function. In some embodiments, the OX40 agonist antibody inhibits Treg suppression of effector T cell function. In some embodiments, effector T cell function is effector T cell proliferation and/or cytokine production. In some embodiments, the effector T cell is a CD4+ effector T cell. In some embodiments, the OX40 agonist antibody increases OX40 signal transduction in a target cell that expresses OX40. In some embodiments, OX40 signal transduction is detected by monitoring NFkB downstream signalling.

"OX40 agonist" means any chemical compound or biological molecule that stimulates an immune reaction through inactivation of OX40 signalling.

To examine the extent of enhancement of, e.g., OX40 activity, samples or assays comprising a given, e.g., protein, gene, cell, or organism, are treated with a potential activating or inhibiting agent and are compared to control samples treated with an inactive control molecule. Control samples are assigned a relative activity value of 100%.

Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 20%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Combining an ADC, which targets a first target protein (FTP) positive lymphomas and leukemias with OX40 agonists is advantageous, because on the one hand the ADC will directly kill the FTP positive tumor cells, while on the other hand the OX40 agonist will engage the patient's own immune system to eliminate the cancer cells. Next to FTP(+) tumor cells, target negative tumor cells in close proximity to FTP(+) tumor cells will potentially be killed by the bystander mechanism of the PBD-dimer released after cell kill of FTP(+) cells. Hence, the ADC will directly kill the tumor. The resulting release of tumor associated antigens from cells killed with the PBD dimer will trigger the immune system, which will be further enhanced by the use of a OX40 agonist.

Specific OX40 agonists suitable for use as secondary agents in the present disclosure include:

a) MED10562 (aka Tavolixizumab, Tavolimab)
   a) CAS Number→1635395-25-3
      (see cas.org/content/chemical-substances/faqs)
   b) Unique Ingredient Identifier (UNII)→4LU9B4-8U4D
      (see fda.gov/ForIndustry/DataStandards/Substance-RegistrationSystem-UniqueIngredientIdentifierUNII/default.htm)
   See clinical trial NCT02318394 at clinicaltrials.gov/ct2/home
   As described in WO2015/095423, WO2015/153514, WO2016/073380 & WO2016/081384
   NCI thesaurus code→C120041
      (see ncit.nci.nih.gov/ncitbrowser/)

```
Heavy Chain sequence:
QVQLQESGPGLVKPSQTLSLTCAVYGGSFSSGYWNWIRKHPGKGLEYIGY

ISYNGITYHNPSLKSRITINRDTSKNQYSLQLNSVTPEDTAVYYCARYKY

DYDGGHAMDYWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKRVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG
(SEQ ID NO: 600)

Light chain sequence:
DIQMTQSPSSLSASVGDRVTITCRASQDISNYLNWYQQKPGKAPKLLIYY

TSKLHSGVPSRFSGSGSGTDYTLTISSLQPEDFATYYCQQGSALPWTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC (SEQ ID NO: 601)
``` b) MED16383 (Efizonerimod alfa)
    a) CAS Number→1635395-27-5
      (see cas.org/content/chemical-substances/faqs)
    b) Unique Ingredient Identifier (UNII)→1MH-7C2X8KE
      (see fda.gov/ForIndustry/DataStandards/Substance-RegistrationSystem-UniqueIngredientIdentifierUNII/default.htm)
    See clinical trial NCT02221960 at clinicaltrials.gov/ct2/home
    As described in WO2015/095423, WO2016/081384, and WO2016/189124
    NCI thesaurus code→C118282
      (see ncit.nci.nih.gov/ncitbrowser/)
    Amino acid sequence (Sequence 17 from WO2016/189124):

```
ESKYGPPCPPCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGKDQDKIEALSSKVQQLERSIGL

KDLAMADLEQKVLEMEASTQVSHRYPRIQSIKVQFTEYKKEKGFILTSQK

EDEIMKVQNNSVIINCDGFYLISLKGYFSQEVNISLHYQKDEEPLFQLKK

VRSVNSLMVASLTYKDKVYLNVTTDNTSLDDFHVNGGELILIHQNPGEFC

VL (SEQ ID NO: 602)
``` c) MOXR0916 (also known as RG7888, Pogalizumab), a humanized anti-OX40 monoclonal antibody
    a) CAS Number→1638935-72-4
      (see cas.org/content/chemical-substances/faqs)
    b) Unique Ingredient Identifier (UNII)→C78148TF1D
      (see fda.gov/ForIndustry/DataStandards/Substance-RegistrationSystem-UniqueIngredientIdentifierUNII/default.htm)

c) NCI thesaurus code→C121376
(see ncit.nci.nih.gov/ncitbrowser/)
d) OX40mAb24 (9B12)
  a) OX40mAb24 is a humanised version of 9B12. 9B12 is a murine IgGI, anti-OX40 mAb directed against the extracellular domain of human OX40 (CD134) (Weinberg, A. D., et al. J Immunother 29, 575-585 (2006)).
  b) See WO2016/057667 Sequence 59 for OX40mAb24 VH sequence, sequence 29 for VL sequence (sequence 32 is an alternative VL):

```
VH sequence
QVQLQESGPGLVKPSQTLSLTCAVYGGSFSSGYWNWIRKHPGKGLEYIGY

ISYNGITYHNPSLKSRITINRDTSKNQYSLQLNSVTPEDTAVYYCARYKY

DYDGGHAMDYWGQGTLVTVSS (SEQ ID NO: 603)

VL sequence
DIQMTQSPSSLSASVGDRVTITCRASQDISNYLNWYQQKPGKAPKLLIYY

TSKLHSGVPSRFSGSGSGTDYTLTISSLQPEDFATYYCQQGSALPWTFGQ

GTKVEIK (SEQ ID NO: 604)
``` e) INCAGN1949
  a) See Gonzalez et al. 2016, DOI: 10.1158/1538-7445.AM2016-3204
  b) See clinical trial NCT02923349 at clinicaltrials.gov/ct2/home
  c) Antibody sequences are disclosed in WO2016/179517 A1:
    i. In particular, an antibody comprising the sequences:

```
VH CDR1 → GSAMH (SEQ ID NO: 605)

VH CDR2 → RIRSKANSYATAYAASVKG
(SEQ ID NO: 606)

VH CDR3 → GIYDSSGYDY
(SEQ ID NO: 607)

VL CDR1 → RSSQSLLHSNGYNYLD
(SEQ ID NO: 608)

VL CDR2 → LGSNRAS
(SEQ ID NO: 609)

VL CDR3 → MQALQTPLT
(SEQ ID NO: 610)
``` ii. Such as, an antibody comprising the sequences:

```
VH →
EVQLVESGGGLVQPGGSLKLSCAASGFTFSGSAMHWVR

QASGKGLEWVGRIRSKANSYATAYAASVKGRFTISRDDS

KNTAYLQMNSLKTEDTAVYYCTSGIYDSSGYDYWGQGTL

VTVSS (SEQ ID NO: 611)

VL →
DIVMTQSPLSLPVTPGEPASISCRSSQSLLHSNGYNYLDW

YLQKPGQSPQLLIYLGSNRASGVPDRFSGSGSGTDFTLKI

SRVEAEDVGVYYCMQALQTPLTFGGGTKVEIK
(SEQ ID NO: 612)
``` g) GSK3174998, a humanized IgG1 agonistic anti-OX40 monoclonal antibody (mAb)

See clinical trial NCT02528357 at clinicaltrials.gov/ct2/home h) PF-04518600 (PF-8600) is an investigational, fully human, monoclonal antibody (mAb) that targets OX40 protein
  See patent WO 2017/130076 A1
  See clinical trial NCT02315066 at clinicaltrials.gov/ct2/home-NCI thesaurus code→C121927
  (see ncit.nci.nih.gov/ncitbrowser/)

In some embodiments, OX40 polypeptide corresponds to Genbank accession no. CAA53576, version no. CAA53576.1, record update date: Feb. 2, 2011 10:10 AM. In one embodiment, the nucleic acid encoding OX40 polypeptide corresponds to Genbank accession no. X75962, version no. X75962.1, record update date: Feb. 2, 2011 10:10 AM. In some embodiments, OX40 polypeptide corresponds to Uniprot/Swiss-Prot accession No. P43489.

CTLA Antagonist

CTLA4 (CD152) is expressed on activated T cells and serves as a co-inhibitor to keep T cell responses in check following CD28-mediated T cell activation. CTLA4 is believed to regulate the amplitude of the early activation of naïve and memory T cells following TCR engagement and to be part of a central inhibitory pathway that affects both antitumor immunity and autoimmunity. CTLA4 is expressed exclusively on T cells, and the expression of its ligands CD80 (B7.1) and CD86 (B7.2), is largely restricted to antigen-presenting cells, T cells, and other immune mediating cells. Antagonistic anti-CTLA4 antibodies that block the CTLA4 signalling pathway have been reported to enhance T cell activation. One such antibody, ipilimumab, was approved by the FDA in 2011 for the treatment of metastatic melanoma. Another anti-CTLA4 antibody, tremelimumab, was tested in phase III trials for the treatment of advanced melanoma, but did not significantly increase the overall survival of patients compared to the standard of care (temozolomide or dacarbazine) at that time.

"CTLA4 agonist" means any chemical compound or biological molecule that stimulates an immune reaction through inhibition of CTLA4 signalling.

To examine the extent of enhancement of, e.g., CTLA4 activity, samples or assays comprising a given, e.g., protein, gene, cell, or organism, are treated with a potential activating or inhibiting agent and are compared to control samples treated with an inactive control molecule. Control samples are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 20%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Combining an ADC, which targets a first target protein (FTP) positive lymphomas and leukemias with CTLA4 inhibitors is advantageous, because on the one hand, the ADC will directly kill the FTP positive tumor cells, while on the other hand the CTLA4 inhibitor will engage the patient's own immune system to eliminate the cancer cells. Next to FTP(+) tumor cells, target negative tumor cells in close proximity to FTP(+) tumor cells will potentially be killed by the bystander mechanism of the PBD-dimer released after cell kill of FTP(+) cells. Hence, the ADC will directly kill the tumor. The resulting release of tumor associated antigens from cells killed with the PBD dimer will trigger the immune system, which will be further enhanced by the use of CTLA4 inhibitors expressed on a large proportion of tumour infiltrating lymphocytes (TILs) from many different tumour types.

The major function of CTLA4 (CD152) is to regulate the amplitude of the early stages of T cell activation, and as such it counteracts the activity of the T cell co-stimulatory receptor, CD28, In the tumor microenvironment. Blockade of the CTLA4 pathway may therefore enhance enhancement of effector CD4+ T cell activity, while it inhibits TReg cell-dependent immunosuppression. Therefore it will be beneficial to target a FTP(+) tumor with the ADC, causing the antigenic cell death, while the CTLA4 blockade induces a stronger immune, durable response.

Specific CTLA4 antagonists suitable for use as secondary agents in the present disclosure include:
  a) ipilimumab
      i. CAS Number→477202-00-9
         (see cas.org/content/chemical-substances/faqs)
      ii. Unique Ingredient Identifier (UNII)→6T8C155666
         (see fda.gov/ForIndustry/DataStandards/Substance-RegistrationSystem-UniqueIngredientIdentifierUNII/default.htm)
  b) Tremelimumab
      i. CAS Number→745013-59-6
         (see cas.org/content/chemical-substances/faqs)
      ii. Unique Ingredient Identifier (UNII)→QEN1-X95CIX
         (see fda.gov/ForIndustry/DataStandards/Substance-RegistrationSystem-UniqueIngredientIdentifierUNII/default.htm)
      iii. VH sequence

```
                                               [SEQ ID NO. 1]
GVVQPGRSLRLSCAASGFTFSSYGMHWVRQAPGKGLEWVAVIWYDGS

NKYYADSVKGRFTISRDNSKNTLYLQMNSLRAEDTAVYYCARDPRGATL

YYYYYGMDVWGQGTTVTVSSASTKGPSVFPLAPCSRSTSESTAALG

CLVKDYFPEPVTVSWNSGALTSGVH (SEQ ID NO: 700)
``` iv. VL sequence

```
                                               [SEQ ID NO. 2]
PSSLSASVGDRVTITCRASQSINSYLDWYQQKPGKAPKLLIYAASSLQSG

VPSRFSGSGSGTDFTLTISSLQPEDFATYYCQQYYSTPFTFGPGTKVEIK

RTVAAPSVFIFPPSDEQLKSGTASVVCLLNNFYPREAKV
(SEQ ID NO: 701)
```

In some embodiments, CTLA polypeptide corresponds to Genbank accession no. AAL07473, version no. AAL07473.1, record update date: Mar. 11, 2010 01:28 AM. In one embodiment, the nucleic acid encoding CTLA4 polypeptide corresponds to Genbank accession no. AF414120, version no. AF414120.1, record update date: Mar. 11, 2010 01:28 AM. In some embodiments, OX40 polypeptide corresponds to Uniprot/Swiss-Prot accession No. P16410.

Fludarabine and Cytarabine

Combination of agents with different action mechanisms is an established therapeutic principle for combating cancer. It can be a way of increasing anti-tumour activity when a synergic effect is shown and/or when reduced toxicity is observed. Antibody-drug conjugates, including those with a PBD warhead, may be particularly suited as combination partners because they are more targeted compared to conventional chemotherapy. As PBD dimers cross-link DNA in a covalent fashion, combining them with other agents that interfere with DNA synthesis via a different mechanism is likely to provide a benefit. Examples of such potential combinations are Fludarabine and Cytarabine.

Fludarabine

Fludarabine or fludarabine phosphate (Fludara) is a chemotherapy drug used in the treatment of hematological malignancies such as leukemias and lymphomas. It is a purine analog, which interferes with DNA by interfering with ribonucleotide reductase (RNAR) and DNA polymerase. It is active against both dividing and resting cells. Fludarabine has also been shown to suppress ERCC1 transcription and this may explain the observed synergy between Fludarabine and the PBD Dimer SJG136 (SG2000) against chronic lymphocytic leukaemia cells. CLAG/CLAG-M-Cladribine is another purine analogue that inhibits RNR.

Combining the ADC, which targets First Target Protein (FTP) positive lymphomas and leukemias, with Fludarabine is advantageous, because on the one hand, the ADC will directly kill the FTP positive tumor cells via a mechanisms depending on DNA cross-linking resulting in apoptosis, while on the other hand the Fludarabine will inhibit the cells RNA and DNA polymerase, while also suppressing the DNA repair enzymes needed to resolve the DNA cross-links induced by the PBD dimer.

To show that the ADC works synergistically with Fludarabine, a panel of FTP(+) cell lines will be co-treated with a range of concentration of both the ADC and Fludarabine. As negative controls, the same panel of cell lines will be co-treated with a range of concentrations of Fludarabine and a non-targeted control ADC or with a range of concentration of the ADC and vehicle. After incubation, two parameters will be measured: the amount of surface FTP (as determined by flow cytometry) and the in vitro cytotoxicity of the combinations (as determined by CellTiter-Glo® or MTS assays). Cytotoxic synergy is calculated by transforming the cell viability data into fraction affected, and calculating the combination index using the CalcuSyn analysis program.

CAS Number→21679-14-1
  (see cas.org/content/chemical-substances/faqs)
  ii. NCBI Pubchem reference→657237
  (see pubchem.ncbi.nlm.nih.gov/)
  iii. IUPHAR/BPS reference→4802
  (see guidetopharmacology.org/)
  iv. Unique Ingredient Identifier (UNII)→1X9VK9O1SC
  (see fda.gov/ForIndustry/DataStandards/SubstanceRegistrationSystem-UniqueIngredientIdentifierUNII/default.htm)

Formula I

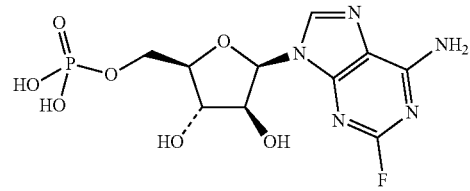

Fludarabine: [(2R, 3R, 4S, 5R)-5-(6-amino-2-fluoro-purin-9-yl)-3,4-dihydroxy-oxolan-2-yl]methoxyphosphonic acid Cytarabine Cytarabine or cytosine arabinoside (Cytosar-U or Depocyt) is a antimetabolic chemotherapy drug used in the treatment of hematological malignancies such as acute myeloid leukemia (AML) and non-Hodgkin lymphoma. It is also known as ara-C (arabinofuranosyl cytidine). It kills cancer cells by interfering with DNA synthesis. It is actively metabolized to cytosine arabinoside triphosphate, which damages DNA when the cell cycle holds in the S phase (synthesis of DNA). Rapidly dividing cells, which require DNA replication for mitosis, are therefore most affected. Cytosine arabinoside also inhibits both DNA and RNA polymerases and nucleotide reductase enzymes needed for DNA synthesis.

Combining the ADC, which targets First Target Protein (FTP) positive lymphomas and leukemias, with Cytarabine is advantageous, because on the one hand, the ADC will directly kill the FTP positive tumor cells via a mechanisms depending on DNA cross-linking resulting in apoptosis, while on the other hand the Cytarabine will inhibit the cells RNA and DNA polymerase, while also suppressing DNA synthesis.

To show that the ADC works synergistically with Cytarabine, a panel of FTP(+) cell lines will be co-treated with a range of concentration of both the ADC and Cytarabine. As negative controls, the same panel of cell lines will be co-treated with a range of concentrations of Cytarabine and a non-targeted control ADC or with a range of concentration of the ADC and vehicle. After incubation, two parameters will be measured: the amount of surface FTP (as determined by flow cytometry) and the in vitro cytotoxicity of the combinations (as determined by CellTiter-Glo® or MTS assays). Cytotoxic synergy is calculated by transforming the cell viability data into fraction affected, and calculating the combination index using the CalcuSyn analysis program (see example 4).

CAS Number→147-94-4
 (see cas.org/content/chemical-substances/faqs)
 ii. NCBI Pubchem reference→6253
 (see pubchem.ncbi.nlm.nih.gov/)
 iii. IUPHAR/BPS reference→4827
 (see guidetopharmacology.org/)
 iv. Unique Ingredient Identifier (UNII)→04079A1RDZ
 (see fda.gov/ForIndustry/DataStandards/SubstanceRegistrationSystem-UniqueIngredientIdentifierUNII/default.htm)

Formula II

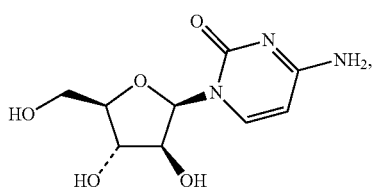

Cytarabine: 4-amino-1-[(2R,3S,4R,5R)-3,4-dihydroxy-5-(hydroxymethyl)oxolan-2-yl] pyrimidin-2-one Hypomethylating Agent The term "hypomethylating agent" refers to a class of compounds that interfere with DNA methylation which is the addition of a methyl group to the 5-position of the cytosine pyrimidine ring or the nitrogen in position 6 of the adenine purine ring. DNA methylation stably alters the gene expression pattern in cells i.e. decrease gene expression (i.e. for the Vitamin D receptor). Hypomethylating agent are compounds that can inhibit methylation, resulting in the expression of the previously hypermethylated silenced genes. Cytidine analogs such as 5-azacytidine (azacitidine) and 5-aza-2'-deoxycytidine (decitabine are the most commonly used Hypomethylating agent. These compounds work by binding to the enzymes that catalyse the methylation reaction, i.e. DNA methyltransferases.

To examine the extent of hypomethylation, samples or assays comprising a given, e.g., protein, gene, cell, or organism, are treated with a potential activating or inhibiting agent and are compared to control samples treated with an inactive control molecule. Control samples are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 20%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Combining an ADC, which targets a first target protein (FTP) positive lymphomas and leukemias with a hypomethylating agent is advantageous, because on the one hand the ADC will directly kill the FTP positive tumor cells, while on the other hand the a hypomethylating agent will interfere with DNA methylation. This interference is by way of causing demethylation in that sequence, which adversely affects the way that cell regulatory proteins are able to bind to the DNA/RNA substrate. This activity synergises with the ADC because PBD dimers cross-link DNA in a covalent fashion, so combining them with other agents that interfere with DNA synthesis via a different mechanism provides a benefit.

Specific Hypomethylating agents suitable for use as secondary agents in the present disclosure include:

a) 5-azacytidine (azacitidine)
  i. CAS Number→320-67-2
  (see cas.org/content/chemical-substances/faqs)
  ii. NCBI Pubchem reference→9444
  (see pubchem.ncbi.nlm.nih.gov/)
  iii. IUPHAR/BPS reference→6796
  (see guidetopharmacology.org/)
  iv. Unique Ingredient Identifier (UNII)→M801H-13NRU
  (see fda.gov/ForIndustry/DataStandards/SubstanceRegistrationSystem-UniqueIngredientIdentifierUNII/default.htm)

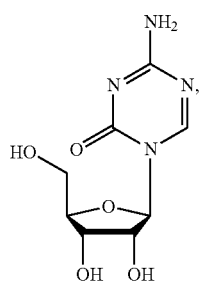

Formula III 5-azacytidine: 4-Amino-1-β-D-ribofuranosyl-1,3,5-triazin-2(1H)-one b) 5-aza-2'-deoxycytidine (decitabine)
  i. CAS Number→2353-33-5
    (see cas.org/content/chemical-substances/faqs)
  ii. NCBI Pubchem reference→451668
    (see pubchem.ncbi.nlm.nih.gov/)
  iii. IUPHAR/BPS reference→6805
    (see guidetopharmacology.org/)
  iv. Unique Ingredient Identifier (UNII)→776B62CQ27
    (see fda.gov/ForIndustry/DataStandards/Substance-RegistrationSystem-UniqueIngredientIdentifierUNII/default.htm)

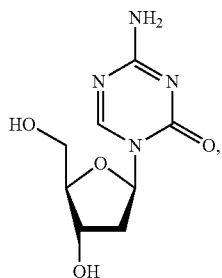

Formula IV b) 5-aza-2'-deoxycytidine: 4-Amino-1-(2-deoxy-β-D-erythropentofuranosyl-1,3,5-triazin-2(1H)-one PARP Inhibitors Poly (adenosine diphosphate [ADP]) ribose polymerase (PARP) are a family of enzymes involved in a wide range of cellular functions including DNA transcription, DNA damage response, genomic stability maintenance, cell cycle regulation, and cell death. PARP-1 is the most abundant and best characterised protein of this group. In oncology, its integral role in the repair of single-strand DNA breaks (SSBs) via the base excision repair (BER) pathway has been a focus of high interest and several PARP-1 inhibitors (PARPi) have been developed (including but not limited to Olaparib, CEP-9722, talazoparib, Rucaparib, Iniparib, Veliparib and Niraparib) and are tested clinically. In cancer therapeutics, PARPi work predominantly by preventing the repair of DNA damage, ultimately causing cell death.

PARP is composed of four domains of interest: a DNA-binding domain, a caspase-cleaved domain, an auto-modification domain, and a catalytic domain. The DNA-binding domain is composed of two zinc finger motifs. In the presence of damaged DNA (base pair-excised), the DNA-binding domain will bind the DNA and induce a conformational shift. It has been shown that this binding occurs independent of the other domains. This is integral in a programmed cell death model based on caspase cleavage inhibition of PARP. The auto-modification domain is responsible for releasing the protein from the DNA after catalysis. Also, it plays an integral role in cleavage-induced inactivation.

PARP is found in the cell nucleus. The main role is to detect and initiate an immediate cellular response to metabolic, chemical, or radiation-induced single-strand DNA breaks (SSB) by signalling the enzymatic machinery involved in the SSB repair. Once PARP detects a SSB, it binds to the DNA, undergoes a structural change, and begins the synthesis of a polymeric adenosine diphosphate ribose (poly (ADP-ribose) or PAR) chain, which acts as a signal for the other DNA-repairing enzymes. Target enzymes include DNA ligase III (LigIII), DNA polymerase beta (polβ), and scaffolding proteins such as X-ray cross-complementing gene 1 (XRCC1). After repairing, the PAR chains are degraded via Poly(ADP-ribose) glycohydrolase (PARG).

NAD+ is required as substrate for generating ADP-ribose monomers. It has been thought that overactivation of PARP may deplete the stores of cellular NAD+ and induce a progressive ATP depletion and necrotic cell death, since glucose oxidation is inhibited. But more recently it was suggested that inhibition of hexokinase activity leads to defects in glycolysis. (see Andrabi, PNAS 2014). Note below that PARP is inactivated by caspase-3 cleavage during programmed cell death.

PARP enzymes are essential in a number of cellular functions, including expression of inflammatory genes: PARP1 is required for the induction of ICAM-1 gene expression by smooth muscle cells, in response to TNF.

PBDs are a class of naturally occurring anti-tumor antibiotics found in *Streptomyces*. PBD dimers exert their cytotoxic mode of action via cross-linking of two strands of DNA, which results in the blockade of replication and tumor cell death. Importantly, the cross-links formed by PBD dimers are relatively non-distorting of the DNA structure, making them hidden to DNA repair mechanisms, which are often impaired in human tumors as opposed to normal tissues.

Combining PBD-based ADCs with PARPi (including but not limited to Olaparib, CEP-9722, talazoparib, Rucaparib, Iniparib, Veliparib and Niraparib) is advantageous because repair of the DNA damaged caused by the PBD dimers is blocked by the PARP inhibition hence resulting in accumulation of DNA damage leading to cancer cell death.

To show that treatment of solid tumor-derived cell lines with PBD-based ADCs and PARPi has an additive or synergistic anti-tumor effect, a panel of solid tumor-derived cell lines will be treated with a range of concentration of each ADC and a PARPi. After incubation, the in vitro cytotoxicity of the combinations (as determined by CellTiter-Glo® or MTS assays) will be measured. Cytotoxic synergy is calculated by transforming the cell viability data into fraction affected, and calculating the combination index using the CalcuSyn analysis program.

"PARP inhibitor" means any chemical compound or biological molecule reduces PARP activity.

To examine the extent of inhibition of, e.g., PARP activity, samples or assays comprising a given, e.g., protein, gene, cell, or organism, are treated with a potential activating or inhibiting agent and are compared to control samples treated with an inactive control molecule. Control samples are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 20%.

Specific PARPi suitable for use in the present disclosure include:

a) Olaparib
   i. CAS Number→763113-22-0
      (see cas.org/content/chemical-substances/faqs)
   ii. NCBI Pubchem reference→23725625
      (see pubchem.ncbi.nlm.nih.gov/)
   iii. Unique Ingredient Identifier (UNII)→WOH-1JD9AR8
      (see fda.gov/ForIndustry/DataStandards/Substance-RegistrationSystem-UniqueIngredientIdentifi-erUNII/default.htm)

Formula V

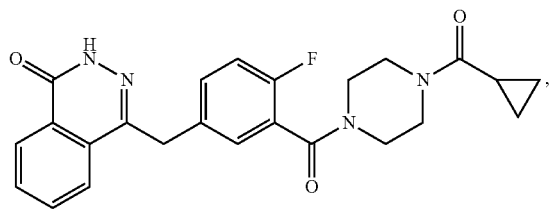

olaparib: 4-[(3-[4-cyclopropylcarbonyl)piperazin-1-yl]carbonyl)-4-fluorophenyl]methyl(2H)phthalazin-1-one b) CEP-9722
   i. CAS Number→916574-83-9
      (see cas.org/content/chemical-substances/faqs)

Formula VI

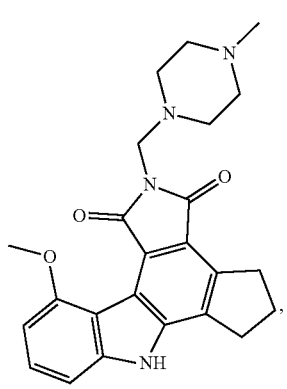

CEP-9722: 11-methoxy-2-((4-methylpiperazin-1-yl)methyl)-4,5,6,7-tetrahydro-1H-cyclopenta[a]pyrrolo[3,4-c]carbazole-1,3(2h)-dione c) BMN-673/talazoparib
   i. CAS Number→1207456-01-6
      (see cas.org/content/chemical-substances/faqs)
   ii. Unique Ingredient Identifier (UNII)→9QHX-048FRV Formula VII

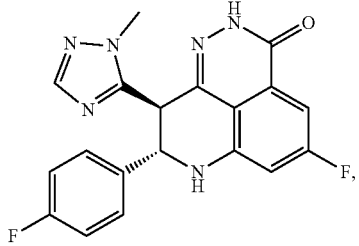

talazoparib: (8S,9R)-5-Fluoro-8-(4-fluorophenyl)-9-(1-methyl-1H-1,2,4-triazol-5-yl)-2,7,8,9,-tetrahydro-3H-pyrido[4,3,2-de]phthalazin-3-one d) Rucaparib
   i. CAS Number→283173-50-2
      (see cas.org/content/chemical-substances/faqs)
   ii. NCBI Pubchem reference→9931954
      (see pubchem.ncbi.nlm.nih.gov/)
   iii. Unique Ingredient Identifier (UNII)→8237F3U7EH
      (see fda.gov/ForIndustry/DataStandards/Substance-RegistrationSystem-UniqueIngredientIdentifi-erUNIII/default.htm)

Formula VIII

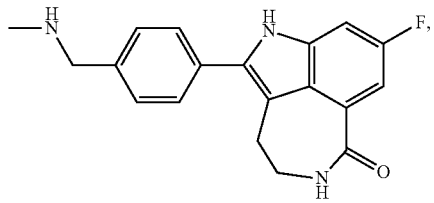

Rucaparib: 8-Fluoro-2-{4-[(methylamino)methyl]phenyl}-1,3,4,5-tetrahydro-6H-azepino[5,4,3-cd]indol-6-one e) Iniparib/SAR24-550/BSI-201
   i. CAS Number→160003-66-7
      (see cas.org/content/chemical-substances/faqs)
   ii. NCBI Pubchem reference→9796068
      (see pubchem.ncbi.nlm.nih.gov/)
   iii. Unique Ingredient Identifier (UNII)→2ZWI7-KHK8F
      (see fda.gov/ForIndustry/DataStandards/Substance-RegistrationSystem-UniqueIngredientIdentifi-erUNIII/default.htm)

Formula IX

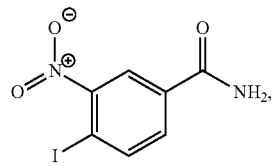

Iniparib: 4-Iodo-3-nitrobenzamide f) Veliparib (ABT-888)
   i. CAS Number→912444-00-9
      (see cas.org/content/chemical-substances/faqs)
   ii. NCBI Pubchem reference→11960529
      (see pubchem.ncbi.nlm.nih.gov/)
   iii. Unique Ingredient Identifier (UNII)→01O4-K0631N
      (see fda.gov/ForIndustry/DataStandards/Substance-RegistrationSystem-UniqueIngredientIdentifierUNII/default.htm)

Formula X

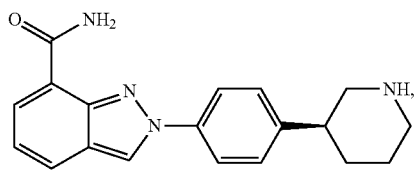

Veliparib: 2-((R)-2-Methylpyrrolidin-2-yl)-1H-benzimidazole-4-carboxamide g) Niraparib/MK-4827
   i. CAS Number→1038915-60-4
      (see cas.org/content/chemical-substances/faqs)
   ii. NCBI Pubchem reference→24958200
      (see pubchem.ncbi.nlm.nih.gov/)
   iii. Unique Ingredient Identifier (UNII)→HMC2-H89N35
      (see fda.gov/ForIndustry/DataStandards/Substance-RegistrationSystem-UniqueIngredientIdentifierUNII/default.htm)

Formula XI

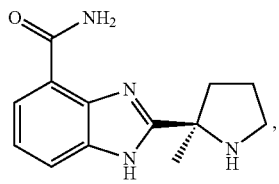

Niraparib: 2-[4-[(3S)-3-Piperidyl]phenyl]indazole-7-carboxamide h) BGB-290
   i. CAS Number→1820833-75-7
      (see cas.org/content/chemical-substances/faqs)
i) 3-aminobenzamide
   i. CAS Number→3544-24-9
      (see cas.org/content/chemical-substances/faqs)
   ii. NCBI Pubchem reference→1645
      (see pubchem.ncbi.nlm.nih.gov/)

Formula XII

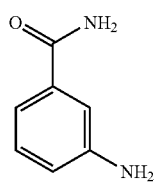

3-Aminobenzamide j) E7016
   i. CAS Number→902128-92-1
      (see cas.org/content/chemical-substances/faqs)

Formula XIII

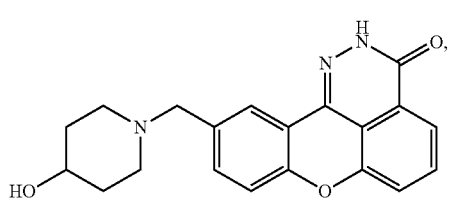

E706: Benzopyrano(4,3,2-de)phthalazin-3(2H)-one, 10-((4-hydroxy-1-piperidinyl)methyl)-

In some embodiments, PARP polypeptide is PARP1, which corresponds to Genbank accession no. AAA60137, version no. AAA60137.1, record update date: Jun. 23, 2010 08:48 AM. In one embodiment, the nucleic acid encoding PARP1 polypeptide corresponds to Genbank accession no. M18112, version no. M18112.1, record update date: Jun. 23, 2010 08:48 AM. In some embodiments, PARP1 polypeptide corresponds to Uniprot/Swiss-Prot accession No. P09874.

Agents that Upregulate HER2 Expression

An agent that "upregulates HER2 expression" means any chemical compound or biological molecule that increase the amount of HER2 protein on a tumour cell surface.

To examine the extent of enhancement samples or assays comprising a given, e.g., protein, gene, cell, or organism, are treated with a potential activating agent and are compared to control samples treated with an inactive control molecule. Control samples are assigned a relative expression value of 100%. Activation is achieved when the expression value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Specific agents that upregulate HER2 expression suitable for use as secondary agents in the present disclosure include:
   a) gemcitabine
      i. CAS Number→95058-81-4
         (see cas.org/content/chemical-substances/faqs)
      ii. NCBI Pubchem reference→60750
         (see pubchem.ncbi.nlm.nih.gov/)
      iii. DrugBank reference→DB00441
         (see drugbank.ca/)
      iv. Unique Ingredient Identifier (UNII)→B76N6SBZ8R
         (see fda.gov/ForIndustry/DataStandards/Substance-RegistrationSystem-UniqueIngredientIdentifierUNII/default.htm)

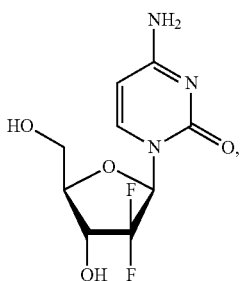

Formula XIV

Gemcitabine: 4-Amino-1-(2-doxy-2,2-
difluoro-β-D-erythro-pentofuranosyl)
pyrimidin-2(1H)-on b) tamoxifen
   i. CAS Number→10540-29-1
     (see cas.org/content/chemical-substances/faqs)
   ii. NCBI Pubchem reference→2733526
     (see pubchem.ncbi.nlm.nih.gov/)
   iii. DrugBank reference→DB00675
     (see drugbank.ca/)
   iv. Unique Ingredient Identifier (UNII)→094Z181Y45
     (see fda.gov/ForIndustry/DataStandards/Substance-RegistrationSystem-UniqueIngredientIdentifi-erUNII/default.htm)

Formula XV

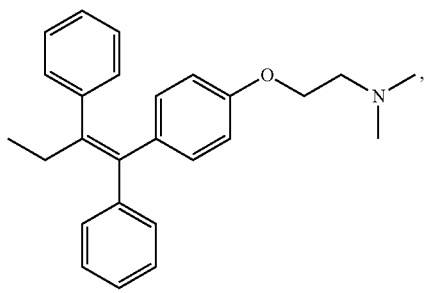

Tamoxifen: (Z)-2-[4-(1,2-diphenylbut-1-enyl)
phenoxy]-N,N-dimethylethanamine

Gemcitabine is the preferred agent that upregulated HER2.

AXLi

The secondary agent as described herein may be an AXL inhibitor.

"AXL inhibitor" means any chemical compound or biological molecule that reduces AXL signalling.

To examine the extent of inhibition of, e.g., AXL activity, samples or assays comprising a given, e.g., protein, gene, cell, or organism, are treated with a potential activating or inhibiting agent and are compared to control samples treated with an inactive control molecule. Control samples are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 20%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Inhibition of AXL with, for example, the AXL inhibitors TP0903 and BGB324 has been shown to decrease expression of DNA repair genes and to diminish the efficiency of the homologous recombination repair machinery. Consequently, AXL inhibition caused a state of HR-deficiency in the cells, making them sensitive to DNA damaging agents.

Combining ADC with AXLi including but not limited to BGB324 and TP0903 is advantageous because on the one hand, ADC will induce DNA damage in AXL-positive cancer cell lines, while on the other hand treatment with the AXLi will diminish the efficiency of the homologous recombination repair machinery making the cells more sensitive to the DNA damage induced by the PBD dimers hence resulting in accumulation of DNA damage leading to cancer cell death.

To show that co-treatment of AXL-positive cancer cell lines with ADC and the AXLi (including but not limited to BGB324 and TP0903) has an additive or synergistic antitumor effect, a panel of cell lines including, but not limited to MDA-MB-157 and SKLU1 will be co-treated with a range of concentration of both ADC and the AXLi BGB324 or TP-093. After incubation the in vitro cytotoxicity of the combinations (as determined by CellTiter-Glo® or MTS assays) will be measured.

Specific AXL inhibitors suitable for use as secondary agents in the present disclosure include:
  c) TP0903
    i. CAS Number→1341200-45-0
      (see cas.org/content/chemical-substances/faqs)

Formula XVI

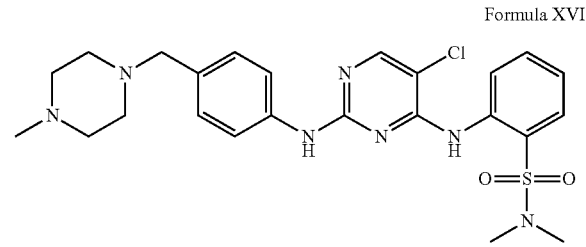

2-((5-chloro-2-((4-((4-methylpiperazin-1-yl)
methyl)phenyl)amino)pyrimidin-4-yl)amino)-
N,N-dimethylbenzenesulfonamide [TP0903]

d) BGB324
    i. CAS Number→1037624-75-1
      (see cas.org/content/chemical-substances/faqs)
    ii. Unique Ingredient Identifier (UNII)→0ICW2-LX8AS
      (see fda.gov/ForIndustry/DataStandards/Substance-RegistrationSystem-UniqueIngredientIdentifi-erUNII/default.htm)

Formula XVII

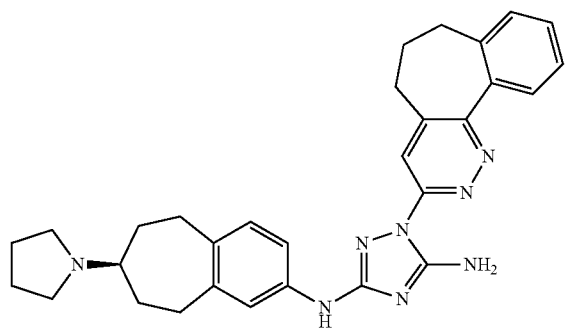

1-(6,7-dihydro-5H-benzo[2,3]cyclohepta[2,4-d]
pyridazin-3-yl)-3-N-[(7S)-7-pyrrolidin-1-yl-
6,7,8,9-tetrahydro-5H-benzo[7]annulen-3-yl]-
1,2,4-triazole-3,5-diamine [BGB324]

e) Gilteritinib (ASP2215)
  i. CAS Number→1254053-43-4
     (see cas.org/content/chemical-substances/faqs)

Formula XVIII

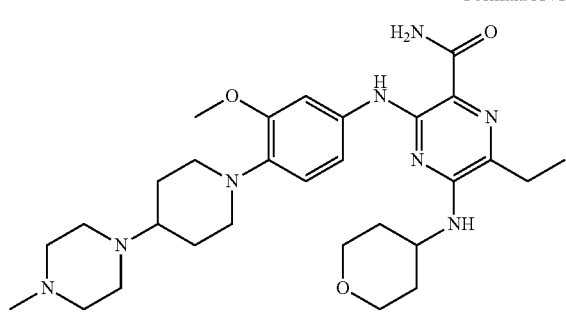

6-ethyl-3-((3-methoxy-4-(4-(4-methylpiperazin-1-yl)
piperidin-1-yl)phenyl)amino)-5-((tetrahydro-2H-pyran-4-yl)
amino)pyrazine-2-carboxamide [Gilteritinib]

f) Cabozantinib
  i. CAS Number→849217-68-1
     (see cas.org/content/chemical-substances/faqs)
  ii. Unique Ingredient Identifier (UNII)→1C39JW444G
     (see fda.gov/ForIndustry/DataStandards/Substance-
     RegistrationSystem-UniqueIngredientIdentifi-
     erUNII/default.htm)

Formula XIX

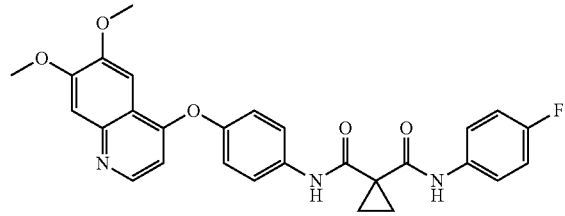

N-(4-((6,7-Dimethoxyquinolin-4-yl)oxy)phenyl)-N′-
(4-fluorophenyl)cyclopropane-1,1-dicarboxamide
[Cabozantinib]

g) SG17079
  i. CAS Number→1239875-86-5
     (see cas.org/content/chemical-substances/faqs)

Formula XX

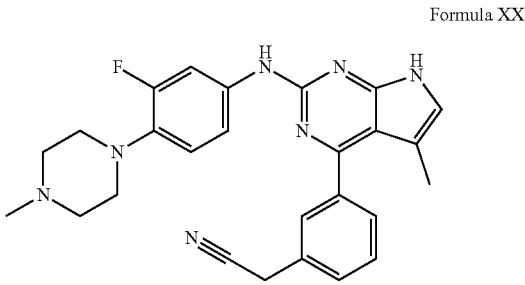

2-(3-(2-((3-fluoro-4-(4-methylpiperazin-1-yl)phenyl)amino)-
5-methyl-7H-pyrrolo[2,3-d]pyrimidin-4-yl)phenyl)
acetonitrile [SG17079]

h) Merestinib
  i. CAS Number→1206799-15-6
     (see cas.org/content/chemical-substances/faqs)

Formula XXI

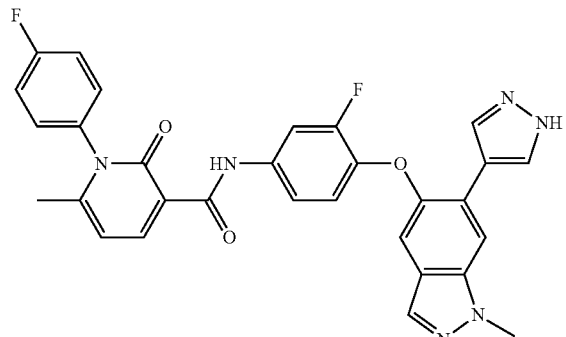

N-(3-Fluoro-4-{[1-methyl-6-(1H-pyrazol-4-yl)-1H-indazol-5-yl]
oxy}phenyl)-1-(4-fluorophenyl)-6-methyl-2-oxo-1,2-
dihydropyridine-3-carboxamide [Merestinib]

i) amuvatinib (MP-470)
  i. CAS Number→850879-09-3
     (see cas.org/content/chemical-substances/faqs)
  ii. Unique Ingredient Identifier (UNII)→SO9-
      S6QZB4R
     (see fda.gov/ForIndustry/DataStandards/Substance-
     RegistrationSystem-UniqueIngredientIdentifi-
     erUNII/default.htm)

Formula XXII

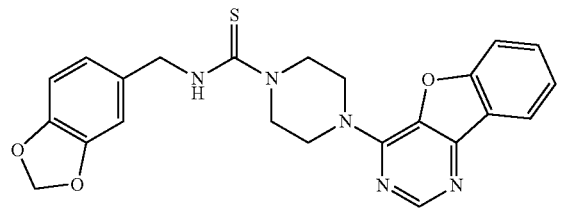

N-(1,3-benzodioxol-5-ylmethyl)-4-([1]benzofuro[3,2-d]
pyrimidin-4-yl)piperazine-1-carbothioamide [Amuvatinib]

j) bosutinib (SKI-606)
  i. CAS Number→380843-75-4
     (see cas.org/content/chemical-substances/faqs)
  ii. Unique Ingredient Identifier (UNII)→5018V4AEZ0
     (see fda.gov/ForIndustry/DataStandards/Substance-RegistrationSystem-UniqueIngredientIdentifierUNII/default.htm)

l) foretinib (GSK1363089/XL880)
  i. CAS Number→849217-64-7
     (see cas.org/content/chemical-substances/faqs)
  ii. Unique Ingredient Identifier (UNII)→81FH7VK1C4
     (see fda.gov/ForIndustry/DataStandards/Substance-RegistrationSystem-UniqueIngredientIdentifierUNII/default.htm)

Formula XXV

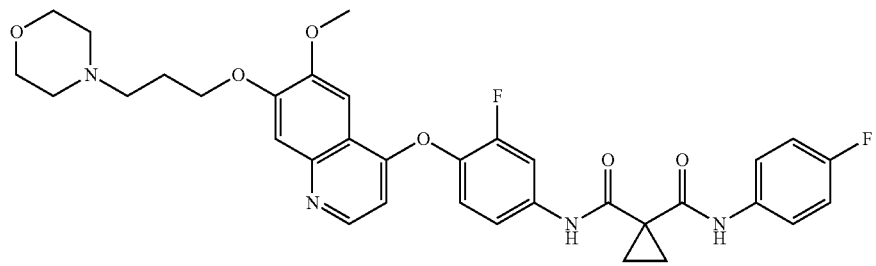

N1'-[3-fluoro-4-[[6-methoxy-7-(3-morpholinopropoxy)-4-quinolyl]oxy]phenyl]-N1-(4-fluorophenyl)cyclopropane-1,1-dicarboxamide [Foretinib]

Formula XXIII

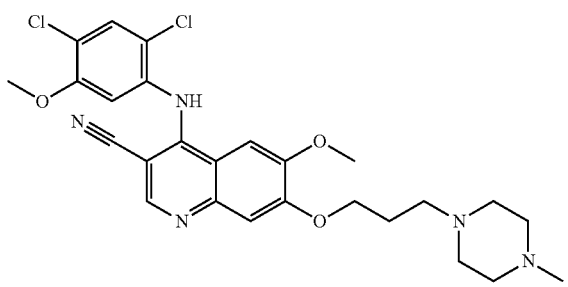

4-[(2,4-dichloro-5-methoxyphenyl)amino]-6-methoxy-7-[3-(4-methylpiperazin-1-yl)propoxy]quinoline-3-carbonitrile [Bosutinib]

k) MGCD265
  i. CAS Number→875337-44-3
     (see cas.org/content/chemical-substances/faqs)
  ii. Unique Ingredient Identifier (UNII)→93M6577H9D
     (see fda.gov/ForIndustry/DataStandards/Substance-RegistrationSystem-UniqueIngredientIdentifierUNII/default.htm)

Formula XXIV

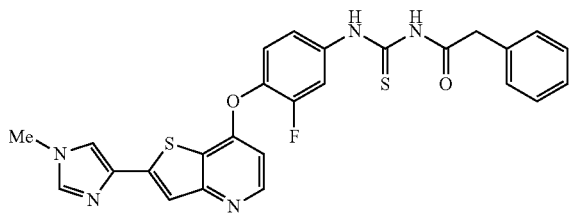

N-(3-fluoro-4-(2-(1-methyl-1H-imidazol-4-yl)thieno(3,2-b)pyridin-7-yloxy)phenylcarbamothioyl)-2-phenylacetamide [MGCD265]

BRAFi

The secondary agent as described herein may be an BRAF inhibitor.

"BRAF inhibitor" means any chemical compound or biological molecule that reduces BRAF activity.

To examine the extent of inhibition of, e.g., BRAF activity, samples or assays comprising a given, e.g., protein, gene, cell, or organism, are treated with a potential activating or inhibiting agent and are compared to control samples treated with an inactive control molecule. Control samples are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 20%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

B-Raf (BRAF) is a member of the Raf kinase family of growth signal transduction protein kinases. This protein plays a role in regulating the MAP kinase/ERKs signaling pathway, which affects cell division, differentiation, and secretion.

B-Raf is a serine/threonine-specific protein kinase. As such, it catalyzes the phosphorylation of serine and threonine residues in a consensus sequence on target proteins by ATP, yielding ADP and a phosphorylated protein as products. Since it is a highly regulated signal transduction kinase, B-Raf must first bind Ras-GTP before becoming active as an enzyme. Once B-Raf is activated, a conserved protein kinase catalytic core phosphorylates protein substrates by promoting the nucleophilic attack of the activated substrate serine or threonine hydroxyl oxygen atom on the γ-phosphate group of ATP through bimolecular nucleophilic substitution.

Mutations in BRAF have been found in cancers, including non-Hodgkin lymphoma, colorectal cancer, malignant melanoma, papillary thyroid carcinoma, non-small-cell lung carcinoma, adenocarcinoma of the lung, brain tumours including glioblastoma and pilocytic astrocytomas as well as inflammatory diseases like erdheim-chester disease. Mutation can lead to uncontrolled growth, especially in melanoma. For example, the V600E mutation in B-RAF is known to drive cell proliferation in melanoma mutated gene. Such mutations makes the mutant BRAF gene constitutively active, driving proliferation of the melanoma. By Inhibiting mutated B-RAF, cell proliferation is blocked and apoptosis (controlled cell death) is induced.

Examples of such potential combinations are BRAF inhibitors such as vemurafenib and dabrafenib. These BRAF inhibitors inhibits the B-RAF protein directly.

Combining ADC, which targets AXL positive tumors, with BRAFi is advantageous, because on the one hand, ADC will directly kill the AXL positive tumor cells via a mechanisms depending on DNA cross-linking resulting in apoptosis, while on the other hand, BRAFi will interfere with cell proliferation through inhibition of BRAF.

To show that ADC works synergistically with BRAFi, a panel of AXL (+) cell lines including, but not limited to MDA-MB231, NCI-H1299 and SNU12 cells, will be co-treated with a range of concentrations of both ADC and BRAFi. As negative controls, the same panel of cell lines will be co-treated with a range of concentrations of MEKi or with a range of concentration of ADC and vehicle. After incubation, the in vitro cytotoxicity of the combinations will be determined by an MTS assay. To determine the cytotoxicity, Cell viability is measured by adding MTS per well and incubating for 4 hours at 37 C. Percentage cell viability is calculated compared to the untreated control. Cytotoxic synergy is calculated by transforming the cell viability data into fraction affected, and calculating the combination index (Table 1) using the CalcuSyn analysis program.

Specific BRAF inhibitors suitable for use as secondary agents in the present disclosure include:
  a) vemurafenib
     i. CAS Number→918504-65-1
        (see cas.org/content/chemical-substances/faqs)
     ii. DrugBank reference→DB08881
        (see drugbank.ca/)
     iii. Unique Ingredient Identifier (UNII)→207SM-Y3FQT
        (see fda.gov/ForIndustry/DataStandards/Substance-RegistrationSystem-UniqueIngredientIdentifierUNII/default.htm)

Formula XXVI

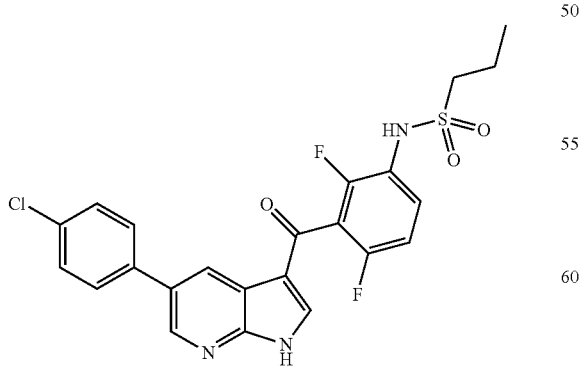

N-(3-{[5-(4-Chlorophenyl)-1H-pyrrolo[2,3-b]pyridin-3-yl]carbonyl}-2,4-difluorophenyl)propane-1-sulfonamide [vemurafenib]

b) PLX4720
   i. CAS Number→918505-84-7
      (see cas.org/content/chemical-substances/faqs)
   ii. Unique Ingredient Identifier (UNII)→EQY31-RO8HA
      (see fda.gov/ForIndustry/DataStandards/Substance-RegistrationSystem-UniqueIngredientIdentifierUNIII/default.htm)

Formula XXVII

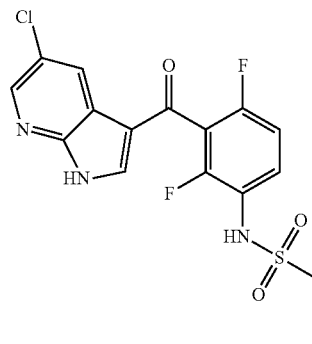

N-(3-(5-chloro-1H-pyrrolo[2,3-b]pyridin-3-carbonyl)-2,4-difluorophenyl)propane-1-sulfonamide [PLX4720]

c) dabrafenib
   i. CAS Number→1195765-45-7
      (see cas.org/content/chemical-substances/faqs)

Formula XXVIII

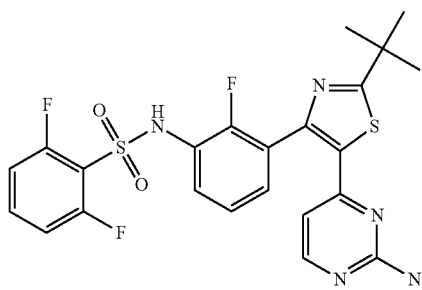

N-{3-[5-(2-aminopyrimidin-4-yl)-2-tert-butyl-1,3-thaizol-4-yl]-2-fluorophenyl}-2,6-difluorobenzenesulfonamide [dabrafenib]

d) Sorafenib
   i. CAS Number→284461-73-0
      (see cas.org/content/chemical-substances/faqs)
   ii. Unique Ingredient Identifier (UNII)→9ZOQ3TZI87
      (see fda.gov/ForIndustry/DataStandards/Substance-RegistrationSystem-UniqueIngredientIdentifierUNIII/default.htm)

Formula XXIX

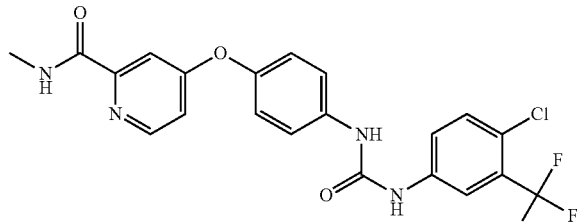

4-[4-[[4-chloro-3-(trifluoromethyl)phenyl]carbamoylamino]phenoxy]-N-methyl-pyridine-2-carboxamide [sorafenib]

e) Encorafenib
   i. CAS Number→1269440-17-6
      (see cas.org/content/chemical-substances/faqs)
   ii. Unique Ingredient Identifier (UNII)→8L7891MRB6
      (see fda.gov/ForIndustry/DataStandards/Substance-RegistrationSystem-UniqueIngredientIdentifierUNIII/default.htm)

Formula XXX

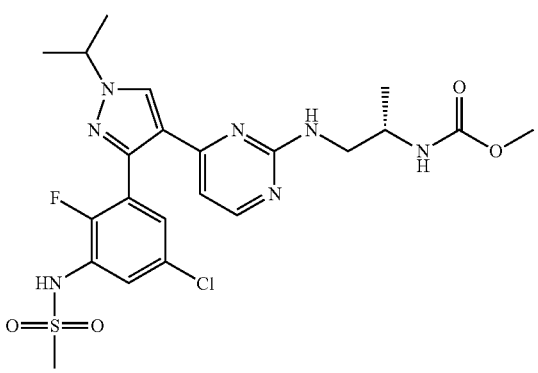

Methyl [(2S)-1-{[4-(3-{5-chloro-2-fluoro-3-[(methylsulfonyl)amino]phenyl}-1-isopropyl-1H-pyrazol-4-yl)-2-pyrimidinyl]amino}-2-propanyl]carbamate [encorafenib]

f)

GDC0879

Formula XXXI i. CAS →

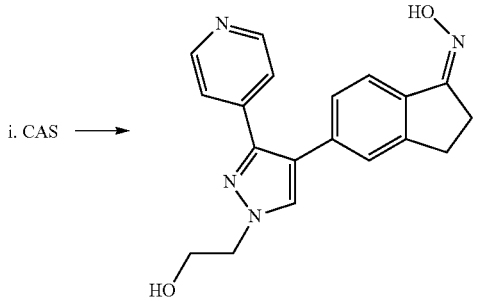

Number 905281-76-7 (see http://www.cas.org/content/chemical-substances/faqs)

(E)-2,3-Dihydro-5-(1-(2-hydroxyethyl)-3-(4-pyridinyl)-1H-pyrazol-4-yl]-1H-inden-1-one oxime [GDC0879]

MEKi

The secondary agent as described herein may be a MEK inhibitor.

"MEK inhibitor" means any chemical compound or biological molecule that reduces MEK1 and/or MEK2 activity.

MEK1 in humans is encoded by the MAP2K1 gene. MEK1 is a member of the dual-specificity protein kinase family that acts as a mitogen-activated protein (MAP) kinase kinase. MAP kinases, also known as extracellular signal-regulated kinases (ERKs), act as an integration point for multiple biochemical signals. This protein kinase lies upstream of MAP kinases and stimulates the enzymatic activity of MAP kinases upon activation by a wide variety of extra- and intracellular signals. As an essential component of the MAP kinase signal transduction pathway, this kinase is involved in many cellular processes such as proliferation, differentiation, transcription regulation and development.

MEK2 in humans is encoded by the MAP2K2 gene. The protein encoded by this gene is a dual specificity protein kinase that belongs to the MAP kinase kinase family. This kinase is known to play a critical role in mitogen growth factor signal transduction. It phosphorylates and thus activates MAPK1/ERK2 and MAPK3/ERK1.

To examine the extent of inhibition of, e.g., MEK activity, samples or assays comprising a given, e.g., protein, gene, cell, or organism, are treated with a potential activating or inhibiting agent and are compared to control samples treated with an inactive control molecule. Control samples are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 20%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Examples of suitable MEK inhibitors are Trametinib, Cobimetinib, Binimetinib and Selumetinib. A MEK inhibitor inhibits the mitogen-activated protein kinase kinase enzymes MEK1 and/or MEK2. Defects in the MAP/ERK pathway can lead uncontrolled growth, especially in melanoma.

Some MEK inhibitors, such as Trametinib, inhibit MEK1 and MEK2 and are approved for the treatment of patients with BRAF V600E mutated metastatic melanoma. As described above, the V600E mutation makes the mutant BRAF gene constitutively active, driven proliferation of the melanoma. By Inhibiting the MAP/ERK pathway, cell proliferation is blocked and apoptosis (controlled cell death) is induced.

Combining ADC, which targets AXL positive tumors, with MEKi is advantageous, because on the one hand, ADC will directly kill the AXL positive tumor cells via a mechanisms depending on DNA cross-linking resulting in apoptosis, while on the other hand, MEKi will interfere with cell proliferation through inhibition of the MAP/ERK cell signalling pathway.

To show that ADC works synergistically with MEKi, a panel of AXL (+) cell lines including, but not limited to MDA-MB231, H1299 and SNU12C cells, will be co-treated with a range of concentration of both ADC and MEKi. As negative controls, the same panel of cell lines will be co-treated with a range of concentrations of MEKi or with a range of concentration of ADC and vehicle. After incubation, the in vitro cytotoxicity of the combinations will be determined by an MTS assay. To determine the cytotoxicity, Cell viability is measured by adding MTS per well and incubating for 4 hours at 37 C. Percentage cell viability is calculated compared to the untreated control. Cytotoxic synergy is calculated by transforming the cell viability data into fraction affected, and calculating the combination index using the CalcuSyn analysis program.

Specific MEK inhibitors suitable for use as secondary agents in the present disclosure include:

a) Trametinib
  i. CAS Number→871700-17-3
    (see cas.org/content/chemical-substances/faqs)
  ii. Unique Ingredient Identifier (UNII)→33E86K87QN
    (see fda.gov/ForIndustry/DataStandards/Substance-RegistrationSystem-UniqueIngredientIdentifierUNII/default.htm)

Formula XXXII

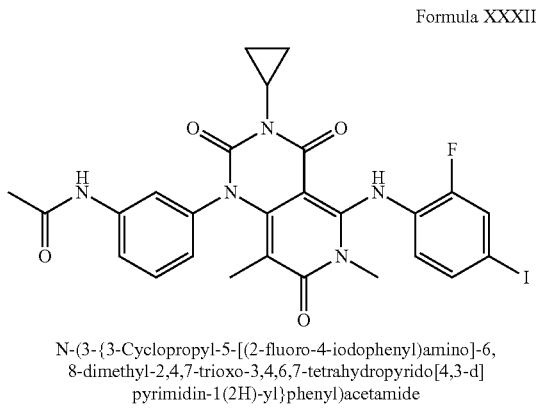 [SMILES: CC(=O)Nc1cccc(-n2c(=O)n(C3CC3)c(=O)c3c(Nc4ccc(I)cc4F)n(C)c(=O)c(C)c32)c1]

N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H)-yl}phenyl)acetamide b) Cobimetinib
  i. CAS Number→934660-93-2
    (see cas.org/content/chemical-substances/faqs)
  ii. Unique Ingredient Identifier (UNII)→ER29L26N1X
    (see fda.gov/ForIndustry/DataStandards/Substance-RegistrationSystem-UniqueIngredientIdentifierUNII/default.htm)

Formula XXXIII

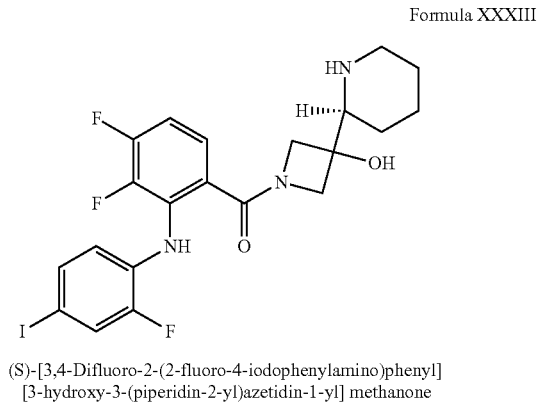 [SMILES: O=C(c1ccc(F)c(F)c1Nc1ccc(I)cc1F)N1CC(O)([C@@H]2CCCCN2)C1]

(S)-[3,4-Difluoro-2-(2-fluoro-4-iodophenylamino)phenyl][3-hydroxy-3-(piperidin-2-yl)azetidin-1-yl] methanone c) Binimetinib
  i. CAS Number→606143-89-9
    (see cas.org/content/chemical-substances/faqs)
  ii. Unique Ingredient Identifier (UNII)→181R97MR71
    (see fda.gov/ForIndustry/DataStandards/Substance-RegistrationSystem-UniqueIngredientIdentifierUNII/default.htm)

Formula XXIV

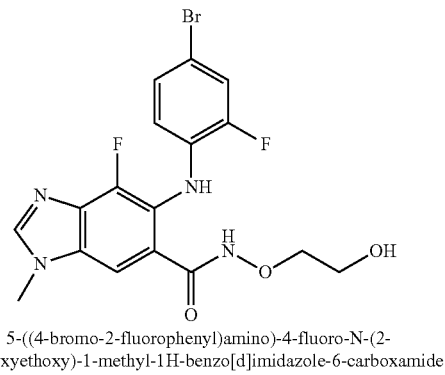

5-((4-bromo-2-fluorophenyl)amino)-4-fluoro-N-(2-hydroxyethoxy)-1-methyl-1H-benzo[d]imidazole-6-carboxamide d) Selumetinib
  i. CAS Number→606143-52-6
    (see cas.org/content/chemical-substances/faqs)
  ii. Unique Ingredient Identifier (UNII)→6UH911579U
    (see fda.gov/ForIndustry/DataStandards/Substance-RegistrationSystem-UniqueIngredientIdentifierUNIII/default.htm)

Formula XXXV

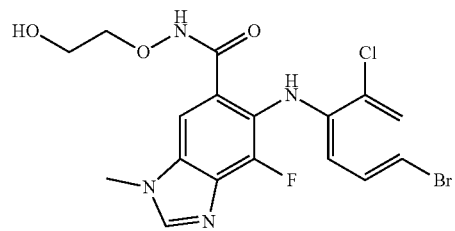

6-(4-bromo-2-chloroanilino)-7-fluoro-N-(2-hydroxyethoxy)-3-methylbenzimidazole-5-carboxamide e) PD-325901
  i. CAS Number→391210-10-9
    (see cas.org/content/chemical-substances/faqs)
  ii. Unique Ingredient Identifier (UNII)→86K0-J5AK6M
    (see fda.gov/ForIndustry/DataStandards/Substance-RegistrationSystem-UniqueIngredientIdentifierUNIII/default.htm)

Formula XXXVI

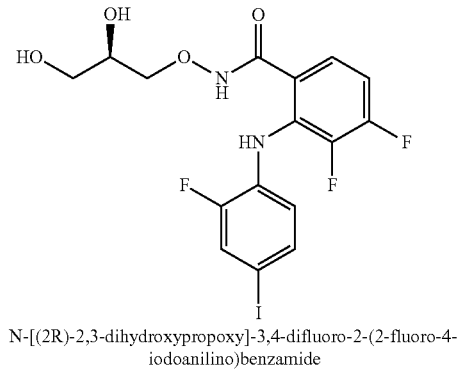

N-[(2R)-2,3-dihydroxypropoxy]-3,4-difluoro-2-(2-fluoro-4-iodoanilino)benzamide f) CI-1040
   i. CAS Number→212631-79-3
      (see cas.org/content/chemical-substances/faqs)
   ii. Unique Ingredient Identifier (UNII)→R3K9Y00J04
      (see fda.gov/ForIndustry/DataStandards/Substance-RegistrationSystem-UniqueIngredientIdentifierUNII/default.htm)

Formula XXXVII

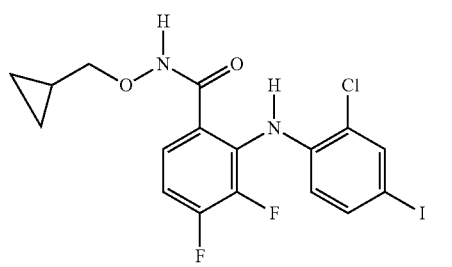

2-[(2-chloro-4-iodophenyl)amino]-N-(cycloprprylmethoxy)-3,4-difluoro-benzamide g) PD035901

PD035901
i. CAS

Formula XXXVIII

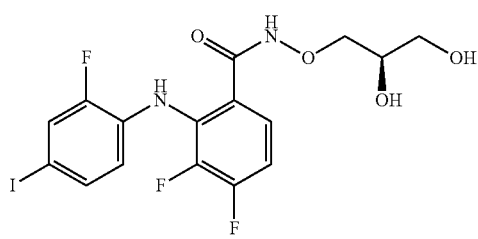

Number → 391210-10-9
(see http://www.cas.org/content/chemical-substances/faqs)
PD035901 h) U0126
   i. CAS Number→218601-62-8
      (see cas.org/content/chemical-substances/faqs)
   ii. Unique Ingredient Identifier (UNII)→8027P94HLL
      (see fda.gov/ForIndustry/DataStandards/Substance-RegistrationSystem-UniqueIngredientIdentifierUNII/default.htm)

Formula XXXIX

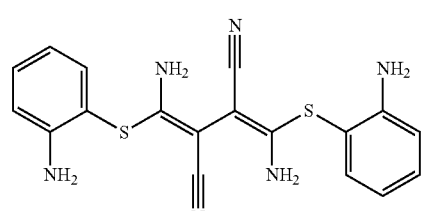

1,4-diamino-2,3-dicyano-1,4-bis (2-aminophenylthio)butadiene i) TAK-733
   iii. CAS Number→1035555-63-5
      (see cas.org/content/chemical-substances/faqs)
   iv. Unique Ingredient Identifier (UNII)→5J61HSP0QJ
      (see fda.gov/ForIndustry/DataStandards/Substance-RegistrationSystem-UniqueIngredientIdentifierUNII/default.htm)

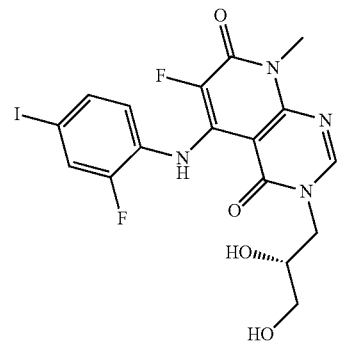

3-[(2R)-2,3-dihydroxypropyl]-6-fluoro-5-(2-fluoro-4-iodoanilino)-8-methylpyrido[2,3-d]pyrimidine-4,7-dione In some embodiments, BRAF polypeptide corresponds to Genbank accession no. AAA35609, version no. AAA35609.2, record update date: Jun. 23, 2010 09:41 AM. In one embodiment, the nucleic acid encoding BRAF polypeptide corresponds to Genbank accession no. M95712, version no. M95712.2, record update date: Jun. 23, 2010 09:41 AM. In some embodiments, BRAF polypeptide corresponds to Uniprot/Swiss-Prot accession No. P15056.

In some embodiments, MEK1 polypeptide corresponds to Genbank accession no. AAA36318, version no. AAA36318.1, record update date: Jun. 23, 2010 08:48 AM. In one embodiment, the nucleic acid encoding MEK1 polypeptide corresponds to Genbank accession no. L05624, version no. L05624.1, record update date: Jun. 23, 2010 08:48 AM. In some embodiments, MEK1 polypeptide corresponds to Uniprot/Swiss-Prot accession No. Q02750.

In some embodiments, MEK2 polypeptide corresponds to Genbank accession no. AAH00471, version no. AAH00471.1, record update date: Sep. 23, 2014 03:30 PM. In one embodiment, the nucleic acid encoding MEK2 polypeptide corresponds to Genbank accession no. BC000471, version no. BC000471.2, record update date: Sep. 23, 2014 03:30 PM. In some embodiments, MEK2 polypeptide corresponds to Uniprot/Swiss-Prot accession No. P36507.

Advantageous Properties of the Described Combinations

Both the ADC and secondary agent when used as a single agent in isolation have demonstrated clinical utility—for example, in the treatment of cancer. However, as described herein, combination of the ADC and secondary agent is expected to provide one or more of the following advantages over treatment with either ADC or secondary agent alone:
  1) effective treatment of a broader range of cancers;
  2) effective treatment of resistant or refractory forms of disorders such as cancer, and individuals with disorders such as cancer who have relapsed after a period of remission;
  3) increased response rate to treatment; and/or
  4) Increased durability of treatment.

Effective treatment of a broader range of cancers as used herein means that following treatment with the combination a complete response is observed with a greater range of recognised cancer types. That is, a complete response is seen from cancer types not previously reported to completely respond to either ADC or secondary agent alone.

Effective treatment of a resistant, refractory, or relapsed forms as used herein means that following treatment with the combination a complete response is observed in individuals that are either partially or completely resistant or refractory to treatment with either ADC or secondary agent alone (for example, individuals who show no response or only partial response following treatment with either agent alone, or those with relapsed disorder). In some embodiments, a complete response following treatment with the ADC/secondary agent combination is observed at least 10% of individuals that are either partially or completely resistant or refractory to treatment with either ADC or secondary agent alone. In some embodiments, a complete response following treatment with the ADC/secondary agent combination is observed at least 20%, at least 30%, at least 40%, at least 50%, at least 60%, at least 70%, at least 80%, at least 90%, at least 95%, at least 98%, or at least 99% of individuals that are either partially or completely resistant or refractory to treatment with either ADC or secondary agent alone.

Increased response rate to treatment as used herein means that following treatment with the combination a complete response is observed in a greater proportion of individuals than is observed following treatment with either ADC or secondary agent alone. In some embodiments, a complete response following treatment with the ADC/secondary agent combination is observed at least 10% of treated individuals. In some embodiments, a complete response following treatment with the ADC/secondary agent combination is observed at least 20%, at least 30%, at least 40%, at least 50%, at least 60%, at least 70%, at least 80%, at least 90%, at least 95%, at least 98%, or at least 99% of treated individuals.

Increased durability of treatment as used herein means that average duration of complete response in individuals treated with the combination is longer than in individuals who achieve complete response following treatment with either ADC or secondary agent alone. In some embodiments, the average duration of a complete response following treatment with the ADC/secondary agent combination is at least 6 months. In some embodiments, the average duration of a complete response following treatment with the ADC/secondary agent combination is at least 12 months, at least 18 months, at least 24 months, at least 3 years, at least 4 years, at least 5 years, at least 6 years, at least 7 years, at least 8 years, at least 9 years, at least 10 years, at least 15 years, or at least 20 years.

'Complete response' is used herein to mean the absence of any clinical evidence of disease in an individual. Evidence may be assessed using the appropriate methodology in the art, for example CT or PET scanning, or biopsy where appropriate. The number of doses required to achieve complete response may be one, two, three, four, five, ten or more. In some embodiments the individuals achieve complete response no more than a year after administration of the first dose, such as no more than 6 months, no more than 3 months, no more than a month, no more than a fortnight, or no more than a week after administration of the first dose.

Treated Disorders

The combined therapies described herein include those with utility for anticancer activity. In particular, in certain aspects the therapies include an antibody conjugated, i.e. covalently attached by a linker, to a PBD drug moiety, i.e. toxin. When the drug is not conjugated to an antibody, the PBD drug has a cytotoxic effect. The biological activity of the PBD drug moiety is thus modulated by conjugation to an antibody. The antibody-drug conjugates (ADC) of the disclosure selectively deliver an effective dose of a cytotoxic agent to tumor tissue whereby greater selectivity, i.e. a lower efficacious dose, may be achieved.

Thus, in one aspect, the present disclosure provides combined therapies comprising administering an ADC which binds a first target protein for use in therapy, wherein the method comprises selecting a subject based on expression of the target protein.

In one aspect, the present disclosure provides a combined therapy with a label that specifies that the therapy is suitable for use with a subject determined to be suitable for such use. The label may specify that the therapy is suitable for use in a subject has expression of the first target protein, such as overexpression of the first target protein. The label may specify that the subject has a particular type of cancer.

The first target protein is preferably AXL. The disorder may be a proliferative disease, for example a cancer such as breast, lung, gastric, head and neck, colorectal, renal, pancreatic, uterine, hepatic, bladder, endometrial and prostate cancers as well as lymphomas (e.g., non-Hodgkin's lymphoma, NHL) and leukemia (particularly acute myeloid leukemia, AML). The disorder may be an immune disorder, cardiovascular disorder, thrombosis, diabetes, immune checkpoint disorder, or fibrotic disorder (fibrosis) such as strabmisus, scleroderma, keloid, Nephrogenic systemic fibrosis, pulmonary fibrosis, idiopathic pulmonary fibrosis (IPF), cystic fibrosis (CF), systemic sclerosis, cardiac fibrosis, non-alcoholic steatohepatitis (NASH), other types of liver fibrosis, primary biliary cirrhosis, renal fibrosis, cancer, and atherosclerosis. The label may specify that the subject has a AXL+ cancer.

In a further aspect there is also provided a combined therapy as described herein for use in the treatment of a proliferative disease. Another aspect of the present disclosure provides the use of a conjugate compound in the manufacture of a medicament for treating a proliferative disease.

One of ordinary skill in the art is readily able to determine whether or not a candidate combined therapy treats a proliferative condition for any particular cell type. For example, assays which may conveniently be used to assess the activity offered by a particular compound are described below.

The combined therapies described herein may be used to treat a proliferative disease. The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g. histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), lymphomas, leukemias, psoriasis, bone diseases, fibroproliferative disorders (e.g. of connective tissues), and atherosclerosis. Cancers of particular interest include, but are not limited to, leukemias and ovarian cancers.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

Disorders of particular interest include, but are not limited to cancers, including metastatic cancers and metastatic cancer cells, such as circulating tumour cells, which may be found circulating in body fluids such as blood or lymph. Cancers of particular interest include breast, lung, gastric, head and neck, colorectal, renal, pancreatic, uterine, hepatic, bladder, endometrial and prostate cancers as well as lymphomas (e.g., non-Hodgkin's lymphoma, NHL) and leukemia (particularly acute myeloid leukemia, AML).

Other disorders of interest include any condition in which Axl is overexpressed, or wherein Axl antagonism will provide a clinical benefit. These include immune disorders, cardiovascular disorders, thrombosis, diabetes, immune checkpoint disorders, fibrotic disorders (fibrosis), or proliferative diseases such as cancer, particularly metastatic cancer. Furthermore, Axl is known to play a role in many cancers of epithelial origin.

Fibrotic disorders of interest include strabmisus, scleroderma, keloid, Nephrogenic systemic fibrosis, pulmonary fibrosis, idiopathic pulmonary fibrosis (IPF), cystic fibrosis (CF), systemic sclerosis, cardiac fibrosis, non-alcoholic steatohepatitis (NASH), other types of liver fibrosis, primary biliary cirrhosis, renal fibrosis, cancer, and atherosclerosis. In these diseases, the chronic development of fibrosis in tissue leads to marked alterations in the architecture of the affected organs and subsequently cause defective organ function. As a result of this process of sustained attrition to organs, many diseases that involve fibrosis are often progressive conditions and have a poor long-term prognosis (see Rockey, D. C., Bell, P. D. and Hill, J. A. (2015), N. Engl. Med., Vol. 372, pp. 1138-1149).

The proliferative disease may be characterised by the presence of a neoplasm comprising both AXL+ve and AXL−ve cells.

The proliferative disease may be characterised by the presence of a neoplasm composed of AXL−ve neoplastic cells, optionally wherein the AXL−ve neoplastic cells are associated with AXL+ve non-neoplastic cells.

The target neoplasm or neoplastic cells may be all or part of a solid tumour.

"Solid tumor" herein will be understood to include solid haematological cancers such as lymphomas (Hodgkin's lymphoma or non-Hodgkin's lymphoma) which are discussed in more detail herein.

Solid tumors may be neoplasms, including non-haematological cancers, comprising or composed of AXL+ve neoplastic cells. Solid tumors may be neoplasms, including non-haematological cancers, infiltrated with AXL+ve cells, such as AXL+ve immune suppressive dendritic cells, NK cells, or macrophages; such solid tumours may lack expression of AXL (that is, comprise or be composed of AXL−ve neoplastic cells).

It is contemplated that the combined therapies of the present disclosure may be used to treat various diseases or disorders, e.g. characterized by the overexpression of a tumor antigen. Exemplary conditions or hyperproliferative disorders include benign or malignant tumors; leukemia, haematological, and lymphoid malignancies. Others include neuronal, glial, astrocytal, hypothalamic, glandular, macrophagal, epithelial, stromal, blastocoelic, inflammatory, angiogenic and immunologic, including autoimmune disorders and graft-versus-host disease (GVHD).

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Autoimmune diseases for which the combined therapies may be used in treatment include rheumatologic disorders (such as, for example, rheumatoid arthritis, Sjögren's syndrome, scleroderma, lupus such as SLE and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, for example, inflammatory bowel diseases (e.g. ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, graft-versus-host disease (GVHD), and autoimmune endocrine disorders (such as, for example, diabetic-related autoimmune diseases such as insulin-dependent diabetes mellitus (IDDM), Addison's disease, and autoimmune thyroid disease (e.g. Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

In some aspects, the subject has a proliferative disorder selected from a cancer such as breast, lung, gastric, head and neck, colorectal, renal, pancreatic, uterine, hepatic, bladder, endometrial and prostate cancers as well as lymphomas (e.g., non-Hodgkin's lymphoma, NHL) and leukemia (particularly acute myeloid leukemia, AML). In some aspects, the subject has a disorder selected from an immune disorder, cardiovascular disorder, thrombosis, diabetes, immune checkpoint disorder, or fibrotic disorder (fibrosis) such as strabmisus, scleroderma, keloid, Nephrogenic systemic fibrosis, pulmonary fibrosis, idiopathic pulmonary fibrosis (IPF), cystic fibrosis (CF), systemic sclerosis, cardiac fibrosis, non-alcoholic steatohepatitis (NASH), other types of liver fibrosis, primary biliary cirrhosis, renal fibrosis, cancer, and atherosclerosis. The label may specify that the subject has a AXL+ cancer. Breast cancer and AML are cancers of particular interest.

In some aspects, the subject has a proliferative disease may be characterised by the presence of a neoplasm comprising both AXL+ve and AXL−ve cells.

The proliferative disease may be characterised by the presence of a neoplasm composed of AXL−ve neoplastic cells, optionally wherein the AXL−ve neoplastic cells are associated with AXL+ve non-neoplastic cells.

The target neoplasm or neoplastic cells may be all or part of a solid tumour.

"Solid tumor" herein will be understood to include solid haematological cancers such as lymphomas (Hodgkin's lymphoma or non-Hodgkin's lymphoma) which are discussed in more detail herein.

Solid tumors may be neoplasms, including non-haematological cancers, comprising or composed of AXL+ve neoplastic cells. Solid tumors may be neoplasms, including non-haematological cancers, infiltrated with AXL+ve cells, such as AXL+ve immune suppressive dendritic cells, NK cells, or macrophages; such solid tumours may lack expression of AXL (that is, comprise or be composed of AXL−ve neoplastic cells).

Patient Selection

In certain aspects, the individuals are selected as suitable for treatment with the combined treatments before the treatments are administered.

As used herein, individuals who are considered suitable for treatment are those individuals who are expected to benefit from, or respond to, the treatment. Individuals may have, or be suspected of having, or be at risk of having cancer. Individuals may have received a diagnosis of cancer. In particular, individuals may have, or be suspected of having, or be at risk of having, lymphoma. In some cases, individuals may have, or be suspected of having, or be at risk of having, a solid cancer that has tumour associated non-tumor cells that express a first target protein, such as infiltrating cells that express a first target protein.

In some aspects, individuals are selected on the basis of the amount or pattern of expression of a first target protein. In some aspects, the selection is based on expression of a first target protein at the cell surface.

In certain aspects, the target is a second target protein. In some aspects, the selection is based on expression of a second target protein at the cell surface.

In some aspects, the selection is based on levels of both a first target protein and a second target protein at the cell surface.

In some cases, expression of the target in a particular tissue of interest is determined.

For example, in a sample of lymphoid tissue or tumor tissue. In some cases, systemic expression of the target is determined. For example, in a sample of circulating fluid such as blood, plasma, serum or lymph.

In some aspects, the individual is selected as suitable for treatment due to the presence of target expression in a sample. In those cases, individuals without target expression may be considered not suitable for treatment.

In other aspects, the level of target expression is used to select a individual as suitable for treatment. Where the level of expression of the target is above a threshold level, the individual is determined to be suitable for treatment.

In some aspects, the presence of a first target protein and/or a second target protein in cells in the sample indicates that the individual is suitable for treatment with a combination comprising an ADC and a secondary agent. In other aspects, the amount of first target protein and/or a second target protein expression must be above a threshold level to indicate that the individual is suitable for treatment. In some aspects, the observation that first target protein and/or a second target protein localisation is altered in the sample as compared to a control indicates that the individual is suitable for treatment.

In some aspects, an individual is indicated as suitable for treatment if cells obtained from lymph node or extra nodal sites react with antibodies against first target protein and/or a second target protein as determined by IHC.

In some aspects, a patient is determined to be suitable for treatment if at least 5%, 10%, 15%, 20%, 25%, 30%, 35%, 40%, 45%, 50%, 55%, 60%, 65%, 70%, 75%, 80%, 85%, 90% or more of all cells in the sample express a first target protein. In some aspects disclosed herein, a patient is determined to be suitable for treatment if at least at least 10% of the cells in the sample express a first target protein.

In some aspects, a patient is determined to be suitable for treatment if at least 5%, 10%, 15%, 20%, 25%, 30%, 35%, 40%, 45%, 50%, 55%, 60%, 65%, 70%, 75%, 80%, 85%, 90% or more of all cells in the sample express a second target protein. In some aspects disclosed herein, a patient is determined to be suitable for treatment if at least at least 10% of the cells in the sample express a second target protein.

The first target protein is preferably AXL.

The second target protein may be PD1, PDL1, GITR, OX40, CTLA, PARPi, MEK1, MEK2, or BRAF. The second target protein is preferably PD-L1.

Samples

The sample may comprise or may be derived from: a quantity of blood; a quantity of serum derived from the individual's blood which may comprise the fluid portion of the blood obtained after removal of the fibrin clot and blood cells; a quantity of pancreatic juice; a tissue sample or biopsy; or cells isolated from said individual.

A sample may be taken from any tissue or bodily fluid. In certain aspects, the sample may include or may be derived from a tissue sample, biopsy, resection or isolated cells from said individual.

In certain aspects, the sample is a tissue sample. The sample may be a sample of tumor tissue, such as cancerous tumor tissue. The sample may have been obtained by a tumor biopsy. In some aspects, the sample is a lymphoid tissue sample, such as a lymphoid lesion sample or lymph node biopsy. In some cases, the sample is a skin biopsy.

In some aspects the sample is taken from a bodily fluid, more preferably one that circulates through the body. Accordingly, the sample may be a blood sample or lymph sample. In some cases, the sample is a urine sample or a saliva sample.

In some cases, the sample is a blood sample or blood-derived sample. The blood derived sample may be a selected fraction of a individual's blood, e.g. a selected cell-containing fraction or a plasma or serum fraction.

A selected cell-containing fraction may contain cell types of interest which may include white blood cells (WBC), particularly peripheral blood mononuclear cells (PBC) and/or granulocytes, and/or red blood cells (RBC). Accordingly, methods according to the present disclosure may involve detection of a first target polypeptide or nucleic acid in the blood, in white blood cells, peripheral blood mononuclear cells, granulocytes and/or red blood cells.

The sample may be fresh or archival. For example, archival tissue may be from the first diagnosis of an individual, or a biopsy at a relapse. In certain aspects, the sample is a fresh biopsy.

The first target polypeptide is preferably AXL.

Individual Status

The individual may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the individual may be any of its forms of development, for example, a foetus. In one preferred embodiment, the individual is a human. The terms "subject", "patient" and "individual" are used interchangeably herein.

In some cases the individual has, is suspected of having, or has received a diagnosis of, a proliferative disease characterised by the presence of a neoplasm comprising both AXL+ve and AXL−ve cells. The neoplasm may be composed of AXL−ve neoplastic cells, optionally wherein the AXL−ve neoplastic cells are associated with AXL+ve non-neoplastic cells. The target neoplasm or neoplastic cells may be all or part of a solid tumour. The solid tumour may be a neoplasm, including a non-haematological cancer, comprising or composed of AXL+ve neoplastic cells. The solid tumour may be a neoplasm, including a non-haematological cancer, infiltrated with AXL+ve cells, such as AXL+ve immune suppressive dendritic cells, NK cells, or macrophages; such solid tumours may lack expression of AXL (that is, comprise or be composed of AXL−ve neoplastic cells).

In some aspects disclosed herein, an individual has, or is suspected as having, or has been identified as being at risk of cancer. In some aspects disclosed herein, the individual has already received a diagnosis of cancer. The individual may have received a diagnosis of a cancer such as breast, lung, gastric, head and neck, colorectal, renal, pancreatic, uterine, hepatic, bladder, endometrial and prostate cancers as well as lymphomas (e.g., non-Hodgkin's lymphoma, NHL) and leukemia (particularly acute myeloid leukemia, AML). Breast cancer and AML are cancers of particular interest.

In some aspects disclosed herein, an individual has, or is suspected as having, or has been identified as being at risk of, or has received a diagnosis of an immune disorder, cardiovascular disorder, thrombosis, diabetes, immune checkpoint disorder, or fibrotic disorder (fibrosis) such as strabmisus, scleroderma, keloid, Nephrogenic systemic fibrosis, pulmonary fibrosis, idiopathic pulmonary fibrosis (IPF), cystic fibrosis (CF), systemic sclerosis, cardiac fibrosis, non-alcoholic steatohepatitis (NASH), other types of liver fibrosis, primary biliary cirrhosis, renal fibrosis, cancer, and atherosclerosis.

In some cases, the individual has received a diagnosis of a solid cancer containing AXL+ expressing infiltrating cells.

The Individual may be undergoing, or have undergone, a therapeutic treatment for that cancer. The subject may, or may not, have previously received ADC×AXL. In some cases the cancer is breast cancer or AML.

Controls

In some aspects, target expression in the individual is compared to target expression in a control. Controls are useful to support the validity of staining, and to identify experimental artefacts.

In some cases, the control may be a reference sample or reference dataset. The reference may be a sample that has been previously obtained from a individual with a known degree of suitability. The reference may be a dataset obtained from analyzing a reference sample.

Controls may be positive controls in which the target molecule is known to be present, or expressed at high level, or negative controls in which the target molecule is known to be absent or expressed at low level.

Controls may be samples of tissue that are from individuals who are known to benefit from the treatment. The tissue may be of the same type as the sample being tested. For example, a sample of tumor tissue from a individual may be compared to a control sample of tumor tissue from a individual who is known to be suitable for the treatment, such as a individual who has previously responded to the treatment.

In some cases the control may be a sample obtained from the same individual as the test sample, but from a tissue known to be healthy. Thus, a sample of cancerous tissue from a individual may be compared to a non-cancerous tissue sample.

In some cases, the control is a cell culture sample.

In some cases, a test sample is analyzed prior to incubation with an antibody to determine the level of background staining inherent to that sample.

In some cases an isotype control is used. Isotype controls use an antibody of the same class as the target specific antibody, but are not immunoreactive with the sample. Such controls are useful for distinguishing non-specific interactions of the target specific antibody.

The methods may include hematopathologist interpretation of morphology and immunohistochemistry, to ensure accurate interpretation of test results. The method may involve confirmation that the pattern of expression correlates with the expected pattern.

For example, where the amount of a first target protein and/or a second target protein expression is analyzed, the method may involve confirmation that in the test sample the expression is observed as membrane staining, with a cytoplasmic component. The method may involve confirmation that the ratio of target signal to noise is above a threshold level, thereby allowing clear discrimination between specific and non-specific background signals.

The first target protein is preferably AXL.

The second target protein may be PD1, PDL1, GITR, OX40, CTLA, PARPi, MEK1, MEK2, or BRAF. The second target protein is preferably PD-L1.

Methods of Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount" or "effective amount" as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

Disclosed herein are methods of therapy. Also provided is a method of treatment, comprising administering to a subject in need of treatment a therapeutically-effective amount of an ADC and a secondary agent. The term "therapeutically effective amount" is an amount sufficient to show benefit to a subject. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors. The subject may have been tested to determine their eligibility to receive the treatment according to the methods disclosed herein. The method of treatment may comprise a step of determining whether a subject is eligible for treatment, using a method disclosed herein.

The ADC may comprise an anti-AXL antibody. The ADC may comprise a drug which is a PBD dimer. The ADC may be an anti-AXL–ADC, and in particular, ADCxAXL. The ADC may be an ADC disclosed in GB1702029.8, GB1719906.8, or PCT/EP2018/053163.

The secondary agent may be:
(a) a PD1 antagonist, such as pembrolizumab, nivolumab, MEDI00680, PDR001 (spartalizumab), Camrelizumab, AUNP12, Pidilizumab, Cemiplimab (REGN-2810), AMP-224, BGB-A317 (Tisleizumab), or BGB-108;
(b) a PD-L1 antagonist, such as atezolizumab (Tecentriq), BMS-936559/MDX-1105, durvalumab/MED14736, or MSB0010718C (Avelumab);
(c) a GITR (Glucocorticoid-Induced TNFR-Related protein) agonist, such as MEDI1873, TRX518, GWN323, MK-1248, MK-4166, BMS-986156 or INCAGN1876;
(d) an OX40 agonist, such as MED10562, MED16383, MOXR0916, RG7888, OX40mAb24, INCAGN1949, GSK3174998, or PF-04518600;
(e) a CTLA-4 antagonist, such as ipilimumab (brand name Yervoy) or Tremelimumab (Originally developed by Pfizer, now Medimmune);
(f) Fludarabine or Cytarabine;
(g) a hypomethylating agent, such as cytidine analogs—for example, 5-azacytidine (azacitidine) and 5-aza-2'-deoxycytidine (decitabine); or
(h) a PARP inhibitor (PARPi), such as Olaparib, CEP-9722, BMN-673/talazoparib, Rucaparib, Iniparib/SAR24-550/BSI-201, Veliparib (ABT-888), Niraparib/MK-4827, BGB-290, 3-aminobenzamide, and E7016;
(i) an agent that upregulates HER2 expression, such as gemcitabine and tamoxifen;
(j) an AXL-kinase inhibitor (AXLi) such as BGB324 (bemcentinib), TP0903, Gilteritinib (ASP2215), Cabozantinib (XL184), SG17079, Merestinib, amuvatinib (MP-470), bosutinib (SKI-606), MGCD265, and foretinib (GSK1363089/XL880);
(k) a BRAF inhibitor (BRAFi), such as vemurafenib, PLX4720, dabrafenib, Sorafenib, Encorafenib, and GDC0879; or
(l) a MEK inhibitor (MEKi), such as Trametinib, Cobimetinib, Binimetinib, Selumetinib, PD-325901, CI-1040, PD035901, U0126, and TAK-733.

The treatment may involve administration of the ADC/secondary agent combination alone or in further combination with other treatments, either simultaneously or sequentially dependent upon the condition to be treated. Examples of treatments and therapies include, but are not limited to, chemotherapy (the administration of active agents, including, e.g. drugs, such as chemotherapeutics); surgery; and radiation therapy.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy.

Examples of chemotherapeutic agents include: Lenalidomide (REVLIMID®, Celgene), Vorinostat (ZOLINZA®, Merck), Panobinostat (FARYDAK®, Novartis), Mocetinostat (MGCD0103), Everolimus (ZORTRESS®, CERTICAN®, Novartis), Bendamustine (TREAKISYM®, RIBOMUSTIN®, LEVACT®, TREANDA®, Mundipharma International), erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo [4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g. calicheamicin, calicheamicin gamma1I, calicheamicin omega1I (*Angew Chem. Intl. Ed. Engl.* (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above. Combinations of agents may be used, such as CHP (doxorubicin, prednisone, cyclophosphamide), or CHOP (doxorubicin, prednisone, cyclophopsphamide, vincristine).

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), ofatumumab (ARZERRA®, GSK), pertuzumab (PERJETA™, OMNITARG™, 2C$_4$, Genentech), trastuzumab (HERCEPTIN®, Genentech), tositumomab (Bexxar, Corixia), MDX-060 (Medarex) and the antibody drug conjugate, gemtuzumab ozogamicin (MYLOTARG®, Wyeth).

Humanized monoclonal antibodies with therapeutic potential as chemotherapeutic agents in combination with the conjugates of the disclosure include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Compositions according to the present disclosure are preferably pharmaceutical compositions. Pharmaceutical compositions according to the present disclosure, and for use in accordance with the present disclosure, may comprise, in addition to the active ingredient, i.e. a conjugate compound, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Dosage

It will be appreciated by one of skill in the art that appropriate dosages of the ADC and/or the secondary agent, and compositions comprising these active elements, can vary from subject to subject. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the subject. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

In certain aspects, the dosage of ADC is determined by the expression of a first target protein observed in a sample obtained from the subject. Thus, the level or localisation of expression of the first target protein in the sample may be indicative that a higher or lower dose of ADC is required. For example, a high expression level of the first target protein may indicate that a higher dose of ADC would be suitable. In some cases, a high expression level of the first target protein may indicate the need for administration of another agent in addition to the ADC. For example, administration of the ADC in conjunction with a chemotherapeutic agent. A high expression level of the first target protein may indicate a more aggressive therapy.

In certain aspects, the dosage of the secondary agent is determined by the expression of a second target protein observed in a sample obtained from the subject. Thus, the level or localisation of expression of the second target protein in the sample may be indicative that a higher or lower dose of secondary agent is required. For example, a high expression level of the second target protein may indicate that a higher dose of secondary agent would be suitable. In some cases, a high expression level of the second target protein may indicate the need for administration of another agent in addition to the secondary agent. For example, administration of the secondary agent in conjunction with a chemotherapeutic agent. A high expression level of the second target protein may indicate a more aggressive therapy.

In certain aspects, the dosage level is determined by the expression of a first target protein on neoplastic cells in a sample obtained from the subject. For example, when the target neoplasm is composed of, or comprises, neoplastic cells expressing the first target protein.

In certain aspects, the dosage level is determined by the expression of a first target protein on cells associated with the target neoplasm. For example, the target neoplasm may be a solid tumour composed of, or comprising, neoplastic cells that express the first target protein. For example, the target neoplasm may be a solid tumour composed of, or comprising, neoplastic cells that do not express the first target protein. The cells expressing the first target protein may be neoplastic or non-neoplastic cells associated with the target neoplasm. For example, the cells expressing the first target protein may be cells infiltrating a solid tumour comprising or composed of neoplastic cells which do not express the first target protein.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of each active compound is in the range of about 100 ng to about 25 mg (more typically about 1 μg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, each active compound is administered to a human subject according to the following dosage regime: about 100 mg, 3 times daily.

In one embodiment, each active compound is administered to a human subject according to the following dosage regime: about 150 mg, 2 times daily.

In one embodiment, each active compound is administered to a human subject according to the following dosage regime: about 200 mg, 2 times daily.

However in one embodiment, each conjugate compound is administered to a human subject according to the following dosage regime: about 50 or about 75 mg, 3 or 4 times daily.

In one embodiment, each conjugate compound is administered to a human subject according to the following dosage regime: about 100 or about 125 mg, 2 times daily.

For the ADC, where it is a PBD bearing ADC, the dosage amounts described above may apply to the conjugate (including the PBD moiety and the linker to the antibody) or to the effective amount of PBD compound provided, for example the amount of compound that is releasable after cleavage of the linker.

The first target protein is preferably AXL. The ADC may comprise an anti-AXL antibody.

The ADC may comprise a drug which is a PBD dimer. The ADC may be an anti-AXL-ADC, and in particular, ADCxAXL. The ADC may be an ADC disclosed in GB1702029.8, GB1719906.8, and PCT/EP2018/053163.

The secondary agent may a PD1 antagonist. Suitable PD1 antagonists include pembrolizumab, nivolumab, MEDI00680, PDR001, Camrelizumab, AUNP12, Pidilizumab REGN-2810, and BGB-108.

Antibodies

The term "antibody" herein is used in the broadest sense and specifically covers monoclonal antibodies, polyclonal antibodies, dimers, multimers, multispecific antibodies (e.g., bispecific antibodies), intact antibodies (also described as "full-length" antibodies) and antibody fragments, so long as they exhibit the desired biological activity, for example, the ability to bind a first target protein (Miller et al (2003) Jour. of Immunology 170:4854-4861). Antibodies may be murine, human, humanized, chimeric, or derived from other species such as rabbit, goat, sheep, horse or camel.

An antibody is a protein generated by the immune system that is capable of recognizing and binding to a specific antigen. (Janeway, C., Travers, P., Walport, M., Shlomchik (2001) Immuno Biology, 5th Ed., Garland Publishing, New York). A target antigen generally has numerous binding sites, also called epitopes, recognized by Complementarity Determining Regions (CDRs) on multiple antibodies. Each antibody that specifically binds to a different epitope has a different structure. Thus, one antigen may have more than one corresponding antibody. An antibody may comprise a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin can be of any type (e.g. IgG, IgE, IgM, IgD, and IgA), class (e.g. IgG1, IgG2, IgG3, IgG4, IgA1 and IgA2) or subclass, or allotype (e.g. human G1m1, G1m2, G1m3, non-G1m1 [that, is any allotype other than G1m1], G1m17, G2m23, G3m21, G3m28, G3m11, G3m5, G3m13, G3m14, G3m10, G3m15, G3m16, G3m6, G3m24, G3m26, G3m27, A2 ml, A2m2, Km1, Km2 and Km3) of immunoglobulin molecule. The immunoglobulins can be derived from any species, including human, murine, or rabbit origin.

"Antibody fragments" comprise a portion of a full length antibody, generally the antigen binding or variable region thereof. Examples of antibody fragments include Fab, Fab', F(ab')$_2$, and scFv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler et al (1975) *Nature* 256:495, or may be made by recombinant DNA methods (see, U.S. Pat. No. 4,816,567). The monoclonal antibodies may also be isolated from phage antibody libraries using the techniques described in Clackson et al (1991) Nature, 352:624-628; Marks et al (1991) J. Mol. Biol., 222:581-597 or from transgenic mice carrying a fully human immunoglobulin system (Lonberg (2008) Curr. Opinion 20(4):450-459).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) *Proc. Natl. Acad. Sci. USA,* 81:6851-6855). Chimeric antibodies include "primatized" antibodies comprising variable domain antigen-binding sequences derived from a non-human primate (e.g. Old World Monkey or Ape) and human constant region sequences.

An "intact antibody" herein is one comprising VL and VH domains, as well as a light chain constant domain (CL) and heavy chain constant domains, CH1, CH2 and CH3. The constant domains may be native sequence constant domains (e.g. human native sequence constant domains) or amino acid sequence variant thereof. The intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called $\alpha$, $\delta$, $\epsilon$, $\gamma$, and $\mu$, respectively. The subunit structures and three-dimensional configurations of different classes of immunoglobulins are well known.

Anti-PD-L1 antibodies are known in the art and are useful in the methods disclosed herein. These antibodies include Atezolizumab (MPDL3280; CAS number 1380723-44-3), Avelumab (MSB0010718C; CAS number 1537032-82-8), and Durvalumab (CAS number 1428935-60-7).

The disclosure includes the combination of the aspects and preferred features described except where such a combination is clearly impermissible or expressly avoided.

The section headings used herein are for organizational purposes only and are not to be construed as limiting the subject matter described.

Aspects and embodiments of the present disclosure will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value.

Similarly, when values are expressed as approximations, by the use of the antecedent "about," it will be understood that the particular value forms another embodiment.

Some Embodiments

The following paragraphs describe some specific embodiments of the present disclosure:

1. A method for treating cancer in an individual, the method comprising administering to the individual an effective amount of ADC×AXL and a secondary agent.

2. A first composition comprising ADC×AXL for use in a method of treating cancer in an individual, wherein the treatment comprises administration of the first composition in combination with a second composition comprising a secondary agent.

3. A first composition comprising a secondary agent for use in a method of treating a disorder in an individual, wherein the treatment comprises administration of the first composition in combination with a second composition comprising ADC×AXL.

4. Use of ADC×AXL in the manufacture of a medicament for treating cancer in an individual, wherein the medicament comprises ADC×AXL, and wherein the treatment comprises administration of the medicament in combination with a composition comprising a secondary agent.

5. Use of a secondary agent in the manufacture of a medicament for treating cancer in an individual, wherein the medicament comprises a secondary agent, and wherein the treatment comprises administration of the medicament in combination with a composition comprising ADC×AXL.

6. A kit comprising:
    a first medicament comprising ADC×AXL;
    a second medicament comprising a secondary agent; and, optionally,
    a package insert comprising instructions for administration of the first medicament to an individual in combination with the second medicament for the treatment of cancer.

7. A kit comprising a medicament comprising ADC×AXL and a package insert comprising instructions for administration of the medicament to an individual in combination with a composition comprising a secondary agent for the treatment of cancer.

8. A kit comprising a medicament comprising a secondary agent and a package insert comprising instructions for administration of the medicament to an individual in combination with a composition comprising ADC×AXL for the treatment of cancer.

9. A pharmaceutical composition comprising ADC×AXL and a secondary agent.

10. A method of treating cancer in an individual, the method comprising administering to the individual an effective amount of the composition of paragraph 9.

11. The composition of paragraph 9 for use in a method of treating cancer in an individual.

12. The use of the composition of paragraph 9 in the manufacture of a medicament for treating cancer in an individual.

13. A kit comprising the composition of paragraph 9 and a set of instructions for administration of the medicament to an individual for the treatment of cancer.

14. The composition, method, use, or kit according to any previous paragraph, wherein the treatment comprises administering ADC×AXL before the secondary agent, simultaneous with the secondary agent, or after the secondary agent.

15. The composition, method, use, or kit according to any previous paragraph, wherein the treatment further comprises administering a chemotherapeutic agent.

16. The composition, method, use, or kit according to any previous paragraph, wherein the individual is human.

17. The composition, method, use, or kit according to any previous paragraph, wherein the individual has a disorder or has been determined to have cancer.

18. The composition, method, use, or kit according any previous paragraph, wherein the individual has, or has been has been determined to have, a cancer characterised by the presence of a neoplasm comprising both AXL+ve and AXL−ve cells.

19. The composition, method, use, or kit according any previous paragraph, wherein the individual has, or has been has been determined to have, a cancer characterised by the presence of a neoplasm comprising, or composed of, AXL−ve neoplastic cells.

20. The composition, method, use, or kit according to any previous paragraph, wherein the cancer or neoplasm is all or part of a solid tumour.

21. The composition, method, use, or kit according to any previous paragraph, wherein the individual has, or has been has been determined to have, a cancer which expresses AXL or AXL+ tumour-associated non-tumour cells, such as AXL+ infiltrating cells.

22. The composition, method, use, or kit according to paragraph 21, wherein the AXL+ infiltrating cells are dendritic cells, NK cells, or macrophages.

23. The composition, method, use, or kit according to any preceding paragraph, wherein the individual has, or has been has been determined to have, a cancer which expresses PD-L1.

24. The composition, method, use, or kit according to any one of the preceding paragraphs, wherein the treatment:
    a) effectively treats a broader range of disorders,
    b) effectively treats resistant, refractory, or relapsed disorders,
    c) has an increased response rate, and/or
    d) has increased durability;

as compared to treatment with either ADCxAXL or the secondary agent alone.

25. The composition, method, use, or kit according to any one of the preceding paragraphs, wherein the cancer is selected from the group comprising: breast cancer, lung cancer, gastric cancer, head and neck cancer, colorectal cancer, renal cancer, pancreatic cancer, uterine cancer, hepatic cancer, bladder cancer, endometrial cancer, prostate cancer, non-Hodgkin's lymphoma, NHL, AML), an immune disorder, cardiovascular disorder, thrombosis, diabetes, immune checkpoint disorder, and fibrotic disorder.

26. A composition, method, use, or kit according to any one of paragraphs 1 to 25, wherein the secondary agent is a PD1 antagonist.

27. A composition, method, use, or kit according to paragraph 26, wherein the PD1 antagonist is selected from pembrolizumab, nivolumab, MEDI0680, PDR001 (spartalizumab), Camrelizumab, AUNP12, Pidilizumab Cemiplimab (REGN-2810), AMP-224, BGB-A317 (Tisleizumab), and BGB-108.

28. A composition, method, use, or kit according to any one of paragraphs 1 to 25, wherein the secondary agent is a PD-L1 antagonist.

29. A composition, method, use, or kit according to paragraph 28, wherein the PD-L1 antagonist is selected from atezolizumab (Tecentriq), BMS-936559/MDX-1105, durvalumab/MEDI4736, and MSB0010718C (Avelumab).

30. A composition, method, use, or kit according to any one of paragraphs 1 to 25, wherein the secondary agent is a GITR (Glucocorticoid-Induced TNFR-Related protein) agonist.

31. A composition, method, use, or kit according to paragraph 30, wherein the GITR (Glucocorticoid-Induced TNFR-Related protein) agonist is selected from MEDI1873, TRX518, GWN323, MK-1248, MK 4166, BMS-986156 and INCAGN1876.

32. A composition, method, use, or kit according to any one of paragraphs 1 to 25, wherein the secondary agent is a OX40 agonist.

33. A composition, method, use, or kit according to paragraph 32, wherein the OX40 agonist is selected from MEDI0562, MEDI6383, MOXR0916, RG7888, OX40mAb24, INCAGN1949, GSK3174998, and PF-04518600.

34. A composition, method, use, or kit according to any one of paragraphs 1 to 25, wherein the secondary agent is a CTLA-4 antagonist.

35. A composition, method, use, or kit according to paragraph 34, wherein the CTLA-4 antagonist is selected from ipilimumab and Tremelimumab.

36. A composition, method, use, or kit according to any one of paragraphs 1 to 25, wherein the secondary agent is Fludarabine.

37. A composition, method, use, or kit according to any one of paragraphs 1 to 25, wherein the secondary agent is Cytarabine.

38. A composition, method, use, or kit according to any one of paragraphs 1 to 25, wherein the secondary agent is a hypomethylating agent.

39. A composition, method, use, or kit according to paragraph 38, wherein the hypomethylating agent is azacitidine.

40. A composition, method, use, or kit according to paragraph 38, wherein the hypomethylating agent is decitabine.

41. A composition, method, use, or kit according to any one of paragraphs 1 to 25, wherein the secondary agent is a PARP inhibitor (PARPi).

42. A composition, method, use, or kit according to paragraph 41, wherein the PARPi is selected from Olaparib, CEP-9722, BMN-673/talazoparib, Rucaparib, Iniparib/SAR24-550/BSI-201, Veliparib (ABT-888), Niraparib/MK-4827, BGB-290, 3-aminobenzamide, and E7016.

43. A composition, method, use, or kit according to any one of paragraphs 1 to 25, wherein the secondary agent is an agent that upregulates HER2 expression.

44. A composition, method, use, or kit according to paragraph 41, wherein the agent that upregulates HER2 expression is selected from gemcitabine and tamoxifen.

45. A composition, method, use, or kit according to any one of paragraphs 1 to 25, wherein the secondary agent is an AXL-kinase inhibitor (AXLi).

46. A composition, method, use, or kit according to paragraph 45, wherein the AXLi is selected from BGB324 (bemcentinib), TP0903, Gilteritinib (ASP2215), Cabozantinib (XL184), SGI7079, Merestinib, amuvatinib (MP-470), bosutinib (SKI-606), MGCD265, and foretinib (GSK1363089/XL880).

47. A composition, method, use, or kit according to any one of paragraphs 1 to 25, wherein the secondary agent is a BRAF inhibitor (BRAFi).

48. A composition, method, use, or kit according to paragraph 47, wherein the BRAFi is selected from vemurafenib, PLX4720, dabrafenib, Sorafenib, Encorafenib, and GDC0879.

49. A composition, method, use, or kit according to any one of paragraphs 1 to 25, wherein the secondary agent is a MEK inhibitor (MEKi).

50. A composition, method, use, or kit according to paragraph 49, wherein the AXLi is selected from Trametinib, Cobimetinib, Binimetinib, Selumetinib, PD-325901, CI-1040, PD035901, U0126, and TAK-733.

STATEMENTS OF INVENTION

1. A method for treating a disorder in an individual, the method comprising administering to the individual an effective amount of an ADC and a secondary agent.

2. A first composition comprising an ADC for use in a method of treating a disorder in an individual, wherein the treatment comprises administration of the first composition in combination with a second composition comprising a secondary agent.

3. A first composition comprising a secondary agent for use in a method of treating a disorder in an individual, wherein the treatment comprises administration of the first composition in combination with a second composition comprising an ADC.

4. Use of an ADC in the manufacture of a medicament for treating a disorder in an individual, wherein the medicament comprises an ADC, and wherein the treatment comprises administration of the medicament in combination with a composition comprising a secondary agent.

5. Use of a secondary agent in the manufacture of a medicament for treating a disorder in an individual, wherein the medicament comprises a secondary agent, and wherein the treatment comprises administration of the medicament in combination with a composition comprising an ADC.

6. A kit comprising:
   a first medicament comprising an ADC;
   a second medicament comprising a secondary agent; and, optionally, a package insert comprising instructions for administration of the first medicament to an individual in combination with the second medicament for the treatment of a disorder.

7. A kit comprising a medicament comprising an ADC and a package insert comprising instructions for administration of the medicament to an individual in combination with a composition comprising a secondary agent for the treatment of a disorder.

8. A kit comprising a medicament comprising a secondary agent and a package insert comprising instructions for administration of the medicament to an individual in combination with a composition comprising an ADC for the treatment of a disorder.

9. A pharmaceutical composition comprising an ADC and a secondary agent.

10. A method of treating a disorder in an individual, the method comprising administering to the individual an effective amount of the composition of paragraph 9.

11. The composition of paragraph 9 for use in a method of treating a disorder in an individual.

12. The use of the composition of paragraph 9 in the manufacture of a medicament for treating a disorder in an individual.

13. A kit comprising the composition of paragraph 9 and a set of instructions for administration of the medicament to an individual for the treatment of a disorder.

14. The composition, method, use, or kit according to any previous paragraph, wherein the treatment comprises administering the ADC before the secondary agent, simultaneous with the secondary agent, or after the secondary agent.

15. The composition, method, use, or kit according to any previous paragraph, wherein the treatment further comprises administering a chemotherapeutic agent.

16. The composition, method, use, or kit according to any previous paragraph, wherein the individual is human.

17. The composition, method, use, or kit according to any preceding paragraph, wherein the individual has a disorder or has been determined to have a disorder.

18. The composition, method, use, or kit according to paragraph 17, wherein the individual has, or has been has been determined to have, a cancer which expresses a first target protein (FTP) or FTP+ tumour-associated non-tumour cells, such as FTP+ infiltrating cells.

19. The composition, method, use, or kit according to any preceding paragraph, wherein the individual has, or has been has been determined to have, a cancer which expresses a second target protein (STP).

20. The composition, method, use, or kit according to any one of the preceding paragraphs, wherein the treatment:
  a) effectively treats a broader range of disorders,
  b) effectively treats resistant, refractory, or relapsed disorders,
  c) has an increased response rate, and/or
  d) has increased durability;
  as compared to treatment with either the ADC or the secondary agent alone.

21. A composition, method, use, or kit according to any previous paragraph, wherein the ADC is an anti-AXL ADC.

22. A composition, method, use, or kit according to paragraph 21, wherein the anti-AXL ADC is ADCxAXL.

23. A composition, method, use, or kit according to any previous paragraph, wherein the FTP is AXL.

24. A composition, method, use, or kit according to any previous paragraph, wherein the disorder is a proliferative disease.

25. The composition, method, use, or kit of paragraph 24, wherein the disorder is cancer.

26. The composition, method, use, or kit according any previous paragraph, wherein the individual has, or has been has been determined to have, a cancer characterised by the presence of a neoplasm comprising both AXL+ve and AXL−ve cells.

27. The composition, method, use, or kit according any previous paragraph, wherein the individual has, or has been has been determined to have, a cancer characterised by the presence of a neoplasm comprising, or composed of AXL−ve neoplastic cells.

28. The composition, method, use, or kit according to any previous paragraph, wherein the cancer or neoplasm is all or part of a solid tumour.

29. The composition, method, use, or kit of any previous paragraph, wherein the disorder is selected from the group comprising: breast cancer, lung cancer, gastric cancer, head and neck cancer, colorectal cancer, renal cancer, pancreatic cancer, uterine cancer, hepatic cancer, bladder cancer, endometrial cancer, prostate cancer, non-Hodgkin's lymphoma, NHL, AML), an immune disorder, cardiovascular disorder, thrombosis, diabetes, immune checkpoint disorder, and fibrotic disorder.

30. A composition, method, use, or kit according to any previous paragraph, wherein the STP is PD-L1.

31. A composition, method, use, or kit according to any one of paragraphs 1 to 30, wherein the secondary agent is a PD1 antagonist.

32. A composition, method, use, or kit according to paragraph 31, wherein the PD1 antagonist is selected from pembrolizumab, nivolumab, MED10680, PDR001 (spartalizumab), Camrelizumab, AUNP12, Pidilizumab Cemiplimab (REGN-2810), AMP-224, BGB-A317 (Tisleizumab), and BGB-108.

33. A composition, method, use, or kit according to any one of paragraphs 1 to 30, wherein the secondary agent is a PD-L1 antagonist.

34. A composition, method, use, or kit according to paragraph 33, wherein the PD-L1 antagonist is selected from atezolizumab (Tecentriq), BMS-936559/MDX-1105, durvalumab/MED14736, and MSB0010718C (Avelumab).

35. A composition, method, use, or kit according to any one of paragraphs 1 to 30, wherein the secondary agent is a GITR (Glucocorticoid-Induced TNFR-Related protein) agonist.

36. A composition, method, use, or kit according to paragraph 35, wherein the GITR (Glucocorticoid-Induced TNFR-Related protein) agonist is selected from MED11873, TRX518, GWN323, MK-1248, MK 4166, BMS-986156 and INCAGN1876.

37. A composition, method, use, or kit according to any one of paragraphs 1 to 30, wherein the secondary agent is a OX40 agonist.

38. A composition, method, use, or kit according to paragraph 37, wherein the OX40 agonist is selected from MED10562, MED16383, MOXR0916, RG7888, OX40mAb24, INCAGN1949, GSK3174998, and PF-04518600.

39. A composition, method, use, or kit according to any one of paragraphs 1 to 30, wherein the secondary agent is a CTLA-4 antagonist.

40. A composition, method, use, or kit according to paragraph 39, wherein the CTLA-4 antagonist is selected from ipilimumab and Tremelimumab.

41. A composition, method, use, or kit according to any one of paragraphs 1 to 30, wherein the secondary agent is Fludarabine.

42. A composition, method, use, or kit according to any one of paragraphs 1 to 30, wherein the secondary agent is Cytarabine.

43. A composition, method, use, or kit according to any one of paragraphs 1 to 30, wherein the secondary agent is a hypomethylating agent.

44. A composition, method, use, or kit according to paragraph 43, wherein the hypomethylating agent is azacitidine.

45. A composition, method, use, or kit according to paragraph 43, wherein the hypomethylating agent is decitabine.

46. A composition, method, use, or kit according to any one of paragraphs 1 to 30, wherein the secondary agent is a PARP inhibitor (PARPi).

47. A composition, method, use, or kit according to paragraph 46, wherein the PARPi is selected from Olaparib, CEP-9722, BMN-673/talazoparib, Rucaparib, Iniparib/SAR24-550/BSI-201, Veliparib (ABT-888), Niraparib/MK-4827, BGB-290, 3-aminobenzamide, and E7016.

48. A composition, method, use, or kit according to any one of paragraphs 1 to 30, wherein the secondary agent is an agent that upregulates HER2 expression.

49. A composition, method, use, or kit according to paragraph 48, wherein the agent that upregulates HER2 expression is selected from gemcitabine and tamoxifen.

50. A composition, method, use, or kit according to any one of paragraphs 1 to 30, wherein the secondary agent is an AXL-kinase inhibitor (AXLi).

51. A composition, method, use, or kit according to paragraph 50, wherein the AXLi is selected from BGB324 (bemcentinib), TP0903, Gilteritinib (ASP2215), Cabozantinib (XL184), SG17079, Merestinib, amuvatinib (MP-470), bosutinib (SKI-606), MGCD265, and foretinib (GSK1363089/XL880).

52. A composition, method, use, or kit according to any one of paragraphs 1 to 30, wherein the secondary agent is a BRAF inhibitor (BRAFi).

53. A composition, method, use, or kit according to paragraph 52, wherein the BRAFi is selected from vemurafenib, PLX4720, dabrafenib, Sorafenib, Encorafenib, and GDC0879.

54. A composition, method, use, or kit according to any one of paragraphs 1 to 30, wherein the secondary agent is a MEK inhibitor (MEKi).

55. A composition, method, use, or kit according to paragraph 54, wherein the AXLi is selected from Trametinib, Cobimetinib, Binimetinib, Selumetinib, PD-325901, CI-1040, PD035901, U0126, and TAK-733.

EXAMPLES

In the following examples:
the FTP is preferably AXL.
Cell lines expressing AxL suitable for use in the examples include MDA-MB231, NCI-H1299 and SN12C.
Disease A—Colorectal
Disease B—Gastric cancer
Disease C—Pancreatic cancer

Example 1

To show that a PBD-ADC can induce ICD and therefore can be a suitable combination agent with immune-oncology (10) drugs, cell lines expressing a first target protein (FTP), will be incubated for 0, 6, 24 and 48 hours with etoposide (negative control) and oxaliplatin (positive control), 1 µg/mL ADC, 1 µg/mL anti-FTP (the antibody in ADC) and 1 µg/mL of B12-SG3249 (a non-binding control ADC with the same PBD payload as ADC).

After Incubation, the amount of AnnexinV−/PI+ (early apoptotic cells) will be measured by Flow cytometry together with the upregulation of surface calreticulin and HSP-70. ER stress will be measured by Northern blot analyses of IRE1 phosphorylation, ATF4 and JNK phosphorylation.

Example 2

In a separate experiment, cell lines expressing FTPs will be incubated for 0, 6, 24 and 48 hours with etoposide (negative control) and oxaliplatin (positive control), 1 µg/mL ADC (ADC targeting FTP with a PBD dimer warhead), 1 µg/mL anti-FTP (the antibody in ADC) and 1 µg/mL of B12-SG3249 (a non-binding control ADC with the same PBD payload as ADC).

After incubation, the cells are washed, and fed to human Dendritic cells (DCs) for an additional 24 h. Activation of the DCs is subsequently measured by increased surface expression of CD86 on the DC population (as determined by Flow cytometry) and by measuring DC mediated release of IL-8 and MIP2.

Example 3

The purpose of this study is to preliminarily assess the safety, tolerability, pharmacological and clinical activity of this combination The following cancer types have been chosen for study: Disease A, Disease B, and Disease C Evidence for efficacy as single agents exists for both drugs:
  ADC (see, for example, GB1702029.8, GB1719906.8, and PCT/EP2018/053163.)
  Secondary agent (see KS Peggs et al. 2009, Clinical and Experimental Immunology, 157: 9-19 [doi:10.1111/j.1365-2249.2009.03912.x])

This primary purpose of this study is to explore whether these agents can be safely combined, and if so, will identify the dose(s) and regimens appropriate for further study. The study will also assess whether each combination induces pharmacologic changes in tumor that would suggest potential clinical benefit, In addition, it will provide preliminary evidence that a combination may increase the response rate and durability of response compared with published data for treatment with single agent ADC or secondary agent.

Each disease group may include a subset of patients previously treated with the secondary agent to explore whether combination therapy might overcome resistance to secondary agent therapy. For each disease, it is not intended to apply specific molecular selection as the data available at present generally do not support excluding patients on the basis of approved molecular diagnostic tests.

Rationale for ADC Starting Dose

The RDE for already established for ADC (in ug/kg administered every three weeks) will be used for all patients in this study. To ensure patient safety, a starting dose below the RDE will be used; the starting dose level will be one where patient benefit could still be demonstrated in study ADC1, suggesting that patients enrolled at such dose level will gain at least some benefit by taking part.

Rationale for Secondary Agent Starting Dose

The RDE for already established for the secondary agent (in ug/kg administered every three weeks) will be used for all patients in this study. To ensure patient safety, a starting dose below the RDE will be used; the starting dose level will be one where patient benefit could still be demonstrated in study SA1, suggesting that patients enrolled at such dose level will gain at least some benefit by taking part.

| Objectives and related endpoints | |
| --- | --- |
| Objective | Endpoint |
| Primary Objective | |
| To characterize the safety and tolerability of ADC in combination with the secondary agent, and to identify the recommended dose and schedules for future studies | Frequency and severity of treatment-emergent AEs and SAEs<br>Changes between baseline and post-baseline laboratory parameters and vital signs<br>Incidence of dose limiting toxicities (DLTs) during the first cycle of treatment (dose escalation only)<br>Frequency of dose interruptions and dose reductions |
| Secondary Objectives | |
| To evaluate the clinical activity of the combination of ADC with the secondary agent | ORR, DOR, PFS, OS |
| To characterize the pharmacokinetic (PK) profile of each of the two compounds ADC and the secondary agent | AUC and Cmax for each compound |
| Evidence for immunogenicity and ADAs to ADC | Anti-Drug-Antibodies (ADAs) before, during and after treatment with ADC |
| Exploratory Objectives | |
| To examine potential correlation of PK profiles with safety/tolerability and efficacy | Correlation coefficients between AUC and/or Cmax of each compound or a compound measure and any of the safety or efficacy variables |
| To characterize changes in the immune infiltrate in tumors | Immunohistochemistry of pre- and on-treatment tumor biopsies, |
| To characterize changes in circulating levels of cytokines in plasma and markers of activation in circulating immune cells | Measurements (e.g. via ELISA) of immunologically relevant cytokines in plasma or serum; staining levels for activation markers of circulating immune cells (e.g. FACS) |

Study Design

This phase Ib, multi-center, open-label study to characterize the safety, tolerability, pharmacokinetics (PK), pharmacodynamics (PD) and antitumor activity of the ADC in combination with the secondary agent, in patients with disease A, disease B, and disease C.

The study is comprised of a dose escalation part followed by a dose expansion part.

Figure 9:
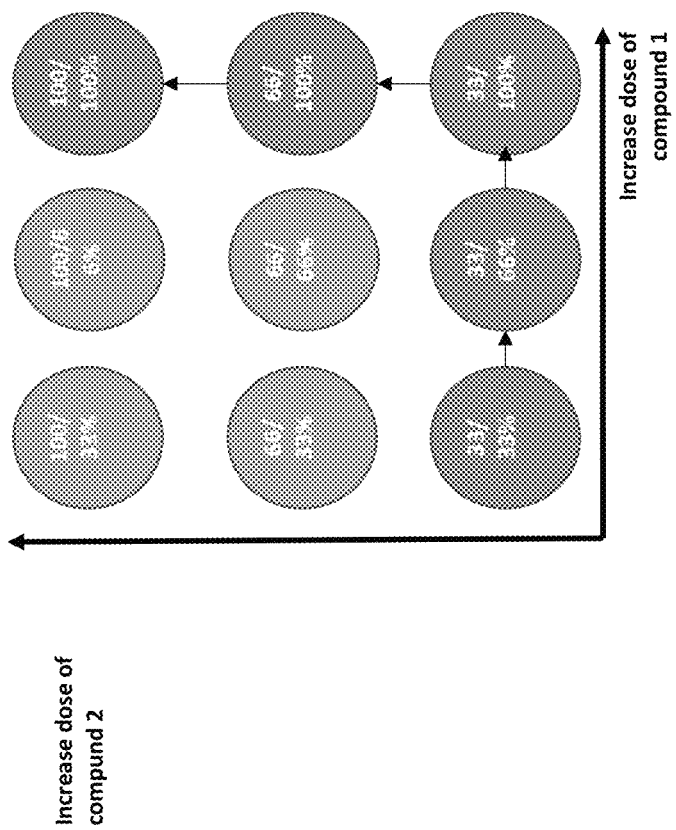
FIG. 9 is a schematic diagram illustrating a dose escalation strategy for an ADC and a secondary agent. A perceived safe starting dose of 33% of the intended efficacious dose is proposed for both compounds, but this may need adaptation to lower or higher, as the individual risk profile for the combination may be. Compound 1 should be the compound for which an efficacious clinical dose has been firmly established (at 100%), and which is therefore aimed to be reached quickly in the trial patients by first escalating the dose of this compound.

Dose escalation will start with reduced starting doses (compared to their respective recommended phase 2 or licensed dose levels), for both ADC and the secondary agent, to guarantee patient safety. Starting doses will be 33% (or 50%) of the RDE for each compound. Subsequently, doses will be first escalated for the secondary agent until the RDE or licensed dose has been reached, or a lower dose if necessary for tolerability reasons. Then, the dose for ADC will be escalated, until the RDE for combination treatment is reached. This is visualized in FIG. 9.

If the dose combination is determined to be safe, it may be tested in additional patients to confirm the safety and tolerability at that dose level. Further tailoring of the dose of each compound may be conducted, and/or the regimen may be modified.

The dose escalation of the combination will be guided by a Bayesian Logistic Regression Model (BLRM) based on any Dose Limiting Toxicities (DLTs) observed in the first (or first two, TBC) cycles of therapy. Use of a BLRM is a well-established method to estimate the maximum tolerated dose (MTD)/ recommended dose for expansion (RDE) in cancer patients. The adaptive BLRM will be guided by the Escalation With Overdose Control (EWOC) principle to control the risk of DLT in future patients on the study. The use of Bayesian response adaptive models for small datasets has been accepted by FDA and EMEA ("Guideline on clinical trials in small populations", Feb. 1, 2007) and endorsed by numerous publications (Babb et al. 1998, Neuenschwander et al. 2008).

The decisions on new dose combinations are made by the Investigators and sponsor study personnel in a dose escalation safety call (DESC) based upon the review of patient tolerability and safety information (including the BLRM summaries of DLT risk, if applicable) along with PK, PD and preliminary activity information available at the time of the decision.

Once the MTD(s)/RDE is determined for the combination, the expansion part of the study may be initiated to further assess the safety, tolerability and preliminary efficacy.

For combinations with IO , changes in the immune infiltrate in tumors will also be characterized following combination treatment in the target disease indications.

Given the available prior clinical experience with the agents in this study, it is expected that in most cases a combination dose can be identified without testing a large number of dose levels or schedules. To assess the pharmacodynamic activity of the combinations, patients will be asked to undergo a tumor biopsy at baseline and again after approximately two cycles of therapy.

For 10 combo: The extent of the change in tumor infiltration by immune cells including lymphocytes and macrophages will contribute to a decision on any potential benefit.

Dose Escalation Part

During the dose escalation part of the study, patients will be treated with a fixed dose of ADC administered i.v., and increasing doses of the secondary agent until the RDE for the secondary agent has been reached. Subsequently, doses of ADC are increased (in different cohorts) while the dose for the secondary agent is kept constant.

Two to approximately 3 or 4 patients with disease A, disease B or disease C will be treated in each escalation cohort until the determination of MTD(s)/RDE(s) is determined.

There will be a 24-hour observation before enrolling the second patient at Dose Level 1. The DLT observation period at each dose level is either 1 cycle (3 weeks) or 2 cycles (6 weeks) as mandated by the appropriate authorities for 10 therapies, after which it will be determined whether to escalate to the next dose level, stay at the current dose level, or de-escalate to the previous dose level for the next cohort. There will be no de-escalation from Dose Level 1. Intrapatient dose escalation is not permitted.

Dose escalation is not permitted unless 2 or more patients have complete DLT information through the first cycle in any given dose level. Dose escalation will be determined by using a mCRM with a target DLT rate of 30% and an equivalence interval of 20% to 35%, and with dose escalation-with-overdose-control (EWOC) and no dose skipping.

Patients will be assigned to a cohort that is actively enrolling. Dose escalation will be performed in each combination following the completion of one cycle of treatment. Safety assessments including adverse events (AEs) and laboratory values will be closely monitored for all enrolled patients in order to identify any DLTs. A single MTD/RDE will be defined; a disease-specific MTD/RDE will not be established.

The mCRM will be implemented for DE under the oversight of a Dose Escalation Steering Committee (DESC). The DESC will confirm each escalating dose level after reviewing all available safety data. PK data from patients in that dose level and prior dose levels may also inform decision making. The DESC may halt dose escalation prior to determining the MTD based on emerging PK, PD, toxicity or response data.

Additional patients may be included at any dose level to further assess the safety and tolerability if at least 1 patient in the study has achieved a partial response or better, or if further evaluation of PK or PD data is deemed necessary by the DESC to determine the RDE.

Dose Escalation will be stopped after 3 cohorts (or at least 6 patients) are consecutively assigned to the same dose level. If the MTD is not reached, the recommended dose for expansion (RDE) will be determined. Prior to the determination of the MTD/RDE a minimum of 6 patients must have been treated with the combination.

It is intended that paired tumor biopsies will be obtained from patients during dose escalation. Analysis of these biopsies will contribute to a better understanding of the relationship between the dose and the pharmacodynamic activity of the combination.

Safety Oversight by the Dose Escalation Steering Committee

A DESC comprised of ADC Therapeutics and the investigators will review patient safety on an ongoing basis during the DE to determine if the dose escalation schedule prescribed by the mCRM warrants modification. In addition to safety observations, PK and/or PD data may also inform decision making. Intermediate doses may be assigned after agreement between ADC Therapeutics and investigators. The DESC may continue to provide oversight during Part 2. No formal Data Safety Monitoring Board (DSMB) will be used.

Dose Expansion Part

Once the MTD/RDE has been declared, dose expansion part may begin. The main objective of the expansion part is to further assess the safety and tolerability of the study treatment at the MTD/RDE and to gain a preliminary understanding of the efficacy of the combination compared to historical single agent efficacy data.

An important exploratory objective is to assess changes in the immune infiltrate in tumor in response to treatment. This will be assessed in paired tumor biopsies collected from patients, with a minimum of ten evaluable biopsy pairs (biopsy specimens must contain sufficient tumor for analysis) in patients treated at the MTD/RDE. If this is not feasible, collection of these biopsies may be stopped. A minimum of 10 to 20 patients are planned to be treated in each investigational arm, Several different investigational arms will open, one per disease. A total of nine investigational arms may be run in the dose expansion. Should enrollment for any of these groups not be feasible, then enrollment to that group may be closed before the 10 to 20 patients target is met.

In each treatment group a maximum of approximately six patients who have received and progressed on prior single administration (i.e. not in combination) secondary agent therapy will be allowed to be treated. This number may be increased if a combination shows promise of overcoming resistance to prior treatment with single administration secondary agent.

Patient Population

The study will be conducted in adult patients with advanced Disease A, Disease B or Disease C as outlined above. The investigator or designee must ensure that only patients who meet all the following inclusion and none of the exclusion criteria are offered treatment in the study.

Inclusion Criteria

Patients eligible for inclusion in this study have to meet all of the following criteria:

1. Written informed consent must be obtained prior to any procedures
2. Age 18 years.
3. Patients with advanced/metastatic cancer, with measurable disease as determined by RECIST version 1.1, who have progressed despite standard therapy or are intolerant to standard therapy, or for whom no standard therapy exists. Patients must fit into one of the following groups:
   Disease A
   Disease B
   Disease C
4. ECOG Performance Status 0-1 (or 2 TBC)
5. TBC: Patient must have a site of disease amenable to biopsy, and be a candidate for tumor biopsy according to the treating institution's guidelines. Patient must be willing to undergo a new tumor biopsy at baseline, and again during therapy on this study.

6. Prior therapy with the secondary agent or related compounds (i.e. same MOA) is allowed Exclusion Criteria Patients eligible for this study must not meet any of the following criteria:
1. History of severe hypersensitivity reactions to other mAbs (OR to same backbone mAb as in ADC OR to same IO mAb if applicable)
2. Known history of positive serum human ADA to backbone of mAb as in ADC
3. Central Nervous System (CNS) disease only (if applicable)
4. Symptomatic CNS metastases or evidence of leptomeningeal disease (brain MRI or previously documented cerebrospinal fluid (CSF) cytology)
   Previously treated asymptomatic CNS metastases are permitted provided that the last treatment (systemic anticancer therapy and-or local radiotherapy) was completed >=8 weeks prior to $1^{st}$ day of dosing, except usage of low dose steroids on a taper is allowed)
   Patients with discrete dural metastases are eligible.
5. Patient having out of range laboratory values defined as:
   Serum creatinine <=1.5×ULN. If serum creatinine >1.5, the creatinine clearance (calculated using Cockcroft-Gault formula, or measured) must be >60 mL/min/1.73m2 for a patient to be eligible
   Total bilirubin >1.5×ULN, except for patients with Gilbert's syndrome who are excluded if total bilirubin >3.0×ULN or direct bilirubin >1.5×ULN
   Alanine aminotransferase (ALT) >3×ULN, except for patients that have tumor involvement of the liver, who are excluded if ALT >5×ULN
   Aspartate aminotransferase (AST) >3×ULN, except for patients that have tumor involvement of the liver, who are excluded if AST >5×ULN
   Absolute neutrophil count<1.0×10e9/L
   Platelet count<75×10e9/L
   Hemoglobin (Hgb)<8 g/dL
   Potassium, magnesium, calcium or phosphate abnormality >CTCAE grade 1 despite appropriate replacement therapy
6. Impaired cardiac function or clinically significant cardiac disease, including any of the following:
   Clinically significant and/or uncontrolled heart disease such as congestive heart failure requiring treatment (NYHA grade III or IV) or uncontrolled hypertension defined by a Systolic Blood Pressure (SBP) 160 mm Hg and/or Diastolic Blood Pressure (DBP) 100 mm Hg, with or without anti-hypertensive medication.
   QTcF >470 msec for females or >450 msec for males on screening ECG using Fridericia's correction, congenital long QT syndrome
   Acute myocardial infarction or unstable angina pectoris <3 months (months prior to study entry
   Clinically significant valvular disease with documented compromise in cardiac function
   Symptomatic pericarditis
   History of or ongoing documented cardiomyopathy
   Left Ventricular Ejection Fraction (LVEF)<40%, as determined by echocardiogram (ECHO) or Multi gated acquisition (MUGA) scan
   History or presence of any clinically significant cardiac arrhythmias, e.g. ventricular, supraventricular, nodal arrhythmias, or conduction abnormality (TBC qualifier: . . . requiring a pacemaker or not controlled with medication)
   Presence of unstable atrial fibrillation (ventricular response rate>100 bpm).
      NOTE: Patients with stable atrial fibrillation can be enrolled provided they do not meet other cardiac exclusion criteria.
   Complete left bundle branch block (LBBB), bifascicular block
   Any clinically significant ST segment and/or T-wave abnormalities
7. Toxicity attributed to prior IO therapy that led to discontinuation of therapy. Adequately treated patients for drug-related skin rash or with replacement therapy for endocrinopathies are not excluded, provided these toxicities did not lead to the discontinuation of prior treatment.
8. Patients with active, known or suspected autoimmune disease. Subjects with vitiligo, type I diabetes mellitus, residual hypothyroidism due to autoimmune condition only requiring hormone replacement, psoriasis not requiring systemic treatment, or conditions not expected to recur in the absence of an external trigger are permitted to enroll, provided the trigger can be avoided.
9. Human Immunodeficiency Virus (HIV), or active Hepatitis B (HBV) or Hepatitis C (HCV) virus infection
   Testing is not mandatory to be eligible. Testing for HCV should be considered if the patient is at risk for having undiagnosed HCV (e.g. history of injection drug use).
10. Malignant disease, other than that being treated in this study. Exceptions to this exclusion include the following: malignancies that were treated curatively and have not recurred within 2 years prior to study treatment; completely resected basal cell and squamous cell skin cancers; any malignancy considered to be indolent and that has never required therapy; and completely resected carcinoma in situ of any type.
11. Systemic anti-cancer therapy within 2 weeks of the first dose of study treatment. For cytotoxic agents that have major delayed toxicity, e.g. mitomycin C and nitrosoureas, 4 weeks is indicated as washout period. For patients receiving anticancer immunotherapies such as CTLA-4 antagonists, 6 weeks is indicated as the washout period.
12. Active diarrhea CTCAE grade 2 or a medical condition associated with chronic diarrhea (such as irritable bowel syndrome, inflammatory bowel disease)
13. Presence of 2: CTCAE grade 2 toxicity (except alopecia, peripheral neuropathy and ototoxicity, which are excluded if >=CTCAE grade 3) due to prior cancer therapy.
14. Active infection requiring systemic antibiotic therapy.
15. Active ulceration of the upper GI tract or GI bleeding
16. Active bleeding diathesis or on oral anti-vitamin K medication (except low-dose warfarin and aspirin or equivalent, as long as the INR <=2.0)
17. Active autoimmune disease, motor neuropathy considered of autoimmune origin, and other CNS autoimmune disease
18. Patients requiring concomitant immunosuppressive agents or chronic treatment with corticoids except:
    replacement dose steroids in the setting of adrenal insufficiency
    topical, inhaled, nasal and ophthalmic steroids are allowed
19. Use of any live vaccines against infectious diseases (e.g. influenza, varicella, pneumococcus) within 4 weeks of initiation of study treatment (NB the use of live vaccines is not allowed through the whole duration of the study)
20. Use of hematopoietic colony-stimulating growth factors (e.g. G-CSF, GMCSF, M-CSF)<2 weeks prior start of study drug. An erythroid stimulating agent is allowed as long as it was initiated at least 2 weeks prior to the first dose of study treatment.
21. Major surgery within 2 weeks of the first dose of study treatment (NB mediastinoscopy, insertion of a central venous access device, or insertion of a feeding tube are not considered major surgery).
22. Radiotherapy within 2 weeks of the first dose of study drug, except for palliative radiotherapy to a limited field, such as for the treatment of bone pain or a focally painful tunlor mass. To allow for assessment of response to treatment, patients must have remaining measurable disease that has not been irradiated
23. Participation in an interventional, investigational study within 2 weeks of the first dose of study treatment.
24. Any medical condition that would, in the investigator's judgment, prevent the patient's participation in the clinical study due to safety concerns, compliance with clinical study procedures or interpretation of study results.
25. Sexually active males unless they use a condom during intercourse while taking drug and for 90 days after stopping study treatment and should not father a child in this period. A condom is required to be used also by vasectomized men in order to prevent delivery of the drug via seminal fluid.
26. Pregnant or lactating women, where pregnancy is defined as the state of a female after conception and until the termination of gestation, confirmed by a positive hCG laboratory test. In rare cases of an endocrine-secreting tumor, hCG levels may be above normal limits but with no pregnancy in the patient. In these cases, there should be a repeat serum hCG test (with a non-rising result) and a vaginal/pelvic ultrasound to rule out pregnancy. Upon confirmation of results and discussion with the Medical representative, these patients may enter the study.
27. Women of child-bearing potential, defined as all women physiologically capable of becoming pregnant, unless they are using highly effective methods of contraception during study treatment and for 90 days after the last any dose of study treatment. Highly effective contraception methods include:
Total abstinence (when this is in line with the preferred and usual lifestyle of the patient. Periodic abstinence (e.g., calendar, ovulation, symptothermal, post-ovulation methods) and withdrawal are not acceptable methods of contraception
Female sterilization (have had surgical bilateral oophorectomy with or without hysterectomy), total hysterectomy or tubal ligation at least 6 weeks before taking study treatment. In case of oophorectomy alone, only when the reproductive status of the woman has been confirmed by follow up hormone level assessment
Male sterilization (at least 6 months prior to screening). For female patients on the study the vasectomized male partner should be the sole partner for that patient.
Use of oral (estrogen and progesterone), injected or implanted combined hormonal methods of contraception or placement of an intrauterine device (IUD) or intrauterine system (IUS) or other forms of hormonal contraception that have comparable efficacy (failure rate <1%), for example hormone vaginal ring or transdermal hormone contraception.
In case of use of oral contraception, women should have been stable on the same pill for a minimum of 3 months before taking study treatment.
Women are considered post-menopausal and not of child bearing potential if they have had 12 months of natural (spontaneous) amenorrhea with an appropriate clinical profile (e.g. age appropriate, history of vasomotor symptoms) or have had surgical bilateral oophorectomy (with or without hysterectomy) or tubal ligation at least 6 weeks ago. In the case of oophorectomy alone, only when the reproductive status of the woman has been confirmed by follow up hormone level assessment is she considered not of child bearing potential.

Dose-Limiting Toxicities and Dose Modification Guidelines

A dose-limiting toxicity (DLT) is defined as any of the following events thought to be at least possibly related to ADC per investigator judgment that occurs during the 21-day DLT evaluation period. Toxicity that is clearly and directly related to the primary disease or to another etiology is excluded from this definition.

DLT Definitions

A hematologic DLT is defined as:
Grade 3 or 4 febrile neutropenia or neutropenic infection
Grade 4 neutropenia lasting >7 days
Grade 4 thrombocytopenia
Grade 3 thrombocytopenia with clinically significant bleeding, or Grade 3 thrombocytopenia requiring a platelet transfusion
Grade 3 anemia that requires transfusion
Grade 4 anemia
A non-hematologic DLT is defined as:
Grade 4 non-hematologic toxicity
Grade 3 non-hematologic toxicity lasting >3 days despite optimal supportive care or medical intervention
A case of Hy's law (AST and/or ALT >3×ULN and bilirubin >2×ULN, and without initial findings of cholestasis (serum alkaline phosphatase (ALP) activity <2×ULN) and no other reason that could explain the combination of increased transaminases and serum total bilirubin, such as viral hepatitis A, B, or C, preexisting or acute liver disease, or another drug capable of causing the observed injury)
Grade 3 or higher hypersensitivity/infusion-related reaction (regardless of premedication). A grade 3 hypersensitivity/infusion-related reaction that resolves within 8 hours after onset with appropriate clinical management does not qualify as a DLT.
LVEF decrease to <40% or >20% decrease from baseline
Grade 4 tumor lysis syndrome (Grade 3 TLS will not constitute DLT unless it leads to irreversible end-organ damage)
The following conditions are not considered non-hematologic DLT:
Grade 3 fatigue for <7 days
Grade 3 diarrhea, nausea, or vomiting in the absence of premedication that responds to therapy and improves by at least 1 grade within 3 days for Grade 3 events or to ≤Grade 1 within 7 days.
AST or ALT elevation >5×ULN but <8×ULN, without concurrent elevation in bilirubin, that downgrades to <Grade 2 within 5 days after onset.
Grade 3 serum lipase or serum amylase for <7 days if without clinical signs or symptoms of pancreatitis
Patients who experience a DLT that resolves or stabilizes with appropriate medical management may continue treatment at the discretion of the investigator in consultation with the sponsor.

Dose Modifications

Guidelines for management of specific toxicities are detailed in the table below. For management of events not specified in the tables, the following may serve as a guidance to investigators:

| AE Grade | ADC Management Guideline |
|---|---|
| 1 | No dose adjustment is required. |
| 2 | First occurrence: Consider holding one or both drugs until improvement to ≤Grade 1 or baseline. Up to 1 dose of one or both drugs may be skipped to permit improvement. If improvement to ≤Grade 1 or baseline occurs within 21 days from the last scheduled (but missed) dose of one or both drugs, continue one or both drugs at the original assigned dose level in subsequent treatment cycles. If improvement to ≤Grade 1 or baseline does not occur within 21 days from the last scheduled (but missed) dose, permanently discontinue one or both drugs. |

| AE Grade | ADC Management Guideline |
|---|---|
| | Second occurrence:<br>Hold one or both drugs until improvement to ≤Grade 1 or baseline. Up to 1 dose of one or both drugs may be skipped to permit resolution. If improvement to ≤Grade 1 or baseline occurs within 21 days from the last scheduled (but missed) dose, continue one or both drugs at 1 dose level below the original assigned dose in subsequent treatment cycles. If improvement to ≤Grade 1 or baseline does not occur within 21 days from the last scheduled (but missed) dose, permanently discontinue one or both drugs.<br>Third occurrence:<br>Permanently discontinue one or both drugs. |
| 3 | First occurrence:<br>Hold one or both drugs until improvement to ≤Grade 1 or baseline. Up to 1 dose of one or both drugs may be skipped to permit improvement, then continue at 1 dose level below the original assigned dose in subsequent treatment cycles.<br>Second occurrence:<br>Permanently discontinue one or both drugs |
| 4 | Permanently discontinue one or both drugs. |

Example 4: Synthesis of Intermediate 3

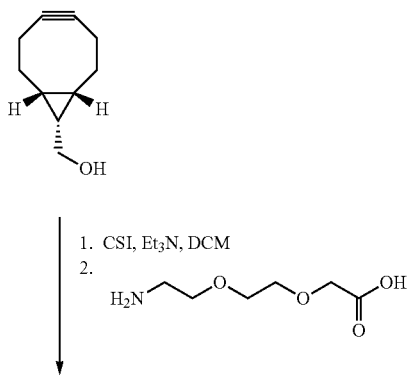

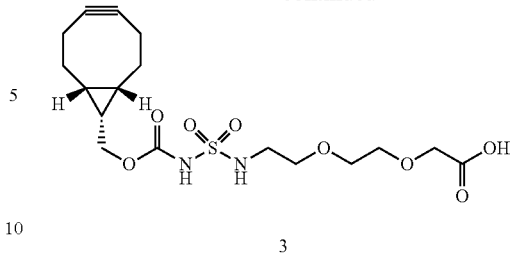

3

A solution of BCN alcohol (0.384 g, 2.55 mmole) in MeCN (25 mL) under a $N_2$ atmosphere was cooled to 0° C., and chlorosulfonyl isocyanate was added (CSI) was added dropwise (0.255 mL, 415 mg, 2.93 mmole, 1.15 equiv.). After stirring for 15 minutes, $Et_3N$ was added dropwise (1.42 mL, 1.03 g, 10.2 mmole, 4 equiv.) and stirring was continued for another 10 minutes. Next, a solution of 2-(2-(2-aminoethoxy)ethoxy)acetic acid (1.0 g, 6.1 mmole, 2.4 equiv.) in $H_2O$ (5 mL) was added and the reaction mixture was stirred to room temperature for 2 h. After this time, $CHCl_3$ (50 mL) and $H_2O$ (100 mL) were added, and the layers were separated. To the aqueous layer in a separatory funnel was added $CH_2Cl_2$ (100 mL) and the pH was adjusted to 4 with 1 N HCl, before separation of layers. The water layer was extracted twice with $CH_2Cl_2$ (2×100 mL), the organic layers were combined and dried ($Na_2SO_4$), filtered and concentrated. The residue was purified by flask column chromatography on silica, elution with $CH_2Cl_2$ to 20% MeOH in $CH_2Cl_2$. Yield 0.42 g (1.0 mmole, 39%) of 3 as a colorless sticky wax.

Example 5: Synthesis of Drug Linker

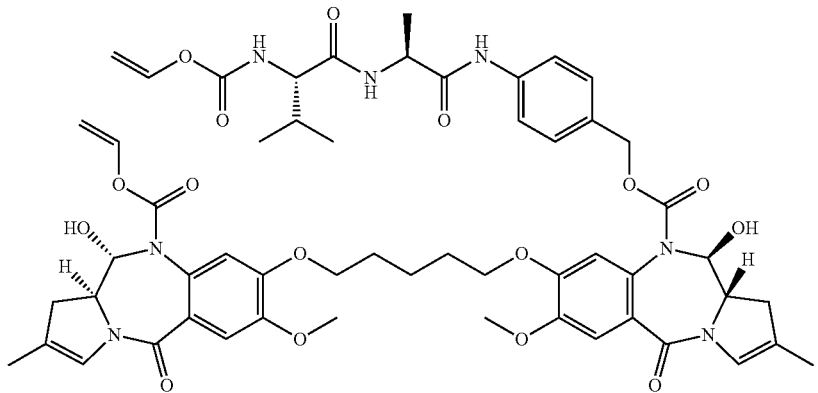

1

↓

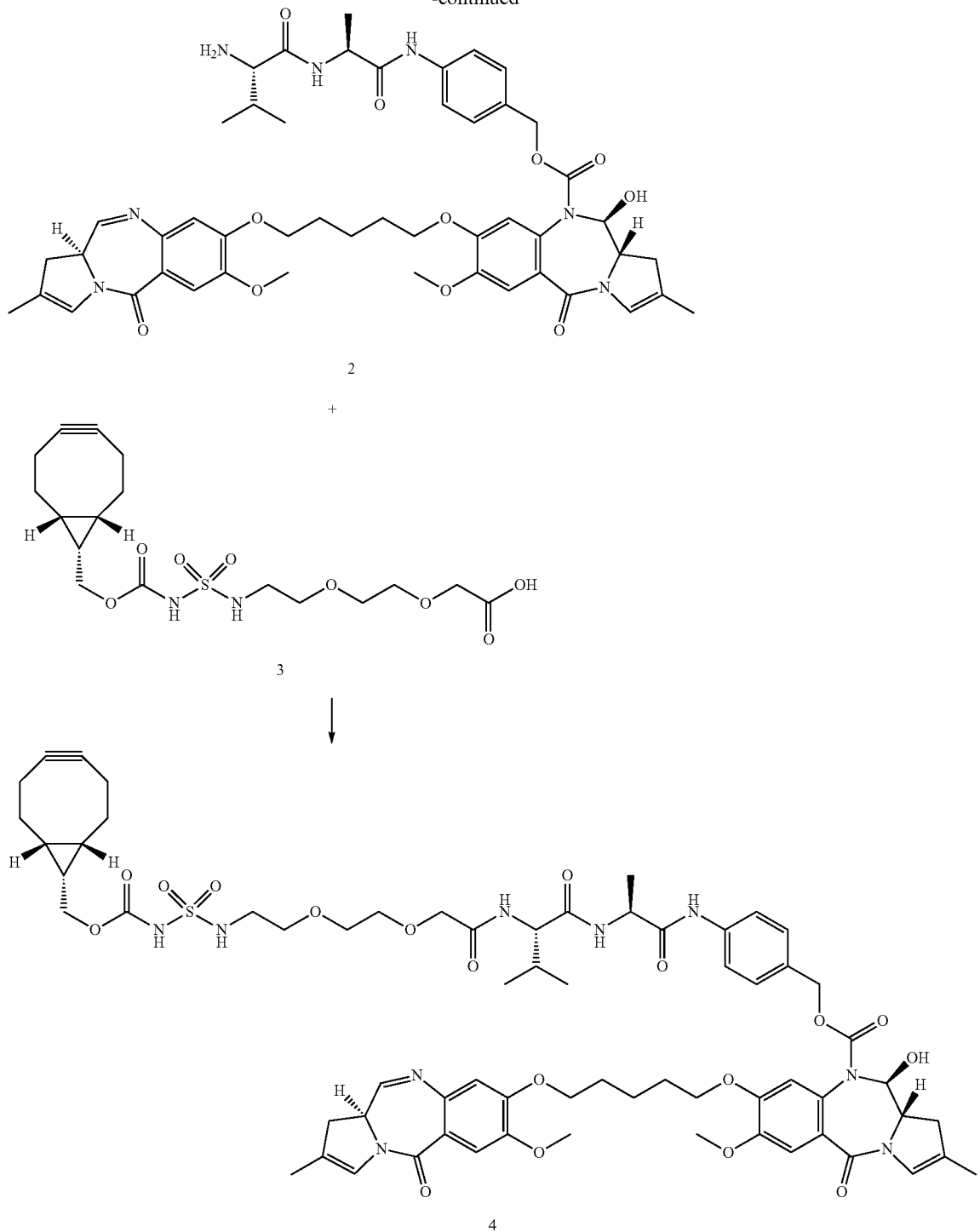

Compound 1 can be synthesised as described in WO2014/057074—see compound 22.

(a) Palladium tetrakistriphenylphosphine (Pd(PPh₃)₄, 4.8 mg, 4.15 µmol) is weighed and put under an inert atmosphere. A solution of pyrrolidine (5.0 µL, 4.3 mg, 60 µmol) in DCM (1 mL) is degassed by bubbling N₂ through the solution. A solution of 1 (27 mg, 24 µmol) in DCM (6 mL) is degassed by bubbling N₂ through the solution. While N₂ is still bubbled through the solution, the degassed solution of pyrrolidine is added. The weighed Pd(PPh₃)₄ is dissolved in DCM (1 mL) and 0.9 mL of this solution is added. After 50 min of bubbling of N₂, DCM (25 mL) is added and the mixture is washed with aqueous saturated NH₄Cl (25 mL). After separation, the aqueous layer is extracted with DCM (2×25 mL). The combined organic layers are dried (Na₂SO₄) and concentrated. The residue is purified by RP-HPLC (30-90% MeCN (0.1% formic acid) in H₂O (0.1% formic acid). The combined fractions are passed through SPE (HCO$_3$) columns and concentrated. After addition of MeCN (50 mL) the mixture is again concentrated. The resulting residue 2 is used in the next step.

The conversion of the reaction can be monitored through LCMS analysis. Column: XBridge BEH C18 Intelligent Speed (IS) Column, 130 Å, 3.5 µm (4.6 mm×20 mm).

Mobile phase A: Water (0.1% formic acid), Mobile phase B (0.1% formic acid). Detection with PDA and ESI+. Samples can be prepared by diluting the reaction mixture with MeCN.

(b) To a solution of the above residue 2 in CHCl$_3$ (5 mL) is added a solution of 3 (15 mg, 36 µmol, mw 418 g/mole) in CHCl$_3$ (0.8 mL). The resulting mixture is added to solid EDC.HCl (4.7 mg, 25 µmol), CHCl$_3$ (5 mL) was added and the mixture stirred for 30 minutes. DCM (30 mL) is added and the resulting mixture is washed with water (30 mL). After separation, the aqueous phase is extracted with DCM (30 mL). The combined organic layers are dried (Na$_2$SO$_4$) and concentrated. The residue is purified by RP-HPLC (30-90% MeCN (no acid) in H$_2$O (0.01% formic acid). The HPLC collection tubes are filled with 5% aqueous (NH$_4$) HCO$_3$ before collection. The combined HPLC fractions are extracted with DCM (3×20 mL). The combined organic layers are dried (Na$_2$SO$_4$) and concentrated. The product 4 is obtained as slightly yellow/white oil (21 mg, 16 µmol, mw 1323 g/mole, 67% over two steps).

The conversion of the reaction can be monitored through LCMS analysis. Column: XBridge BEH C18 Intelligent Speed (IS) Column, 130 Å, 3.5 µm (4.6 mm×20 mm). Mobile phase A: Water (0.1% formic acid), Mobile phase B (0.1% formic acid). Detection with PDA and ESI+.

Example 6: Antibody Modification

Reaction Conditions

The reaction conditions for the one-pot glycan remodelling are:

15 mg/ml AXL Antibody (~0.1 mM)
0.15 mg/mL EndoSH (1% w/w) from *Streptococcus pyogenes*
1.13 mg/mL His-TnGalNAcT (7.5% w/w) Galactose-N-acetyl Transferase (GalNAcT) enzyme
2.5 mM 6-N$_3$GalNAc-UDP (25 eq. compared to IgG)
10 mM MnCl$_2$
25 mM TrisHCl ph 8.0
150 mM NaCl
Incubate 16 hours at 30° C.

Procedure

This example is on a 25 mg-scale, which may be altered as necessary. The individual components are added in order and mixed:

106.5 µL 25 mM Tris pH 8.0, 150 mM NaCl (to obtain a final volume of 1667 µL)
1 mL 25 mg/mL AXL Antibody in 25 mM Tris pH 8.0, 150 mM NaCl
71.4 µL 3.5 mg/mL EndoSH in 25 mM Tris pH 8.0
389 µL 4.82 mg/mL His-TnGalNAcT in 25 mM Tris pH 8.0
16.7 µL 1M MnCl$_2$ in MQ
83.4 µL 0.1 M 6-N$_3$GalNAc-UDP in MQ This mixture for approximately 16 hours at 30° C. Completion of the modified galactose residue may be assessed by subjecting a sample to MS analysis. After protein A affinity purification, a small sample of the product may be reduced with DTT and subsequently subjected to MS analysis. A typical mass spectrum of a successful transfer reaction shows the formation of a one major product of (90% of total heavy chain), resulting from modified galactose transfer to core GlcNAc(Fuc) substituted Ab, and a minor product (±10% of total heavy chain), resulting from modified galactose transfer to core GlcNAc (without Fucose) substituted Ab.

Purification Procedure

Buffers

Binding/wash buffer (TBS pH 7.5):
20 mM TrisHCIl ph 7.5
150 mM NaCl
Wash buffer for endotoxin removal (TBS pH 7.5+Triton-X100):
20 mM TrisHCIl pH 7.5
150 mM NaCl
0.2% Triton X-100
Elution buffer:
0.1 M Glycine pH 2.7
CIP buffer:
0.5 M NaOH Procedure 1. Wash the MabSelectSure 5 mL column (5 mL/min) with the following buffers in order to clean the column before applying the sample:
Wash column with at least 5 column volumes (CV) TBS pH 7.5
Wash column with 15 CV 0.5 M NaOH
Wash column with 5 CV TBS pH 7.5
Wash column with 5 CV Glycine pH 2.7
Wash column with TBS pH 7.5 until a natural pH is obtained
2. Remove precipitation from reaction mixture by centrifugation (5 min at 4000 g) or by filtration (0.22 or 0.45 µm filter)
3. Load sample at 2 mL/min and perform the following steps with 5 mL/min:
Wash with at least 20 CV TBS=0.2% Triton X-100
Wash with at least 20 CV TBS
Elute with 0.1 M Glycine ph 2.7
4. Immediately neutralize fractions by adding ⅕ volume of 1 M Tric-HCl ph 8.0 and mixing
5. Dialyze sample against 3×≥50 volumes of PBS pH 7.4 at 4° C. (3×>1 hour)
6. Concentrate sample using spinfilter devices to ~20 mg/mL Example 7: Conjugation of 4 to Modified Antibody to Produce ConjA Reaction Conditions 15 mg/ml azido-modified AXL antibody (0.1 M IgG)
0.5 mM 4 (5 eq. compared to IgG=2.5 eq per azide)
10% DMF or 25% propylenegycol
PBS pH7.4

Procedure

1. Add 9 vols of 16.67 mg/ml azido-modified antibody in PBS pH7
2. Add 1 vol of 5 mM 4 in DMF and mix immediately.
3. Incubate overnight.
4. Measure conversion by RP-HPLC and MS.

Example 8: Purification of ADC

Sample Preparation

The following requirements should be met before loading onto the column: Organic solvent ≤5% Total sample volume ≤3% of the CV (≤720 µL for Superdex 200 10/300 GL, and ≤10 ml for Superdex 200 HiLoad 26/600)

No precipitants

The above requirements can be accomplished using the following procedure:

1. Dilute sample with PBS pH7.4 to a final organic solvent concentration of 55%
2. If volume exceeds 3% of the CV, the sample was concentrated using Amicon Ultra centrifugal filters (MWCO 10 kDa)
3. Potential precipitation is removed by centrifugation (10 min at 13000 rpm in a table top centrifuge)

Purification

The purification was carried out using a Superdex 200 10/300 GL column (CV=23 ml, GE healthcare) on an Akta Purifier-10. The following washing steps are performed with a flow rate of 0.5 ml/min:

Wash column with 1 CV water
Wash column with 1 CV 0.5 M NaOH.
Equilibrate column with PBS pH 7.4 (Sigma, D8537) until neutral pH is obtained.

The sample is injected with 0.5 ml/min PBS pH7.4 and 1 ml fractions are collected (total run=1.5CV). Monomer fractions are pooled and dialysed at 4° C. against 3×1 L of formulation buffer (30 mM histidine, 200 mM sorbitol, 0.02% (w/v) tween-20, pH 6.0). Samples are filter-sterilized using 0.22 μm filter, snapfrozen using liquid nitrogen and stored at −80° C.

Mass spectral analysis of the fabricator-digested sample showed one major product (observed mass 25691 Da, approximately 90% of total Fc/2 fragment), corresponding to the conjugated Fc/2 fragment. RP-HPLC analysis of the reduced sample indicated an average DAR of 1.98.

Example 9: In Vitro Cytotoxicity

H1299 cells were obtained from ATCC (ATCC number CRL-5803). H1299 medium was Dulbecco's Modified Eagle Medium (DMEM) supplemented with 10% Gibco FBS. Cells were grown at 37° C., 5% $CO_2$ in a humidified incubator. Cell suspensions were dispensed into 96-well flat bottomed plates (104 cells per well). A set of 8×10-fold dilutions of stock ADC were prepared in cell culture medium. Each ADC dilution (50 μl per well) was dispensed into 4 replicate wells of the 96-well plate containing cell suspension. Control wells were prepared by adding the same volume of culture medium only. After incubation for 96 hours, cell viability was measured by 3-(4,5-dimethylthiazol-2-yl)-5-(3-carboxymethoxy-phenyl)-2-(4-sulfophenyl)-2H-tetrazolium (MTS) assay (Promega, catalogue number G5421) following manufacturer's instructions. Absorbance was measured at 490 nm. Cell survival (%) was calculated from the mean absorbance in the 4 ADC-treated wells compared to the mean absorbance in the 4 control wells (100%). Dose response curves were generated from the mean data of 3 replicate experiments and the $EC_{50}$ values were determined by fitting data to a sigmoidal dose-response curve with variable slope using Prism (GraphPad, San Diego, Calif.). Error bars indicate standard deviation (SD).

The $EC_{50}$ of ConjA was found to be 0.0554 μg/mL.

Example 10: Antigen Binding Study

Maxisorp plates were coated at +4° C. overnight with human Axl antigen (50 ng/well; batch in PBS. Non-reactive sites were blocked with SuperBlock buffer (overnight at +4° C. or room temperature). A set of 8×3-fold or 5-fold dilutions of stock ADC were prepared in sample buffer/PBS/Tween20. Each ADC dilution (60 μL/well) was dispensed into 4 replicate wells of the coated plate. Control wells were prepared by adding the same volume of sample buffer/PBS/Tween20. Anti-human kappa IgG-horseradish peroxidase (HRP) conjugate was used as secondary antibody (1:5000, 1 hour at room temperature). HRP was detected with 1-Step Ultra TMB-ELISA substrate solution (75 μL/well; 5 minutes at room temperature). Substrate reaction was stopped with 0.6 M HCl (75 μL/well). Optical density was measured at 450 nm on Envision using 450 nm Peroxidase program. Antigen binding curves were generated from the mean data of 3 replicate experiments using Prism (GraphPad, San Diego, Calif.). FIG. 2 shows the results obtained, where ▲ is ConjA. Error bars indicate standard error of the mean (SEM). ConjA bound with high affinity to the extracellular domain of AXL coated on plates.

Figure 3:
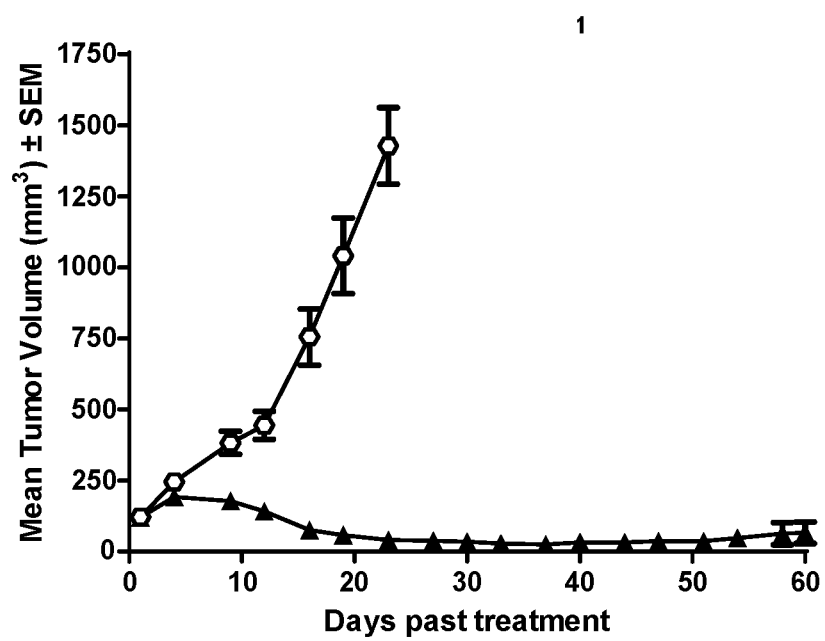
FIG. 3. Graph showing in vivo efficacy of a conjugate according to the invention.

Example 11: In Vivo Efficacy Study $5 \times 10^6$ MDA-MB-231 tumor cells were subcutaneously implanted to female athymic nude mice. ADC dosing with vehicle or test item was initiated when tumor volumes reached 88-172 $mm^3$. ConjA was administrated intravenously (i.v.) via tail vein injection once at a dose level of 1 mg/kg. The dosing volume was 10 mL/kg of body weight and was escalated to the body weight of each individual animal. Animals were euthanized if their tumor volume reached the endpoint volume of 1500 $mm^3$ or at the end of the study, whichever came first. Animals weight, signs of any adverse, treatment-related side effects and clinical signs were monitored during the study period. For the calculation of mean tumour volume of the group, the following rule was applied: when an animal exited the study due to tumour size, the final tumour volume recorded for the animal was included with the data used to calculate the mean volume at subsequent time points. Tumour volume and body weight values were not used to calculate a group mean tumour volumes/body weight when fewer than 50% of the animals in a group remained in the study. Prism (GraphPad, San Diego, Calif.) was used for graphical presentations and statistical analyses. FIG. 3 shows the results obtained, where ▲ is ConjA, and ○ is the vehicle alone. Error bars indicate SEM.

A single dose of 1 mg/kg of ConjA strongly inhibited tumor growth with 10/10 mice being tumor-free 60 days after dosing.

Example 12: Rat Toxicology Study

Method

ConjA was evaluated in a single intravenous dose rat tolerability study. Male sprague-dawley rats (n=3/group) were dosed 3 & 6 mg/kg for ConjA on day 1, with necropsy on day 21 following dosing. Bodyweights and food consumption were monitored frequently with in-life sampling for clinical pathology (blood on days 8 and 21) and repeated sampling for pharmacokinetics. At necropsy, macroscopic observations were taken with selected organs weighed and retained for possible histopathology.

ConjA was clinically well tolerated at 3 & 6 mg/kg. Bodyweight gain was reduced by 11 and 21% in the 3 and 6 mg/kg groups respectively, consistent with reduced food consumption. Several haematology parameters were reduced on day 8, mainly in the 6 mg/kg dose group (reticulocytes (−76%), haemoglobin (−29%) white blood cells (−66%) and platelets (−37%)), with some evidence of recovery by day 21. At necropsy, reduced thymus weight was observed in all animals. Therefore, the maximum tolerated dose (MTD) for ConjA was 6 mg/kg.

Example 13: Synergy in SN12C Cells (Axl High-Expressing) Between ADC×AXL and Each of Cytarabine, Decitabine, Gemcitabine, Olaparib, and Fludarabine Cells were plated on day 1 at 10,000 cells/well in 96-well plates, three replicates per experiment and total n of 3. Combination drug was added on day 2 at various doses (see figures) and incubated for 24 hours at 37° C., 5% $CO_2$. Drug only control was added in the following dosage range at the same time, all at a 10 fold dilution.

On day 3 ADC×AXL was added to cells containing drug, or media only as a control in the dosage range 0.001 pM-100 nM at a 10 fold dilution and incubated for a further 5 days (3×cell doubling time). Absorption was analysed at 492 nM on a Thermo Labsystems Multiscan Ascent plate reader using the MTT assay.

Data was analysed using Graphpad Prism v5.02, and synergism was plotted using Calcusyn v2.11. Strong synergism is indicative of a CI value of <0.7—moderate synergism carries a CI value of >0.7 and <1.

Figure 4:
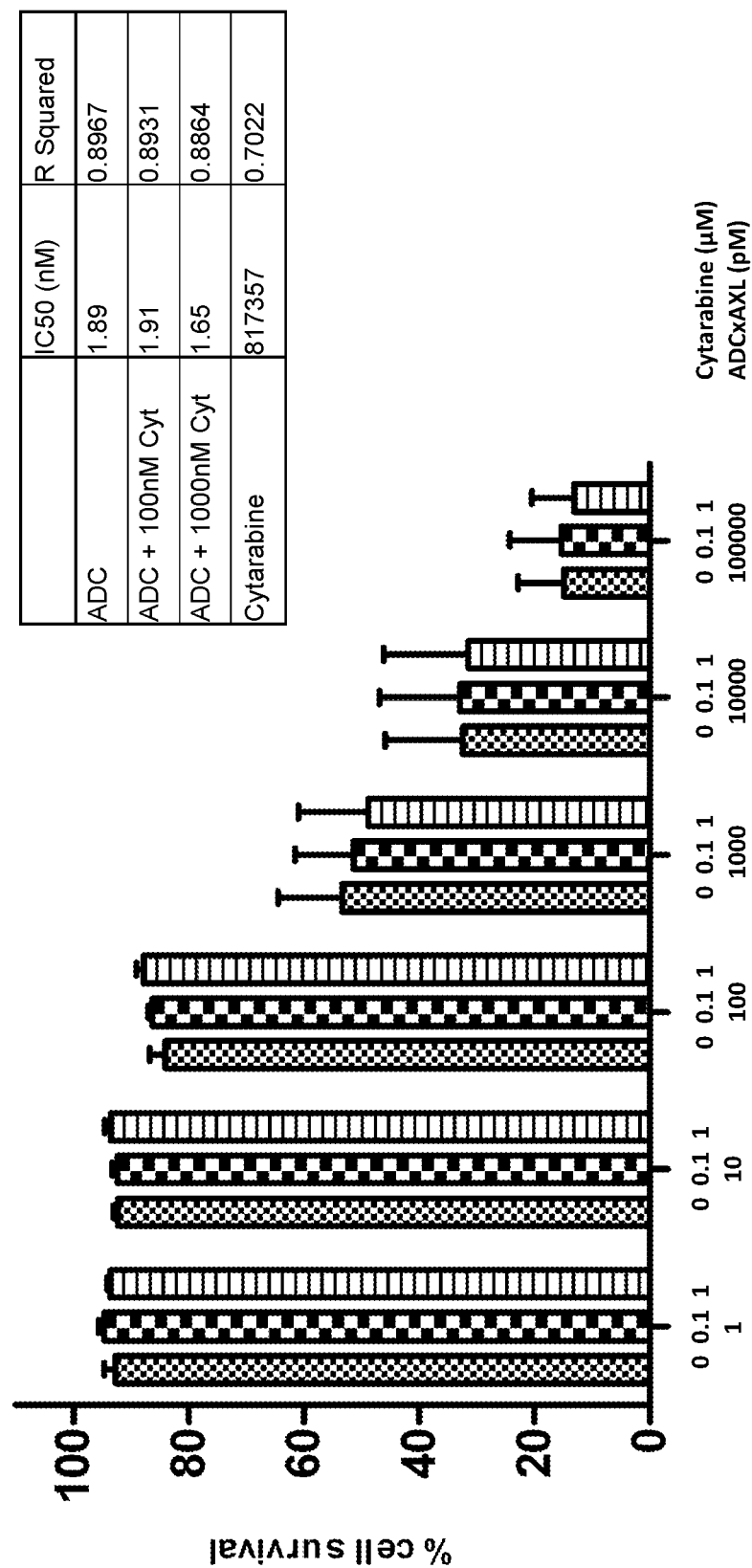
FIG. 4. Graph showing in vitro synergy between ADCx AXL and Cytarabine in SN12C cells.
Figure 5:
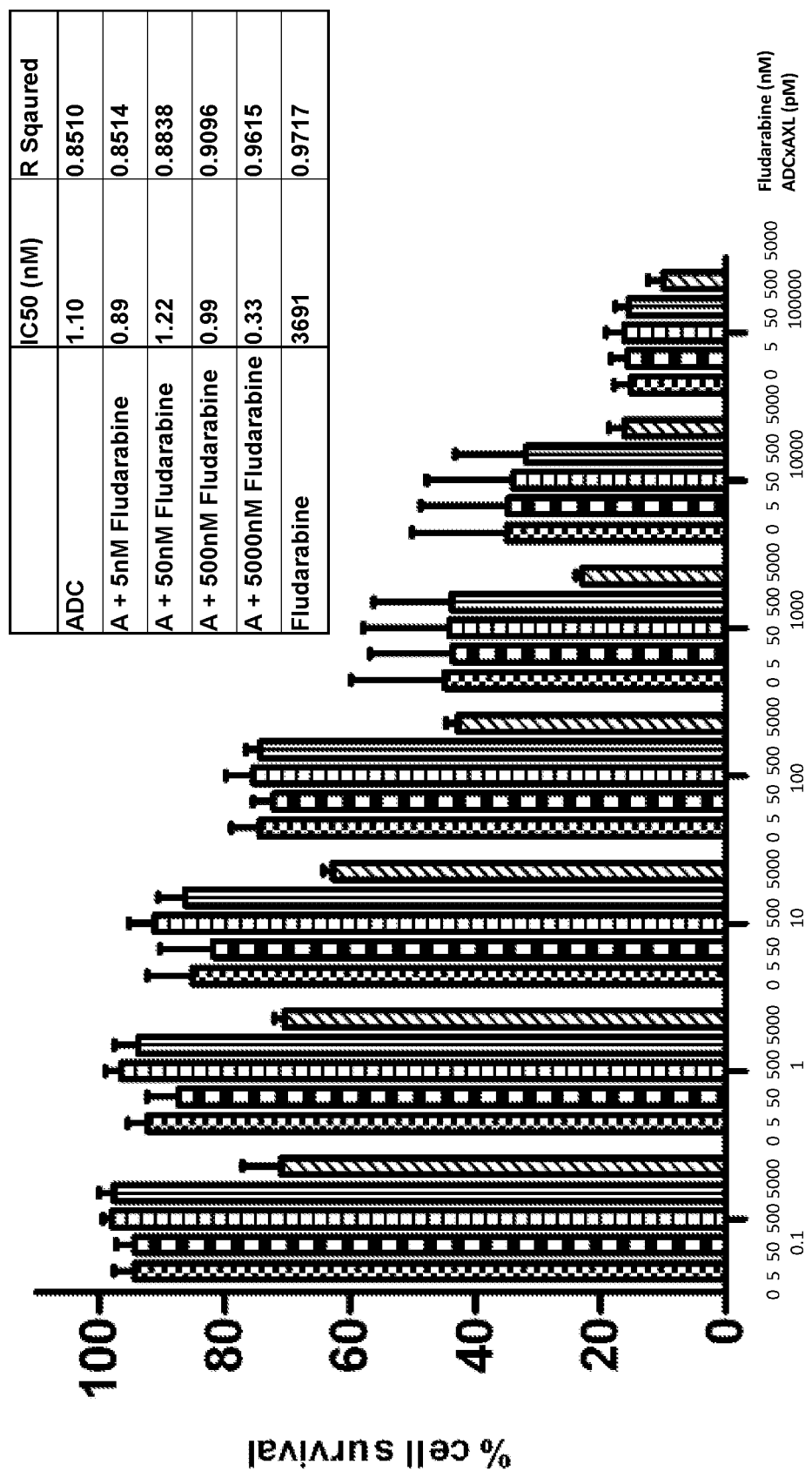
FIG. 5. Graph showing in vitro synergy between ADCx AXL and Fludarabine in SN12C cells.
Figure 6:
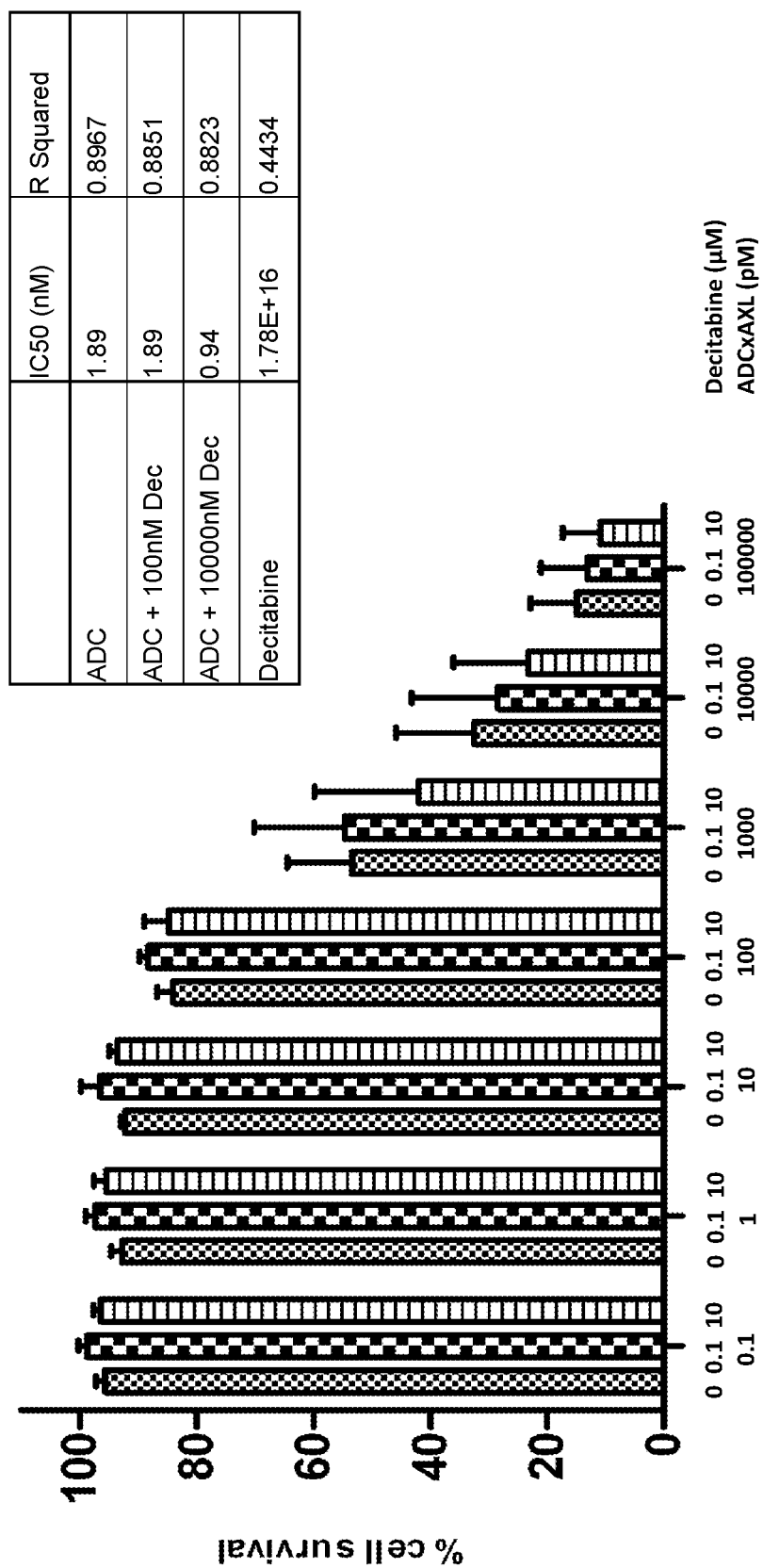
FIG. 6. Graph showing in vitro synergy between ADCx AXL and Decitabine in SN12C cells.
Figure 7:
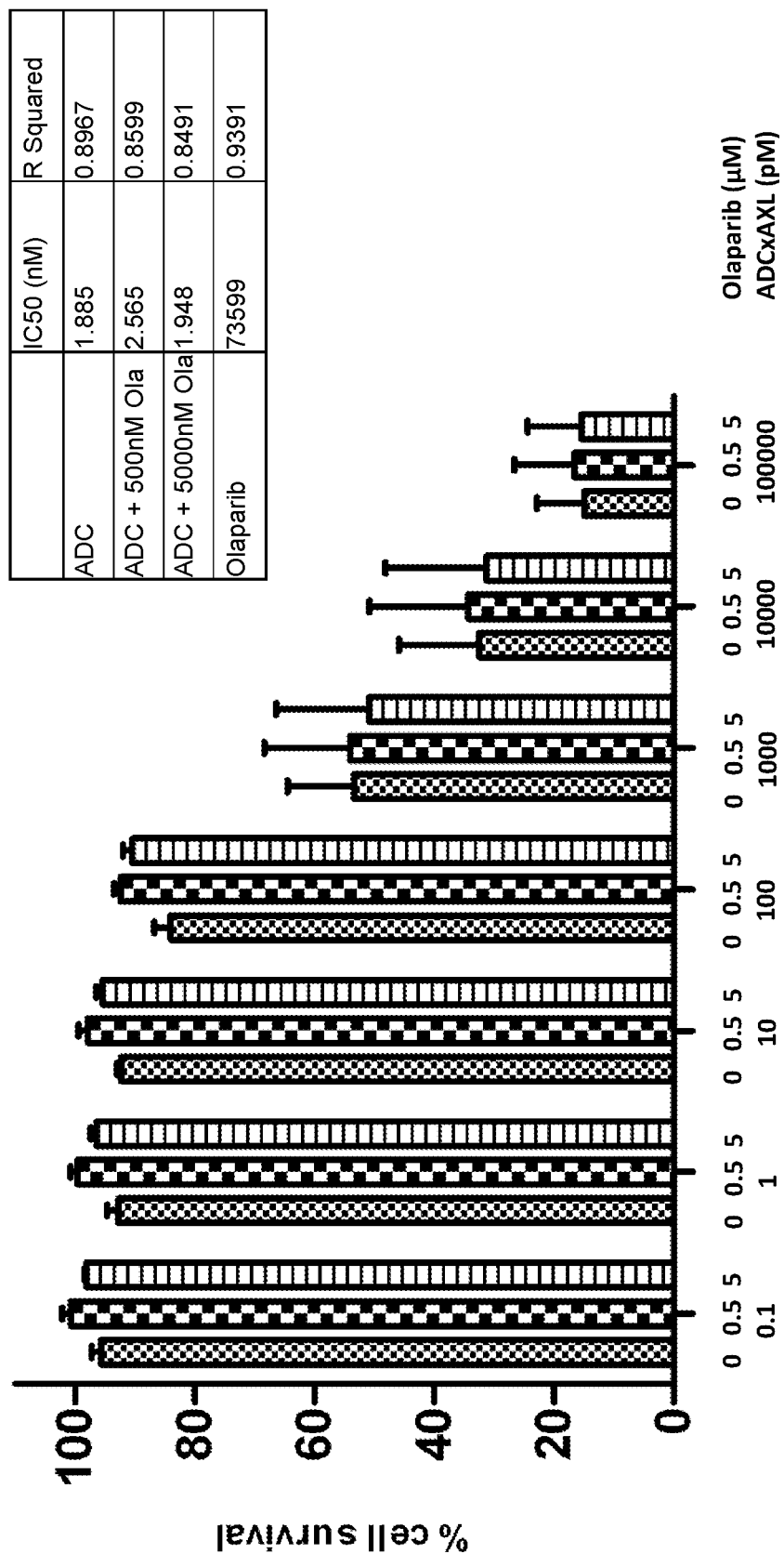
FIG. 7. Graph showing in vitro synergy between ADCx AXL and Olaparib in SN12C cells.
Figure 8:
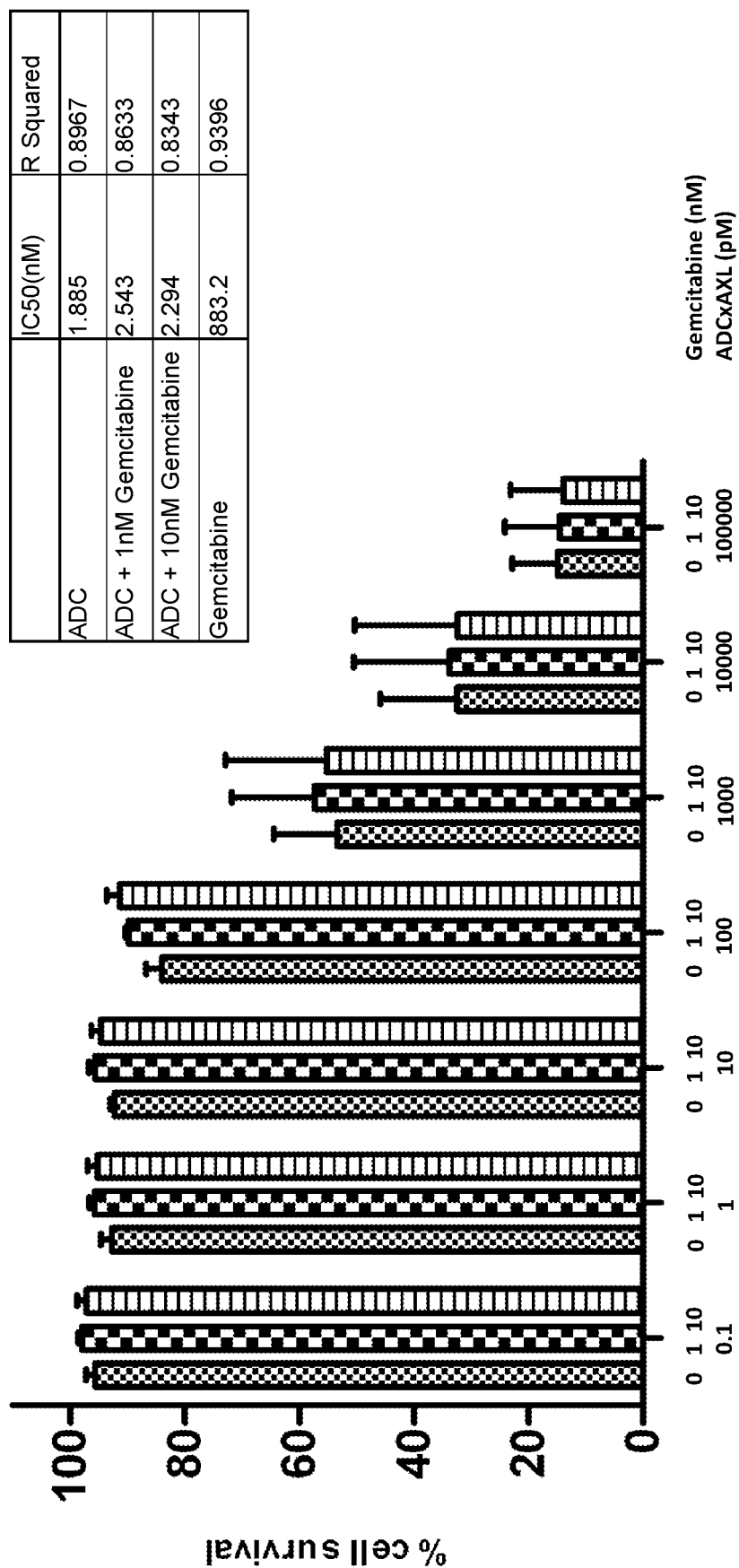
FIG. 8. Graph showing in vitro synergy between ADCx AXL and Gemcitabine in SN12C cells.

Results are shown in FIG. 4 (Cytarabine), FIG. 5 (Fludarabine), FIG. 6 (Decitabine), FIG. 7 (Olaparib), and FIG. 8 (Gemcitabine).

Example 14: Synergy Between ADC×AXL and Each of MEKi and BRAFi

MEKi

Examples of suitable MEK inhibitors such as Trametinib, Cobimetinib, Binimetinib, Selumetinib, U0126 or PD325901.

MEK inhibitors (MEKi) inhibit the mitogen-activated protein kinase enzymes MEK1 and/or MEK2. They can be used to affect the MAPK/ERK pathway which is often overactive in some cancers. Defects in the MAP/ERK pathway can lead uncontrolled growth, especially in melanoma. Hence MEK inhibitors have potential for treatment of some cancers especially BRAF-mutated melanoma and KRAS/BRAF mutated colorectal cancer (Wang et al., Biochim. Biophys Acta 1773(8): 1248-1255 (2007). Interestingly, according Miller et al (Cancer Discovery 6(4):382-399, 2016) incubation of tumor cells with MEKi (U0126 or PD325901) induced a strong accumulation of AXL on the membrane of tumor cells.

Trametinib

Trametinib (trade name Mekinist) is a MEK inhibitor, inhibiting MEK1 and MEK2. It is approved for the treatment of patients with BRAF V600E mutated metastatic melanoma. The V600E mutation makes the mutant BRAF gene constitutively active, driven proliferation of the melanoma. By Inhibiting the MAP/ERK pathway, cell proliferation is blocked and apoptosis (controlled cell death) is induced.

Combining ADC×AXL, which targets AXL positive tumors, with MEKi is advantageous, because on the one hand, ADC×AXL will directly kill the AXL positive tumor cells via a mechanisms depending on DNA cross-linking resulting in apoptosis, while on the other hand, MEKi will induce apoptosis through interference with cell proliferation through inhibition of the MAP/ERK cell signalling pathway. Also, combining ADC×AXL with MEKi is advantageous because the upregulation of AXL by MEKi will increase the uptake of ADC×AXL into the tumor cells resulting in higher accumulation of PBD dimer and subsequent DNA damage leading to higher cancer cell death.

To show that co-treatment of AXL-positive cancer cell lines with ADC×AXL and MEKi has an additive or synergistic anti-tumor effect, a panel of cell lines including, but not limited to MDA-MB231, SN12C, MDA-MB-157 and SKLU1 will be pre-incubated with cells with MEKi for up to 24h (1 or 10 uM) and then serial dilutions of ADC×AXL (or B12-PL1601 as control) will be added. After incubation the in vitro cytotoxicity of the combinations (as determined by CellTiter-Glo® or MTS assays) will be measured.

Alternatively, a panel of cell lines including, but not limited to MDA-MB231, SN12C, MDA-MB-157 and SKLU1 will be co-treated with a range of concentrations of both ADC×AXL and MEKi.

As negative controls, the same panel of cell lines will be co-treated with a range of concentrations of Trametinib or with a range of concentration of ADC×AXL and vehicle.

After incubation the in vitro cytotoxicity of the combinations (as determined by CellTiter-Glo® or MTS assays) will be measured. Percentage cell viability is calculated compared to the untreated control. Cytotoxic synergy is calculated by transforming the cell viability data into fraction affected, and calculating the combination index using the CalcuSyn analysis program.

BRAFi

Examples of suitable BRAF inhibitors such as vemurafenib and dabrafenib. A BRAF inhibitor inhibits the (mutated) B-RAF protein directly. Mutations in BRAF can lead to uncontrolled growth, especially in melanoma.

Vemurafenib

Vemurafenib (trade name Zelboraf) directly inhibits B-RAF. It is approved for the treatment of patients with late-stage melanoma driven by a V600E B-RAF mutated gene.

Mutations makes the mutant BRAF gene constitutively active, driving proliferation of the melanoma. By Inhibiting mutated B-RAF, cell proliferation is blocked and apoptosis (controlled cell death) is induced.

Combining ADC×AXL, which targets AXL positive tumors, with Vemurafenib is advantageous, because on the one hand, ADC×AXL will directly kill the AXL positive tumor cells via a mechanisms depending on DNA cross-linking resulting in apoptosis, while on the other hand, Vemurafenib will induce apoptosis via interference with cell proliferation through inhibition of BRAF.

To show that ADC×AXL works synergistically with Vemurafenib, a panel of AXL (+) cell lines including, but not limited to MDA-MB231, NCI-H1299 and SNU12 cells, will be co-treated with a range of concentrations of both ADC×AXL and Vemurafenib.

As negative controls, the same panel of cell lines will be co-treated with a range of concentrations of Trametinib or with a range of concentration of ADC×AXL and vehicle.

After incubation, the in vitro cytotoxicity of the combinations will be determined by an MTS assay. To determine the cytotoxicity, Cell viability is measured by adding MTS per well and incubating for 4 hours at 37 C. Percentage cell viability is calculated compared to the untreated control. Cytotoxic synergy is calculated by transforming the cell viability data into fraction affected, and calculating the combination index using the CalcuSyn analysis program.

Example 15: Synergy Against AXL+ Ve Neoplastic Cells Between ADC×AXL and Each of the Immunooncology (110) Secondary Agents PD1 Antagonists, PDL1 Antagonists, CTLA4 Antagonists, OX40 Agonists, and GITR Agonists PD1 Antagonists To test whether a PBD-based ADC against AXL combined with a PD1 antagonist shows additive or synergistic effect, the combination is tested in vivo in a syngeneic tumor model in immunocompetent mice (for AXL, potentially suitable models include 4T1, EMT-6, EMT-6-BRCA1(−/−), EMT-6-BRCA1(+/−), 4T1-BRCA1(+/−), KLN 205, Lewis Lung, Madisonl09 Colon26, CT26, MC38, GL261, B16F10, CloudmanS91, Pan02, Renca, and MBT-2). For this purpose, an antibody cross reactive with mouse AXL is conjugated to a PBD warhead and this ADC is administered with the PD1 antagonist to mice grafted with a mouse tumor cell line expressing AXL. The ADC is administered before the PD1 antagonist, concomitantly with the PD1 antagonist, or after the PD1 antagonist, as decided by the experimenter.

Typically, the ADC is dosed as a single dose between 0.1 and 1 mg/kg, while the PD1 antagonist is dosed Q3d x 3 at doses between 1 and 10 mg/kg. Control groups include the ADC or PD1 antagonist alone. Tumor volumes and body weight is subsequently measured up to 60 days for all groups and the number of partially responding (PR), completely responding (CR) tumor free surviving (TFS mice is determined in each group.

Statistical analysis (typically a log-rank test) is performed to determine whether the mice treated with the combination have outperformed the mice treated with either ADC or PD1 antagonist alone.

PDL1 Antagonists

To test whether a PBD-based ADC against AXL combined with a PDL1 antagonist shows additive or synergistic effect, the combination is tested in vivo in a syngeneic tumor model in immunocompetent mice. For this purpose, an antibody cross reactive with mouse AXL is conjugated to a PBD warhead and this ADC is administered with the PDL1 antagonist to mice grafted with a mouse tumor cell line expressing AXL. The ADC is administered before the PDL1 antagonist, concomitantly with the PDL1 antagonist, or after the PDL1 antagonist, as decided by the experimenter.

Typically, the ADC is dosed as a single dose between 0.1 and 1 mg/kg, while the PD1 antagonist is dosed Q3d x 3 at doses between 1 and 10 mg/kg. Control groups include the ADC or PDL1 antagonist alone. Tumor volumes and body weight is subsequently measured up to 60 days for all groups and the number of partially responding (PR), completely responding (CR) tumor free surviving (TFS mice is determined in each group.

Statistical analysis (typically a log-rank test) is performed to determine whether the mice treated with the combination have outperformed the mice treated with either ADC or PDL1 antagonist alone.

CTLA4 Antagonists

To test whether a PBD-based ADC against AXL combined with a CTLA4 antagonist shows additive or synergistic effect, the combination is tested in vivo in a syngeneic tumor model in immunocompetent mice. For this purpose, an antibody cross reactive with mouse AXL is conjugated to a PBD warhead and this ADC is administered with the CTLA4 antagonist to mice grafted with a mouse tumor cell line expressing AXL. The ADC is administered before the CTLA4 antagonist, concomitantly with the CTLA4 antagonist, or after the CTLA4 antagonist, as decided by the experimenter.

Typically, the ADC is dosed as a single dose between 0.1 and 1 mg/kg, while the CLTA4 antagonist is dosed Q3d x 3 at doses between 1 and 10 mg/kg. Control groups include the ADC or CTLA4 antagonist alone. Tumor volumes and body weight is subsequently measured up to 60 days for all groups and the number of partially responding (PR), completely responding (CR) tumor free surviving (TFS mice is determined in each group.

Statistical analysis (typically a log-rank test) is performed to determine whether the mice treated with the combination have outperformed the mice treated with either ADC or CTLA4 antagonist alone.

OX40 Agonists

To test whether a PBD-based ADC against AXL combined with a OX40 agonist shows additive or synergistic effect, the combination is tested in vivo in a syngeneic tumor model in immunocompetent mice. or this purpose, an antibody cross reactive with mouse AXL is conjugated to a PBD warhead and this ADC is administered with the OX40 agonist to mice grafted with a mouse tumor cell line expressing AXL. The ADC is administered before the OX40 agonist, concomitantly with the OX40 agonist, or after the OX40 agonist, as decided by the experimenter.

Typically, the ADC is dosed as a single dose between 0.1 and 1 mg/kg, while the OX40 agonist is dosed Q3d x 3 at doses between 1 and 10 mg/kg. Control groups include the ADC or OX40 agonist alone. Tumor volumes and body weight is subsequently measured up to 60 days for all groups and the number of partially responding (PR), completely responding (CR) tumor free surviving (TFS mice is determined in each group.

Statistical analysis (typically a log-rank test) is performed to determine whether the mice treated with the combination have outperformed the mice treated with either ADC or OX40 agonist alone.

GITR Agonists

To test whether a PBD-based ADC against AXL combined with a GITR agonist shows additive or synergistic effect, the combination is tested in vivo in a syngeneic tumor model in immunocompetent mice. For this purpose, an antibody cross reactive with mouse AXL is conjugated to a PBD warhead and this ADC is administered with the GITR agonist to mice grafted with a mouse tumor cell line expressing AXL. The ADC is administered before the GITR agonist, concomitantly with the GITR agonist, or after the GITR agonist, as decided by the experimenter.

Typically, the ADC is dosed as a single dose between 0.1 and 1 mg/kg, while the GITR agonist is dosed Q3d x 3 at doses between 1 and 10 mg/kg. Control groups include the ADC or GITR agonist alone. Tumor volumes and body weight is subsequently measured up to 60 days for all groups and the number of partially responding (PR), completely responding (CR) tumor free surviving (TFS mice is determined in each group.

Statistical analysis (typically a log-rank test) is performed to determine whether the mice treated with the combination have outperformed the mice treated with either ADC or GITR agonist alone.

Example 16: Synergy Against AXL−Ve Neoplastic Cells Between ADC×AXL and Each of the Immunooncology (110) Secondary Agents PD1 Antagonists, PDL1 Antagonists, CTLA4 Antagonists, OX40 Agonists, and GITR Agonists AXL is also expressed on immune cells that infiltrate the local tumor environment and which can have a suppressive impact on the innate immune response against the tumor. Examples of such cells are NK cells, DC cells or macrophages. ADC×AXL can be used to target these immune cells, which will kill the immune suppressive cells, boosting the immune response.

In addition to this 'release of immune suppression' effect, killing of the immune cells by ADC×AXL will release local PBD warhead will kill neighboring neoplastic cells via bystander kill.

Accordingly, through these two mechanisms, tumors not expressing AXL can be killed by targeting immune cells in the local tumor environment. Also, AXL−ve tumor cells killed by PBD released from neighboring immune cells will induce additional immunogenic cell death, further strengthening the anti-tumor immune response.

PD1 Antagonists

To test whether a PBD-based ADC against AXL combined with a PD1 antagonist shows additive or synergistic effect against tumors not expressing AXL, the combination is tested in vivo in a syngeneic tumor model in immunocompetent mice. For this purpose, an antibody cross reactive with mouse AXL is conjugated to a PBD warhead and this ADC is administered with the PD1 antagonist to mice grafted with a mouse tumor cell line know to have high levels of infiltrating cells (e.g dendritic cells, NK cells, or macrophages), such as but not limited to MC38 and CT26. The ADC is administered before the PD1 antagonist, concomitantly with the PD1 antagonist, or after the PD1 antagonist, as decided by the experimenter.

Typically, the ADC is dosed as a single dose between 0.1 and 1 mg/kg, while the PD1 antagonist is dosed Q3d x 3 at doses between 1 and 10 mg/kg. Control groups include the ADC or PD1 antagonist alone. Tumor volumes and body weight is subsequently measured up to 60 days for all groups and the number of partially responding (PR), completely responding (CR) tumor free surviving (TFS mice is determined in each group.

Statistical analysis (typically a log-rank test) is performed to determine whether the mice treated with the combination have outperformed the mice treated with either ADC or PD1 antagonist alone.

PD-L1 Antagonists

To test whether a PBD-based ADC against AXL combined with a PDL1 antagonist shows additive or synergistic effect against tumors not expressing AXL, the combination is tested in vivo in a syngeneic tumor model in immunocompetent mice. For this purpose, an antibody cross reactive with mouse AXL is conjugated to a PBD warhead and this ADC is administered with the PDL1 antagonist to mice grafted with a mouse tumor cell line know to have high levels of infiltrating cells (e.g dendritic cells, NK cells, or macrophages), such as but not limited to MC38 and CT26. The ADC is administered before the PDL1 antagonist, concomitantly with the PDL1 antagonist, or after the PDL1 antagonist, as decided by the experimenter.

Typically, the ADC is dosed as a single dose between 0.1 and 1 mg/kg, while the PDL1 antagonist is dosed Q3d x 3 at doses between 1 and 10 mg/kg. Control groups include the ADC or PDL1 antagonist alone. Tumor volumes and body weight is subsequently measured up to 60 days for all groups and the number of partially responding (PR), completely responding (CR) tumor free surviving (TFS mice is determined in each group.

Statistical analysis (typically a log-rank test) is performed to determine whether the mice treated with the combination have outperformed the mice treated with either ADC or PDL1 antagonist alone.

CTLA4 Antagonists

To test whether a PBD-based ADC against AXL combined with a CTLA4 antagonist shows additive or synergistic effect against tumors not expressing AXL, the combination is tested in vivo in a syngeneic tumor model in immunocompetent mice. For this purpose, an antibody cross reactive with mouse AXL is conjugated to a PBD warhead and this ADC is administered with the CTLA4 antagonist to mice grafted with a mouse tumor cell line know to have high levels of infiltrating cells (e.g dendritic cells, NK cells, or macrophages), such as but not limited to MC38 and CT26. The ADC is administered before the CTLA4 antagonist, concomitantly with the CTLA4 antagonist, or after the CTLA4 antagonist, as decided by the experimenter.

Typically, the ADC is dosed as a single dose between 0.1 and 1 mg/kg, while the CTLA4 antagonist is dosed Q3d x 3 at doses between 1 and 10 mg/kg. Control groups include the ADC or CTLA4 antagonist alone. Tumor volumes and body weight is subsequently measured up to 60 days for all groups and the number of partially responding (PR), completely responding (CR) tumor free surviving (TFS mice is determined in each group.

Statistical analysis (typically a log-rank test) is performed to determine whether the mice treated with the combination have outperformed the mice treated with either ADC or CTLA4 antagonist alone.

OX40 Agonists

To test whether a PBD-based ADC against AXL combined with a OX40 agonist shows additive or synergistic effect against tumors not expressing AXL, the combination is tested in vivo in a syngeneic tumor model in immunocompetent mice. For this purpose, an antibody cross reactive with mouse AXL is conjugated to a PBD warhead and this ADC is administered with the OX40 agonist to mice grafted with a mouse tumor cell line know to have high levels of infiltrating cells (e.g dendritic cells, NK cells, or macrophages), such as but not limited to MC38 and CT26. The ADC is administered before the OX40 agonist, concomitantly with the OX40 agonist, or after the OX40 agonist, as decided by the experimenter.

Typically, the ADC is dosed as a single dose between 0.1 and 1 mg/kg, while the OX40 agonist is dosed Q3d x 3 at doses between 1 and 10 mg/kg. Control groups include the ADC or OX40 agonist alone. Tumor volumes and body weight is subsequently measured up to 60 days for all groups and the number of partially responding (PR), completely responding (CR) tumor free surviving (TFS mice is determined in each group.

Statistical analysis (typically a log-rank test) is performed to determine whether the mice treated with the combination have outperformed the mice treated with either ADC or OX40 agonist alone.

GITR Agonists

To test whether a PBD-based ADC against AXL combined with a GITR agonist shows additive or synergistic effect against tumors not expressing AXL, the combination is tested in vivo in a syngeneic tumor model in immunocompetent mice. For this purpose, an antibody cross reactive with mouse AXL is conjugated to a PBD warhead and this ADC is administered with the GITR agonist to mice grafted with a mouse tumor cell line know to have high levels of infiltrating cells (e.g dendritic cells, NK cells, or macrophages), such as but not limited to MC38 and CT26. The ADC is administered before the GITR agonist, concomitantly with the GITR agonist, or after the GITR agonist, as decided by the experimenter.

Typically, the ADC is dosed as a single dose between 0.1 and 1 mg/kg, while the GITR agonist is dosed Q3d x 3 at doses between 1 and 10 mg/kg. Control groups include the ADC or GITR agonist alone. Tumor volumes and body weight is subsequently measured up to 60 days for all groups and the number of partially responding (PR), completely responding (CR) tumor free surviving (TFS mice is determined in each group.

Statistical analysis (typically a log-rank test) is performed to determine whether the mice treated with the combination have outperformed the mice treated with either ADC or GITR agonist alone.

The invention claimed is:

1. A method for treating cancer in an individual, the method comprising administering to the individual an effective amount of ADCxAXL and a secondary agent; wherein ADCxAXL has the chemical structure:

Ab-(DL)$_p$ wherein:
DL is:

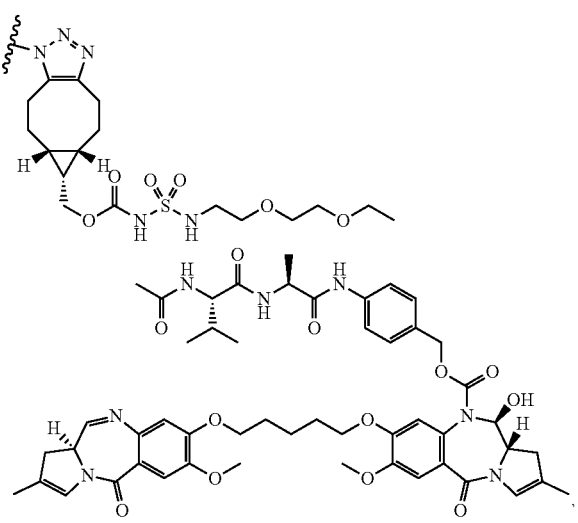

p is from 1 to 8;
and Ab is an antibody that binds to AXL, the antibody comprising:
(a) a heavy chain having the sequence according to SEQ ID NO. 3; and
(b) a light chain having the sequence according to SEQ ID NO. 4.

2. A method according to claim 1, wherein the secondary agent is Fludarabine or Cytarabine.

3. A method according to claim 1, wherein the secondary agent is a PD1 antagonist.

4. A method according to claim 3, wherein the PD 1 antagonist is selected from the group consisting of pembrolizumab, nivolumab, MEDI0680, PDR001 (spartalizumab), Camrelizumab, AUNP12, Pidilizumab Cemiplimab (REGN-2810), AMP-224, BGB-A317 (Tisleizumab), and BGB-108.

5. A method according to claim 1, wherein the secondary agent is a PD-L1 antagonist.

6. A method according to claim 5, wherein the PD-L1 antagonist is selected from the group consisting of atezolizumab (Tecentriq), BMS-936559/MDX-1105, durvalumab/MEDI4736, and MSB0010718C (Avelumab).

7. A method according to claim 1, wherein the secondary agent is a GITR (Glucocorticoid-Induced TNFR-Related protein) agonist.

8. A method according to claim 7, wherein the GITR (Glucocorticoid-Induced TNFR-Related protein) agonist is selected from the group consisting of MEDI1873, TRX518, GWN323, MK-1248, MK 4166, BMS-986156 and INCAGN1876.

9. A method according to claim 1, wherein the secondary agent is an OX40 agonist.

10. A method according to claim 9, wherein the OX40 agonist is selected from the group consisting of MEDI0562, MEDI6383, MOXR0916, RG7888, OX40mAb24, INCAGN1949, GSK3174998, and PF-04518600.

11. A method according to claim 1, wherein the secondary agent is a CTLA-4 antagonist.

12. A method according to claim 11, wherein the CTLA-4 antagonist is ipilimumab or Tremelimumab.

13. A method according to claim 1, wherein the secondary agent is a hypomethylating agent.

14. A method according to claim 13, wherein the hypomethylating agent is azacitidine or decitabine.

15. A method according to claim 1, wherein the secondary agent is a PARP inhibitor (PARPi).

16. A method according to claim 15, wherein the PARPi is selected from the group consisting of Olaparib, CEP-9722, BMN-673/talazoparib, Rucaparib, Iniparib/SAR240550/BSI-201, Veliparib (ABT-888), Niraparib/MK-4827, BGB-290, 3-aminobenzamide, and E7016.

17. A method according to claim 1, wherein the secondary agent is an agent that upregulates HER2 expression.

18. A method according to claim 17, wherein the agent that upregulates HER2 expression is gemcitabine or tamoxifen.

19. A method according to claim 1, wherein the secondary agent is an AXL-kinase inhibitor (AXLi), a BRAF inhibitor (BRAFi), or a MEK inhibitor (MEKi).

20. A method according to claim 19, wherein:
the AXLi is selected from the group consisting of BGB324 (bemcentinib), TP0903, Gilteritinib (ASP2215), Cabozantinib (XL184), SGI7079, Merestinib, amuvatinib (MP-470), bosutinib (SKI-606), MGCD265, and foretinib (GSK1363089/XL880);
the BRAFi is selected from the group consisting of vemurafenib, PLX4720, dabrafenib, Sorafenib, Encorafenib, and GDC0879; and
the MEKi is selected from the group consisting of Trametinib, Cobimetinib, Binimetinib, Selumetinib, PD-325901, CI-1040, PD035901, U0126, and TAK-733.

21. A method according to claim 1, wherein the cancer comprises AXL+ve neoplastic cells, both AXL+ve and AXL−ve neoplastic cells, or AXL−ve neoplastic cells infiltrated with AXL+ve cells.

* * * * *

```
                        SEQUENCE LISTING

<160> NUMBER OF SEQ ID NOS: 701

<210> SEQ ID NO 1
<211> LENGTH: 122
<212> TYPE: PRT
<213> ORGANISM: Artificial Sequence
<220> FEATURE:
<223> OTHER INFORMATION: 1H12 VH, CDR underline

<400> SEQUENCE: 1

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Pro Ile Tyr Tyr Thr Tyr Asp Asp Thr Met Asp Tyr Trp
            100                 105                 110

Gly Gln Gly Thr Thr Val Thr Val Ser Ser
        115                 120

<210> SEQ ID NO 2
<211> LENGTH: 108
<212> TYPE: PRT
<213> ORGANISM: Artificial Sequence
<220> FEATURE:
<223> OTHER INFORMATION: 1H12 VL, CDR underline

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Ser Ala Ser Ser Ser Val Ser Ser Gly
            20                  25                  30

Asn Phe His Trp Tyr Gln Gln Lys Pro Gly Leu Ala Pro Arg Leu Leu
        35                  40                  45

Ile Tyr Arg Thr Ser Asn Leu Ala Ser Gly Ile Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Trp Ser Gly Tyr Pro
                85                  90                  95

Trp Thr Phe Gly Gly Gly Thr Lys Leu Glu Ile Lys
            100                 105
```

```
<210> SEQ ID NO 3
<211> LENGTH: 451
<212> TYPE: PRT
<213> ORGANISM: Artificial Sequence
<220> FEATURE:
<223> OTHER INFORMATION: 1H12 Heavy Chain
<220> FEATURE:
<221> NAME/KEY: MISC_FEATURE
<222> LOCATION: (302)..(302)
<223> OTHER INFORMATION: Xaa - Asn297 (numbering according to Kabat)

<400> SEQUENCE: 3
```

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Pro Ile Tyr Tyr Thr Tyr Asp Asp Thr Met Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Xaa Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
        405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 4
<211> LENGTH: 215
<212> TYPE: PRT
<213> ORGANISM: Artificial Sequence
<220> FEATURE:
<223> OTHER INFORMATION: 1H12 Light Chain

<400> SEQUENCE: 4

Glu Ile Val Leu Thr Gln Ser Pro Gly Thr Leu Ser Leu Ser Pro Gly
1               5                   10                  15

Glu Arg Ala Thr Leu Ser Cys Ser Ala Ser Ser Ser Val Ser Ser Gly
            20                  25                  30

Asn Phe His Trp Tyr Gln Gln Lys Pro Gly Leu Ala Pro Arg Leu Leu
        35                  40                  45

Ile Tyr Arg Thr Ser Asn Leu Ala Ser Gly Ile Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Trp Ser Gly Tyr Pro
                85                  90                  95

Trp Thr Phe Gly Gly Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 5
<211> LENGTH: 5
<212> TYPE: PRT
<213> ORGANISM: Artificial Sequence
<220> FEATURE:

<223> OTHER INFORMATION: 1H12 VH CDR1

<400> SEQUENCE: 5

Ser Tyr Gly Met Ser
1               5

<210> SEQ ID NO 6
<211> LENGTH: 17
<212> TYPE: PRT
<213> ORGANISM: Artificial Sequence
<220> FEATURE:
<223> OTHER INFORMATION: 1H12 VH CDR2

<400> SEQUENCE: 6

Thr Ile Ser Ser Gly Gly Ser Tyr Thr Tyr Tyr Pro Asp Ser Val Lys
1               5                   10                  15

Gly

<210> SEQ ID NO 7
<211> LENGTH: 13
<212> TYPE: PRT
<213> ORGANISM: Artificial Sequence
<220> FEATURE:
<223> OTHER INFORMATION: 1H12 VH CDR3

<400> SEQUENCE: 7

His Pro Ile Tyr Tyr Thr Tyr Asp Asp Thr Met Asp Tyr
1               5                   10

<210> SEQ ID NO 8
<211> LENGTH: 12
<212> TYPE: PRT
<213> ORGANISM: Artificial Sequence
<220> FEATURE:
<223> OTHER INFORMATION: 1H12 VL CDR1

<400> SEQUENCE: 8

Ser Ala Ser Ser Ser Val Ser Ser Gly Asn Phe His
1               5                   10

<210> SEQ ID NO 9
<211> LENGTH: 7
<212> TYPE: PRT
<213> ORGANISM: Artificial Sequence
<220> FEATURE:
<223> OTHER INFORMATION: 1H12 VL CDR2

<400> SEQUENCE: 9

Arg Thr Ser Asn Leu Ala Ser
1               5

<210> SEQ ID NO 10
<211> LENGTH: 9
<212> TYPE: PRT
<213> ORGANISM: Artificial Sequence
<220> FEATURE:
<223> OTHER INFORMATION: 1H12 VL CDR3

<400> SEQUENCE: 10

Gln Gln Trp Ser Gly Tyr Pro Trp Thr
1               5

<210> SEQ ID NO 11
<211> LENGTH: 118
<212> TYPE: PRT
<213> ORGANISM: Artificial Sequence
<220> FEATURE:
<223> OTHER INFORMATION: murine 5F11 VH, CDR underline

<400> SEQUENCE: 11

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Ser Pro Tyr Tyr Tyr Gly Pro Phe Ala Tyr Trp Gly Gln Gly Thr
            100                 105                 110

Leu Val Thr Val Ser Ser
        115

<210> SEQ ID NO 12
<211> LENGTH: 111
<212> TYPE: PRT
<213> ORGANISM: Artificial Sequence
<220> FEATURE:
<223> OTHER INFORMATION: murine 5F11 VL, CDR underline

<400> SEQUENCE: 12

Asp Ile Val Leu Thr Gln Ser Pro Ala Ser Leu Ala Val Ser Leu Gly
1               5                   10                  15

Gln Arg Ala Ile Ile Ser Cys Lys Ala Ser Gln Ser Val Ser Phe Ala
            20                  25                  30

Gly Thr Ser Leu Met His Trp Tyr Gln Gln Lys Pro Gly Gln Gln Pro
        35                  40                  45

Lys Leu Leu Ile Tyr Arg Ala Ser Asn Leu Glu Ala Gly Phe Pro Thr
    50                  55                  60

Arg Phe Ser Gly Ser Gly Ser Arg Thr Asp Phe Thr Leu Asn Ile His
65                  70                  75                  80

Pro Val Glu Glu Glu Asp Ala Ala Thr Tyr Tyr Cys Gln Gln Ser Arg
                85                  90                  95

Glu Tyr Pro Arg Thr Phe Gly Gly Gly Thr Lys Leu Glu Val Lys
            100                 105                 110

<210> SEQ ID NO 13
<211> LENGTH: 5
<212> TYPE: PRT
<213> ORGANISM: Artificial Sequence
<220> FEATURE:
<223> OTHER INFORMATION: 5F11 VH CDR1

<400> SEQUENCE: 13

Arg Tyr Trp Met Ser
1               5

<210> SEQ ID NO 14
<211> LENGTH: 17
<212> TYPE: PRT
<213> ORGANISM: Artificial Sequence
<220> FEATURE:

<223> OTHER INFORMATION: 5F11 VH CDR2

<400> SEQUENCE: 14

Glu Ile Asn Pro Asp Ser Ser Thr Ile Asn Tyr Thr Pro Ser Leu Lys
1               5                   10                  15
Asp

<210> SEQ ID NO 15
<211> LENGTH: 9
<212> TYPE: PRT
<213> ORGANISM: Artificial Sequence
<220> FEATURE:
<223> OTHER INFORMATION: 5F11 VH CDR3

<400> SEQUENCE: 15

Pro Tyr Tyr Tyr Gly Pro Phe Ala Tyr
1               5

<210> SEQ ID NO 16
<211> LENGTH: 15
<212> TYPE: PRT
<213> ORGANISM: Artificial Sequence
<220> FEATURE:
<223> OTHER INFORMATION: 5F11 VL CDR1

<400> SEQUENCE: 16

Lys Ala Ser Gln Ser Val Ser Phe Ala Gly Thr Ser Leu Met His
1               5                   10                  15

<210> SEQ ID NO 17
<211> LENGTH: 7
<212> TYPE: PRT
<213> ORGANISM: Artificial Sequence
<220> FEATURE:
<223> OTHER INFORMATION: 5F11 VL CDR2

<400> SEQUENCE: 17

Arg Ala Ser Asn Leu Glu Ala
1               5

<210> SEQ ID NO 18
<211> LENGTH: 9
<212> TYPE: PRT
<213> ORGANISM: Artificial Sequence
<220> FEATURE:
<223> OTHER INFORMATION: 5F11 VL CDR3

<400> SEQUENCE: 18

Gln Gln Ser Arg Glu Tyr Pro Arg Thr
1               5

<210> SEQ ID NO 19
<211> LENGTH: 117
<212> TYPE: PRT
<213> ORGANISM: Artificial Sequence
<220> FEATURE:
<223> OTHER INFORMATION: 5F11 RHA

<400> SEQUENCE: 19

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
                20                  25                  30

Trp Met Ser Trp Val Arg Gln Ala Pro Gly Lys Gly Leu Glu Trp Val
            35                  40                  45

```
Ala Glu Ile Asn Pro Asp Ser Ser Thr Ile Asn Tyr Thr Pro Ser Leu
        50                  55                  60

Lys Asp Arg Phe Ala Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ser Pro Tyr Tyr Tyr Gly Pro Phe Ala Tyr Trp Gly Gln Gly Thr
            100                 105                 110

Leu Val Thr Val Ser
        115

<210> SEQ ID NO 20
<211> LENGTH: 117
<212> TYPE: PRT
<213> ORGANISM: Artificial Sequence
<220> FEATURE:
<223> OTHER INFORMATION: 5F11 RHB

<400> SEQUENCE: 20

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Glu Ile Asn Pro Asp Ser Ser Thr Ile Asn Tyr Thr Pro Ser Leu
    50                  55                  60

Lys Asp Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Ser Pro Tyr Tyr Tyr Gly Pro Phe Ala Tyr Trp Gly Gln Gly Thr
            100                 105                 110

Leu Val Thr Val Ser
        115

<210> SEQ ID NO 21
<211> LENGTH: 117
<212> TYPE: PRT
<213> ORGANISM: Artificial Sequence
<220> FEATURE:
<223> OTHER INFORMATION: 5F11 RHC

<400> SEQUENCE: 21

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ser Glu Ile Asn Pro Asp Ser Ser Thr Ile Asn Tyr Thr Pro Ser Leu
    50                  55                  60

Lys Asp Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ser Pro Tyr Tyr Tyr Gly Pro Phe Ala Tyr Trp Gly Gln Gly Thr
```

```
                    100                 105                 110

Leu Val Thr Val Ser
            115

<210> SEQ ID NO 22
<211> LENGTH: 111
<212> TYPE: PRT
<213> ORGANISM: Artificial Sequence
<220> FEATURE:
<223> OTHER INFORMATION: 5F11 RKA

<400> SEQUENCE: 22

Glu Ile Val Leu Thr Gln Ser Pro Leu Ser Leu Pro Val Thr Pro Gly
1               5                   10                  15

Glu Pro Ala Ser Ile Ser Cys Lys Ala Ser Gln Ser Val Ser Phe Ala
            20                  25                  30

Gly Thr Ser Leu Met His Trp Tyr Leu Gln Lys Pro Gly Gln Ser Pro
        35                  40                  45

Gln Leu Leu Ile Tyr Arg Ala Ser Asn Leu Glu Ala Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Arg
                85                  90                  95

Glu Tyr Pro Arg Thr Phe Gly Gln Gly Thr Lys Val Glu Ile Lys
            100                 105                 110

<210> SEQ ID NO 23
<211> LENGTH: 894
<212> TYPE: PRT
<213> ORGANISM: Homo sapiens

<400> SEQUENCE: 23

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
            20                  25                  30

Glu Glu Ser Pro Phe Val Gly Asn Pro Gly Asn Ile Thr Gly Ala Arg
        35                  40                  45

Gly Leu Thr Gly Thr Leu Arg Cys Gln Leu Gln Val Gln Gly Glu Pro
    50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Thr Ser Leu Gln Leu Ser Asp Thr
            100                 105                 110

Gly Gln Tyr Gln Cys Leu Val Phe Leu Gly His Gln Thr Phe Val Ser
        115                 120                 125

Gln Pro Gly Tyr Val Gly Leu Glu Gly Leu Pro Tyr Phe Leu Glu Glu
    130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
            180                 185                 190
```

His Val Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
    210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asp Asp Gly Met Gly Ile Gln
            260                 265                 270

Ala Gly Glu Pro Asp Pro Pro Glu Glu Pro Leu Thr Ser Gln Ala Ser
        275                 280                 285

Val Pro Pro His Gln Leu Arg Leu Gly Ser Leu His Pro His Thr Pro
    290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                325                 330                 335

Pro Glu Asn Ile Ser Ala Thr Arg Asn Gly Ser Gln Ala Phe Val His
            340                 345                 350

Trp Gln Glu Pro Arg Ala Pro Leu Gln Gly Thr Leu Leu Gly Tyr Arg
        355                 360                 365

Leu Ala Tyr Gln Gly Gln Asp Thr Pro Glu Val Leu Met Asp Ile Gly
    370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Gly Gln Ala Gln
            420                 425                 430

Pro Val His Gln Leu Val Lys Glu Pro Ser Thr Pro Ala Phe Ser Trp
        435                 440                 445

Pro Trp Trp Tyr Val Leu Leu Gly Ala Val Val Ala Ala Ala Cys Val
    450                 455                 460

Leu Ile Leu Ala Leu Phe Leu Val His Arg Arg Lys Lys Glu Thr Arg
465                 470                 475                 480

Tyr Gly Glu Val Phe Glu Pro Thr Val Glu Arg Gly Glu Leu Val Val
                485                 490                 495

Arg Tyr Arg Val Arg Lys Ser Tyr Ser Arg Arg Thr Thr Glu Ala Thr
            500                 505                 510

Leu Asn Ser Leu Gly Ile Ser Glu Glu Leu Lys Glu Lys Leu Arg Asp
        515                 520                 525

Val Met Val Asp Arg His Lys Val Ala Leu Gly Lys Thr Leu Gly Glu
    530                 535                 540

Gly Glu Phe Gly Ala Val Met Glu Gly Gln Leu Asn Gln Asp Asp Ser
545                 550                 555                 560

Ile Leu Lys Val Ala Val Lys Thr Met Lys Ile Ala Ile Cys Thr Arg
                565                 570                 575

Ser Glu Leu Glu Asp Phe Leu Ser Glu Ala Val Cys Met Lys Glu Phe
            580                 585                 590

Asp His Pro Asn Val Met Arg Leu Ile Gly Val Cys Phe Gln Gly Ser
        595                 600                 605

```
Glu Arg Glu Ser Phe Pro Ala Pro Val Val Ile Leu Pro Phe Met Lys
610                 615                 620
His Gly Asp Leu His Ser Phe Leu Leu Tyr Ser Arg Leu Gly Asp Gln
625                 630                 635                 640
Pro Val Tyr Leu Pro Thr Gln Met Leu Val Lys Phe Met Ala Asp Ile
                645                 650                 655
Ala Ser Gly Met Glu Tyr Leu Ser Thr Lys Arg Phe Ile His Arg Asp
                660                 665                 670
Leu Ala Ala Arg Asn Cys Met Leu Asn Glu Asn Met Ser Val Cys Val
                675                 680                 685
Ala Asp Phe Gly Leu Ser Lys Lys Ile Tyr Asn Gly Asp Tyr Tyr Arg
690                 695                 700
Gln Gly Arg Ile Ala Lys Met Pro Val Lys Trp Ile Ala Ile Glu Ser
705                 710                 715                 720
Leu Ala Asp Arg Val Tyr Thr Ser Lys Ser Asp Val Trp Ser Phe Gly
                725                 730                 735
Val Thr Met Trp Glu Ile Ala Thr Arg Gly Gln Thr Pro Tyr Pro Gly
                740                 745                 750
Val Glu Asn Ser Glu Ile Tyr Asp Tyr Leu Arg Arg Gly Asn Arg Leu
                755                 760                 765
Lys Gln Pro Ala Asp Cys Leu Asp Gly Leu Tyr Ala Leu Met Ser Arg
                770                 775                 780
Cys Trp Glu Leu Asn Pro Gln Asp Arg Pro Ser Phe Thr Glu Leu Arg
785                 790                 795                 800
Glu Asp Leu Glu Asn Thr Leu Lys Ala Leu Pro Pro Ala Gln Glu Pro
                805                 810                 815
Asp Glu Ile Leu Tyr Val Asn Met Asp Glu Gly Gly Gly Tyr Pro Glu
                820                 825                 830
Pro Pro Gly Ala Ala Gly Gly Ala Asp Pro Pro Thr Gln Pro Asp Pro
                835                 840                 845
Lys Asp Ser Cys Ser Cys Leu Thr Ala Ala Glu Val His Pro Ala Gly
                850                 855                 860
Arg Tyr Val Leu Cys Pro Ser Thr Thr Pro Ser Pro Ala Gln Pro Ala
865                 870                 875                 880
Asp Arg Gly Ser Pro Ala Ala Pro Gly Gln Glu Asp Gly Ala
                885                 890
```

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28
<400> SEQUENCE: 28
000

<210> SEQ ID NO 29
<400> SEQUENCE: 29
000

<210> SEQ ID NO 30
<400> SEQUENCE: 30
000

<210> SEQ ID NO 31
<400> SEQUENCE: 31
000

<210> SEQ ID NO 32
<400> SEQUENCE: 32
000

<210> SEQ ID NO 33
<400> SEQUENCE: 33
000

<210> SEQ ID NO 34
<400> SEQUENCE: 34
000

<210> SEQ ID NO 35
<400> SEQUENCE: 35
000

<210> SEQ ID NO 36
<400> SEQUENCE: 36
000

<210> SEQ ID NO 37
<400> SEQUENCE: 37
000

<210> SEQ ID NO 38
<400> SEQUENCE: 38
000

-continued

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

```
<210> SEQ ID NO 50
<400> SEQUENCE: 50
000

<210> SEQ ID NO 51
<400> SEQUENCE: 51
000

<210> SEQ ID NO 52
<400> SEQUENCE: 52
000

<210> SEQ ID NO 53
<400> SEQUENCE: 53
000

<210> SEQ ID NO 54
<400> SEQUENCE: 54
000

<210> SEQ ID NO 55
<400> SEQUENCE: 55
000

<210> SEQ ID NO 56
<400> SEQUENCE: 56
000

<210> SEQ ID NO 57
<400> SEQUENCE: 57
000

<210> SEQ ID NO 58
<400> SEQUENCE: 58
000

<210> SEQ ID NO 59
<400> SEQUENCE: 59
000

<210> SEQ ID NO 60
<400> SEQUENCE: 60
000

<210> SEQ ID NO 61
```

```
<400> SEQUENCE: 61

000

<210> SEQ ID NO 62
<400> SEQUENCE: 62

000

<210> SEQ ID NO 63
<400> SEQUENCE: 63

000

<210> SEQ ID NO 64
<400> SEQUENCE: 64

000

<210> SEQ ID NO 65
<400> SEQUENCE: 65

000

<210> SEQ ID NO 66
<400> SEQUENCE: 66

000

<210> SEQ ID NO 67
<400> SEQUENCE: 67

000

<210> SEQ ID NO 68
<400> SEQUENCE: 68

000

<210> SEQ ID NO 69
<400> SEQUENCE: 69

000

<210> SEQ ID NO 70
<400> SEQUENCE: 70

000

<210> SEQ ID NO 71
<400> SEQUENCE: 71

000

<210> SEQ ID NO 72
<400> SEQUENCE: 72
```

000

<210> SEQ ID NO 73
<400> SEQUENCE: 73
000

<210> SEQ ID NO 74
<400> SEQUENCE: 74
000

<210> SEQ ID NO 75
<400> SEQUENCE: 75
000

<210> SEQ ID NO 76
<400> SEQUENCE: 76
000

<210> SEQ ID NO 77
<400> SEQUENCE: 77
000

<210> SEQ ID NO 78
<400> SEQUENCE: 78
000

<210> SEQ ID NO 79
<400> SEQUENCE: 79
000

<210> SEQ ID NO 80
<400> SEQUENCE: 80
000

<210> SEQ ID NO 81
<400> SEQUENCE: 81
000

<210> SEQ ID NO 82
<400> SEQUENCE: 82
000

<210> SEQ ID NO 83
<400> SEQUENCE: 83
000

-continued

<210> SEQ ID NO 84
<400> SEQUENCE: 84
000

<210> SEQ ID NO 85
<400> SEQUENCE: 85
000

<210> SEQ ID NO 86
<400> SEQUENCE: 86
000

<210> SEQ ID NO 87
<400> SEQUENCE: 87
000

<210> SEQ ID NO 88
<400> SEQUENCE: 88
000

<210> SEQ ID NO 89
<400> SEQUENCE: 89
000

<210> SEQ ID NO 90
<400> SEQUENCE: 90
000

<210> SEQ ID NO 91
<400> SEQUENCE: 91
000

<210> SEQ ID NO 92
<400> SEQUENCE: 92
000

<210> SEQ ID NO 93
<400> SEQUENCE: 93
000

<210> SEQ ID NO 94
<400> SEQUENCE: 94
000

<210> SEQ ID NO 95

```
<400> SEQUENCE: 95
000

<210> SEQ ID NO 96
<400> SEQUENCE: 96
000

<210> SEQ ID NO 97
<400> SEQUENCE: 97
000

<210> SEQ ID NO 98
<400> SEQUENCE: 98
000

<210> SEQ ID NO 99
<400> SEQUENCE: 99
000

<210> SEQ ID NO 100
<400> SEQUENCE: 100
000

<210> SEQ ID NO 101
<400> SEQUENCE: 101
000

<210> SEQ ID NO 102
<400> SEQUENCE: 102
000

<210> SEQ ID NO 103
<400> SEQUENCE: 103
000

<210> SEQ ID NO 104
<400> SEQUENCE: 104
000

<210> SEQ ID NO 105
<400> SEQUENCE: 105
000

<210> SEQ ID NO 106
<400> SEQUENCE: 106
```

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

<210> SEQ ID NO 113

<400> SEQUENCE: 113

000

<210> SEQ ID NO 114

<400> SEQUENCE: 114

000

<210> SEQ ID NO 115

<400> SEQUENCE: 115

000

<210> SEQ ID NO 116

<400> SEQUENCE: 116

000

<210> SEQ ID NO 117

<400> SEQUENCE: 117

000

-continued

<210> SEQ ID NO 118

<400> SEQUENCE: 118

000

<210> SEQ ID NO 119

<400> SEQUENCE: 119

000

<210> SEQ ID NO 120

<400> SEQUENCE: 120

000

<210> SEQ ID NO 121

<400> SEQUENCE: 121

000

<210> SEQ ID NO 122

<400> SEQUENCE: 122

000

<210> SEQ ID NO 123

<400> SEQUENCE: 123

000

<210> SEQ ID NO 124

<400> SEQUENCE: 124

000

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

```
<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140
```

-continued

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163
<400> SEQUENCE: 163
000

<210> SEQ ID NO 164
<400> SEQUENCE: 164
000

<210> SEQ ID NO 165
<400> SEQUENCE: 165
000

<210> SEQ ID NO 166
<400> SEQUENCE: 166
000

<210> SEQ ID NO 167
<400> SEQUENCE: 167
000

<210> SEQ ID NO 168
<400> SEQUENCE: 168
000

<210> SEQ ID NO 169
<400> SEQUENCE: 169
000

<210> SEQ ID NO 170
<400> SEQUENCE: 170
000

<210> SEQ ID NO 171
<400> SEQUENCE: 171
000

<210> SEQ ID NO 172
<400> SEQUENCE: 172
000

<210> SEQ ID NO 173
<400> SEQUENCE: 173
000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201

<400> SEQUENCE: 201

000

<210> SEQ ID NO 202

<400> SEQUENCE: 202

000

<210> SEQ ID NO 203

<400> SEQUENCE: 203

000

<210> SEQ ID NO 204

<400> SEQUENCE: 204

000

<210> SEQ ID NO 205

<400> SEQUENCE: 205

000

<210> SEQ ID NO 206

<400> SEQUENCE: 206

000

<210> SEQ ID NO 207

<400> SEQUENCE: 207

000

```
<210> SEQ ID NO 208
<400> SEQUENCE: 208
000

<210> SEQ ID NO 209
<400> SEQUENCE: 209
000

<210> SEQ ID NO 210
<400> SEQUENCE: 210
000

<210> SEQ ID NO 211
<400> SEQUENCE: 211
000

<210> SEQ ID NO 212
<400> SEQUENCE: 212
000

<210> SEQ ID NO 213
<400> SEQUENCE: 213
000

<210> SEQ ID NO 214
<400> SEQUENCE: 214
000

<210> SEQ ID NO 215
<400> SEQUENCE: 215
000

<210> SEQ ID NO 216
<400> SEQUENCE: 216
000

<210> SEQ ID NO 217
<400> SEQUENCE: 217
000

<210> SEQ ID NO 218
<400> SEQUENCE: 218
000

<210> SEQ ID NO 219
```

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231
<400> SEQUENCE: 231
000

<210> SEQ ID NO 232
<400> SEQUENCE: 232
000

<210> SEQ ID NO 233
<400> SEQUENCE: 233
000

<210> SEQ ID NO 234
<400> SEQUENCE: 234
000

<210> SEQ ID NO 235
<400> SEQUENCE: 235
000

<210> SEQ ID NO 236
<400> SEQUENCE: 236
000

<210> SEQ ID NO 237
<400> SEQUENCE: 237
000

<210> SEQ ID NO 238
<400> SEQUENCE: 238
000

<210> SEQ ID NO 239
<400> SEQUENCE: 239
000

<210> SEQ ID NO 240
<400> SEQUENCE: 240
000

<210> SEQ ID NO 241
<400> SEQUENCE: 241
000

```
<210> SEQ ID NO 242
<400> SEQUENCE: 242
000

<210> SEQ ID NO 243
<400> SEQUENCE: 243
000

<210> SEQ ID NO 244
<400> SEQUENCE: 244
000

<210> SEQ ID NO 245
<400> SEQUENCE: 245
000

<210> SEQ ID NO 246
<400> SEQUENCE: 246
000

<210> SEQ ID NO 247
<400> SEQUENCE: 247
000

<210> SEQ ID NO 248
<400> SEQUENCE: 248
000

<210> SEQ ID NO 249
<400> SEQUENCE: 249
000

<210> SEQ ID NO 250
<400> SEQUENCE: 250
000

<210> SEQ ID NO 251
<400> SEQUENCE: 251
000

<210> SEQ ID NO 252
<400> SEQUENCE: 252
000

<210> SEQ ID NO 253
```

```
<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264
```

000

<210> SEQ ID NO 265
<400> SEQUENCE: 265
000

<210> SEQ ID NO 266
<400> SEQUENCE: 266
000

<210> SEQ ID NO 267
<400> SEQUENCE: 267
000

<210> SEQ ID NO 268
<400> SEQUENCE: 268
000

<210> SEQ ID NO 269
<400> SEQUENCE: 269
000

<210> SEQ ID NO 270
<400> SEQUENCE: 270
000

<210> SEQ ID NO 271
<400> SEQUENCE: 271
000

<210> SEQ ID NO 272
<400> SEQUENCE: 272
000

<210> SEQ ID NO 273
<400> SEQUENCE: 273
000

<210> SEQ ID NO 274
<400> SEQUENCE: 274
000

<210> SEQ ID NO 275
<400> SEQUENCE: 275
000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

-continued

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

```
<400> SEQUENCE: 298

000

<210> SEQ ID NO 299

<400> SEQUENCE: 299

000

<210> SEQ ID NO 300
<211> LENGTH: 7
<212> TYPE: PRT
<213> ORGANISM: Artificial Sequence
<220> FEATURE:
<223> OTHER INFORMATION: AUNP12 peptide

<400> SEQUENCE: 300

Phe Ser Glu Ser Thr Asn Ser
1               5

<210> SEQ ID NO 301
<211> LENGTH: 7
<212> TYPE: PRT
<213> ORGANISM: Artificial Sequence
<220> FEATURE:
<223> OTHER INFORMATION: AUNP12 peptide

<400> SEQUENCE: 301

Ser Asn Thr Ser Glu Ser Phe
1               5

<210> SEQ ID NO 302
<211> LENGTH: 14
<212> TYPE: PRT
<213> ORGANISM: Artificial Sequence
<220> FEATURE:
<223> OTHER INFORMATION: AUNP12 peptide

<400> SEQUENCE: 302

Phe Arg Val Thr Gln Leu Ala Pro Lys Ala Gln Ile Lys Glu
1               5                   10

<210> SEQ ID NO 303
<211> LENGTH: 22
<212> TYPE: PRT
<213> ORGANISM: Artificial Sequence
<220> FEATURE:
<223> OTHER INFORMATION: AUNP12 peptide

<400> SEQUENCE: 303

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 304

<400> SEQUENCE: 304

000

<210> SEQ ID NO 305

<400> SEQUENCE: 305

000
```

-continued

<210> SEQ ID NO 306

<400> SEQUENCE: 306

000

<210> SEQ ID NO 307

<400> SEQUENCE: 307

000

<210> SEQ ID NO 308

<400> SEQUENCE: 308

000

<210> SEQ ID NO 309

<400> SEQUENCE: 309

000

<210> SEQ ID NO 310

<400> SEQUENCE: 310

000

<210> SEQ ID NO 311

<400> SEQUENCE: 311

000

<210> SEQ ID NO 312

<400> SEQUENCE: 312

000

<210> SEQ ID NO 313

<400> SEQUENCE: 313

000

<210> SEQ ID NO 314

<400> SEQUENCE: 314

000

<210> SEQ ID NO 315

<400> SEQUENCE: 315

000

<210> SEQ ID NO 316

<400> SEQUENCE: 316

000

```
<210> SEQ ID NO 317
<400> SEQUENCE: 317
000

<210> SEQ ID NO 318
<400> SEQUENCE: 318
000

<210> SEQ ID NO 319
<400> SEQUENCE: 319
000

<210> SEQ ID NO 320
<400> SEQUENCE: 320
000

<210> SEQ ID NO 321
<400> SEQUENCE: 321
000

<210> SEQ ID NO 322
<400> SEQUENCE: 322
000

<210> SEQ ID NO 323
<400> SEQUENCE: 323
000

<210> SEQ ID NO 324
<400> SEQUENCE: 324
000

<210> SEQ ID NO 325
<400> SEQUENCE: 325
000

<210> SEQ ID NO 326
<400> SEQUENCE: 326
000

<210> SEQ ID NO 327
<400> SEQUENCE: 327
000

<210> SEQ ID NO 328
```

```
<400> SEQUENCE: 328

000

<210> SEQ ID NO 329

<400> SEQUENCE: 329

000

<210> SEQ ID NO 330

<400> SEQUENCE: 330

000

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339

<400> SEQUENCE: 339
```

000

<210> SEQ ID NO 340
<400> SEQUENCE: 340
000

<210> SEQ ID NO 341
<400> SEQUENCE: 341
000

<210> SEQ ID NO 342
<400> SEQUENCE: 342
000

<210> SEQ ID NO 343
<400> SEQUENCE: 343
000

<210> SEQ ID NO 344
<400> SEQUENCE: 344
000

<210> SEQ ID NO 345
<400> SEQUENCE: 345
000

<210> SEQ ID NO 346
<400> SEQUENCE: 346
000

<210> SEQ ID NO 347
<400> SEQUENCE: 347
000

<210> SEQ ID NO 348
<400> SEQUENCE: 348
000

<210> SEQ ID NO 349
<400> SEQUENCE: 349
000

<210> SEQ ID NO 350
<400> SEQUENCE: 350
000

```
<210> SEQ ID NO 351
<400> SEQUENCE: 351
000

<210> SEQ ID NO 352
<400> SEQUENCE: 352
000

<210> SEQ ID NO 353
<400> SEQUENCE: 353
000

<210> SEQ ID NO 354
<400> SEQUENCE: 354
000

<210> SEQ ID NO 355
<400> SEQUENCE: 355
000

<210> SEQ ID NO 356
<400> SEQUENCE: 356
000

<210> SEQ ID NO 357
<400> SEQUENCE: 357
000

<210> SEQ ID NO 358
<400> SEQUENCE: 358
000

<210> SEQ ID NO 359
<400> SEQUENCE: 359
000

<210> SEQ ID NO 360
<400> SEQUENCE: 360
000

<210> SEQ ID NO 361
<400> SEQUENCE: 361
000

<210> SEQ ID NO 362
```

<400> SEQUENCE: 362

000

<210> SEQ ID NO 363

<400> SEQUENCE: 363

000

<210> SEQ ID NO 364

<400> SEQUENCE: 364

000

<210> SEQ ID NO 365

<400> SEQUENCE: 365

000

<210> SEQ ID NO 366

<400> SEQUENCE: 366

000

<210> SEQ ID NO 367

<400> SEQUENCE: 367

000

<210> SEQ ID NO 368

<400> SEQUENCE: 368

000

<210> SEQ ID NO 369

<400> SEQUENCE: 369

000

<210> SEQ ID NO 370

<400> SEQUENCE: 370

000

<210> SEQ ID NO 371

<400> SEQUENCE: 371

000

<210> SEQ ID NO 372

<400> SEQUENCE: 372

000

<210> SEQ ID NO 373

<400> SEQUENCE: 373

000

<210> SEQ ID NO 374
<400> SEQUENCE: 374
000

<210> SEQ ID NO 375
<400> SEQUENCE: 375
000

<210> SEQ ID NO 376
<400> SEQUENCE: 376
000

<210> SEQ ID NO 377
<400> SEQUENCE: 377
000

<210> SEQ ID NO 378
<400> SEQUENCE: 378
000

<210> SEQ ID NO 379
<400> SEQUENCE: 379
000

<210> SEQ ID NO 380
<400> SEQUENCE: 380
000

<210> SEQ ID NO 381
<400> SEQUENCE: 381
000

<210> SEQ ID NO 382
<400> SEQUENCE: 382
000

<210> SEQ ID NO 383
<400> SEQUENCE: 383
000

<210> SEQ ID NO 384
<400> SEQUENCE: 384
000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<400> SEQUENCE: 388

000

<210> SEQ ID NO 389

<400> SEQUENCE: 389

000

<210> SEQ ID NO 390

<400> SEQUENCE: 390

000

<210> SEQ ID NO 391

<400> SEQUENCE: 391

000

<210> SEQ ID NO 392

<400> SEQUENCE: 392

000

<210> SEQ ID NO 393

<400> SEQUENCE: 393

000

<210> SEQ ID NO 394

<400> SEQUENCE: 394

000

<210> SEQ ID NO 395

<400> SEQUENCE: 395

000

```
<210> SEQ ID NO 396
<400> SEQUENCE: 396

000

<210> SEQ ID NO 397
<400> SEQUENCE: 397

000

<210> SEQ ID NO 398
<400> SEQUENCE: 398

000

<210> SEQ ID NO 399
<400> SEQUENCE: 399

000

<210> SEQ ID NO 400
<211> LENGTH: 5
<212> TYPE: PRT
<213> ORGANISM: Artificial Sequence
<220> FEATURE:
<223> OTHER INFORMATION: BMS-936559/MDX-1105 Antibody 1 VH CDR1

<400> SEQUENCE: 400

Asp Tyr Gly Phe Ser
1               5

<210> SEQ ID NO 401
<211> LENGTH: 17
<212> TYPE: PRT
<213> ORGANISM: Artificial Sequence
<220> FEATURE:
<223> OTHER INFORMATION: BMS-936559/MDX-1105 Antibody 1 VH CDR2

<400> SEQUENCE: 401

Trp Ile Thr Ala Tyr Asn Gly Asn Thr Asn Tyr Ala Gln Lys Leu Gln
1               5                   10                  15

Gly

<210> SEQ ID NO 402
<211> LENGTH: 8
<212> TYPE: PRT
<213> ORGANISM: Artificial Sequence
<220> FEATURE:
<223> OTHER INFORMATION: BMS-936559/MDX-1105 Antibody 1 VH CDR3

<400> SEQUENCE: 402

Asp Tyr Phe Tyr Gly Met Asp Val
1               5

<210> SEQ ID NO 403
<211> LENGTH: 11
<212> TYPE: PRT
<213> ORGANISM: Artificial Sequence
<220> FEATURE:
<223> OTHER INFORMATION: BMS-936559/MDX-1105 Antibody 1 VL CDR1

<400> SEQUENCE: 403

Arg Ala Ser Gln Ser Val Ser Ser Tyr Leu Val
```

```
1               5                  10
```

<210> SEQ ID NO 404
<211> LENGTH: 7
<212> TYPE: PRT
<213> ORGANISM: Artificial Sequence
<220> FEATURE:
<223> OTHER INFORMATION: BMS-936559/MDX-1105 Antibody 1 VL CDR2

<400> SEQUENCE: 404

```
Asp Ala Ser Asn Arg Ala Thr
1               5
```

<210> SEQ ID NO 405
<211> LENGTH: 9
<212> TYPE: PRT
<213> ORGANISM: Artificial Sequence
<220> FEATURE:
<223> OTHER INFORMATION: BMS-936559/MDX-1105 Antibody 1 VL CDR3

<400> SEQUENCE: 405

```
Gln Gln Arg Ser Asn Trp Pro Arg Thr
1               5
```

<210> SEQ ID NO 406
<211> LENGTH: 5
<212> TYPE: PRT
<213> ORGANISM: Artificial Sequence
<220> FEATURE:
<223> OTHER INFORMATION: BMS-936559/MDX-1105 Antibody 2 VH CDR1

<400> SEQUENCE: 406

```
Thr Tyr Ala Ile Ser
1               5
```

<210> SEQ ID NO 407
<211> LENGTH: 17
<212> TYPE: PRT
<213> ORGANISM: Artificial Sequence
<220> FEATURE:
<223> OTHER INFORMATION: BMS-936559/MDX-1105 Antibody 2 VH CDR2

<400> SEQUENCE: 407

```
Gly Ile Ile Pro Ile Phe Gly Lys Ala His Tyr Ala Gln Lys Phe Gln
1               5                   10                  15

Gly
```

<210> SEQ ID NO 408
<211> LENGTH: 14
<212> TYPE: PRT
<213> ORGANISM: Artificial Sequence
<220> FEATURE:
<223> OTHER INFORMATION: BMS-936559/MDX-1105 Antibody 2 VH CDR3

<400> SEQUENCE: 408

```
Lys Phe His Phe Val Ser Gly Ser Pro Phe Gly Met Asp Val
1               5                   10
```

<210> SEQ ID NO 409
<211> LENGTH: 11
<212> TYPE: PRT
<213> ORGANISM: Artificial Sequence
<220> FEATURE:
<223> OTHER INFORMATION: BMS-936559/MDX-1105 Antibody 2 VL CDR1

<400> SEQUENCE: 409

Arg Ala Ser Gln Ser Val Ser Ser Tyr Leu Ala
1               5                   10

<210> SEQ ID NO 410
<211> LENGTH: 7
<212> TYPE: PRT
<213> ORGANISM: Artificial Sequence
<220> FEATURE:
<223> OTHER INFORMATION: BMS-936559/MDX-1105 Antibody 2 VL CDR2

<400> SEQUENCE: 410

Asp Ala Ser Asn Arg Ala Thr
1               5

<210> SEQ ID NO 411
<211> LENGTH: 8
<212> TYPE: PRT
<213> ORGANISM: Artificial Sequence
<220> FEATURE:
<223> OTHER INFORMATION: BMS-936559/MDX-1105 Antibody 2 VL CDR3

<400> SEQUENCE: 411

Gln Gln Arg Ser Asn Trp Pro Thr
1               5

<210> SEQ ID NO 412
<211> LENGTH: 5
<212> TYPE: PRT
<213> ORGANISM: Artificial Sequence
<220> FEATURE:
<223> OTHER INFORMATION: BMS-936559/MDX-1105 Antibody 3 VH CDR1

<400> SEQUENCE: 412

Ser Tyr Asp Val His
1               5

<210> SEQ ID NO 413
<211> LENGTH: 17
<212> TYPE: PRT
<213> ORGANISM: Artificial Sequence
<220> FEATURE:
<223> OTHER INFORMATION: BMS-936559/MDX-1105 Antibody 3 VH CDR2

<400> SEQUENCE: 413

Trp Leu His Ala Asp Thr Gly Ile Thr Lys Phe Ser Gln Lys Phe Gln
1               5                   10                  15

Gly

<210> SEQ ID NO 414
<211> LENGTH: 9
<212> TYPE: PRT
<213> ORGANISM: Artificial Sequence
<220> FEATURE:
<223> OTHER INFORMATION: BMS-936559/MDX-1105 Antibody 3 VH CDR3

<400> SEQUENCE: 414

Glu Arg Ile Gln Leu Trp Phe Asp Tyr
1               5

<210> SEQ ID NO 415
<211> LENGTH: 11
<212> TYPE: PRT
<213> ORGANISM: Artificial Sequence
<220> FEATURE:
<223> OTHER INFORMATION: BMS-936559/MDX-1105 Antibody 3 VL CDR1

<400> SEQUENCE: 415

```
Arg Ala Ser Gln Gly Ile Ser Ser Trp Leu Ala
1               5                   10

<210> SEQ ID NO 416
<211> LENGTH: 7
<212> TYPE: PRT
<213> ORGANISM: Artificial Sequence
<220> FEATURE:
<223> OTHER INFORMATION: BMS-936559/MDX-1105 Antibody 3 VL CDR2

<400> SEQUENCE: 416

Ala Ala Ser Ser Leu Gln Ser
1               5

<210> SEQ ID NO 417
<211> LENGTH: 9
<212> TYPE: PRT
<213> ORGANISM: Artificial Sequence
<220> FEATURE:
<223> OTHER INFORMATION: BMS-936559/MDX-1105 Antibody 3 VL CDR3

<400> SEQUENCE: 417

Gln Gln Tyr Asn Ser Tyr Pro Tyr Thr
1               5

<210> SEQ ID NO 418
<211> LENGTH: 121
<212> TYPE: PRT
<213> ORGANISM: Artificial Sequence
<220> FEATURE:
<223> OTHER INFORMATION: durvalumab/MEDI4736 VH Sequence

<400> SEQUENCE: 418

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120

<210> SEQ ID NO 419
<211> LENGTH: 108
<212> TYPE: PRT
<213> ORGANISM: Artificial Sequence
<220> FEATURE:
<223> OTHER INFORMATION: durvalumab/MEDI4736 VL Sequence

<400> SEQUENCE: 419

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30
```

-continued

```
Tyr Leu Ala Trp Tyr Gln Gln Lys Pro Gly Gln Ala Pro Arg Leu Leu
            35                  40                  45
Ile Tyr Asp Ala Ser Ser Arg Ala Thr Gly Ile Pro Asp Arg Phe Ser
        50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Tyr Gly Ser Leu Pro
                 85                  90                  95
Trp Thr Phe Gly Gln Gly Thr Lys Val Glu Ile Lys
            100                 105
```

<210> SEQ ID NO 420

<400> SEQUENCE: 420

000

<210> SEQ ID NO 421

<400> SEQUENCE: 421

000

<210> SEQ ID NO 422

<400> SEQUENCE: 422

000

<210> SEQ ID NO 423

<400> SEQUENCE: 423

000

<210> SEQ ID NO 424

<400> SEQUENCE: 424

000

<210> SEQ ID NO 425

<400> SEQUENCE: 425

000

<210> SEQ ID NO 426

<400> SEQUENCE: 426

000

<210> SEQ ID NO 427

<400> SEQUENCE: 427

000

<210> SEQ ID NO 428

<400> SEQUENCE: 428

000

```
<210> SEQ ID NO 429
<400> SEQUENCE: 429
000

<210> SEQ ID NO 430
<400> SEQUENCE: 430
000

<210> SEQ ID NO 431
<400> SEQUENCE: 431
000

<210> SEQ ID NO 432
<400> SEQUENCE: 432
000

<210> SEQ ID NO 433
<400> SEQUENCE: 433
000

<210> SEQ ID NO 434
<400> SEQUENCE: 434
000

<210> SEQ ID NO 435
<400> SEQUENCE: 435
000

<210> SEQ ID NO 436
<400> SEQUENCE: 436
000

<210> SEQ ID NO 437
<400> SEQUENCE: 437
000

<210> SEQ ID NO 438
<400> SEQUENCE: 438
000

<210> SEQ ID NO 439
<400> SEQUENCE: 439
000

<210> SEQ ID NO 440
```

-continued

<400> SEQUENCE: 440

000

<210> SEQ ID NO 441

<400> SEQUENCE: 441

000

<210> SEQ ID NO 442

<400> SEQUENCE: 442

000

<210> SEQ ID NO 443

<400> SEQUENCE: 443

000

<210> SEQ ID NO 444

<400> SEQUENCE: 444

000

<210> SEQ ID NO 445

<400> SEQUENCE: 445

000

<210> SEQ ID NO 446

<400> SEQUENCE: 446

000

<210> SEQ ID NO 447

<400> SEQUENCE: 447

000

<210> SEQ ID NO 448

<400> SEQUENCE: 448

000

<210> SEQ ID NO 449

<400> SEQUENCE: 449

000

<210> SEQ ID NO 450

<400> SEQUENCE: 450

000

<210> SEQ ID NO 451

<400> SEQUENCE: 451

000

<210> SEQ ID NO 452

<400> SEQUENCE: 452

000

<210> SEQ ID NO 453

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458

<400> SEQUENCE: 458

000

<210> SEQ ID NO 459

<400> SEQUENCE: 459

000

<210> SEQ ID NO 460

<400> SEQUENCE: 460

000

<210> SEQ ID NO 461

<400> SEQUENCE: 461

000

<210> SEQ ID NO 462

<400> SEQUENCE: 462

000

<210> SEQ ID NO 463

<400> SEQUENCE: 463

000

<210> SEQ ID NO 464

<400> SEQUENCE: 464

000

<210> SEQ ID NO 465

<400> SEQUENCE: 465

000

<210> SEQ ID NO 466

<400> SEQUENCE: 466

000

<210> SEQ ID NO 467

<400> SEQUENCE: 467

000

<210> SEQ ID NO 468

<400> SEQUENCE: 468

000

<210> SEQ ID NO 469

<400> SEQUENCE: 469

000

<210> SEQ ID NO 470

<400> SEQUENCE: 470

000

<210> SEQ ID NO 471

<400> SEQUENCE: 471

000

<210> SEQ ID NO 472

<400> SEQUENCE: 472

000

<210> SEQ ID NO 473

<400> SEQUENCE: 473

000

<210> SEQ ID NO 474

<400> SEQUENCE: 474

000

<210> SEQ ID NO 475

<400> SEQUENCE: 475

000

<210> SEQ ID NO 476

<400> SEQUENCE: 476

000

<210> SEQ ID NO 477

<400> SEQUENCE: 477

000

<210> SEQ ID NO 478

<400> SEQUENCE: 478

000

<210> SEQ ID NO 479

<400> SEQUENCE: 479

000

<210> SEQ ID NO 480

<400> SEQUENCE: 480

000

<210> SEQ ID NO 481

<400> SEQUENCE: 481

000

<210> SEQ ID NO 482

<400> SEQUENCE: 482

000

<210> SEQ ID NO 483

<400> SEQUENCE: 483

000

<210> SEQ ID NO 484

<400> SEQUENCE: 484

000

<210> SEQ ID NO 485

<400> SEQUENCE: 485

000

<210> SEQ ID NO 486

<400> SEQUENCE: 486

000

<210> SEQ ID NO 487

<400> SEQUENCE: 487

000

<210> SEQ ID NO 488

<400> SEQUENCE: 488

000

<210> SEQ ID NO 489

<400> SEQUENCE: 489

000

<210> SEQ ID NO 490

<400> SEQUENCE: 490

000

<210> SEQ ID NO 491

<400> SEQUENCE: 491

000

<210> SEQ ID NO 492

<400> SEQUENCE: 492

000

<210> SEQ ID NO 493

<400> SEQUENCE: 493

000

<210> SEQ ID NO 494

<400> SEQUENCE: 494

000

<210> SEQ ID NO 495

<400> SEQUENCE: 495

000

<210> SEQ ID NO 496

<400> SEQUENCE: 496

<210> SEQ ID NO 497

<400> SEQUENCE: 497

000

<210> SEQ ID NO 498

<400> SEQUENCE: 498

000

<210> SEQ ID NO 499

<400> SEQUENCE: 499

000

<210> SEQ ID NO 500
<211> LENGTH: 107
<212> TYPE: PRT
<213> ORGANISM: Artificial Sequence
<220> FEATURE:
<223> OTHER INFORMATION: TRX518 VL seuqence

<400> SEQUENCE: 500

```
Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asn Val Gly Thr Asn
            20                  25                  30

Val Ala Trp Tyr Gln Gln Lys Pro Gly Gln Ala Pro Arg Leu Leu Ile
        35                  40                  45

Tyr Ser Ala Ser Tyr Arg Tyr Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Thr Asp Pro Leu
                85                  90                  95

Thr Phe Gly Gly Gly Thr Lys Val Glu Ile Lys
            100                 105
```

<210> SEQ ID NO 501
<211> LENGTH: 118
<212> TYPE: PRT
<213> ORGANISM: Artificial Sequence
<220> FEATURE:
<223> OTHER INFORMATION: TRX518 VH sequence

<400> SEQUENCE: 501

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Gln Val
65                  70                  75                  80
```

```
Val Leu Thr Met Thr Asn Met Asp Pro Val Asp Ala Thr Tyr Tyr
             85                  90                  95

Cys Ala Arg Thr Arg Arg Tyr Phe Pro Phe Ala Tyr Trp Gly Gln Gly
            100                 105                 110

Thr Leu Val Thr Val Ser
            115

<210> SEQ ID NO 502
<211> LENGTH: 118
<212> TYPE: PRT
<213> ORGANISM: Artificial Sequence
<220> FEATURE:
<223> OTHER INFORMATION: TRX518 VH sequence

<400> SEQUENCE: 502

Gln Val Thr Leu Arg Glu Ser Gly Pro Ala Leu Val Lys Pro Thr Gln
1               5                  10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Lys Tyr Tyr Gln Pro Ser
50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
             85                  90                  95

Cys Ala Arg Thr Arg Arg Tyr Phe Pro Phe Ala Tyr Trp Gly Gln Gly
            100                 105                 110

Thr Leu Val Thr Val Ser
            115

<210> SEQ ID NO 503

<400> SEQUENCE: 503

000

<210> SEQ ID NO 504

<400> SEQUENCE: 504

000

<210> SEQ ID NO 505

<400> SEQUENCE: 505

000

<210> SEQ ID NO 506

<400> SEQUENCE: 506

000

<210> SEQ ID NO 507

<400> SEQUENCE: 507

000
```

<210> SEQ ID NO 508
<400> SEQUENCE: 508
000

<210> SEQ ID NO 509
<400> SEQUENCE: 509
000

<210> SEQ ID NO 510
<400> SEQUENCE: 510
000

<210> SEQ ID NO 511
<400> SEQUENCE: 511
000

<210> SEQ ID NO 512
<400> SEQUENCE: 512
000

<210> SEQ ID NO 513
<400> SEQUENCE: 513
000

<210> SEQ ID NO 514
<400> SEQUENCE: 514
000

<210> SEQ ID NO 515
<400> SEQUENCE: 515
000

<210> SEQ ID NO 516
<400> SEQUENCE: 516
000

<210> SEQ ID NO 517
<400> SEQUENCE: 517
000

<210> SEQ ID NO 518
<400> SEQUENCE: 518
000

<210> SEQ ID NO 519

```
<400> SEQUENCE: 519

000

<210> SEQ ID NO 520

<400> SEQUENCE: 520

000

<210> SEQ ID NO 521

<400> SEQUENCE: 521

000

<210> SEQ ID NO 522

<400> SEQUENCE: 522

000

<210> SEQ ID NO 523

<400> SEQUENCE: 523

000

<210> SEQ ID NO 524

<400> SEQUENCE: 524

000

<210> SEQ ID NO 525

<400> SEQUENCE: 525

000

<210> SEQ ID NO 526

<400> SEQUENCE: 526

000

<210> SEQ ID NO 527

<400> SEQUENCE: 527

000

<210> SEQ ID NO 528

<400> SEQUENCE: 528

000

<210> SEQ ID NO 529

<400> SEQUENCE: 529

000

<210> SEQ ID NO 530

<400> SEQUENCE: 530
```

000

<210> SEQ ID NO 531

<400> SEQUENCE: 531

000

<210> SEQ ID NO 532

<400> SEQUENCE: 532

000

<210> SEQ ID NO 533

<400> SEQUENCE: 533

000

<210> SEQ ID NO 534

<400> SEQUENCE: 534

000

<210> SEQ ID NO 535

<400> SEQUENCE: 535

000

<210> SEQ ID NO 536

<400> SEQUENCE: 536

000

<210> SEQ ID NO 537

<400> SEQUENCE: 537

000

<210> SEQ ID NO 538

<400> SEQUENCE: 538

000

<210> SEQ ID NO 539

<400> SEQUENCE: 539

000

<210> SEQ ID NO 540

<400> SEQUENCE: 540

000

<210> SEQ ID NO 541

<400> SEQUENCE: 541

000

```
<210> SEQ ID NO 542
<400> SEQUENCE: 542
000

<210> SEQ ID NO 543
<400> SEQUENCE: 543
000

<210> SEQ ID NO 544
<400> SEQUENCE: 544
000

<210> SEQ ID NO 545
<400> SEQUENCE: 545
000

<210> SEQ ID NO 546
<400> SEQUENCE: 546
000

<210> SEQ ID NO 547
<400> SEQUENCE: 547
000

<210> SEQ ID NO 548
<400> SEQUENCE: 548
000

<210> SEQ ID NO 549
<400> SEQUENCE: 549
000

<210> SEQ ID NO 550
<400> SEQUENCE: 550
000

<210> SEQ ID NO 551
<400> SEQUENCE: 551
000

<210> SEQ ID NO 552
<400> SEQUENCE: 552
000

<210> SEQ ID NO 553
```

```
<400> SEQUENCE: 553
000

<210> SEQ ID NO 554
<400> SEQUENCE: 554
000

<210> SEQ ID NO 555
<400> SEQUENCE: 555
000

<210> SEQ ID NO 556
<400> SEQUENCE: 556
000

<210> SEQ ID NO 557
<400> SEQUENCE: 557
000

<210> SEQ ID NO 558
<400> SEQUENCE: 558
000

<210> SEQ ID NO 559
<400> SEQUENCE: 559
000

<210> SEQ ID NO 560
<400> SEQUENCE: 560
000

<210> SEQ ID NO 561
<400> SEQUENCE: 561
000

<210> SEQ ID NO 562
<400> SEQUENCE: 562
000

<210> SEQ ID NO 563
<400> SEQUENCE: 563
000

<210> SEQ ID NO 564
<400> SEQUENCE: 564
```

000

<210> SEQ ID NO 565
<400> SEQUENCE: 565
000

<210> SEQ ID NO 566
<400> SEQUENCE: 566
000

<210> SEQ ID NO 567
<400> SEQUENCE: 567
000

<210> SEQ ID NO 568
<400> SEQUENCE: 568
000

<210> SEQ ID NO 569
<400> SEQUENCE: 569
000

<210> SEQ ID NO 570
<400> SEQUENCE: 570
000

<210> SEQ ID NO 571
<400> SEQUENCE: 571
000

<210> SEQ ID NO 572
<400> SEQUENCE: 572
000

<210> SEQ ID NO 573
<400> SEQUENCE: 573
000

<210> SEQ ID NO 574
<400> SEQUENCE: 574
000

<210> SEQ ID NO 575
<400> SEQUENCE: 575
000

<210> SEQ ID NO 576

<400> SEQUENCE: 576

000

<210> SEQ ID NO 577

<400> SEQUENCE: 577

000

<210> SEQ ID NO 578

<400> SEQUENCE: 578

000

<210> SEQ ID NO 579

<400> SEQUENCE: 579

000

<210> SEQ ID NO 580

<400> SEQUENCE: 580

000

<210> SEQ ID NO 581

<400> SEQUENCE: 581

000

<210> SEQ ID NO 582

<400> SEQUENCE: 582

000

<210> SEQ ID NO 583

<400> SEQUENCE: 583

000

<210> SEQ ID NO 584

<400> SEQUENCE: 584

000

<210> SEQ ID NO 585

<400> SEQUENCE: 585

000

<210> SEQ ID NO 586

<400> SEQUENCE: 586

000

<210> SEQ ID NO 587

<400> SEQUENCE: 587

000

<210> SEQ ID NO 588

<400> SEQUENCE: 588

000

<210> SEQ ID NO 589

<400> SEQUENCE: 589

000

<210> SEQ ID NO 590

<400> SEQUENCE: 590

000

<210> SEQ ID NO 591

<400> SEQUENCE: 591

000

<210> SEQ ID NO 592

<400> SEQUENCE: 592

000

<210> SEQ ID NO 593

<400> SEQUENCE: 593

000

<210> SEQ ID NO 594

<400> SEQUENCE: 594

000

<210> SEQ ID NO 595

<400> SEQUENCE: 595

000

<210> SEQ ID NO 596

<400> SEQUENCE: 596

000

<210> SEQ ID NO 597

<400> SEQUENCE: 597

000

<210> SEQ ID NO 598

<400> SEQUENCE: 598

000

<210> SEQ ID NO 599

<400> SEQUENCE: 599

000

<210> SEQ ID NO 600
<211> LENGTH: 450
<212> TYPE: PRT
<213> ORGANISM: Artificial Sequence
<220> FEATURE:
<223> OTHER INFORMATION: MEDI0562 Heavy chain sequence

<400> SEQUENCE: 600

```
Gln Val Gln Leu Gln Glu Ser Gly Pro Gly Leu Val Lys Pro Ser Gln
  1               5                  10                  15

Thr Leu Ser Leu Thr Cys Ala Val Tyr Gly Gly Ser Phe Ser Ser Gly
             20                  25                  30

Tyr Trp Asn Trp Ile Arg Lys His Pro Gly Lys Gly Leu Glu Tyr Ile
         35                  40                  45

Gly Tyr Ile Ser Tyr Asn Gly Ile Thr Tyr His Asn Pro Ser Leu Lys
     50                  55                  60

Ser Arg Ile Thr Ile Asn Arg Asp Thr Ser Lys Asn Gln Tyr Ser Leu
 65                  70                  75                  80

Gln Leu Asn Ser Val Thr Pro Glu Asp Thr Ala Val Tyr Tyr Cys Ala
                 85                  90                  95

Arg Tyr Lys Tyr Asp Tyr Asp Gly Gly His Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
```

```
                305                 310                 315                 320
Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly
    450

<210> SEQ ID NO 601
<211> LENGTH: 214
<212> TYPE: PRT
<213> ORGANISM: Artificial Sequence
<220> FEATURE:
<223> OTHER INFORMATION: MEDI0562 Light Chain sequence

<400> SEQUENCE: 601

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Lys Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Ser Ala Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
```

-continued

```
<210> SEQ ID NO 602
<211> LENGTH: 402
<212> TYPE: PRT
<213> ORGANISM: Artificial Sequence
<220> FEATURE:
<223> OTHER INFORMATION: MEDI6383

<400> SEQUENCE: 602
```

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Asp Gln Asp Lys Ile Glu Ala Leu Ser Ser Lys
225                 230                 235                 240

Val Gln Gln Leu Glu Arg Ser Ile Gly Leu Lys Asp Leu Ala Met Ala
                245                 250                 255

Asp Leu Glu Gln Lys Val Leu Glu Met Glu Ala Ser Thr Gln Val Ser
            260                 265                 270

His Arg Tyr Pro Arg Ile Gln Ser Ile Lys Val Gln Phe Thr Glu Tyr
        275                 280                 285

Lys Lys Glu Lys Gly Phe Ile Leu Thr Ser Gln Lys Glu Asp Glu Ile
    290                 295                 300

Met Lys Val Gln Asn Asn Ser Val Ile Ile Asn Cys Asp Gly Phe Tyr
305                 310                 315                 320

Leu Ile Ser Leu Lys Gly Tyr Phe Ser Gln Glu Val Asn Ile Ser Leu
                325                 330                 335

His Tyr Gln Lys Asp Glu Glu Pro Leu Phe Gln Leu Lys Lys Val Arg
            340                 345                 350

Ser Val Asn Ser Leu Met Val Ala Ser Leu Thr Tyr Lys Asp Lys Val

```
                355                 360                 365
Tyr Leu Asn Val Thr Thr Asp Asn Thr Ser Leu Asp Asp Phe His Val
            370                 375                 380

Asn Gly Gly Glu Leu Ile Leu Ile His Gln Asn Pro Gly Glu Phe Cys
385                 390                 395                 400

Val Leu

<210> SEQ ID NO 603
<211> LENGTH: 121
<212> TYPE: PRT
<213> ORGANISM: Artificial Sequence
<220> FEATURE:
<223> OTHER INFORMATION: Ox40mAb24 VH sequence

<400> SEQUENCE: 603

Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Ser Gly
            20                  25                  30

Tyr Trp Asn Trp Ile Arg Lys His Pro Gly Lys Gly Leu Glu Tyr Ile
        35                  40                  45

Gly Tyr Ile Ser Tyr Asn Gly Ile Thr Tyr His Asn Pro Ser Leu Lys
    50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Tyr Cys Ala
                85                  90                  95

Arg Tyr Lys Tyr Asp Tyr Asp Gly Gly His Ala Met Asp Tyr Trp Gly
            100                 105                 110

Gln Gly Thr Leu Val Thr Val Ser Ser
        115                 120

<210> SEQ ID NO 604
<211> LENGTH: 107
<212> TYPE: PRT
<213> ORGANISM: Artificial Sequence
<220> FEATURE:
<223> OTHER INFORMATION: OX40mAb24 VL sequence

<400> SEQUENCE: 604

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Ser Ala Leu Pro Trp
                85                  90                  95

Thr Phe Gly Gln Gly Thr Lys Val Glu Ile Lys
            100                 105

<210> SEQ ID NO 605
<211> LENGTH: 5
<212> TYPE: PRT
```

<213> ORGANISM: Artificial Sequence
<220> FEATURE:
<223> OTHER INFORMATION: INCAGN1949 Antibody a VH CDR1

<400> SEQUENCE: 605

Gly Ser Ala Met His
1               5

<210> SEQ ID NO 606
<211> LENGTH: 19
<212> TYPE: PRT
<213> ORGANISM: Artificial Sequence
<220> FEATURE:
<223> OTHER INFORMATION: INCAGN1949 Antibody a VH CDR2

<400> SEQUENCE: 606

Arg Ile Arg Ser Lys Ala Asn Ser Tyr Ala Thr Ala Tyr Ala Ala Ser
1               5                   10                  15

Val Lys Gly

<210> SEQ ID NO 607
<211> LENGTH: 10
<212> TYPE: PRT
<213> ORGANISM: Artificial Sequence
<220> FEATURE:
<223> OTHER INFORMATION: INCAGN1949 Antibody a VH CDR3

<400> SEQUENCE: 607

Gly Ile Tyr Asp Ser Ser Gly Tyr Asp Tyr
1               5                   10

<210> SEQ ID NO 608
<211> LENGTH: 16
<212> TYPE: PRT
<213> ORGANISM: Artificial Sequence
<220> FEATURE:
<223> OTHER INFORMATION: INCAGN1949 Antibody a VL CDR1

<400> SEQUENCE: 608

Arg Ser Ser Gln Ser Leu Leu His Ser Asn Gly Tyr Asn Tyr Leu Asp
1               5                   10                  15

<210> SEQ ID NO 609
<211> LENGTH: 7
<212> TYPE: PRT
<213> ORGANISM: Artificial Sequence
<220> FEATURE:
<223> OTHER INFORMATION: INCAGN1949 Antibody a VL CDR2

<400> SEQUENCE: 609

Leu Gly Ser Asn Arg Ala Ser
1               5

<210> SEQ ID NO 610
<211> LENGTH: 9
<212> TYPE: PRT
<213> ORGANISM: Artificial Sequence
<220> FEATURE:
<223> OTHER INFORMATION: INCAGN1949 Antibody a VL CDR3

<400> SEQUENCE: 610

Met Gln Ala Leu Gln Thr Pro Leu Thr
1               5

<210> SEQ ID NO 611
<211> LENGTH: 121

```
<212> TYPE: PRT
<213> ORGANISM: Artificial Sequence
<220> FEATURE:
<223> OTHER INFORMATION: INCAGN1949 Antibody b VH sequence

<400> SEQUENCE: 611

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ser
        115                 120

<210> SEQ ID NO 612
<211> LENGTH: 112
<212> TYPE: PRT
<213> ORGANISM: Artificial Sequence
<220> FEATURE:
<223> OTHER INFORMATION: INCAGN1949 Antibody b VL sequence

<400> SEQUENCE: 612

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 613

<400> SEQUENCE: 613

000

<210> SEQ ID NO 614

<400> SEQUENCE: 614

000

<210> SEQ ID NO 615
```

<400> SEQUENCE: 615

000

<210> SEQ ID NO 616

<400> SEQUENCE: 616

000

<210> SEQ ID NO 617

<400> SEQUENCE: 617

000

<210> SEQ ID NO 618

<400> SEQUENCE: 618

000

<210> SEQ ID NO 619

<400> SEQUENCE: 619

000

<210> SEQ ID NO 620

<400> SEQUENCE: 620

000

<210> SEQ ID NO 621

<400> SEQUENCE: 621

000

<210> SEQ ID NO 622

<400> SEQUENCE: 622

000

<210> SEQ ID NO 623

<400> SEQUENCE: 623

000

<210> SEQ ID NO 624

<400> SEQUENCE: 624

000

<210> SEQ ID NO 625

<400> SEQUENCE: 625

000

<210> SEQ ID NO 626

<400> SEQUENCE: 626

000

<210> SEQ ID NO 627
<400> SEQUENCE: 627
000

<210> SEQ ID NO 628
<400> SEQUENCE: 628
000

<210> SEQ ID NO 629
<400> SEQUENCE: 629
000

<210> SEQ ID NO 630
<400> SEQUENCE: 630
000

<210> SEQ ID NO 631
<400> SEQUENCE: 631
000

<210> SEQ ID NO 632
<400> SEQUENCE: 632
000

<210> SEQ ID NO 633
<400> SEQUENCE: 633
000

<210> SEQ ID NO 634
<400> SEQUENCE: 634
000

<210> SEQ ID NO 635
<400> SEQUENCE: 635
000

<210> SEQ ID NO 636
<400> SEQUENCE: 636
000

<210> SEQ ID NO 637
<400> SEQUENCE: 637
000

<210> SEQ ID NO 638

<400> SEQUENCE: 638

000

<210> SEQ ID NO 639

<400> SEQUENCE: 639

000

<210> SEQ ID NO 640

<400> SEQUENCE: 640

000

<210> SEQ ID NO 641

<400> SEQUENCE: 641

000

<210> SEQ ID NO 642

<400> SEQUENCE: 642

000

<210> SEQ ID NO 643

<400> SEQUENCE: 643

000

<210> SEQ ID NO 644

<400> SEQUENCE: 644

000

<210> SEQ ID NO 645

<400> SEQUENCE: 645

000

<210> SEQ ID NO 646

<400> SEQUENCE: 646

000

<210> SEQ ID NO 647

<400> SEQUENCE: 647

000

<210> SEQ ID NO 648

<400> SEQUENCE: 648

000

<210> SEQ ID NO 649

<400> SEQUENCE: 649

000

<210> SEQ ID NO 650

<400> SEQUENCE: 650

000

<210> SEQ ID NO 651

<400> SEQUENCE: 651

000

<210> SEQ ID NO 652

<400> SEQUENCE: 652

000

<210> SEQ ID NO 653

<400> SEQUENCE: 653

000

<210> SEQ ID NO 654

<400> SEQUENCE: 654

000

<210> SEQ ID NO 655

<400> SEQUENCE: 655

000

<210> SEQ ID NO 656

<400> SEQUENCE: 656

000

<210> SEQ ID NO 657

<400> SEQUENCE: 657

000

<210> SEQ ID NO 658

<400> SEQUENCE: 658

000

<210> SEQ ID NO 659

<400> SEQUENCE: 659

000

<210> SEQ ID NO 660

<400> SEQUENCE: 660

000

<210> SEQ ID NO 661

<400> SEQUENCE: 661

000

<210> SEQ ID NO 662

<400> SEQUENCE: 662

000

<210> SEQ ID NO 663

<400> SEQUENCE: 663

000

<210> SEQ ID NO 664

<400> SEQUENCE: 664

000

<210> SEQ ID NO 665

<400> SEQUENCE: 665

000

<210> SEQ ID NO 666

<400> SEQUENCE: 666

000

<210> SEQ ID NO 667

<400> SEQUENCE: 667

000

<210> SEQ ID NO 668

<400> SEQUENCE: 668

000

<210> SEQ ID NO 669

<400> SEQUENCE: 669

000

<210> SEQ ID NO 670

<400> SEQUENCE: 670

000

<210> SEQ ID NO 671

<400> SEQUENCE: 671

000

<210> SEQ ID NO 672

<400> SEQUENCE: 672

000

<210> SEQ ID NO 673

<400> SEQUENCE: 673

000

<210> SEQ ID NO 674

<400> SEQUENCE: 674

000

<210> SEQ ID NO 675

<400> SEQUENCE: 675

000

<210> SEQ ID NO 676

<400> SEQUENCE: 676

000

<210> SEQ ID NO 677

<400> SEQUENCE: 677

000

<210> SEQ ID NO 678

<400> SEQUENCE: 678

000

<210> SEQ ID NO 679

<400> SEQUENCE: 679

000

<210> SEQ ID NO 680

<400> SEQUENCE: 680

000

<210> SEQ ID NO 681

<400> SEQUENCE: 681

000

<210> SEQ ID NO 682

<400> SEQUENCE: 682

000

```
<210> SEQ ID NO 683
<400> SEQUENCE: 683
000

<210> SEQ ID NO 684
<400> SEQUENCE: 684
000

<210> SEQ ID NO 685
<400> SEQUENCE: 685
000

<210> SEQ ID NO 686
<400> SEQUENCE: 686
000

<210> SEQ ID NO 687
<400> SEQUENCE: 687
000

<210> SEQ ID NO 688
<400> SEQUENCE: 688
000

<210> SEQ ID NO 689
<400> SEQUENCE: 689
000

<210> SEQ ID NO 690
<400> SEQUENCE: 690
000

<210> SEQ ID NO 691
<400> SEQUENCE: 691
000

<210> SEQ ID NO 692
<400> SEQUENCE: 692
000

<210> SEQ ID NO 693
<400> SEQUENCE: 693
000

<210> SEQ ID NO 694
```

```
<400> SEQUENCE: 694

000

<210> SEQ ID NO 695

<400> SEQUENCE: 695

000

<210> SEQ ID NO 696

<400> SEQUENCE: 696

000

<210> SEQ ID NO 697

<400> SEQUENCE: 697

000

<210> SEQ ID NO 698

<400> SEQUENCE: 698

000

<210> SEQ ID NO 699

<400> SEQUENCE: 699

000

<210> SEQ ID NO 700
<211> LENGTH: 167
<212> TYPE: PRT
<213> ORGANISM: Artificial Sequence
<220> FEATURE:
<223> OTHER INFORMATION: Tremelimumab VH sequence

<400> SEQUENCE: 700

Gly Val Val Gln Pro Gly Arg Ser Leu Arg Leu Ser Cys Ala Ala Ser
1               5                   10                  15

Gly Phe Thr Phe Ser Ser Tyr Gly Met His Trp Val Arg Gln Ala Pro
            20                  25                  30

Gly Lys Gly Leu Glu Trp Val Ala Val Ile Trp Tyr Asp Gly Ser Asn
        35                  40                  45

Lys Tyr Tyr Ala Asp Ser Val Lys Gly Arg Phe Thr Ile Ser Arg Asp
    50                  55                  60

Asn Ser Lys Asn Thr Leu Tyr Leu Gln Met Asn Ser Leu Arg Ala Glu
65                  70                  75                  80

Asp Thr Ala Val Tyr Tyr Cys Ala Arg Asp Pro Arg Gly Ala Thr Leu
                85                  90                  95

Tyr Tyr Tyr Tyr Tyr Gly Met Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160
```

```
<210> SEQ ID NO 701
<211> LENGTH: 139
<212> TYPE: PRT
<213> ORGANISM: Artificial Sequence
<220> FEATURE:
<223> OTHER INFORMATION: Tremelimumab VL sequence

<400> SEQUENCE: 701

Pro Ser Ser Leu Ser Ala Ser Val Gly Asp Arg Val Thr Ile Thr Cys
1               5                   10                  15
Arg Ala Ser Gln Ser Ile Asn Ser Tyr Leu Asp Trp Tyr Gln Gln Lys
            20                  25                  30
Pro Gly Lys Ala Pro Lys Leu Leu Ile Tyr Ala Ala Ser Ser Leu Gln
        35                  40                  45
Ser Gly Val Pro Ser Arg Phe Ser Gly Ser Gly Ser Gly Thr Asp Phe
    50                  55                  60
Thr Leu Thr Ile Ser Ser Leu Gln Pro Glu Asp Phe Ala Thr Tyr Tyr
65                  70                  75                  80
Cys Gln Gln Tyr Tyr Ser Thr Pro Phe Thr Phe Gly Pro Gly Thr Lys
                85                  90                  95
Val Glu Ile Lys Arg Thr Val Ala Ala Pro Ser Val Phe Ile Phe Pro
            100                 105                 110
Pro Ser Asp Glu Gln Leu Lys Ser Gly Thr Ala Ser Val Val Cys Leu
        115                 120                 125
Leu Asn Asn Phe Tyr Pro Arg Glu Ala Lys Val
        130                 135
```